United States Patent
Liu et al.

(10) Patent No.: US 10,465,176 B2
(45) Date of Patent: *Nov. 5, 2019

(54) CAS VARIANTS FOR GENE EDITING

(71) Applicant: President and Fellows of Harvard College, Cambridge, MA (US)

(72) Inventors: David R. Liu, Lexington, MA (US); Alexis Christine Komor, Pasadena, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 133 days.

This patent is subject to a terminal disclaimer.

(21) Appl. No.: 15/103,608

(22) PCT Filed: Dec. 12, 2014

(86) PCT No.: PCT/US2014/070038
§ 371 (c)(1),
(2) Date: Jun. 10, 2016

(87) PCT Pub. No.: WO2015/089406
PCT Pub. Date: Jun. 18, 2015

(65) Prior Publication Data
US 2016/0304846 A1    Oct. 20, 2016

Related U.S. Application Data

(63) Continuation of application No. 14/325,815, filed on Jul. 8, 2014, and a continuation of application No. 14/326,109, filed on Jul. 8, 2014, now Pat. No. 9,840,699, and a continuation of application No. 14/326,140, filed on Jul. 8, 2014, now abandoned, and a continuation of application No. 14/326,269, filed on Jul. 8, 2014, now Pat. No. 9,068,179, and a continuation of application No. 14/326,290, filed on Jul. 8, 2014, now abandoned, and a continuation of application No. 14/326,318, filed on Jul. 8, 2014, and a continuation of application No. 14/326,303, filed on Jul. 8, 2014, now abandoned.

(60) Provisional application No. 61/980,333, filed on Apr. 16, 2014, provisional application No. 61/915,386, filed on Dec. 12, 2013.

(51) Int. Cl.
| | |
|---|---|
| C12N 9/22 | (2006.01) |
| C12N 9/64 | (2006.01) |
| C12N 9/78 | (2006.01) |
| A61K 38/46 | (2006.01) |
| A61K 38/50 | (2006.01) |
| A61K 47/61 | (2017.01) |
| C12N 15/01 | (2006.01) |
| C12N 15/10 | (2006.01) |
| C12P 19/34 | (2006.01) |
| C12Q 1/6883 | (2018.01) |

(52) U.S. Cl.
CPC ............. *C12N 9/22* (2013.01); *A61K 38/465* (2013.01); *A61K 38/50* (2013.01); *A61K 47/61* (2017.08); *C12N 9/6472* (2013.01); *C12N 9/78* (2013.01); *C12N 15/01* (2013.01); *C12N 15/102* (2013.01); *C12P 19/34* (2013.01); *C12Q 1/6883* (2013.01); *C12Y 301/00* (2013.01); *C12Y 304/22062* (2013.01); *C12Y 305/04* (2013.01); *C12Y 305/04001* (2013.01); *C12Y 305/04004* (2013.01); *C12Y 305/04005* (2013.01); *C07K 2319/00* (2013.01); *C07K 2319/80* (2013.01); *C12Q 2600/156* (2013.01); *C12Y 301/22* (2013.01)

(58) Field of Classification Search
None
See application file for complete search history.

(56) References Cited

U.S. PATENT DOCUMENTS

| | | | |
|---|---|---|---|
| 4,182,449 | A | 1/1980 | Kozlow |
| 4,235,871 | A | 11/1980 | Papahadjopoulos et al. |
| 4,880,635 | A | 11/1989 | Janoff et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |

(Continued)

FOREIGN PATENT DOCUMENTS

| | | |
|---|---|---|
| AU | 2012244264 A1 | 11/2012 |
| AU | 2015252023 A1 | 11/2015 |

(Continued)

OTHER PUBLICATIONS

U.S. Appl. No. 61/716,256, Jinek et al., filed Oct. 19, 2012.

(Continued)

*Primary Examiner* — Anand U Desai
(74) *Attorney, Agent, or Firm* — Wolf, Greenfield & Sacks, P.C.

(57) ABSTRACT

Some aspects of this disclosure provide strategies, systems, reagents, methods, and kits that are useful for the targeted editing of nucleic acids, including editing a single site within the genome of a cell or subject, e.g., within the human genome. In some embodiments, fusion proteins of Cas9 and nucleic acid editing enzymes or enzyme domains, e.g., deaminase domains, are provided. In some embodiments, methods for targeted nucleic acid editing are provided. In some embodiments, reagents and kits for the generation of targeted nucleic acid editing proteins, e.g., fusion proteins of Cas9 and nucleic acid editing enzymes or domains, are provided.

44 Claims, 4 Drawing Sheets
Specification includes a Sequence Listing.

(56) References Cited

U.S. PATENT DOCUMENTS

| | | |
|---|---|---|
| 4,921,757 A | 5/1990 | Wheatley et al. |
| 5,139,941 A | 8/1992 | Muzyczka et al. |
| 5,449,639 A | 9/1995 | Wei et al. |
| 5,780,053 A | 7/1998 | Ashley et al. |
| 5,835,699 A | 11/1998 | Kimura |
| 5,962,313 A | 10/1999 | Podsakoff et al. |
| 6,057,153 A | 5/2000 | George et al. |
| 6,453,242 B1 | 9/2002 | Eisenberg et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,163,824 B2 | 1/2007 | Cox, III et al. |
| 7,479,573 B2 | 1/2009 | Chu et al. |
| 7,794,931 B2 | 9/2010 | Breaker et al. |
| 7,919,277 B2 | 4/2011 | Russell et al. |
| 7,993,672 B2 | 8/2011 | Huang et al. |
| 8,097,648 B2 | 1/2012 | Littlefield et al. |
| 8,361,725 B2 | 1/2013 | Russell et al. |
| 8,394,604 B2 | 3/2013 | Liu et al. |
| 8,492,082 B2 | 7/2013 | De Franciscis et al. |
| 8,546,553 B2 | 10/2013 | Terns et al. |
| 8,569,256 B2 | 10/2013 | Heyes et al. |
| 8,680,069 B2 | 3/2014 | de Fougerolles et al. |
| 8,691,750 B2 | 4/2014 | Constien et al. |
| 8,697,359 B1 | 4/2014 | Zhang |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,846,578 B2 | 9/2014 | McCray et al. |
| 8,993,233 B2 | 3/2015 | Zhang et al. |
| 8,999,641 B2 | 4/2015 | Zhang et al. |
| 9,068,179 B1 * | 6/2015 | Liu ................. C12Y 304/22062 |
| 9,163,284 B2 | 10/2015 | Liu et al. |
| 9,228,207 B2 | 1/2016 | Liu et al. |
| 9,234,213 B2 | 1/2016 | Wu |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,388,430 B2 | 7/2016 | Liu et al. |
| 9,512,446 B1 | 12/2016 | Joung et al. |
| 9,526,724 B2 | 12/2016 | Oshlack et al. |
| 9,737,604 B2 | 8/2017 | Liu et al. |
| 9,816,093 B1 | 11/2017 | Donohoue et al. |
| 9,822,372 B2 | 11/2017 | Zhang et al. |
| 9,840,690 B2 | 12/2017 | Karli et al. |
| 9,840,699 B2 * | 12/2017 | Liu ......................... A61K 47/61 |
| 9,840,713 B2 | 12/2017 | Zhang |
| 9,873,907 B2 | 1/2018 | Zeiner et al. |
| 9,879,270 B2 | 1/2018 | Hittinger et al. |
| 9,938,288 B1 | 4/2018 | Kishi et al. |
| 9,944,933 B2 | 4/2018 | Storici et al. |
| 9,982,279 B1 | 5/2018 | Gill et al. |
| 9,999,671 B2 | 6/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,167,457 B2 | 1/2019 | Liu et al. |
| 10,227,581 B2 | 3/2019 | Liu et al. |
| 2004/0003420 A1 | 1/2004 | Kuhn et al. |
| 2004/0115184 A1 | 6/2004 | Smith et al. |
| 2005/0222030 A1 | 10/2005 | Allison et al. |
| 2006/0088864 A1 | 4/2006 | Smolke et al. |
| 2006/0104984 A1 | 5/2006 | Littlefield et al. |
| 2006/0246568 A1 | 11/2006 | Honjo et al. |
| 2007/0264692 A1 | 11/2007 | Liu et al. |
| 2008/0124725 A1 | 5/2008 | Barrangou et al. |
| 2008/0182254 A1 | 7/2008 | Hall et al. |
| 2009/0130718 A1 | 5/2009 | Short |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0316643 A1 | 12/2010 | Eckert et al. |
| 2011/0059160 A1 | 3/2011 | Essner et al. |
| 2011/0104787 A1 | 5/2011 | Church et al. |
| 2011/0189776 A1 | 8/2011 | Terns et al. |
| 2011/0217739 A1 | 9/2011 | Terns et al. |
| 2012/0129759 A1 | 5/2012 | Liu et al. |
| 2012/0141523 A1 | 6/2012 | Castado et al. |
| 2012/0244601 A1 | 9/2012 | Bertozzi et al. |
| 2012/0270273 A1 | 10/2012 | Zhang et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0309720 A1 | 11/2013 | Schultz et al. |
| 2013/0344117 A1 | 12/2013 | Mirosevich et al. |
| 2014/0004280 A1 | 1/2014 | Loomis |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0186843 A1 | 7/2014 | Zhang et al. |
| 2014/0186958 A1 | 7/2014 | Zhang et al. |
| 2014/0234289 A1 | 8/2014 | Liu et al. |
| 2014/0248702 A1 | 9/2014 | Cong |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |

(56) References Cited

U.S. PATENT DOCUMENTS

| | | |
|---|---|---|
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens et al. |
| 2015/0218573 A1 | 8/2015 | Loque et al. |
| 2015/0225773 A1 | 8/2015 | Farmer et al. |
| 2015/0252358 A1 | 9/2015 | Maeder et al. |
| 2015/0307889 A1 | 10/2015 | Petolino et al. |
| 2015/0315252 A1 | 11/2015 | Haugwitz et al. |
| 2016/0015682 A2 | 1/2016 | Cawthorne et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |
| 2016/0115488 A1 | 4/2016 | Zhang et al. |
| 2016/0138046 A1 | 5/2016 | Wu et al. |
| 2016/0186214 A1 | 6/2016 | Brouns et al. |
| 2016/0200779 A1 | 7/2016 | Liu et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0272965 A1 | 9/2016 | Zhang et al. |
| 2016/0281072 A1 | 9/2016 | Zhang |
| 2016/0304855 A1 | 10/2016 | Stark et al. |
| 2016/0312304 A1 | 10/2016 | Sorrentino et al. |
| 2016/0333389 A1 | 11/2016 | Liu et al. |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0350476 A1 | 12/2016 | Quake et al. |
| 2016/0369262 A1 | 12/2016 | Reik et al. |
| 2017/0009242 A1 | 1/2017 | McKinley et al. |
| 2017/0014449 A1 | 1/2017 | Bangera et al. |
| 2017/0020922 A1 | 1/2017 | Wagner et al. |
| 2017/0037432 A1 | 2/2017 | Donohoue et al. |
| 2017/0044520 A1 | 2/2017 | Liu et al. |
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0087224 A1 | 3/2017 | Quake |
| 2017/0087225 A1 | 3/2017 | Quake |
| 2017/0088587 A1 | 3/2017 | Quake |
| 2017/0088828 A1 | 3/2017 | Quake |
| 2017/0107536 A1 | 4/2017 | Zhang et al. |
| 2017/0107560 A1 | 4/2017 | Peter et al. |
| 2017/0114367 A1 | 4/2017 | Hu et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0226522 A1 | 8/2017 | Hu et al. |
| 2017/0233703 A1 | 8/2017 | Xie et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0283797 A1 | 10/2017 | Robb et al. |
| 2017/0314016 A1 | 11/2017 | Kim et al. |
| 2017/0362635 A1 | 12/2017 | Chamberlain et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127780 A1 | 5/2018 | Liu et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237787 A1 | 8/2018 | Maianti et al. |
| 2018/0245066 A1 | 8/2018 | Yao et al. |
| 2018/0265864 A1 | 9/2018 | Li et al. |
| 2018/0273939 A1 | 9/2018 | Yu et al. |
| 2018/0282722 A1 | 10/2018 | Jakimo et al. |
| 2018/0305688 A1 | 10/2018 | Zhong |
| 2018/0305704 A1 | 10/2018 | Zhang |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2019/0093099 A1 | 3/2019 | Liu et al. |

FOREIGN PATENT DOCUMENTS

| | | |
|---|---|---|
| AU | 2015101792 | 1/2016 |
| BR | 112015013786 A2 | 7/2017 |
| CA | 2894668 A1 | 6/2014 |
| CA | 2894681 A1 | 6/2014 |
| CA | 2894684 A1 | 6/2014 |
| CA | 2 852 593 A1 | 11/2015 |
| CN | 1069962 A | 3/1993 |
| CN | 103224947 A | 7/2013 |
| CN | 103233028 A | 8/2013 |
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 103981211 A | 8/2014 |
| CN | 103981212 A | 8/2014 |
| CN | 104004778 A | 8/2014 |
| CN | 104004782 A | 8/2014 |
| CN | 104017821 A | 9/2014 |
| CN | 104109687 A | 10/2014 |
| CN | 104178461 A | 12/2014 |

(56) References Cited

FOREIGN PATENT DOCUMENTS

| | | |
|---|---|---|
| CN | 104342457 | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104561095 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |
| CN | 104725626 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 105039339 A | 11/2015 |
| CN | 105039399 A | 11/2015 |
| CN | 105063061 A | 11/2015 |
| CN | 105087620 A | 11/2015 |
| CN | 105112422 A | 12/2015 |
| CN | 105112445 A | 12/2015 |
| CN | 105112519 A | 12/2015 |
| CN | 105121648 A | 12/2015 |
| CN | 105132427 A | 12/2015 |
| CN | 105132451 A | 12/2015 |
| CN | 105177038 A | 12/2015 |
| CN | 105177126 A | 12/2015 |
| CN | 105210981 A | 1/2016 |
| CN | 105219799 A | 1/2016 |
| CN | 105238806 A | 1/2016 |
| CN | 105255937 A | 1/2016 |
| CN | 105274144 A | 1/2016 |
| CN | 105296518 A | 2/2016 |
| CN | 105296537 A | 2/2016 |
| CN | 105316324 A | 2/2016 |
| CN | 105316327 A | 2/2016 |
| CN | 105316337 A | 2/2016 |
| CN | 105331607 A | 2/2016 |
| CN | 105331608 A | 2/2016 |
| CN | 105331609 A | 2/2016 |
| CN | 105331627 A | 2/2016 |
| CN | 105400773 A | 3/2016 |
| CN | 105400779 A | 3/2016 |
| CN | 105400810 A | 3/2016 |
| CN | 105441451 A | 3/2016 |
| CN | 105462968 A | 4/2016 |
| CN | 105463003 A | 4/2016 |
| CN | 105463027 A | 4/2016 |
| CN | 105492608 A | 4/2016 |
| CN | 105492609 A | 4/2016 |
| CN | 105505976 A | 4/2016 |
| CN | 105505979 A | 4/2016 |
| CN | 105518134 A | 4/2016 |
| CN | 105518135 A | 4/2016 |
| CN | 105518137 A | 4/2016 |
| CN | 105518138 A | 4/2016 |
| CN | 105518139 A | 4/2016 |
| CN | 105518140 A | 4/2016 |
| CN | 105543228 A | 5/2016 |
| CN | 105543266 A | 5/2016 |
| CN | 105543270 A | 5/2016 |
| CN | 105567688 A | 5/2016 |
| CN | 105567689 | 5/2016 |
| CN | 105567734 A | 5/2016 |
| CN | 105567735 A | 5/2016 |
| CN | 105567738 A | 5/2016 |
| CN | 105593367 A | 5/2016 |
| CN | 105594664 A | 5/2016 |
| CN | 105602987 A | 5/2016 |
| CN | 105624146 A | 6/2016 |
| CN | 105624187 A | 6/2016 |
| CN | 105646719 A | 6/2016 |
| CN | 105647922 A | 6/2016 |
| CN | 105647962 A | 6/2016 |
| CN | 105647968 A | 6/2016 |
| CN | 105647969 A | 6/2016 |
| CN | 105671070 A | 6/2016 |
| CN | 105671083 A | 6/2016 |
| CN | 105695485 A | 6/2016 |
| CN | 105779448 A | 7/2016 |
| CN | 105779449 A | 7/2016 |
| CN | 105802980 A | 7/2016 |
| CN | 105821039 A | 8/2016 |
| CN | 105821040 A | 8/2016 |
| CN | 105821049 A | 8/2016 |
| CN | 105821072 A | 8/2016 |
| CN | 105821075 A | 8/2016 |
| CN | 105821116 A | 8/2016 |
| CN | 105838733 A | 8/2016 |
| CN | 105861547 A | 8/2016 |
| CN | 105861552 A | 8/2016 |
| CN | 105861554 A | 8/2016 |
| CN | 105886498 A | 8/2016 |
| CN | 105886534 A | 8/2016 |
| CN | 105886616 A | 8/2016 |
| CN | 105907758 A | 8/2016 |
| CN | 105907785 A | 8/2016 |
| CN | 105925608 A | 9/2016 |
| CN | 105950560 A | 9/2016 |
| CN | 105950626 A | 9/2016 |
| CN | 105950633 A | 9/2016 |
| CN | 105950639 A | 9/2016 |
| CN | 105985985 A | 10/2016 |
| CN | 106011104 A | 10/2016 |
| CN | 106011150 A | 10/2016 |
| CN | 106011167 A | 10/2016 |
| CN | 106011171 A | 10/2016 |
| CN | 106032540 A | 10/2016 |
| CN | 106047803 A | 10/2016 |
| CN | 106047877 A | 10/2016 |
| CN | 106047930 A | 10/2016 |
| CN | 106086008 A | 11/2016 |
| CN | 106086028 A | 11/2016 |
| CN | 106086061 A | 11/2016 |
| CN | 106086062 A | 11/2016 |
| CN | 106109417 A | 11/2016 |
| CN | 106119275 A | 11/2016 |
| CN | 106119283 A | 11/2016 |
| CN | 106148286 A | 11/2016 |
| CN | 106148370 A | 11/2016 |
| CN | 106148416 A | 11/2016 |
| CN | 106167525 A | 11/2016 |
| CN | 106167808 A | 11/2016 |
| CN | 106167810 A | 11/2016 |
| CN | 106167821 A | 11/2016 |
| CN | 106172238 A | 12/2016 |
| CN | 106190903 A | 12/2016 |
| CN | 106191057 A | 12/2016 |
| CN | 106191061 A | 12/2016 |
| CN | 106191062 A | 12/2016 |
| CN | 106191064 A | 12/2016 |
| CN | 106191071 A | 12/2016 |
| CN | 106191099 A | 12/2016 |
| CN | 106191107 A | 12/2016 |
| CN | 106191113 A | 12/2016 |
| CN | 106191114 A | 12/2016 |
| CN | 106191116 A | 12/2016 |
| CN | 106191124 A | 12/2016 |
| CN | 106222177 A | 12/2016 |

(56) References Cited

FOREIGN PATENT DOCUMENTS

| | | | |
|---|---|---|---|
| CN | 106222193 A | 12/2016 |
| CN | 106222203 A | 12/2016 |
| CN | 106244555 A | 12/2016 |
| CN | 106244591 A | 12/2016 |
| CN | 106244609 A | 12/2016 |
| CN | 106282241 A | 1/2017 |
| CN | 106318934 A | 1/2017 |
| CN | 106318973 A | 1/2017 |
| CN | 106350540 A | 1/2017 |
| CN | 106367435 A | 2/2017 |
| CN | 106399306 A | 2/2017 |
| CN | 106399311 A | 2/2017 |
| CN | 106399360 A | 2/2017 |
| CN | 106399367 A | 2/2017 |
| CN | 106399375 A | 2/2017 |
| CN | 106399377 A | 2/2017 |
| CN | 106434651 A | 2/2017 |
| CN | 106434663 A | 2/2017 |
| CN | 106434688 A | 2/2017 |
| CN | 106434737 A | 2/2017 |
| CN | 106434748 A | 2/2017 |
| CN | 106434752 A | 2/2017 |
| CN | 106434782 A | 2/2017 |
| CN | 106446600 A | 2/2017 |
| CN | 106479985 A | 3/2017 |
| CN | 106480027 A | 3/2017 |
| CN | 106480036 A | 3/2017 |
| CN | 106480067 A | 3/2017 |
| CN | 106480080 A | 3/2017 |
| CN | 106480083 A | 3/2017 |
| CN | 106480097 A | 3/2017 |
| CN | 106544351 A | 3/2017 |
| CN | 106544353 A | 3/2017 |
| CN | 106544357 A | 3/2017 |
| CN | 106554969 A | 4/2017 |
| CN | 106566838 A | 4/2017 |
| CN | 106701763 A | 5/2017 |
| CN | 106701808 A | 5/2017 |
| CN | 106701818 A | 5/2017 |
| CN | 106701823 A | 5/2017 |
| CN | 106701830 A | 5/2017 |
| CN | 106754912 A | 5/2017 |
| CN | 106755026 A | 5/2017 |
| CN | 106755077 A | 5/2017 |
| CN | 106755088 A | 5/2017 |
| CN | 106755091 A | 5/2017 |
| CN | 106755097 A | 5/2017 |
| CN | 106755424 A | 5/2017 |
| CN | 106801056 A | 6/2017 |
| CN | 106834323 A | 6/2017 |
| CN | 106834341 A | 6/2017 |
| CN | 106834347 A | 6/2017 |
| CN | 106845151 A | 6/2017 |
| CN | 106868008 A | 6/2017 |
| CN | 106868031 A | 6/2017 |
| CN | 106906240 A | 6/2017 |
| CN | 106906242 A | 6/2017 |
| CN | 106916820 A | 7/2017 |
| CN | 106916852 A | 7/2017 |
| CN | 106939303 A | 7/2017 |
| CN | 106947750 A | 7/2017 |
| CN | 106947780 A | 7/2017 |
| CN | 106957830 A | 7/2017 |
| CN | 106957831 A | 7/2017 |
| CN | 106957844 A | 7/2017 |
| CN | 106957855 A | 7/2017 |
| CN | 106957858 A | 7/2017 |
| CN | 106967697 A | 7/2017 |
| CN | 106967726 A | 7/2017 |
| CN | 106978428 A | 7/2017 |
| CN | 106987570 A | 7/2017 |
| CN | 106987757 A | 7/2017 |
| CN | 107012164 A | 8/2017 |
| CN | 107012174 A | 8/2017 |
| CN | 107012213 A | 8/2017 |
| CN | 107012250 A | 8/2017 |
| CN | 107022562 A | 8/2017 |
| CN | 107034188 A | 8/2017 |
| CN | 107034218 A | 8/2017 |
| CN | 107034229 A | 8/2017 |
| CN | 107043775 A | 8/2017 |
| CN | 107043779 A | 8/2017 |
| CN | 107043787 A | 8/2017 |
| CN | 107058320 A | 8/2017 |
| CN | 107058328 A | 8/2017 |
| CN | 107058358 A | 8/2017 |
| CN | 107058372 A | 8/2017 |
| CN | 107083392 A | 8/2017 |
| CN | 107099533 A | 8/2017 |
| CN | 107099850 A | 8/2017 |
| CN | 107119053 A | 9/2017 |
| CN | 107119071 A | 9/2017 |
| CN | 107129999 A | 9/2017 |
| CN | 107130000 A | 9/2017 |
| CN | 107142272 A | 9/2017 |
| CN | 107142282 A | 9/2017 |
| CN | 107177591 A | 9/2017 |
| CN | 107177595 A | 9/2017 |
| CN | 107177631 A | 9/2017 |
| CN | 107190006 A | 9/2017 |
| CN | 107190008 A | 9/2017 |
| CN | 107217042 A | 9/2017 |
| CN | 107217075 A | 9/2017 |
| CN | 107227307 A | 10/2017 |
| CN | 107227352 A | 10/2017 |
| CN | 107236737 A | 10/2017 |
| CN | 107236739 A | 10/2017 |
| CN | 107236741 A | 10/2017 |
| CN | 107245502 A | 10/2017 |
| CN | 107254485 A | 10/2017 |
| CN | 107266541 A | 10/2017 |
| CN | 107267515 A | 10/2017 |
| CN | 107287245 A | 10/2017 |
| CN | 107298701 A | 10/2017 |
| CN | 107299114 A | 10/2017 |
| CN | 107304435 A | 10/2017 |
| CN | 107312785 A | 11/2017 |
| CN | 107312793 A | 11/2017 |
| CN | 107312795 A | 11/2017 |
| CN | 107312798 A | 11/2017 |
| CN | 107326042 A | 11/2017 |
| CN | 107326046 A | 11/2017 |
| CN | 107354156 A | 11/2017 |
| CN | 107354173 A | 11/2017 |
| CN | 107356793 A | 11/2017 |
| CN | 107362372 A | 11/2017 |
| CN | 107365786 A | 11/2017 |
| CN | 107365804 A | 11/2017 |
| CN | 107384894 A | 11/2017 |
| CN | 107384922 A | 11/2017 |
| CN | 107384926 A | 11/2017 |
| CN | 107400677 A | 11/2017 |
| CN | 107418974 A | 12/2017 |
| CN | 107435051 A | 12/2017 |
| CN | 107435069 A | 12/2017 |
| CN | 107446922 A | 12/2017 |
| CN | 107446923 A | 12/2017 |
| CN | 107446924 A | 12/2017 |
| CN | 107446932 A | 12/2017 |
| CN | 107446951 A | 12/2017 |
| CN | 107446954 A | 12/2017 |
| CN | 107460196 A | 12/2017 |
| CN | 107474129 A | 12/2017 |
| CN | 107475300 A | 12/2017 |
| CN | 107488649 A | 12/2017 |
| CN | 107502608 A | 12/2017 |
| CN | 107502618 A | 12/2017 |
| CN | 107513531 A | 12/2017 |
| CN | 107519492 A | 12/2017 |
| CN | 107523567 A | 12/2017 |
| CN | 107523583 A | 12/2017 |
| CN | 107541525 A | 1/2018 |
| CN | 107557373 A | 1/2018 |
| CN | 107557378 A | 1/2018 |

(56) References Cited

FOREIGN PATENT DOCUMENTS

| | | |
|---|---|---|
| CN | 107557381 A | 1/2018 |
| CN | 107557390 A | 1/2018 |
| CN | 107557393 A | 1/2018 |
| CN | 107557394 A | 1/2018 |
| CN | 107557455 A | 1/2018 |
| CN | 107574179 | 1/2018 |
| CN | 107586777 | 1/2018 |
| CN | 107586779 | 1/2018 |
| CN | 107604003 | 1/2018 |
| CN | 107619829 A | 1/2018 |
| CN | 107619837 A | 1/2018 |
| CN | 107630006 A | 1/2018 |
| CN | 107630041 A | 1/2018 |
| CN | 107630042 A | 1/2018 |
| CN | 107630043 A | 1/2018 |
| CN | 107641631 A | 1/2018 |
| CN | 107653256 A | 2/2018 |
| CN | 107686848 A | 2/2018 |
| CN | 206970581 | 2/2018 |
| CN | 107760652 A | 3/2018 |
| CN | 107760663 A | 3/2018 |
| CN | 107760684 A | 3/2018 |
| CN | 107760715 A | 3/2018 |
| CN | 107784200 A | 3/2018 |
| CN | 107794272 A | 3/2018 |
| CN | 107794276 A | 3/2018 |
| CN | 107815463 A | 3/2018 |
| CN | 107828738 A | 3/2018 |
| CN | 107828794 A | 3/2018 |
| CN | 107828826 A | 3/2018 |
| CN | 107828874 A | 3/2018 |
| CN | 107858346 A | 3/2018 |
| CN | 107858373 A | 3/2018 |
| CN | 107880132 A | 4/2018 |
| CN | 107881184 A | 4/2018 |
| CN | 107893074 A | 4/2018 |
| CN | 107893075 A | 4/2018 |
| CN | 107893076 A | 4/2018 |
| CN | 107893080 A | 4/2018 |
| CN | 107893086 A | 4/2018 |
| CN | 107904261 A | 4/2018 |
| CN | 107937427 A | 4/2018 |
| CN | 107937432 A | 4/2018 |
| CN | 107937501 A | 4/2018 |
| CN | 107974466 A | 5/2018 |
| CN | 107988229 A | 5/2018 |
| CN | 107988246 A | 5/2018 |
| CN | 107988256 A | 5/2018 |
| CN | 107988268 A | 5/2018 |
| CN | 108018316 A | 5/2018 |
| CN | 108034656 A | 5/2018 |
| CN | 108048466 A | 5/2018 |
| CN | 108102940 A | 6/2018 |
| CN | 108103092 A | 6/2018 |
| CN | 108103098 A | 6/2018 |
| CN | 108103586 A | 6/2018 |
| CN | 108148835 A | 6/2018 |
| CN | 108148837 A | 6/2018 |
| CN | 108148873 A | 6/2018 |
| CN | 108192956 A | 6/2018 |
| CN | 108251423 A | 7/2018 |
| CN | 108251451 A | 7/2018 |
| CN | 108251452 A | 7/2018 |
| CN | 108342480 A | 7/2018 |
| CN | 108359691 A | 8/2018 |
| CN | 108359712 A | 8/2018 |
| CN | 108384784 A | 8/2018 |
| CN | 108396027 A | 8/2018 |
| CN | 108410877 A | 8/2018 |
| CN | 108410906 A | 8/2018 |
| CN | 108410907 A | 8/2018 |
| CN | 108410911 A | 8/2018 |
| CN | 108424931 A | 8/2018 |
| CN | 108441519 A | 8/2018 |
| CN | 108441520 A | 8/2018 |
| CN | 108486108 A | 9/2018 |
| CN | 108486111 A | 9/2018 |
| CN | 108486145 A | 9/2018 |
| CN | 108486146 A | 9/2018 |
| CN | 108486154 A | 9/2018 |
| CN | 108486159 A | 9/2018 |
| CN | 108486234 A | 9/2018 |
| CN | 108504657 A | 9/2018 |
| CN | 108504685 A | 9/2018 |
| CN | 108504693 A | 9/2018 |
| CN | 108546712 A | 9/2018 |
| CN | 108546717 A | 9/2018 |
| CN | 108546718 A | 9/2018 |
| CN | 108559730 A | 9/2018 |
| CN | 108559732 A | 9/2018 |
| CN | 108559745 A | 9/2018 |
| CN | 108559760 A | 9/2018 |
| CN | 108570479 A | 9/2018 |
| CN | 108588071 A | 9/2018 |
| CN | 108588123 A | 9/2018 |
| CN | 108588128 A | 9/2018 |
| CN | 108588182 A | 9/2018 |
| CN | 108610399 A | 10/2018 |
| CN | 108611364 A | 10/2018 |
| CN | 108624622 A | 10/2018 |
| CN | 108642053 A | 10/2018 |
| CN | 108642055 A | 10/2018 |
| CN | 108642077 A | 10/2018 |
| CN | 108642078 A | 10/2018 |
| CN | 108642090 A | 10/2018 |
| CN | 108690844 A | 10/2018 |
| CN | 108707604 A | 10/2018 |
| CN | 108707620 A | 10/2018 |
| CN | 108707621 A | 10/2018 |
| CN | 108707628 A | 10/2018 |
| CN | 108707629 A | 10/2018 |
| CN | 108715850 A | 10/2018 |
| CN | 108728476 A | 11/2018 |
| CN | 108728486 A | 11/2018 |
| CN | 108753772 A | 11/2018 |
| CN | 108753783 A | 11/2018 |
| CN | 108753813 A | 11/2018 |
| CN | 108753817 A | 11/2018 |
| CN | 108753832 A | 11/2018 |
| CN | 108753835 A | 11/2018 |
| CN | 108753836 A | 11/2018 |
| CN | 108795902 A | 11/2018 |
| CN | 108822217 A | 11/2018 |
| CN | 108823248 A | 11/2018 |
| CN | 108823249 A | 11/2018 |
| CN | 108823291 A | 11/2018 |
| CN | 108841845 A | 11/2018 |
| CN | 108853133 A | 11/2018 |
| CN | 108866093 A | 11/2018 |
| CN | 108893529 A | 11/2018 |
| CN | 108913664 A | 11/2018 |
| CN | 108913691 A | 11/2018 |
| CN | 108913714 A | 11/2018 |
| CN | 108913717 A | 11/2018 |
| CN | 208034188 | 11/2018 |
| EP | 2 604 255 A1 | 6/2013 |
| EP | 2840140 A1 | 2/2015 |
| EP | 2 966 170 A1 | 1/2016 |
| EP | 3 009 511 A2 | 4/2016 |
| EP | 3031921 A1 | 6/2016 |
| EP | 3045537 A1 | 7/2016 |
| EP | 3144390 A1 | 3/2017 |
| EP | 3199632 A1 | 8/2017 |
| EP | 3216867 A1 | 9/2017 |
| EP | 3252160 A1 | 12/2017 |
| GB | 2 528 177 A | 1/2016 |
| GB | 2 531 454 A | 4/2016 |
| GB | 2531454 A | 4/2016 |
| GB | 2542653 A | 3/2017 |
| HK | 1208045 A1 | 2/2016 |
| JP | 2007-501626 A | 2/2007 |
| JP | 2008-515405 A | 5/2008 |
| JP | 2010-539929 A | 12/2010 |
| JP | 2011-081011 A | 4/2011 |

(56) References Cited

FOREIGN PATENT DOCUMENTS

| | | |
|---|---|---|
| JP | 2011-523353 A | 8/2011 |
| JP | 2012-525146 A | 10/2012 |
| JP | 2012-531909 A | 12/2012 |
| KR | 101584933 B1 | 1/2016 |
| KR | 20160133380 A | 11/2016 |
| KR | 20170037025 A | 4/2017 |
| KR | 20170037028 A | 4/2017 |
| KR | 101748575 B1 | 6/2017 |
| KR | 2018-0022465 A | 3/2018 |
| RU | 2016104674 A | 8/2017 |
| RU | 2634395 C1 | 10/2017 |
| RU | 2652899 C1 | 5/2018 |
| TW | 1608100 B | 12/2017 |
| TW | 2018-29773 A | 8/2018 |
| WO | WO 2001/036452 A2 | 5/2001 |
| WO | WO 2001/38547 A2 | 5/2001 |
| WO | WO 2002/059296 A2 | 8/2002 |
| WO | WO 2002/068676 A2 | 9/2002 |
| WO | WO 2002/103028 A2 | 12/2002 |
| WO | WO 2004/007684 A2 | 1/2004 |
| WO | WO 2005/014791 A2 | 2/2005 |
| WO | WO 2006/002547 A1 | 1/2006 |
| WO | WO 2006/042112 A2 | 4/2006 |
| WO | WO 2007/025097 A2 | 3/2007 |
| WO | WO 2007/136815 A2 | 11/2007 |
| WO | WO 2008/108989 A2 | 9/2008 |
| WO | WO 2010/011565 A2 | 1/2010 |
| WO | WO 2010/011961 A2 | 1/2010 |
| WO | WO 2010/054108 A2 | 5/2010 |
| WO | WO 2010/054154 A2 | 5/2010 |
| WO | WO 2010/068289 A2 | 6/2010 |
| WO | WO 2010/075424 A2 | 7/2010 |
| WO | WO 2010/102257 A2 | 9/2010 |
| WO | WO 2010/129019 A2 | 11/2010 |
| WO | WO 2010/129023 A2 | 11/2010 |
| WO | WO 2010/132092 A2 | 11/2010 |
| WO | WO 2010/144150 A2 | 12/2010 |
| WO | WO 2011/002503 A1 | 1/2011 |
| WO | WO 2011/017293 A2 | 2/2011 |
| WO | WO 2011/053868 A1 | 5/2011 |
| WO | WO 2011/053982 A2 | 5/2011 |
| WO | WO 2011/075627 A1 | 6/2011 |
| WO | WO 2011/091311 A2 | 7/2011 |
| WO | WO 2011/109031 A1 | 9/2011 |
| WO | WO 2011/143124 A2 | 11/2011 |
| WO | WO 2012/054726 A1 | 4/2012 |
| WO | WO 2012/065043 A2 | 5/2012 |
| WO | WO 2012/125445 A2 | 9/2012 |
| WO | WO 2012/138927 A2 | 10/2012 |
| WO | WO 2012/149470 A1 | 11/2012 |
| WO | WO 2012/158985 A2 | 11/2012 |
| WO | WO 2012/158986 A2 | 11/2012 |
| WO | WO 2012/164565 A1 | 12/2012 |
| WO | WO 2013/012674 A1 | 1/2013 |
| WO | WO 2013/013105 A2 | 1/2013 |
| WO | WO 2013/047844 A1 | 4/2013 |
| WO | WO 2013/066438 A2 | 5/2013 |
| WO | WO 2013/098244 A1 | 7/2013 |
| WO | WO 2013/119602 A1 | 8/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142378 A9 | 9/2013 |
| WO | WO 2013/142578 A1 | 9/2013 |
| WO | WO 2013/142578 A2 | 9/2013 |
| WO | WO 2013/160230 A1 | 10/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A1 | 11/2013 |
| WO | WO 2013/176772 A2 | 11/2013 |
| WO | WO 2013/176915 A1 | 11/2013 |
| WO | WO 2013/176916 A1 | 11/2013 |
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2014/005042 A2 | 1/2014 |
| WO | WO 2014/011237 A1 | 1/2014 |
| WO | WO 2014/011901 A1 | 1/2014 |
| WO | WO 2014/018423 A2 | 1/2014 |
| WO | WO 2014/020608 A1 | 2/2014 |
| WO | WO 2014/022120 A1 | 2/2014 |
| WO | WO 2014/022702 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |
| WO | WO 2014/043143 A1 | 3/2014 |
| WO | WO 2014/047103 A2 | 3/2014 |
| WO | WO 2014/059173 A2 | 4/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/110006 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/125668 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |

(56) References Cited

FOREIGN PATENT DOCUMENTS

| | | |
|---|---|---|
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/153118 A1 | 9/2014 |
| WO | WO 2014/153470 A2 | 9/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/007194 A1 | 1/2015 |
| WO | WO 2015/010114 A1 | 1/2015 |
| WO | WO 2015/011483 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/048707 A2 | 4/2015 |
| WO | WO 2015/049897 A1 | 4/2015 |
| WO | WO 2015/051191 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/054315 A1 | 4/2015 |
| WO | WO 2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066634 A2 | 5/2015 |
| WO | WO 2015/066636 A2 | 5/2015 |
| WO | WO 2015/066637 A1 | 5/2015 |
| WO | WO 2015/066638 A2 | 5/2015 |
| WO | WO 2015/066643 A1 | 5/2015 |
| WO | WO 2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075175 A1 | 5/2015 |
| WO | WO 2015/075195 A1 | 5/2015 |
| WO | WO 2015/075557 A2 | 5/2015 |
| WO | WO 2015/077058 A2 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A2 | 6/2015 |
| WO | WO 2015/086798 A1 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A1 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |

(56) References Cited

FOREIGN PATENT DOCUMENTS

| | | |
|---|---|---|
| WO | WO 2015/109752 A1 | 7/2015 |
| WO | WO 2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/114365 A1 | 8/2015 |
| WO | WO 2015/115903 A1 | 8/2015 |
| WO | WO 2015/116686 A1 | 8/2015 |
| WO | WO 2015/116969 A2 | 8/2015 |
| WO | WO 2015/117021 A1 | 8/2015 |
| WO | WO 2015/117041 A1 | 8/2015 |
| WO | WO 2015/117081 A2 | 8/2015 |
| WO | WO 2015/118156 A1 | 8/2015 |
| WO | WO 2015/119941 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/124715 A1 | 8/2015 |
| WO | WO 2015/124718 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/129686 A1 | 9/2015 |
| WO | WO 2015/131101 A1 | 9/2015 |
| WO | WO 2015/133554 A1 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO 2015/143177 A1 | 9/2015 |
| WO | WO 2015/145417 A1 | 10/2015 |
| WO | WO 2015/148431 A1 | 10/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153889 A2 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164740 A1 | 10/2015 |
| WO | WO 2015/164748 A1 | 10/2015 |
| WO | WO 2015/165274 A1 | 11/2015 |
| WO | WO 2015/165275 A1 | 11/2015 |
| WO | WO 2015/165276 A1 | 11/2015 |
| WO | WO 2015/166272 A2 | 11/2015 |
| WO | WO 2015/167766 A1 | 11/2015 |
| WO | WO 2015/167956 A1 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |
| WO | WO 2015/171894 A1 | 11/2015 |
| WO | WO 2015/171932 A1 | 11/2015 |
| WO | WO 2015/172128 A1 | 11/2015 |
| WO | WO 2015/173436 A1 | 11/2015 |
| WO | WO 2015/175642 A2 | 11/2015 |
| WO | WO 2015/179540 A1 | 11/2015 |
| WO | WO 2015/183025 A1 | 12/2015 |
| WO | WO 2015/183026 A1 | 12/2015 |
| WO | WO 2015/183885 A1 | 12/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188056 A1 | 12/2015 |
| WO | WO 2015/188065 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A1 | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 A2 | 12/2015 |
| WO | WO 2015/193858 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A2 | 12/2015 |
| WO | WO 2016/001978 A1 | 1/2016 |
| WO | WO 2016/004010 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO 2016/011210 A2 | 1/2016 |
| WO | WO 2016/011428 A1 | 1/2016 |
| WO | WO 2016/012544 A2 | 1/2016 |
| WO | WO 2016/012552 A1 | 1/2016 |
| WO | WO 2016/014409 A1 | 1/2016 |
| WO | WO 2016/014565 A2 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |
| WO | WO 2016/022363 A2 | 2/2016 |
| WO | WO 2016/022866 A1 | 2/2016 |
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |
| WO | WO 2016/026444 A1 | 2/2016 |
| WO | WO 2016/028682 A1 | 2/2016 |
| WO | WO 2016/028843 A1 | 2/2016 |
| WO | WO 2016/028887 A1 | 2/2016 |
| WO | WO 2016/033088 A1 | 3/2016 |
| WO | WO 2016/033230 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/036754 A1 | 3/2016 |
| WO | WO 2016/037157 A2 | 3/2016 |
| WO | WO 2016/040030 A1 | 3/2016 |
| WO | WO 2016/040594 A1 | 3/2016 |
| WO | WO 2016/044182 A1 | 3/2016 |
| WO | WO 2016/044416 A1 | 3/2016 |
| WO | WO 2016/046635 A1 | 3/2016 |
| WO | WO 2016/049024 A2 | 3/2016 |
| WO | WO 2016/049163 A2 | 3/2016 |
| WO | WO 2016/049230 A1 | 3/2016 |
| WO | WO 2016/049251 A1 | 3/2016 |
| WO | WO 2016/049258 A2 | 3/2016 |
| WO | WO 2015/048801 A2 | 4/2016 |
| WO | WO 2016/053397 A2 | 4/2016 |
| WO | WO 2016/054326 A1 | 4/2016 |

(56) References Cited

FOREIGN PATENT DOCUMENTS

| | | |
|---|---|---|
| WO | WO 2016/057061 A2 | 4/2016 |
| WO | WO 2016/057821 A2 | 4/2016 |
| WO | WO 2016/057835 A2 | 4/2016 |
| WO | WO 2016/057850 A2 | 4/2016 |
| WO | WO 2016/057951 A2 | 4/2016 |
| WO | WO 2016/057961 A2 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/064894 A2 | 4/2016 |
| WO | WO 2016/069282 A1 | 5/2016 |
| WO | WO 2016/069283 A1 | 5/2016 |
| WO | WO 2016/069591 A2 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/072399 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO 2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO 2016/080795 A1 | 5/2016 |
| WO | WO 2016/081923 A2 | 5/2016 |
| WO | WO 2016/081924 A1 | 5/2016 |
| WO | WO 2016/082135 A1 | 6/2016 |
| WO | WO 2016/083811 A1 | 6/2016 |
| WO | WO 2016/084084 A1 | 6/2016 |
| WO | WO 2016/084088 A1 | 6/2016 |
| WO | WO 2016/086177 A2 | 6/2016 |
| WO | WO 2016/089433 A1 | 6/2016 |
| WO | WO 2016/089866 A1 | 6/2016 |
| WO | WO 2016/089883 A1 | 6/2016 |
| WO | WO 2016/090385 A1 | 6/2016 |
| WO | WO 2016/094679 A1 | 6/2016 |
| WO | WO 2016/094845 A2 | 6/2016 |
| WO | WO 2016/094867 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/094888 A1 | 6/2016 |
| WO | WO 2016/097212 A1 | 6/2016 |
| WO | WO 2016/097231 A2 | 6/2016 |
| WO | WO 2016/097751 A1 | 6/2016 |
| WO | WO 2016/099887 A1 | 6/2016 |
| WO | WO 2016/100272 A1 | 6/2016 |
| WO | WO 2016/100389 A1 | 6/2016 |
| WO | WO 2016/100568 A1 | 6/2016 |
| WO | WO 2016/100571 A1 | 6/2016 |
| WO | WO 2016/100951 A2 | 6/2016 |
| WO | WO 2016/100955 A2 | 6/2016 |
| WO | WO 2016/100974 A1 | 6/2016 |
| WO | WO 2016/103233 A2 | 6/2016 |
| WO | WO 2016/104716 A1 | 6/2016 |
| WO | WO 2016/106236 A1 | 6/2016 |
| WO | WO 2016/106239 A1 | 6/2016 |
| WO | WO 2016/106244 A1 | 6/2016 |
| WO | WO 2016/106338 A2 | 6/2016 |
| WO | WO 2016/108926 A1 | 7/2016 |
| WO | WO 2016/109255 A1 | 7/2016 |
| WO | WO 2016/109840 A2 | 7/2016 |
| WO | WO 2016/110214 A1 | 7/2016 |
| WO | WO 2016/110453 A1 | 7/2016 |
| WO | WO 2016/110511 A1 | 7/2016 |
| WO | WO 2016/110512 A1 | 7/2016 |
| WO | WO 2016/111546 A2 | 7/2016 |
| WO | WO 2016/112242 A1 | 7/2016 |
| WO | WO 2016/112351 A1 | 7/2016 |
| WO | WO 2016/112963 A1 | 7/2016 |
| WO | WO 2016/114972 A1 | 7/2016 |
| WO | WO 2016/115179 A1 | 7/2016 |
| WO | WO 2016/115326 A1 | 7/2016 |
| WO | WO 2016/115355 A1 | 7/2016 |
| WO | WO 2016/116032 A1 | 7/2016 |
| WO | WO 2016/120480 A1 | 8/2016 |
| WO | WO 2016/123071 A1 | 8/2016 |
| WO | WO 2016/123230 A1 | 8/2016 |
| WO | WO 2016/123243 A1 | 8/2016 |
| WO | WO 2016/123578 A1 | 8/2016 |
| WO | WO 2016/126747 A1 | 8/2016 |
| WO | WO 2016/130600 A2 | 8/2016 |
| WO | WO 2016/130697 A1 | 8/2016 |
| WO | WO 2016/131009 A1 | 8/2016 |
| WO | WO 2016/132122 A1 | 8/2016 |
| WO | WO 2016/133165 A1 | 8/2016 |
| WO | WO 2016/135507 A1 | 9/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/137774 A1 | 9/2016 |
| WO | WO 2016/137949 A1 | 9/2016 |
| WO | WO 2016/141224 A1 | 9/2016 |
| WO | WO 2016/141893 A1 | 9/2016 |
| WO | WO 2016/142719 A1 | 9/2016 |
| WO | WO 2016/145150 A2 | 9/2016 |
| WO | WO 2016/148994 A1 | 9/2016 |
| WO | WO 2016/149484 A2 | 9/2016 |
| WO | WO 2016/149547 A1 | 9/2016 |
| WO | WO 2016/150336 A1 | 9/2016 |
| WO | WO 2016/150855 A1 | 9/2016 |
| WO | WO 2016/154016 A2 | 9/2016 |
| WO | WO 2016/154579 A2 | 9/2016 |
| WO | WO 2016/154596 A1 | 9/2016 |
| WO | WO 2016/155482 A1 | 10/2016 |
| WO | WO 2016/161004 A1 | 10/2016 |
| WO | WO 2016/161207 A1 | 10/2016 |
| WO | WO 2016/161260 A1 | 10/2016 |
| WO | WO 2016/161380 A1 | 10/2016 |
| WO | WO 2016/161446 A1 | 10/2016 |
| WO | WO 2016/164356 A1 | 10/2016 |
| WO | WO 2016/164797 A1 | 10/2016 |
| WO | WO 2016/166340 A1 | 10/2016 |
| WO | WO 2016/167300 A1 | 10/2016 |
| WO | WO 2016/170484 A1 | 10/2016 |
| WO | WO 2016/172359 A2 | 10/2016 |
| WO | WO 2016/172727 A1 | 10/2016 |
| WO | WO 2016/174056 A1 | 11/2016 |
| WO | WO 2016/174151 A1 | 11/2016 |
| WO | WO 2016/174250 A1 | 11/2016 |
| WO | WO 2016/176191 A1 | 11/2016 |
| WO | WO 2016/176404 A1 | 11/2016 |
| WO | WO 2016/176690 A2 | 11/2016 |
| WO | WO 2016/177682 A1 | 11/2016 |
| WO | WO 2016/178207 A1 | 11/2016 |
| WO | WO 2016/179038 A1 | 11/2016 |
| WO | WO 2016/179112 A1 | 11/2016 |
| WO | WO 2016/181357 A1 | 11/2016 |
| WO | WO 2016/182893 A1 | 11/2016 |
| WO | WO 2016/182917 A1 | 11/2016 |
| WO | WO 2016/182959 A1 | 11/2016 |
| WO | WO 2016/183236 A1 | 11/2016 |
| WO | WO 2016/183298 A2 | 11/2016 |
| WO | WO 2016/183345 A1 | 11/2016 |
| WO | WO 2016/183402 A2 | 11/2016 |
| WO | WO 2016/183438 A1 | 11/2016 |
| WO | WO 2016/183448 A1 | 11/2016 |
| WO | WO 2016/184955 A2 | 11/2016 |
| WO | WO 2016/184989 A1 | 11/2016 |
| WO | WO 2016/185411 A1 | 11/2016 |
| WO | WO 2016/186745 A1 | 11/2016 |
| WO | WO 2016/186772 A2 | 11/2016 |
| WO | WO 2016/186946 A1 | 11/2016 |
| WO | WO 2016/186953 A1 | 11/2016 |
| WO | WO 2016/187717 A1 | 12/2016 |
| WO | WO 2016/187904 A1 | 12/2016 |
| WO | WO 2016/191684 A1 | 12/2016 |
| WO | WO 2016/191869 A1 | 12/2016 |

(56) References Cited

FOREIGN PATENT DOCUMENTS

| | | |
|---|---|---|
| WO | WO 2016/196273 A1 | 12/2016 |
| WO | WO 2016/196282 A1 | 12/2016 |
| WO | WO 2016/196308 A1 | 12/2016 |
| WO | WO 2016/196361 A1 | 12/2016 |
| WO | WO 2016/196499 A1 | 12/2016 |
| WO | WO 2016/196539 A2 | 12/2016 |
| WO | WO 2016/196655 A1 | 12/2016 |
| WO | WO 2016/196805 A1 | 12/2016 |
| WO | WO 2016/196887 A1 | 12/2016 |
| WO | WO 2016/197132 A1 | 12/2016 |
| WO | WO 2016/197133 A1 | 12/2016 |
| WO | WO 2016/197354 A1 | 12/2016 |
| WO | WO 2016/197355 A1 | 12/2016 |
| WO | WO 2016/197356 A1 | 12/2016 |
| WO | WO 2016/197357 A1 | 12/2016 |
| WO | WO 2016/197358 A1 | 12/2016 |
| WO | WO 2016/197359 A1 | 12/2016 |
| WO | WO 2016/197360 A1 | 12/2016 |
| WO | WO 2016/197361 A1 | 12/2016 |
| WO | WO 2016/197362 A1 | 12/2016 |
| WO | WO 2016/198361 A1 | 12/2016 |
| WO | WO 2016/198500 A1 | 12/2016 |
| WO | WO 2016/200263 A1 | 12/2016 |
| WO | WO 2016/201047 A1 | 12/2016 |
| WO | WO 2016/201138 A1 | 12/2016 |
| WO | WO 2016/201152 A1 | 12/2016 |
| WO | WO 2016/201153 A1 | 12/2016 |
| WO | WO 2016/201155 A1 | 12/2016 |
| WO | WO 2016/205276 A1 | 12/2016 |
| WO | WO 2016/205613 A1 | 12/2016 |
| WO | WO 2016/205623 A1 | 12/2016 |
| WO | WO 2016/205680 A1 | 12/2016 |
| WO | WO 2016/205688 A2 | 12/2016 |
| WO | WO 2016/205703 A1 | 12/2016 |
| WO | WO 2016/205711 A1 | 12/2016 |
| WO | WO 2016/205728 A1 | 12/2016 |
| WO | WO 2016/205745 A2 | 12/2016 |
| WO | WO 2016/205749 A1 | 12/2016 |
| WO | WO 2016/205759 A1 | 12/2016 |
| WO | WO 2016/205764 A1 | 12/2016 |
| WO | WO 2017/001572 A1 | 1/2017 |
| WO | WO 2017/001988 A1 | 1/2017 |
| WO | WO 2017/004261 A1 | 1/2017 |
| WO | WO 2017/004279 A2 | 1/2017 |
| WO | WO 2017/004616 A1 | 1/2017 |
| WO | WO 2017/005807 A1 | 1/2017 |
| WO | WO 2017/009399 A1 | 1/2017 |
| WO | WO 2017/010556 A1 | 1/2017 |
| WO | WO 2017/011519 A1 | 1/2017 |
| WO | WO 2017/011721 A1 | 1/2017 |
| WO | WO 2017/011804 A1 | 1/2017 |
| WO | WO 2017/015015 A1 | 1/2017 |
| WO | WO 2017/015101 A1 | 1/2017 |
| WO | WO 2017/015567 A1 | 1/2017 |
| WO | WO 2017/015637 A1 | 1/2017 |
| WO | WO 2017/017016 A1 | 2/2017 |
| WO | WO 2017/019867 A1 | 2/2017 |
| WO | WO 2017/019895 A1 | 2/2017 |
| WO | WO 2017/023803 A1 | 2/2017 |
| WO | WO 2017/023974 A1 | 2/2017 |
| WO | WO 2017/024047 A1 | 2/2017 |
| WO | WO 2017/024319 A1 | 2/2017 |
| WO | WO 2017/024343 A1 | 2/2017 |
| WO | WO 2017/024602 A1 | 2/2017 |
| WO | WO 2017/025323 A1 | 2/2017 |
| WO | WO 2017/027423 A1 | 2/2017 |
| WO | WO 2017/028768 A1 | 2/2017 |
| WO | WO 2017/029664 A1 | 2/2017 |
| WO | WO 2017/031360 A1 | 2/2017 |
| WO | WO 2017/031483 A1 | 2/2017 |
| WO | WO 2017/035416 A2 | 3/2017 |
| WO | WO 2017/040348 A1 | 3/2017 |
| WO | WO 2017/040511 A1 | 3/2017 |
| WO | WO 2017/040709 A1 | 3/2017 |
| WO | WO 2017/040786 A1 | 3/2017 |
| WO | WO 2017/040793 A1 | 3/2017 |
| WO | WO 2017/040813 A2 | 3/2017 |
| WO | WO 2017/043573 A1 | 3/2017 |
| WO | WO 2017/043656 A1 | 3/2017 |
| WO | WO 2017/044419 A1 | 3/2017 |
| WO | WO 2017/044776 A1 | 3/2017 |
| WO | WO 2017/044857 A2 | 3/2017 |
| WO | WO 2017/049129 A2 | 3/2017 |
| WO | WO 2017/050963 A1 | 3/2017 |
| WO | WO 2017/053312 A1 | 3/2017 |
| WO | WO 2017/053431 A2 | 3/2017 |
| WO | WO 2017/053713 A1 | 3/2017 |
| WO | WO 2017/053729 A1 | 3/2017 |
| WO | WO 2017/053753 A1 | 3/2017 |
| WO | WO 2017/053762 A1 | 3/2017 |
| WO | WO 2017/053879 A1 | 3/2017 |
| WO | WO 2017/054721 A1 | 4/2017 |
| WO | WO 2017/058658 A2 | 4/2017 |
| WO | WO 2017/059241 A1 | 4/2017 |
| WO | WO 2017/062605 A1 | 4/2017 |
| WO | WO 2017/062723 A1 | 4/2017 |
| WO | WO 2017/062754 A1 | 4/2017 |
| WO | WO 2017/062855 A1 | 4/2017 |
| WO | WO 2017/062886 A1 | 4/2017 |
| WO | WO 2017/062983 A1 | 4/2017 |
| WO | WO 2017/064439 A1 | 4/2017 |
| WO | WO 2017/064546 A1 | 4/2017 |
| WO | WO 2017/064566 A2 | 4/2017 |
| WO | WO 2017/066175 A1 | 4/2017 |
| WO | WO 2017/066497 A2 | 4/2017 |
| WO | WO 2017/066588 A2 | 4/2017 |
| WO | WO 2017/066707 A1 | 4/2017 |
| WO | WO 2017/068077 A1 | 4/2017 |
| WO | WO 2017/068377 A1 | 4/2017 |
| WO | WO 2017/069829 A2 | 4/2017 |
| WO | WO 2017/070029 A1 | 4/2017 |
| WO | WO 2017/070032 A1 | 4/2017 |
| WO | WO 2017/070169 A1 | 4/2017 |
| WO | WO 2017/070284 A1 | 4/2017 |
| WO | WO 2017/070598 A1 | 4/2017 |
| WO | WO 2017/070605 A1 | 4/2017 |
| WO | WO 2017/070632 A2 | 4/2017 |
| WO | WO 2017/070633 A2 | 4/2017 |
| WO | WO 2017/072590 A1 | 5/2017 |
| WO | WO 2017/074526 A1 | 5/2017 |
| WO | WO 2017/074962 A1 | 5/2017 |
| WO | WO 2017/075261 A1 | 5/2017 |
| WO | WO 2017/075335 A1 | 5/2017 |
| WO | WO 2017/075475 A1 | 5/2017 |
| WO | WO 2017/077135 A1 | 5/2017 |
| WO | WO 2017/077329 A2 | 5/2017 |
| WO | WO 2017/078751 A1 | 5/2017 |
| WO | WO 2017/079400 A1 | 5/2017 |
| WO | WO 2017/079428 A1 | 5/2017 |
| WO | WO 2017/079673 A1 | 5/2017 |
| WO | WO 2017/079724 A1 | 5/2017 |
| WO | WO 2017/081097 A1 | 5/2017 |
| WO | WO 2017/081288 A1 | 5/2017 |
| WO | WO 2017/083368 A1 | 5/2017 |
| WO | WO 2017/083722 A1 | 5/2017 |
| WO | WO 2017/083766 A1 | 5/2017 |
| WO | WO 2017/087395 A1 | 5/2017 |
| WO | WO 2017/090724 A1 | 6/2017 |
| WO | WO 2017/091510 A1 | 6/2017 |
| WO | WO 2017/091630 A1 | 6/2017 |
| WO | WO 2017/092201 A1 | 6/2017 |
| WO | WO 2017/093370 A1 | 6/2017 |
| WO | WO 2017/095111 A1 | 6/2017 |
| WO | WO 2017/096041 A1 | 6/2017 |
| WO | WO 2017/096237 A1 | 6/2017 |
| WO | WO 2017/100158 A1 | 6/2017 |
| WO | WO 2017/100431 A2 | 6/2017 |
| WO | WO 2017/104404 A1 | 6/2017 |
| WO | WO 2017/105251 A1 | 6/2017 |
| WO | WO 2017/105350 A1 | 6/2017 |
| WO | WO 2017/105991 A1 | 6/2017 |
| WO | WO 2017/106414 A1 | 6/2017 |
| WO | WO 2017/106528 A2 | 6/2017 |
| WO | WO 2017/106537 A2 | 6/2017 |

(56) References Cited

FOREIGN PATENT DOCUMENTS

| | | |
|---|---|---|
| WO | WO 2017/106569 A1 | 6/2017 |
| WO | WO 2017/106616 A1 | 6/2017 |
| WO | WO 2017/106657 A1 | 6/2017 |
| WO | WO 2017/106767 A1 | 6/2017 |
| WO | WO 2017/109134 A1 | 6/2017 |
| WO | WO 2017/109757 A1 | 6/2017 |
| WO | WO 2017/112620 A1 | 6/2017 |
| WO | WO 2017/115268 A1 | 7/2017 |
| WO | WO 2017/115268 A2 | 7/2017 |
| WO | WO 2017/117395 A1 | 7/2017 |
| WO | WO 2017/118598 A1 | 7/2017 |
| WO | WO 2017/118720 A1 | 7/2017 |
| WO | WO 2017/123609 A1 | 7/2017 |
| WO | WO 2017/123910 A1 | 7/2017 |
| WO | WO 2017/124086 A1 | 7/2017 |
| WO | WO 2017/124100 A1 | 7/2017 |
| WO | WO 2017/124652 A1 | 7/2017 |
| WO | WO 2017/126987 A1 | 7/2017 |
| WO | WO 2017/127807 A1 | 7/2017 |
| WO | WO 2017/131237 A1 | 8/2017 |
| WO | WO 2017/132112 A1 | 8/2017 |
| WO | WO 2017/136520 A1 | 8/2017 |
| WO | WO 2017/136629 A1 | 8/2017 |
| WO | WO 2017/136794 A1 | 8/2017 |
| WO | WO 2017/139264 A1 | 8/2017 |
| WO | WO 2017/139505 A2 | 8/2017 |
| WO | WO 2017/141173 A2 | 8/2017 |
| WO | WO 2017/142835 A1 | 8/2017 |
| WO | WO 2017/142999 A2 | 8/2017 |
| WO | WO 2017/143042 A2 | 8/2017 |
| WO | WO 2017/147278 A1 | 8/2017 |
| WO | WO 2017/147432 A1 | 8/2017 |
| WO | WO 2017/147446 A1 | 8/2017 |
| WO | WO 2017/147555 A1 | 8/2017 |
| WO | WO 2017/151444 A1 | 9/2017 |
| WO | WO 2017/152015 A1 | 9/2017 |
| WO | WO 2017/155717 A1 | 9/2017 |
| WO | WO 2017/157422 A1 | 9/2017 |
| WO | WO 2017/158153 A1 | 9/2017 |
| WO | WO 2017/160689 A1 | 9/2017 |
| WO | WO 2017/160752 A1 | 9/2017 |
| WO | WO 2017/160890 A1 | 9/2017 |
| WO | WO 2017/161068 A1 | 9/2017 |
| WO | WO 2017/165826 A1 | 9/2017 |
| WO | WO 2017/165862 A1 | 9/2017 |
| WO | WO 2017/172644 A2 | 10/2017 |
| WO | WO 2017/172645 A2 | 10/2017 |
| WO | WO 2017/172860 A1 | 10/2017 |
| WO | WO 2017/173004 A1 | 10/2017 |
| WO | WO 2017/173054 A1 | 10/2017 |
| WO | WO 2017/173092 A1 | 10/2017 |
| WO | WO 2017/174329 A1 | 10/2017 |
| WO | WO 2017/176529 A1 | 10/2017 |
| WO | WO 2017/176806 A1 | 10/2017 |
| WO | WO 2017/178590 A1 | 10/2017 |
| WO | WO 2017/180694 A1 | 10/2017 |
| WO | WO 2017/180711 A1 | 10/2017 |
| WO | WO 2017/180915 A2 | 10/2017 |
| WO | WO 2017/180926 A1 | 10/2017 |
| WO | WO 2017/181107 A2 | 10/2017 |
| WO | WO 2017/181735 A2 | 10/2017 |
| WO | WO 2017/182468 A1 | 10/2017 |
| WO | WO 2017/184334 A1 | 10/2017 |
| WO | WO 2017/184768 A1 | 10/2017 |
| WO | WO 2017/184786 A1 | 10/2017 |
| WO | WO 2017/186550 A1 | 11/2017 |
| WO | WO 2017/189308 A1 | 11/2017 |
| WO | WO 2017/189336 A1 | 11/2017 |
| WO | WO 2017/190257 A1 | 11/2017 |
| WO | WO 2017/190664 A1 | 11/2017 |
| WO | WO 2017/191210 A1 | 11/2017 |
| WO | WO 2017/192172 A1 | 11/2017 |
| WO | WO 2017/192512 A2 | 11/2017 |
| WO | WO 2017/192544 A1 | 11/2017 |
| WO | WO 2017/192573 A1 | 11/2017 |
| WO | WO 2017/193029 A2 | 11/2017 |
| WO | WO 2017/193053 A1 | 11/2017 |
| WO | WO 2017/196768 A1 | 11/2017 |
| WO | WO 2017/197038 A1 | 11/2017 |
| WO | WO 2017/197238 A1 | 11/2017 |
| WO | WO 2017/197301 A1 | 11/2017 |
| WO | WO 2017/201476 A1 | 11/2017 |
| WO | WO 2017/205290 A1 | 11/2017 |
| WO | WO 2017/205423 A1 | 11/2017 |
| WO | WO 2017/207589 A1 | 12/2017 |
| WO | WO 2017/208247 A1 | 12/2017 |
| WO | WO 2017/209809 A1 | 12/2017 |
| WO | WO 2017/213896 A1 | 12/2017 |
| WO | WO 2017/213898 A2 | 12/2017 |
| WO | WO 2017/214460 A1 | 12/2017 |
| WO | WO 2017/216392 A1 | 12/2017 |
| WO | WO 2017/216771 A2 | 12/2017 |
| WO | WO 2017/218185 A1 | 12/2017 |
| WO | WO 2017/219027 A1 | 12/2017 |
| WO | WO 2017/219033 A1 | 12/2017 |
| WO | WO 2017/220751 A1 | 12/2017 |
| WO | WO 2017/222370 A1 | 12/2017 |
| WO | WO 2017/222773 A1 | 12/2017 |
| WO | WO 2017/222834 A1 | 12/2017 |
| WO | WO 2017/223107 A1 | 12/2017 |
| WO | WO 2017/223330 A1 | 12/2017 |
| WO | WO 2018/000657 A1 | 1/2018 |
| WO | WO 2018/002719 A1 | 1/2018 |
| WO | WO 2018/005117 A1 | 1/2018 |
| WO | WO 2018/005289 A2 | 1/2018 |
| WO | WO 2018/005691 A1 | 1/2018 |
| WO | WO 2018/005782 A1 | 1/2018 |
| WO | WO 2018/005873 A1 | 1/2018 |
| WO | WO 2018/06693 A1 | 1/2018 |
| WO | WO 2018/009520 A1 | 1/2018 |
| WO | WO 2018/009562 A1 | 1/2018 |
| WO | WO 2018/009822 A1 | 1/2018 |
| WO | WO 2018/013821 A1 | 1/2018 |
| WO | WO 2018/013990 A1 | 1/2018 |
| WO | WO 2018/014384 A1 | 1/2018 |
| WO | WO 2018/015444 A1 | 1/2018 |
| WO | WO 2018/015936 A2 | 1/2018 |
| WO | WO 2018/017754 A1 | 1/2018 |
| WO | WO 2018/018979 A1 | 2/2018 |
| WO | WO 2018/020248 A1 | 2/2018 |
| WO | WO 2018/022480 A1 | 2/2018 |
| WO | WO 2018/022634 A1 | 2/2018 |
| WO | WO 2018/025206 A1 | 2/2018 |
| WO | WO 2018/026723 A1 | 2/2018 |
| WO | WO 2018/026976 A1 | 2/2018 |
| WO | WO 2018/027078 A1 | 2/2018 |
| WO | WO 2018/030608 A1 | 2/2018 |
| WO | WO 2018/031683 A1 | 2/2018 |
| WO | WO 2018/035250 A1 | 2/2018 |
| WO | WO 2018/035300 A1 | 2/2018 |
| WO | WO 2018/035423 A1 | 2/2018 |
| WO | WO 2018/035503 A1 | 2/2018 |
| WO | WO 2018/039145 A1 | 3/2018 |
| WO | WO 2018/039438 A1 | 3/2018 |
| WO | WO 2018/039440 A1 | 3/2018 |
| WO | WO 2018/039448 A1 | 3/2018 |
| WO | WO 2018/045630 A1 | 3/2018 |
| WO | WO 2018/048827 A1 | 3/2018 |
| WO | WO 2018/049168 A1 | 3/2018 |
| WO | WO 2018/051347 A1 | 3/2018 |
| WO | WO 2018/058064 A1 | 3/2018 |
| WO | WO 2018/062866 A2 | 4/2018 |
| WO | WO 2018/064352 A1 | 4/2018 |
| WO | WO 2018/064371 A1 | 4/2018 |
| WO | WO 2018/064516 A1 | 4/2018 |
| WO | WO 2018/067546 A1 | 4/2018 |
| WO | WO 2018/067846 A1 | 4/2018 |
| WO | WO 2018/068053 A2 | 4/2018 |
| WO | WO 2018/069474 A1 | 4/2018 |
| WO | WO 2018/071623 A2 | 4/2018 |
| WO | WO 2018/071663 A1 | 4/2018 |
| WO | WO 2018/071868 A1 | 4/2018 |
| WO | WO 2018/071892 A1 | 4/2018 |
| WO | WO 2018/074979 A1 | 4/2018 |

(56) References Cited

FOREIGN PATENT DOCUMENTS

| | | |
|---|---|---|
| WO | WO 2018/079134 A1 | 5/2018 |
| WO | WO 2018/080573 A1 | 5/2018 |
| WO | WO 2018/081504 A1 | 5/2018 |
| WO | WO 2018/081535 A2 | 5/2018 |
| WO | WO 2018/081728 A1 | 5/2018 |
| WO | WO 2018/083128 A2 | 5/2018 |
| WO | WO 2018/083606 A1 | 5/2018 |
| WO | WO 2018/085288 A1 | 5/2018 |
| WO | WO 2018/086623 A1 | 5/2018 |
| WO | WO 2018/093990 A1 | 5/2018 |
| WO | WO 2018/098383 A1 | 5/2018 |
| WO | WO 2018/098480 A1 | 5/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018/108272 A1 | 6/2018 |
| WO | WO 2018/109101 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | WO 2018/119354 A1 | 6/2018 |
| WO | WO 2018/119359 A1 | 6/2018 |
| WO | WO 2018/130830 A1 | 7/2018 |
| WO | WO 2018/135838 A2 | 7/2018 |
| WO | WO 2018/136396 A2 | 7/2018 |
| WO | WO 2018/138385 A1 | 8/2018 |
| WO | WO 2018/148246 A1 | 8/2018 |
| WO | WO 2018/148256 A1 | 8/2018 |
| WO | WO 2018/148647 A2 | 8/2018 |
| WO | WO 2018/149418 A1 | 8/2018 |
| WO | WO 2018/149888 A1 | 8/2018 |
| WO | WO 2018/152418 A1 | 8/2018 |
| WO | WO 2018/154380 A1 | 8/2018 |
| WO | WO 2018/154387 A1 | 8/2018 |
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A2 | 8/2018 |
| WO | WO 2018/156372 A1 | 8/2018 |
| WO | WO 2018/161009 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/195545 A2 | 10/2018 |
| WO | WO 2018/195555 A1 | 10/2018 |
| WO | WO 2018/197020 A1 | 11/2018 |
| WO | WO 2018/197495 A1 | 11/2018 |
| WO | WO 2018/202800 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |

OTHER PUBLICATIONS

U.S. Appl. No. 61/717,324, Cho et al., filed Oct. 23, 2012.
U.S. Appl. No. 61/734,256, Chen et al., filed Dec. 6, 2012.
U.S. Appl. No. 61/758,624, Chen et al., filed Jan. 30, 2013.
U.S. Appl. No. 61/761,046, Knight et al., filed Feb. 5, 2013.
U.S. Appl. No. 61/794,422, Knight et al., filed Mar. 15, 2013.
U.S. Appl. No. 61/803,599, Kim et al., filed Mar. 20, 2013.
U.S. Appl. No. 61/837,481, Cho et al., filed Jun. 20, 2013.
Partial Supplementary European Search Report for Application No. EP 12845790.0, dated Mar. 18, 2015.
Supplementary European Search Report for Application No. EP 12845790.0, dated Oct. 12, 2015.
International Search Report and Written Opinion for PCT/US2012/047778, dated May 30, 2013.
International Preliminary Report on Patentability for PCT/US2012/047778, dated Feb. 6, 2014.
International Search Report and Written Opinion for PCT/US2014/052231, dated Dec. 4, 2014.
International Search Report and Written Opinion for PCT/US2014/052231, dated Jan. 30, 2015 (Corrected Version).
International Preliminary Report on Patentability for PCT/US2014/052231, dated Mar. 3, 2016.
International Search Report and Written Opinion for PCT/US2014/050283, dated Nov. 6, 2014.
International Preliminary Report on Patentability for PCT/US2014/050283, dated Feb. 18, 2016.
International Search Report and Written Opinion for PCT/US2014/054247, dated Mar. 27, 2015.
International Preliminary Report on Patentability for PCT/US2014/054247, dated Mar. 17, 2016.
Invitation to Pay Additional Fees for PCT/US2014/054291, dated Dec. 18, 2014.
International Search Report and Written Opinion for PCT/US2014/054291, dated Mar. 27, 2015.
International Preliminary Report on Patentability for PCT/US2014/054291, dated Mar. 17, 2016.
International Search Report and Written Opinion for PCT/US2014/054252, dated Mar. 5, 2015.
International Preliminary Report on Patentability or PCT/US2014/054252, dated Mar. 17, 2016.
International Search Report and Written Opinion for PCT/US2014/070038, dated Apr. 14, 2015.
International Preliminary Report on Patentability for PCT/US2014/070038, dated Jun. 23, 2016.
International Search Report and Written Opinion for PCT/US2015/042770, dated Feb. 23, 2016.
International Search Report and Written Opinion for PCT/US2015/058479, dated Feb. 11, 2016.
International Search Report for PCT/US2013/032589, dated Jul. 26, 2013.
Alexandrov et al., Signatures of mutational processes in human cancer. Nature. Aug. 22, 2013;500(7463):415-21. doi: 10.1038/nature12477. Epub Aug. 14, 2013.
Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Bedell et al., In vivo genome editing using a high-efficiency TALEN system. Nature. Nov. 1, 2012;491(7422):114-8. Doi: 10.1038/nature11537. Epub Sep. 23, 2012.
Beumer et al., Efficient gene targeting in *Drosophila* with zinc-finger nucleases. Genetics. Apr. 2006;172(4):2391-403. Epub Feb. 1, 2006.
Bhagwat, DNA-cytosine deaminases: from antibody maturation to antiviral defense. DNA Repair (Amst). Jan. 5, 2004;3(1):85-9.
Boch, TALEs of genome targeting. Nat Biotechnol. Feb. 2011;29(2):135-6. Doi: 10.1038/nbt.1767.

(56) References Cited

OTHER PUBLICATIONS

Boeckle et al., Melittin analogs with high lytic activity at endosomal pH enhance transfection with purified targeted PEI polyplexes. J Control Release. May 15, 2006;112(2):240-8. Epub Mar. 20, 2006.
Branden and Tooze, Introduction to Protein Structure. 1999; 2nd edition. Garland Science Publisher: 3-12.
Brown et al., Serine recombinases as tools for genome engineering. Methods. Apr. 2011;53(4):372-9. doi: 10.1016/j.ymeth.2010.12.031. Epub Dec. 30, 2010.
Bulow et al., Multienzyme systems obtained by gene fusion. Trends Biotechnol. Jul. 1991;9(7):226-31.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cameron, Recent advances in transgenic technology. Mol Biotechnol. Jun. 1997;7(3):253-65.
Cargill et al.,Characterization of single-nucleotide polymorphisms in coding regions of human genes. Nat Genet. Jul. 1999;22(3):231-8.
Caron et al., Intracellular delivery of a Tat-eGFP fusion protein into muscle cells. Mol Ther. Mar. 2001;3(3):310-8.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Charpentier et al., Biotechnology: Rewriting a genome. Nature. Mar. 7, 2013;495(7439):50-1. doi: 10.1038/495050a.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Chichili et al., Linkers in the structural biology of protein-protein interactions. Protein Science. 2013;22:153-67.
Chipev et al., A leucine-proline mutation in the H1 subdomain of keratin 1 causes epidermolytic hyperkeratosis. Cell. Sep. 4, 1992;70(5):821-8.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Christian et al, Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cole-Strauss et al., Correction of the mutation responsible for sickle cell anemia by an RNA-DNA oligonucleotide. Science. Sep. 6, 1996;273(5280):1386-9.

Cong et al., Multiplex genome engineering using CRISPR/Cas systems. Science. Feb. 15, 2013;339(6121):819-23. doi: 10.1126/science.1231143. Epub Jan. 3, 2013.
Conticello, The AID/APOBEC family of nucleic acid mutators. Genome Biol. 2008;9(6):229. doi: 10.1186/gb-2008-9-6-229. Epub Jun. 17, 2008.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
De Souza, Primer: genome editing with engineered nucleases. Nat Methods. Jan. 2012;9(1):27.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fuchs et al., Polyarginine as a multifunctional fusion tag. Protein Sci. Jun. 2005;14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.

(56) References Cited

OTHER PUBLICATIONS

Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Genbank Submission; NIH/NCBI, Accession No. J04623. Kita et al., Apr. 26, 1993. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
Gerber et al., RNA editing by base deamination: more enzymes, more targets, new mysteries. Trends Biochem Sci. Jun. 2001;26(6):376-84.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Guo et al., Protein tolerance to random amino acid change. Proc Natl Acad Sci U S A. Jun. 22, 2004;101(25):9205-10. Epub Jun. 14, 2004.
Hale et al., RNA-guided RNA cleavage by a CRISPR RNA-Cas protein complex. Cell. Nov. 25, 2009;139(5):945-56. doi: 10.1016/j.cell.2009.07.040.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.

Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hill et al., Functional analysis of conserved histidines in ADP-glucose pyrophosphorylase from *Escherichia coli*.Biochem Biophys Res Commun. Mar. 17, 1998;244(2):573-7.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.
Horvath et al., CRISPR/Cas, the immune system of bacteria and archaea. Science. Jan. 8, 2010;327(5962):167-70. doi: 10.1126/science.1179555.
Houdebine, The methods to generate transgenic animals and to control transgene expression. J Biotechnol. Sep. 25, 2002;98(2-3):145-60.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Huang et al., Heritable gene targeting in zebrafish using customized TALENs. Nat Biotechnol. Aug. 5, 2011;29(8):699-700. doi: 10.1038/nbt.1939.
Humbert et al., Targeted gene therapies: tools, applications, optimization. Crit Rev Biochem Mol Biol. May-Jun. 2012;47(3):264-81. doi: 10.3109/10409238.2012.658112.
Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Ikediobi et al., Mutation analysis of 24 known cancer genes in the NCI-60 cell line set. Mol Cancer Ther. Nov. 2006;5(11):2606-12. Epub Nov. 6, 2006.
Irrthum et al., Congenital hereditary lymphedema caused by a mutation that inactivates VEGFR3 tyrosine kinase. Am J Hum Genet. Aug. 2000;67(2):295-301. Epub Jun. 9, 2000.
Jamieson et al., Drug discovery with engineered zinc-finger proteins. Nat Rev Drug Discov. May 2003;2(5):361-8.
Jansen et al., Backbone and nucleobase contacts to glucosamine-6-phosphate in the glmS ribozyme. Nat Struct Mol Biol. Jun. 2006;13(6):517-23. Epub May 14, 2006.
Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al.,TALENs: a widely applicable technology for targeted genome editing. Nat Rev Mol Cell Biol. Jan. 2013;14(1):49-55. doi: 10.1038/nrm3486. Epub Nov. 21, 2012.
Kaiser et al., Gene therapy. Putting the fingers on gene repair. Science. Dec. 23, 2005;310(5756):1894-6.

(56) References Cited

OTHER PUBLICATIONS

Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.

Kappel et al., Regulating gene expression in transgenic animals. Curr Opin Biotechnol. Oct. 1992;3(5):548-53.

Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.

Kim et al., A library of TAL effector nucleases spanning the human genome. Nat Biotechnol. Mar. 2013;31(3):251-8. Doi: 10.1038/nbt.2517. Epub Feb. 17, 2013.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Kim et al., TALENs and ZFNs are associated with different mutationsignatures. Nat Methods. Mar. 2013;10(3):185. doi: 10.1038/nmeth.2364. Epub Feb. 10, 2013.

Kim et al., Targeted genome editing in human cells with zinc finger nucleases constructed via modular assembly. Genome Res. Jul. 2009;19(7):1279-88. doi: 10.1101/gr.089417.108. Epub May 21, 2009.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Kumar et al., Structural and functional consequences of the mutation of a conserved arginine residue in alphaA and alphaB crystallins. J Biol Chem. Aug. 20, 1999;274(34):24137-41.

Kundu et al., Leucine to proline substitution by SNP at position 197 in Caspase-9 gene expression leads to neuroblastoma: a bioinformatics analysis. 3 Biotech. 2013; 3:225-34.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.

Lazar et al., Transforming growth factor alpha: mutation of aspartic acid 47 and leucine 48 results in different biological activities. Mol Cell Biol. Mar. 1988;8(3):1247-52.

Lee et al., PIK3CA gene is frequently mutated in breast carcinomas and hepatocellular carcinomas. Oncogene. Feb. 17, 2005;24(8):1477-80.

Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.

Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Lewis et al., Codon 129 polymorphism of the human prion protein influences the kinetics of amyloid formation. J Gen Virol. Aug. 2006;87(Pt 8):2443-9.

Li et al., Current approaches for engineering proteins with diverse biological properties. Adv Exp Med Biol. 2007;620:18-33.

Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.

Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Design of polydactyl zinc-finger proteins for unique addressing within complex genomes. Proc Natl Acad Sci U S A. May 27, 1997;94(11):5525-30.

Liu et al., Fast Colorimetric Sensing of Adenosine and Cocaine Based on a General Sensor Design Involving Aptamers and Nanoparticles. Angew Chem. 2006;118(1):96-100.

Lombardo et al., Gene editing in human stem cells using zinc finger nucleases and integrase-defective lentiviral vector delivery. Nat Biotechnol. Nov. 2007;25(11):1298-306. Epub Oct. 28, 2007.

Lundberg et al., Delivery of short interfering RNA using endosomolytic cell-penetrating peptides. FASEB J. Sep. 2007;21(11):2664-71. Epub Apr. 26, 2007.

Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.

Maeder et al., Robust, synergistic regulation of human gene expression using TALE activators. Nat Methods. Mar. 2013;10(3):243-5. doi: 10.1038/nmeth.2366. Epub Feb. 10, 2013.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.

Mali et al., Cas9 as a versatile tool for engineering biology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science.1232033. Epub Jan. 3, 2013.

Mani et al., Design, engineering, and characterization of zinc finger nucleases. Biochem Biophys Res Commun. Sep. 23, 2005;335(2):447-57.

Meng et al., Targeted gene inactivation in zebrafish using engineered zinc-finger nucleases. Nat Biotechnol. Jun. 2008;26(6):695-701. doi: 10.1038/nbt1398. Epub May 25, 2008.

Miller et al., A TALE nuclease architecture for efficient genome editing. Nat Biotechnol. Feb. 2011;29(2):143-8. doi:10.1038/nbt.1755. Epub Dec. 22, 2010.

Miller et al., An improved zinc-finger nuclease architecture for highly specific genome editing. Nat Biotechnol. Jul. 2007;25(7):778-85. Epub Jul. 1, 2007.

Minoretti et al., A W148R mutation in the human FOXD4 gene segregating with dilated cardiomyopathy, obsessive-compulsive disorder, and suicidality. Int J Mol Med. Mar. 2007;19(3):369-72.

Moore et al., Improved somatic mutagenesis in zebrafish using transcription activator-like effector nucleases (TALENs). PLoS One. 2012;7(5):e37877. Doi: 10.1371/journal.pone.0037877. Epub May 24, 2012.

Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.

Morris et al., A peptide carrier for the delivery of biologically active proteins into mammalian cells. Nat Biotechnol. Dec. 2001;19(12):1173-6.

Moscou et al., A simple cipher governs DNA recognition by TAL effectors. Science. Dec. 11, 2009;326(5959):1501. doi: 10.1126/science.1178817.

Mullins et al., Transgenesis in nonmurine species. Hypertension. Oct. 1993;22(4):630-3.

(56) References Cited

OTHER PUBLICATIONS

Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Noris et al., A phenylalanine-55 to serine amino-acid substitution in the human glycoprotein IX leucine-rich repeat is associated with Bernard-Soulier syndrome. Br J Haematol. May 1997;97(2):312-20.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
Osborn et al., TALEN-based gene correction for epidermolysis bullosa. Mol Ther. Jun. 2013;21(6):1151-9. doi: 10.1038/mt.2013.56. Epub Apr. 2, 2013.
Pan et al., Biological and biomedical applications of engineered nucleases. Mol Biotechnol. Sep. 2013;55(1):54-62. doi: 10.1007/s12033-012-9613-9.
Pattanayak et al., Determining the specificities of TALENs, Cas9, and other genome-editing enzymes. Methods Enzymol. 2014;546:47-78. doi: 10.1016/B978-0-12-801185-0.00003-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Petek et al., Frequent endonuclease cleavage at off-target locations in vivo. Mol Ther. May 2010;18(5):983-6. Doi: 10.1038/mt.2010.35. Epub Mar. 9, 2010.
Phillips, The challenge of gene therapy and DNA delivery. J Pharm Pharmacol. Sep. 2001;53(9):1169-74.
Poller et al., A leucine-to-proline substitution causes a defective alpha 1-antichymotrypsin allele associated with familial obstructive lung disease. Genomics. Sep. 1993;17(3):740-3.
Porteus, Design and testing of zinc finger nucleases for use in mammalian cells. Methods Mol Biol. 2008;435:47-61. doi: 10.1007/978-1-59745-232-8_4.
Proudfoot et al., Zinc finger recombinases with adaptable DNA sequence specificity. PLoS One. Apr. 29, 2011;6(4):e19537. doi: 10.1371/journal.pone.0019537.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ramirez et al., Unexpected failure rates for modular assembly of engineered zinc fingers. Nat Methods. May 2008;5(5):374-5. Doi: 10.1038/nmeth0508-374.
Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.
Reynaud et al., What role for AID: mutator, or assembler of the immunoglobulin mutasome? Nat Immunol. Jul. 2003;4(7):631-8.
Reyon et al., FLASH assembly of TALENs for high-throughput genome editing. Nat Biotechnol. May 2012;30(5):460-5. doi: 10.1038/nbt.2170.
Sage et al., Proliferation of functional hair cells in vivo in the absence of the retinoblastoma protein. Science. Feb. 18, 2005;307(5712):1114-8. Epub Jan. 13, 2005.
Samal et al., Cationic polymers and their therapeutic potential. Chem Soc Rev. Nov. 7, 2012;41(21):7147-94. doi: 10.1039/c2cs35094g. Epub Aug. 10, 2012.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang, Prospects for transgenesis in the chick. Mech Dev. Sep. 2004;121(9):1179-86.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

(56) References Cited

OTHER PUBLICATIONS

Schriefer et al., Low pressure DNA shearing: a method for random DNA sequence analysis. Nucleic Acids Res. Dec. 25, 1990;18(24):7455-6.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schwarze et al., In vivo protein transduction: delivery of a biologically active protein into the mouse. Science. Sep. 3, 1999;285(5433):1569-72.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.

Sells et al., Delivery of protein into cells using polycationic liposomes. Biotechniques. Jul. 1995;19(1):72-6, 78.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.

Shalem et al., Genome-scale CRISPR-Cas9 knockout screening in human cells. Science. Jan. 3, 2014;343(6166):84-7. doi: 10.1126/science.1247005. Epub Dec. 12, 2013.

Sheridan, First CRISPR-Cas patent opens race to stake out intellectual property. Nat Biotechnol. 2014;32(7):599-601.

Sheridan, Gene therapy finds its niche. Nat Biotechnol. Feb. 2011;29(2):121-8. doi: 10.1038/nbt.1769.

Siebert et al., An improved PCR method for walking in uncloned genomic DNA. Nucleic Acids Res. Mar. 25, 1995;23(6):1087-8.

Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.

Szczepek et al., Structure-based redesign of the dimerization interface reduces the toxicity of zinc-finger nucleases. Nat Biotechnol. Jul. 2007;25(7):786-93. Epub Jul. 1, 2007.

Tebas et al., Gene editing of CCR5 in autologous CD4 T cells of persons infected with HIV. N Engl J Med. Mar. 6, 2014;370(10):901-10. doi: 10.1056/NEJMoa1300662.

Tessarollo et al., Targeted mutation in the neurotrophin-3 gene results in loss of muscle sensory neurons. Proc Natl Acad Sci U S A. Dec. 6, 1994;91(25):11844-8.

Tesson et al., Knockout rats generated by embryo microinjection of TALENs. Nat Biotechnol. Aug. 5, 2011;29(8):695-6. doi: 10.1038/nbt.1940.

Thompson et al., Engineering and identifying supercharged proteins for macromolecule delivery into mammalian cells. Methods Enzymol. 2012;503:293-319. doi: 10.1016/B978-0-12-396962-0.00012-4.

Thorpe et al., Functional correction of episomal mutations with short DNA fragments and RNA-DNA oligonucleotides. J Gene Med. Mar.-Apr. 2002;4(2):195-204.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.

Uniprot Submission; UniProt, Accession No. P01011. Last modified Jun. 11, 2014, version 2. 15 pages.

UniProt Submission; UniProt, Accession No. P01011. Last modified Sep. 18, 2013, version 2. 15 pages.

UniProt Submission; UniProt, Accession No. P04264. Last modified Jun. 11, 2014, version 6. 15 pages.

UniProt Submission; UniProt, Accession No. P04275. Last modified Jul. 9, 2014, version 107. 29 pages.

Urnov et al., Genome editing with engineered zinc finger nucleases. Nat Rev Genet. Sep. 2010;11(9):636-46. doi: 10.1038/nrg2842.

Urnov et al., Highly efficient endogenous human gene correction using designed zinc-finger nucleases. Nature. Jun. 2, 2005;435(7042):646-51. Epub Apr. 3, 2005.

Vanamee et al., FokI requires two specific DNA sites for cleavage. J Mol Biol. May 25, 2001;309(1):69-78.

Wacey et al., Disentangling the perturbational effects of amino acid substitutions in the DNA-binding domain of p53. Hum Genet. Jan. 1999;104(1):15-22.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Wah et al., Structure of FokI has implications for DNA cleavage. Proc Natl Acad Sci U S A. Sep. 1, 1998 ;95(18):10564-9.

Wang et al., Genetic screens in human cells using the CRISPR-Cas9 system. Science. Jan. 3, 2014;343(6166):80-4. doi: 10.1126/science.1246981. Epub Dec. 12, 2013.

Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.

Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.

Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.

Wang et al., Efficient delivery of genome-editing proteins using bioreducible lipid nanoparticles. Proc Natl Acad Sci U S A. Feb. 29, 2016. pii: 201520244. [Epub ahead of print].

Weber et al., Assembly of designer TAL effectors by Golden Gate cloning. PLoS One. 2011;6(5):e19722. doi:10.1371/journal.pone.0019722. Epub May 19, 2011.

Weinberger et al., Disease-causing mutations C277R and C277Y modify gating of human ClC-1 chloride channels in myotonia congenita. J Physiol. Aug. 1, 2012;590(Pt 15):3449-64. doi: 0.1113/jphysiol.2012.232785. Epub May 28, 2012.

Wiedenheft et al., RNA-guided genetic silencing systems in bacteria and archaea. Nature. Feb. 15, 2012;482(7385):331-8. doi: 10.1038/nature10886. Review.

Wolfe et al., Analysis of zinc fingers optimized via phage display: evaluating the utility of a recognition code. J Mol Biol. Feb. 5, 1999;285(5):1917-34.

Wood et al., Targeted genome editing across species using ZFNs and TALENs. Science. Jul. 15, 2011;333(6040):307. doi: 10.1126/science.1207773. Epub Jun. 23, 2011.

Wu et al., Correction of a genetic disease in mouse via use of CRISPR-Cas9. Cell Stem Cell. Dec. 5, 2013;13(6):659-62. doi: 10.1016/j.stem.2013.10.016.

Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.

Yazaki et al., Hereditary systemic amyloidosis associated with a new apolipoprotein AII stop codon mutation Stop78Arg. Kidney Int. Jul. 2003;64(1):11-6.

Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.

Zhang et al., Conditional gene manipulation: Cre-ating a new biological era. J Zhejiang Univ Sci B. Jul. 2012;13(7):511-24. doi: 10.1631/jzus.B1200042. Review.

Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.

Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.

(56) References Cited

OTHER PUBLICATIONS

Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Abudayyeh et al., C2c2 is a single-component programmable RNA-guided RNA-targeting CRISPR effector. Science Aug. 2016;353(6299):aaf5573. DOI: 10.1126/science.aaf5573.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Barnes et al., Repair and genetic consequences of endogenous DNA base damage in mammalian cells. Annu Rev Genet. 2004;38:445-76.
Beale et al., Comparison of the differential context-dependence of DNA deamination by APOBEC enzymes: correlation with mutation spectra in vivo. J Mol Biol. Mar. 26, 2004;337(3):585-96.
Begley, Scientists unveil the 'most clever CRISPR gadget' so far. STAT, Apr. 20, 2016. https://www.statnews.com/2016/04/20/clever-crispr-advance-unveiled/.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Bitinaite et al., FokI dimerization is required for DNA cleavage. Proc Natl Acad Sci U S A. Sep. 1, 1998;95(18):10570-5.
Bolotin et al., Clustered regularly interspaced short palindrome repeats (CRISPRs) have spacers of extrachromosomal origin. Microbiology. Aug. 2005;151(Pt 8):2551-61.
Borman, Improved route to single-base genome editing. Chemical & Engineering News, Apr. 25, 2016;94(17)p5. http://cen.acs.org/articles/94/i17/Improved-route-single-base-genome.html.
Briner et al., Guide RNA functional modules direct Cas9 activity and orthogonality. Mol Cell. Oct. 23, 2014;56(2):333-339. doi: 10.1016/j.molcel.2014.09.019 . . . .
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brusse et al., Spinocerebellar ataxia associated with a mutation in the fibroblast growth factor 14 gene (SCA27): A new phenotype. Mov Disord. Mar. 2006;21(3):396-401.
Buchholz et al., Alteration of Cre recombinase site specificity by substrate-linked protein evolution. Nat Biotechnol. Nov. 2001;19(11):1047-52.
Buchwald et al., Long-term, continuous intravenous heparin administration by an implantable infusion pump in ambulatory patients with recurrent venous thrombosis. Surgery. Oct. 1980;88(4):507-16.
Burstein et al., New CRISPR-Cas systems from uncultivated microbes. Nature Feb. 2017;542(7640):237-240.
Caldecott et al., Single-strand break repair and genetic disease. Nat Rev Genet. Aug. 2008;9(8):619-31. doi: 10.1038/nrg2380.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.

Chavez et al., Highly efficient Cas9-mediated transcriptional programming. Nat Methods. Apr. 2015;12(4):326-8. doi: 10.1038/nmeth.3312. Epub Mar. 2, 2015.
Chavez et al., Precise Cas9 targeting enables genomic mutation prevention. Jun. 14, 2016. doi:https://doi.org/10.1101/058974. [Preprint].
Chavez et al., Precise Cas9 targeting enables genomic mutation prevention. Proc Natl Acad Sci U S A. Apr. 3, 2018;115(14):3669-3673. doi: 10.1073/pnas.1718148115. Epub Mar. 19, 2018.
Chavez et al., Therapeutic applications of the PhiC31 integrase system. Curr Gene Ther. Oct. 2011;11(5):375-81. Review.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Chew et al., A multifunctional AAV-CRISPR-Cas9 and its host response. Nat Methods. Oct. 2016;13(10):868-74. doi: 10.1038/nmeth.3993. Epub Sep. 5, 2016.
Chu et al., Increasing the efficiency of homology-directed repair for CRISPR-Cas9-induced precise gene editing in mammalian cells. Nat Biotech. Feb. 13, 2015;33:543-8.
Covino et al., The CCL2/CCR2 Axis in the Pathogenesis of HIV-1 Infection: A New Cellular Target for Therapy? Current Drug Targets Dec. 2016;17(1):76-110. DOI: 10.2174/1389450117011512171109178.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Cox et al., Therapeutic genome editing: prospects and challenges. Nat Med. Feb. 2015;21(2):121-31. doi: 10.1038/nm.3793.
Cunningham et al., Ensembl 2015. Nucleic Acids Res. Jan. 2015;43(Database issue):D662-9. doi: 10.1093/nar/gku1010. Epub Oct. 28, 2014.
Davis et al., DNA double strand break repair via non-homologous end-joining. Transl Cancer Res. Jun. 2013;2(3):130-143.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
Dicarlo et al., Genome engineering in *Saccharomyces cerevisiae* using CRISPR-Cas systems. Nucleic Acids Research Apr. 2013;41(7):4336-43.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Doench et al., Optimized sgRNA design to maximize activity and minimize off-target effects of CRISPR-Cas9. Nat Biotechnol. Feb. 2016;34(2):184-191. doi: 10.1038/nbt.3437.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Doudna et al., Genome editing. The new frontier of genome engineering with CRISPR-Cas9. Science. Nov. 28, 2014;346(6213):1258096. doi: 10.1126/science.1258096.
Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Endo et al., Toward establishing an efficient and versatile gene targeting system in higher plants. Biocatalysis and Agricultural Biotechnology 2014;3,(1):2-6.
Extended European Search Report for EP 15830407.1, dated Mar. 2, 2018.
Fang et al., Synthetic Studies Towards Halichondrins: Synthesis of the Left Halves of Norhalichondrins and Homohalichondrins. Tetrahedron Letters 1992;33(12):1557-1560.

(56) References Cited

OTHER PUBLICATIONS

Ferretti et al., Complete genome sequence of an M1 strain of *Streptococcus pyogenes*. Proc Natl Acad Sci U S A. Apr. 10, 2001;98(8):4658-63.

Ferry et al., Rational design of inducible CRISPR guide RNAs for de novo assembly of transcriptional programs. Nat Commun. Mar. 3, 2017;8:14633. doi: 10.1038/ncomms14633.

Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.

Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.

Freshney, Culture of Animal Cells. A Manual of Basic Technique. Alan R. Liss, Inc. New York. 1983;4.

Fukui et al., DNA Mismatch Repair in Eukaryotes and Bacteria. J Nucleic Acids. Jul. 27, 2010;2010. pii: 260512. doi: 10.4061/2010/260512.

Fung et al., Repair at single targeted DNA double-strand breaks in pluripotent and differentiated human cells. PLoS One. 2011;6(5):e20514. doi: 10.1371/journal.pone.0020514. Epub May 25, 2011.

Gaj et al., A comprehensive approach to zinc-finger recombinase customization enables genomic targeting in human cells. Nucleic Acids Res. Feb. 6, 2013;41(6):3937-46.

Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.

Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.

Gao et al., DNA-guided genome editing using the Natronobacterium gregoryi Argonaute. Nat Biotechnol. Jul. 2016;34(7):768-73. doi: 10.1038/nbt.3547. Epub May 2, 2016.

Gardlik et al., Vectors and delivery systems in gene therapy. Med Sci Monit. Apr. 2005;11(4):RA110-21. Epub Mar. 24, 2005.

Garneau et al., The CRISPR/Cas bacterial immune system cleaves bacteriophage and plasmid DNA. Nature. Nov. 4, 2010;468(7320):67-71. doi: 10.1038/nature09523.

Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.

Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.

Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.

Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.

Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.

Harris et al., RNA editing enzyme APOBEC1 and some of its homologs can act as DNA mutators. Mol Cell. Nov. 2002;10(5):1247-53.

Heller et al., Replisome assembly and the direct restart of stalled replication forks. Nat Rev Mol Cell Biol. Dec. 2006;7(12):932-43. Epub Nov. 8, 2006.

Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.

Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.

Hilton et al., Enabling functional genomics with genome engineering. Genome Res. Oct. 2015;25(10):1442-55. doi: 10.1101/gr.190124.115.

Hondares et al., Peroxisome Proliferator-activated Receptor α (PPARα) Induces PPARγ Coactivator 1α (PGC-1α) Gene Expression and Contributes to Thermogenic Activation of Brown Fat. J Biol. Chem Oct. 2011; 286(50):43112-22. doi: 10.1074/jbc.M111.252775.

Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.

Howard et al., Intracerebral drug delivery in rats with lesion-induced memory deficits. J Neurosurg. Jul. 1989;71(1):105-12.

Hower et al., Shape-based peak identification for ChIP-Seq. BMC Bioinformatics. Jan. 12, 2011;12:15. doi: 10.1186/1471-2105-12-15.

Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.

Hwang et al., Efficient In Vivo Genome Editing Using RNA-Guided Nucleases. Nat Biotechnol. Mar. 2013; 31(3): 227-229. doi: 10.1038/nbt.2501. Epub Jan. 29, 2013.

International Preliminary Report on Patentability for PCT/US2016/058344, dated May 3, 2018.

International Preliminary Report on Patentability for PCT/US2015/042770, dated Dec. 19, 2016.

International Preliminary Report on Patentability for PCT/US2015/058479, dated May 11, 2017.

International Search Report and Written Opinion for PCT/US2016/044546, dated Dec. 28, 2016.

International Search Report and Written Opinion for PCT/US2016/058344, dated Apr. 20, 2017.

International Search Report and Written Opinion for PCT/US2017/045381, dated Oct. 26, 2017.

International Search Report and Written Opinion for PCT/US2017/046144, dated Oct. 10, 2017.

International Search Report and Written Opinion for PCT/US2017/056671, dated Feb. 20, 2018.

International Search Report and Written Opinion for PCT/US2017/068105, dated Apr. 4, 2018.

International Search Report and Written Opinion for PCT/US2017/068114, dated Mar. 20, 2018.

International Search Report and Written Opinion for PCT/US2017/48390, dated Jan. 9, 2018.

International Search Report for PCT/US2018/021664, dated Jun. 21, 2018.

International Search Report for PCT/US2018/021878, dated Aug. 20, 2018.

International Search Report for PCT/US2018/021880, dated Jun. 20, 2018.

International Search Report for PCT/US2018/024208, dated Aug. 23, 2018.

International Search Report for PCT/US2018/025887, dated Jun. 21, 2018.

International Search Report for PCT/US2018/032460, dated Jul. 11, 2018.

Invitation to Pay Additional Fees for PCT/US2016/058344, dated Mar. 1, 2017.

Invitation to Pay Additional Fees for PCT/US2017/056671, dated Dec. 21, 2017.

Invitation to Pay Additional Fees for PCT/US2017/48390, dated Nov. 7, 2017.

Invitation to Pay Additional Fees for PCT/US2018/021878, dated Jun. 8, 2018.

Ishino et al., Nucleotide sequence of the iap gene, responsible for alkaline phosphatase isozyme conversion in *Escherichia coli*, and identification of the gene product. J Bacteriol. Dec. 1987;169(12):5429-33.

Jansen et al., Identification of genes that are associated with DNA repeats in prokaryotes. Mol Microbiol. Mar. 2002;43(6):1565-75.

(56) References Cited

OTHER PUBLICATIONS

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

Kaya et al., A bacterial Argonaute with noncanonical guide RNA specificity. Proc. Natl. Acad. Sci. USA Apr. 2016;113(15):4057-62.

Kellendonk et al., Regulation of Cre recombinase activity by the synthetic steroid RU 486. Nucleic Acids Res. Apr. 15, 1996;24(8):1404-11.

Kim et al., Genome-wide target specificities of CRISPR RNA-guided programmable deaminases. Nat Biotechnol. May 2017;35(5):475-480. doi: 10.1038/nbt.3852. Epub Apr. 10, 2017.

Kim et al., Highly efficient RNA-guided base editing in mouse embryos. Nat Biotechnol. May 2017;35(5):435-437. doi: 10.1038/nbt.3816. Epub Feb. 27, 2017.

Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.

Kim et al., The role of apolipoprotein E in Alzheimer's disease. Neuron. Aug. 13, 2009;63(3):287-303. doi: 10.1016/j.neuron.2009.06.026.

Kim et al., Transcriptional repression by zinc finger peptides. Exploring the potential for applications in gene therapy. J Biol Chem. Nov. 21, 1997;272(47):29795-800.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.

Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.

Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. EMBO J. Apr. 1988;7(4):1229-37.

Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.

Komor et al., CRISPR-Based Technologies for the Manipulation of Eukaryotic Genomes. Cell. Jan. 12, 2017;168(1-2):20-36. doi: 10.1016/j.cell.2016.10.044.

Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.

Komor et al., Programmable editing of a target base in genomic DNA without double-stranded DNA cleavage. Nature. Apr. 20, 2016;533(7603):420-4. doi: 10.1038/nature17946.

Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.

Kunz et al., DNA Repair in mammalian cells: Mismatched repair: variations on a theme. Cell Mol Life Sci. Mar. 2009;66(6):1021-38. doi: 10.1007/s00018-009-8739-9.

Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.

Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.

Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.

Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.

Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.

Langer et al., New methods of drug delivery. Science. Sep. 28, 1990;249(4976):1527-33.

Lau et al., Molecular basis for discriminating between normal and damaged bases by the human alkyladenine glycosylase, AAG. Proc Natl Acad Sci U S A. Dec. 5, 2000;97(25):13573-8.

Ledford, Gene-editing hack yields pinpoint precision. Nature, Apr. 20, 2016. http://www.nature.com/news/gene-editing-hack-yields-pinpoint-precision-1.19773.

Lee et al., A chimeric thyroid hormone receptor constitutively bound to DNA requires retinoid X receptor for hormone-dependent transcriptional activation in yeast. Mol Endocrinol. Sep. 1994;8(9):1245-52.

Lee et al., Failure to detect DNA-guided genome editing using Natronobacterium gregoryi Argonaute. Nat Biotechnol. Nov. 28, 2016;35(1):17-18. doi: 10.1038/nbt.3753.

Lee et al., Recognition of liposomes by cells: in vitro binding and endocytosis mediated by specific lipid headgroups and surface charge density. Biochim Biophys Acta. Jan. 31, 1992;1103(2):185-97.

Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.

Levy et al., Inhibition of calcification of bioprosthetic heart valves by local controlled-release diphosphonate. Science. Apr. 12, 1985;228(4696):190-2.

Lewis et al., Building the Class 2 CRISPR-Cas Arsenal. Mol Cell 2017;65(3);377-379.

Li et al., Base editing with a Cpf1-cytidine deaminase fusion. Nat Biotechnol. Apr. 2018;36(4):324-327. doi: 10.1038/nbt.4102. Epub Mar. 19, 2018.

Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.

Li et al., Highly efficient and precise base editing in discarded human tripronuclear embryos. Protein Cell. Aug. 19, 2017. doi: 10.1007/s13238-017-0458-7. [Epub ahead of print].

Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.

Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.

Lieber et al., Mechanism and regulation of human non-homologous DNA end-joining. Nat Rev Mol Cell Biol. Sep. 2003;4(9):712-20.

Lin et al., Enhanced homology-directed human genome engineering by controlled timing of CRISPR/Cas9 delivery. Elife. Dec. 15, 2014;3:e04766. doi: 10.7554/eLife.04766.

(56) References Cited

OTHER PUBLICATIONS

Liu et al., C2c1-sgRNA Complex Structure Reveals RNA-Guided DNA Cleavage Mechanism. Molecular Cell Jan. 2017;65(2):310-22.
Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.
Liu et al., Balancing AID and DNA repair during somatic hypermutation. Trends Immunol. Apr. 2009;30(4):173-81. doi: 10.1016/j.it.2009.01.007.
Liu et al., Distance determination by GIY-YIG intron endonucleases: discrimination between repression and cleavage functions. Nucleic Acids Res. Mar. 31, 2006;34(6):1755-64. Print 2006.
Losey et al., Crystal structure of *Staphylococcus sureus* tRNA adenosine deaminase tadA in complex with RNA. Nature Struct. Mol. Biol. Feb. 2006;13(2):153-9.
Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Lyons et al., Efficient Recognition of an Unpaired Lesion by a DNA Repair Glycosylase. J. Am. Chem. Soc., 2009;131(49):17742-3. DOI: 10.1021/ja908378y.
Ma et al., Targeted AID-mediated mutagenesis (TAM) enables efficient genomic diversification in mammalian cells. Nature Methods. Oct. 2016;13:1029-35. doi:10.1038/nmeth.4027.
Makarova et al., Prokaryotic homologs of Argonaute proteins are predicted to function as key components of a novel system of defense against mobile genetic elements. Biology Direct 2009;4:29.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Makarova et al., Evolution and classification of the CRISPR-Cas systems. Nat Rev Microbiol. Jun. 2011;9(6):467-77. doi: 10.1038/nrmicro2577. Epub May 9, 2011.
Marioni et al., DNA methylation age of blood predicts all-cause mortality in later life. Genome Biol. Jan. 30, 2015;16:25. doi: 10.1186/s13059-015-0584-6.
Marraffini et al., CRISPR interference limits horizontal gene transfer in *Staphylococci* by targeting DNA. Science. Dec. 19, 2008;322(5909):1843-5. doi: 10.1126/science.1165771.
Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.
Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.
Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.
Minoche et al., Evaluation of genomic high-throughput sequencing data generated on Illumina HiSeq and genome analyzer systems. Genome Biol. Nov. 8, 2011;12(11):R112. doi: 10.1186/gb-2011-12-11-r112.
Mojica et al., Intervening sequences of regularly spaced prokaryotic repeats derive from foreign genetic elements. J Mol Evol. Feb. 2005;60(2):174-82.
Mol et al., Crystal structure of human uracil-DNA glycosylase in complex with a protein inhibitor: protein mimicry of DNA. Cell. Sep. 8, 1995;82(5):701-8.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Offord, Advances in Genome Editing. The Scientist, Apr. 20, 2016. http://www.the-scientist.com/?articles.view/articleNo/45903/title/Advances-in-Genome-Editing/.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Pearl, Structure and function in the uracil-DNA glycosylase superfamily. Mutat Res. Aug. 30, 2000;460(3-4):165-81.
Petolino et al., Editing Plant Genomes: a new era of crop improvement. Plant Biotechnol J. Feb. 2016;14(2):435-6. doi: 10.1111/pbi.12542.
Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.
Ran et al., Genome engineering using the CRISPR-Cas9 system. Nat Protoc. Nov. 2013;8(11):2281-308. doi: 10.1038/nprot.2013.143. Epub Oct. 24, 2013.
Ran et al., In vivo genome editing using *Staphylococcus aureus* Cas9. Nature. Apr. 9, 2015;520(7546):186-91. doi: 10.1038/nature14299. Epub Apr. 1, 2015.
Rath et al., Fidelity of end joining in mammalian episomes and the impact of Metnase on joint processing. BMC Mol Biol. Mar. 22, 2014;15:6. doi: 10.1186/1471-2199-15-6.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).
Ray et al., Homologous recombination: ends as the means. Trends Plant Sci. Oct. 2002;7(10):435-40.
Rebuzzini et al., New mammalian cellular systems to study mutations introduced at the break site by non-homologous end-joining. DNA Repair (Amst). May 2, 2005;4(5):546-55.
Rees et al., Improving the DNA specificity and applicability of base editing through protein engineering and protein delivery. Nat Commun. Jun. 6, 2017;8:15790. doi: 10.1038/ncomms15790.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.

(56) References Cited

OTHER PUBLICATIONS

Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.

Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.

Sadelain et al., Safe harbours for the integration of new DNA in the human genome. Nat Rev Cancer. Dec. 1, 2011;12(1):51-8. doi: 10.1038/nrc3179.

Sanjana et al., A transcription activator-like effector toolbox for genome engineering. Nat Protoc. Jan. 5, 2012;7(1):171-92. doi: 10.1038/nprot.2011.431.

Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.

Saudek et al., A preliminary trial of the programmable implantable medication system for insulin delivery. N Engl J Med. Aug. 31, 1989;321(9):574-9.

Sclimenti et al., Directed evolution of a recombinase for improved genomic integration at a native human sequence. Nucleic Acids Res. Dec. 15, 2001;29(24):5044-51.

Sefton et al., Implantable pumps. Crit Rev Biomed Eng. 1987;14(3):201-40.

Seripa et al., The missing ApoE allele. Ann Hum Genet. Jul. 2007;71(Pt 4):496-500. Epub Jan. 22, 2007.

Shah et al., Inteins: nature's gift to protein chemists. Chem Sci. 2014;5(1):446-461.

Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.

Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.

Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.

Shee et al., Engineered proteins detect spontaneous DNA breakage in human and bacterial cells. Elife. Oct. 29, 2013;2:e01222. doi: 10.7554/eLife.01222.

Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.

Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.

Shmakov et al., Discovery and Functional Characterization of Diverse Class 2 CRISPR Cas Systems. Molecular Cell Nov. 2015;60(3):385-97.

Simonelli et al., Base excision repair intermediates are mutagenic in mammalian cells. Nucleic Acids Res. Aug. 2, 2005;33(14):4404-11. Print 2005.

Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.

Sjoblom et al., The consensus coding sequences of human breast and colorectal cancers. Science. Oct. 13, 2006;314(5797):268-74. Epub Sep. 7, 2006.

Slaymaker et al., Rationally engineered Cas9 nucleases with improved specificity. Science. Jan. 1, 2016;351(6268):84-8. doi: 10.1126/science.aad5227. Epub Dec. 1, 2015.

Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.

Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.

Stephens et al., The landscape of cancer genes and mutational processes in breast cancer. Nature Jun. 2012;486:400-404. doi:10.1038/nature11017.

Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.

Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.

Swarts et al., DNA-guided DNA interference by a prokaryotic Argonaute. Nature. Mar. 13, 2014;507(7491):258-61. doi: 10.1038/nature12971. Epub Feb. 16, 2014.

Swarts et al., The evolutionary journey of Argonaute proteins. Nat Struct Mol Biol. Sep. 2014;21(9):743-53. doi: 10.1038/nsmb.2879.

Tagalakis et al., Lack of RNA-DNA oligonucleotide (chimeraplast) mutagenic activity in mouse embryos. Mol Reprod Dev. Jun. 2005;71(2):140-4.

Tang et al., Aptazyme-embedded guide RNAs enable ligand-responsive genome editing and transcriptional activation. Nat Commun. Jun. 28, 2017;8:15939. doi: 10.1038/ncomms15939.

Thyagarajan et al., Mammalian genomes contain active recombinase recognition sites. Gene. Feb. 22, 2000;244(1-2):47-54.

Thyagarajan et al., Site-specific genomic integration in mammalian cells mediated by phage phiC31 integrase. Mol Cell Biol. Jun. 2001;21(12):3926-34.

Tirumalai et al., Recognition of core-type DNA sites by lambda integrase. J Mol Biol. Jun. 12, 1998;279(3):513-27.

Tourdot et al., A general strategy to enhance immunogenicity of low-affinity HLA-A2.1-associated peptides: implication in the identification of cryptic tumor epitopes. Eur J Immunol. Dec. 2000;30(12):3411-21.

Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.

Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.

Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.

Vagner et al., Efficiency of homologous DNA recombination varies along the Bacillus subtilis chromosome. J Bacteriol. Sep. 1988;170(9):3978-82.

Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.

Wang et al., CRISPR-Cas9 Targeting of PCSK9 in Human Hepatocytes In Vivo—Brief Report. Arterioscler Thromb Vasc Biol. May 2016;36(5):783-6. doi: 10.1161/ATVBAHA.116.307227. Epub Mar. 3, 2016.

Wang et al., Nucleation, propagation and cleavage of target RNAs in Ago silencing complexes. Nature. Oct. 8, 2009;461(7265):754-61. doi: 10.1038/nature08434.

Wang et al., Recombinase technology: applications and possibilities. Plant Cell Rep. Mar. 2011;30(3):267-85. doi: 10.1007/s00299-010-0938-1. Epub Oct. 24, 2010.

Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.

Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.

(56) References Cited

OTHER PUBLICATIONS

Warren et al., Mutations in the amino-terminal domain of lambda-integrase have differential effects on integrative and excisive recombination. Mol Microbiol. Feb. 2005;55(4):1104-12.
Wijnker et al., Managing meiotic recombination in plant breeding. Trends Plant Sci. Dec. 2008;13(12):640-6. doi: 10.1016/j.tplants. 2008.09.004. Epub Oct. 22, 2008.
Wolf et al., tadA, an essential tRNA-specific adenosine deaminase from Escherichia coli. EMBO J. Jul. 15, 2002;21(14):3841-51.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Xu et al., Sequence determinants of improved CRISPR sgRNA design. Genome Res. Aug. 2015;25(8):1147-57. doi: 10.1101/gr. 191452.115. Epub Jun. 10, 2015.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamamoto et al., Virological and immunological bases for HIV-1 vaccine design. Uirusu 2007;57(2):133-139. https://doi.org/10.2222/jsv.57.133.
Yamano et al., Crystal Structure of Cpf1 in Complex with Guide RNA and Target DNA. Cell May 2016;165(4)949-62.
Yang et al., Engineering and optimising deaminase fusions for genome editing. Nat Commun. Nov. 2, 2016;7:13330. doi: 10.1038/ncomms13330.
Yang et al., Genome editing with targeted deaminases. BioRxiv. Preprint. First posted online Jul. 28, 2016.
Yang et al., New CRISPR-Cas systems discovered. Cell Res. Mar. 2017;27(3):313-314. doi: 10.1038/cr.2017.21. Epub Feb. 21, 2017.
Yang et al., PAM-dependent Target DNA Recognition and Cleavage by C2C1 CRISPR-Cas endonuclease. Cell Dec. 2016;167(7):1814-28.
Yuan et al., Tetrameric structure of a serine integrase catalytic domain. Structure. Aug. 6, 2008;16(8):1275-86. doi: 10.1016/j.str. 2008.04.018.
Yuen et al., Control of transcription factor activity and osteoblast differentiation in mammalian cells using an evolved small-molecule-dependent intein. J Am Chem Soc. Jul. 12, 2006;128(27):8939-46.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zhang et al., Comparison of non-canonical PAMs for CRISPR/Cas9-mediated DNA cleavage in human cells. Sci Rep. Jun. 2014;4:5405.
Zhang et al., Programmable base editing of zebrafish genome using a modified CRISPR-Cas9 system. Nat Commun. Jul. 25, 2017;8(1):118. doi: 10.1038/s41467-017-00175-6.
Zhang et al., Stabilized plasmid-lipid particles for regional gene therapy: formulation and transfection properties. Gene Ther. Aug. 1999;6(8):1438-47.
Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zuris et al., Cationic lipid-mediated delivery of proteins enables efficient protein-based genome editing in vitro and in vivo. Nat Biotechnol. 2015;33:73-80.
Chavez et al., Precise Cas9 targeting enables genomic mutation prevention. Jun. 14, 2016. [Preprint].
Nishida et al., Targeted nucleotide editing using hybrid prokaryotic and vertebrate adaptive immune systems. Science. Sep. 16, 2016;353(6305). pii: aaf8729. doi: 10.1126/science.aaf8729. Epub Aug. 4, 2016.
Qi et al., Engineering naturally occuring trans-acting non-coding RNAs to sense molecular signals. Nucleic Acids Res. Jul. 2012;40(12):5775-86. doi: 10.1093/nar/gks168. Epub Mar. 1, 2012.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Aihara et al., A conformational switch controls the DNA cleavage activity of lambda integrase. Mol Cell. 2003 Jul;12(1):187-98.
Ames et al., A eubacterial riboswich class that senses the coenzyme tetrahydrofolate. Chem Bio Jul. 30, 2010; 17(7);681-5. doi: 10.1016/j.chembio.2010.05.020.
Batey et al., Structure of a natural guanine-responsive riboswitch complexed with the metabolite hypoxanthine. Nature. Nov. 18, 2004;432(7015):411-5.
Bershtein et al., Advances in laboratory evolution of enzymes. Curr Opin Chem Biol. Apr. 2008;12(2):151-8. doi: 10.1016/j.cbpa.2008. 01.027. Epub Mar. 7, 2008. Review.
Bogdanove et al., TAL effectors: customizable proteins for DNA targeting. Science. Sep. 30, 2011;333(6051):1843-6. doi: 10.1126/science.1204094.
Burstein et al.: New CRISPR-Cas systems from uncultivated microbes. Nature. vol. 542. no. 7640. Dec. 22, 2016 (Dec. 22, 2016). Pages 237-241. XP055480893.GB ISSN: 00280836. DOI: 10.1038jnature21059.
Buskirk et al., Directed evolution of ligand dependence: small-molecule-activated protein splicing. Proc Natl Acad Sci U.S.A. Jul. 20, 2004;101(29):10505-10. Epub Jul. 9, 2004 .
Chen et al., Fusion protein linkers: property, design and functionality. Adv Drug Deliv Rev. Oct. 2013;65(10):1357-69. doi:10.1016/j.addr.2012.09.039. Epub Sep. 29, 2012.
Cobb et al., Directed evolution an enabling synthetic biology tool. Curr Opin chem Biol. Aug. 2012;16(3-4):285-91. doi:10.1016/j.cbpa.2012.05.186.Epub Jun. 4, 2012. Review.
Cobb et al., Directed evolution as a powerful synthetic biology tool. Methods. Mar. 15, 2013;60(1):81-90. doi: 10.1016/j.ymeth.2012. 03.009. Epub Mar. 23, 2012.
Dixon et al., Reengineering orthogonally selective riboswitches. Proc Natl Acad Sci U.S.A. Feb. 16, 2010;107(7):2830-5. doi: 10.1073/pnas.0911209107. Epub Jan. 26, 2010.
Edwards et al., Crystal structures of the thi-box riboswitch bound to thiamine pyrophosphate analogs reveal adaptive RNA-small molecule recognition. Structure. Sep. 2006;14(9):1459-68.
Esvelt et al., A system for the continuous directed evolution of biomolecules. Nature. Apr. 28, 2011;472(7344):499-503. doi: 10.1038/nature09929. Epub Apr. 10, 2011.
Fischer et al., Cryptic epitopes induce high-titer humoral immune response in patients with cancer. J Immunol. Sep. 1, 2010;185(5):3095-102. doi: 10.4049/jimmunol.0902166. Epub 2010.
Hida et al., Directed evolution for drug and nucleic acid delivery. Adv Drug Deliv Rev. Dec. 22, 2007;59(15):1562-78. Epub Aug. 28, 2007. Review.
Husimi, Selection and evolution of bacteriophages in cellstat. Adv Biophys. 1989;25:1-43. Review.
Kakiyama et al., A peptide release system using a photo-cleavable linker in a cell array format for cell-toxicity analysis. Polymer J. Feb. 27, 2013;45:535-9.
Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.
Klein et al., Cocrystal structure of a class I preQi riboswitch reveals a pseudoknot recognizing an essential hypermodified nucleobase. Nat Struct Mol Biol. Mar. 2009;16(3):343-4. doi: 10.1038/nsmb. 1563.Epub Feb. 22, 2009.
Kwon et al., Chemical basis of glycine riobswitch cooperativitiy. RNA. Jan. 2008; 14(1):25-34.Epub Nov. 27, 2007.
Lee et al., An allosteric self-splicing ribozyme triggered by a bacterial second messenger. Science. Aug. 13, 2010;329(5993):845-8. doi: 10.1126/science.1190713.

(56) References Cited

OTHER PUBLICATIONS

Liu et al., Fast Colorimetric Sensing of Adenosine and Cocaine Based on a General Sensor Design Involving Aptamers and Nanoparticles. AngewChem. Dec. 16, 2006;45(1):90-4. DOI: 10.1002/anie.200502589.
Meyer et al., Confirmation of a second natuarl preQ1 aptamer class in Streptococcacae bacterial. RNA. 2008 Apri; 14(4):685-95. doi: 10.1261/rna.937308. Epub Feb. 27, 2008.
Montage et al., Structure of the S-adenosylemethionine riboswitch regulatory mRNA element. Nature. Jun. 29, 2006;441(7079):1172-5.
Mootz et al. Conditional proten splicing; a new tool to control protein structure and fuction in vitro and invivo. J. Am Chem Soc. Sep. 3, 2003:125(35):10560-9.
Mootz et al., Protein splicing triggered by a small molecule. J Am Chem Soc. Aug. 7, 2002;124(31):9044-5.
Nahvi et al., Coenzyme B12 riboswitchen are widespread genetic control elements in proaryotes. Nucleic Acids Res. Jan. 2, 2004;32(1):143-50.
Neel et al., Riboswitches: Classification, function and in silico approach, International Journal of Pharma Sciences and Research. 2010;1(9):409-420.
Nelson et al., Filamentous phage DNA cloning vectors: a noninfective mutant with a nonpolar deletion in gene III. Virology. 1981; 108(2): 338-50.
Ni et al., Nucleic acid aptamers: clinical applications and promising new horizons. Curr Med Chem. 2011;18(27):4206-14. Review.
Peck et al., Directed evolution of a small-molecule-triggered intein with improved splicing properties in mammalian cells. Chem Biol. May 27, 2011;18(5):619-30. doi: 10.1016/j.chembiol.2011.02.014.
Rakonjac et al., Roles of PIII in filamentous phage assembly. J Mol Biol. 1998; 282(1)25-41.
Riechmann et al.,. The C-terminal domain of TolA is the coreceptor for filamentous phage infection of *E. coli*. Cell. 1997; 90(2):351-60. PMID:9244308.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Serganov et al., Structural basis for discriminative regulation of gene expression by adenine and guanine-sensing mRNAs. Chem biol. Dec. 2004;11(12):1729-41.
Serganov et al., Coenzyme recognition and gene regulation by a flavin mononucleotide riboswitch. Nature. 2009 Mar. 12;458(7235):233-7. doi: 10.1038/nature07642. Epub Jan. 25, 2009.
Serganov et al., Structural basis for gene regulation by a thiamine pyrophosphate-sensing riboswitch. Nature. Jun. 29, 2006;441(7097):1167-71. Epub May 21, 2006.
Skretas et al., Regulation of protein activity with small-molecule-controlled inteins. Protein Sci. Feb. 2005;14(2):523-32. Epub Jan. 4, 2005.
Smith, Filamentous fusion phage: novel expression vectors that display cloned antigens on the virion surface. Science. Jun. 14, 1985;228(4705):1315-7.
Sudarsan et al., An mRNA structure in bacteria that controls gene expression by binding lysine. Genes Dev. Nov. 1, 2003;17(21):2688-97.
Sudarsan et al., Riboswitches in eubacteria sense the second messenger cyclic di-GMP. Science. Jul. 18, 2008 18;321(5887):411-3. doi: 10.1126/science.1159519.
Suess et al., A theophylline responsive riboswitch based on helix slipping controls gene expression in vivo. Nucleic Acids Res. Mar. 5, 2004;32(4):1610-4.
Trausch et al., the structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Weinberg et al., The aptamer core of SAM-IV riboswitchees mimics the ligand-binding site of SAM-I riboswitches. RNA. May 2008: 14(5):822-8. doi: 10.1261/rna.988608. Epub Mar. 27, 2008.

Winkler et al., an mRNA structure that controls gene expression by binding FMN. Proc Natl Acad Sci U.S.A. Dec. 10, 2002;99(25):15908-13. Epub Nov. 27, 2002.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Yuan et al., Laboratory-directed protein evolution. Microbiol Mol Biol Rev. 2005; 69(3):373-92. PMID: 16148303.
Zimmermann et al., Molecular interactions and metal binding in the theophylline-binding core of an RNA aptamer. RNA. May 2000;6(5):659-67.
Extended European Search Report for EP18199195.1, dated Feb. 12, 2019.
International Preliminary Report on Patentability for PCT/US2014/048390, dated Mar. 7, 2019.
International Preliminary Report on Patentability for PCT/US2017/046144, dated Feb. 21, 2019.
International Preliminary Report on Patentability for PCT/US2017/045381, dated Feb. 14, 2019.
International Preliminary Report on Patentability for PCT/US2017/056671, dated Apr. 25, 2019.
Requirement for Restriction/Election, dated Nov. 24, 2014, in connection with U.S. Appl. No. 14/325,815.
Office Action, dated Feb. 11, 2015, in connection with U.S. Appl. No. 14/325,815.
Office Action, dated Jun. 4, 2015, in connection with U.S. Appl. No. 14/325,815.
Advisory Action dated Sep. 16, 2015 in connection with U.S. Appl. No. 14/325,815.
Office Action, dated Jan. 5, 2016, in connection with U.S. Appl. No. 14/325,815.
Office Action, dated Jun. 7, 2016, in connection with U.S. Appl. No. 14/325,815.
Advisory Action dated Nov. 28, 2016 in connection with U.S. Appl. No. 14/325,815.
Office Action, dated Jan. 12, 2017, in connection with U.S. Appl. No. 14/325,815.
Applicant Initiated Interview Summary, dated May 2, 2017, in connection with U.S. Appl. No. 14/325,815.
Office Action, dated Sep. 27, 2017, in connection with U.S. Appl. No. 14/325,815.
Office Action, dated Jan. 17, 2018, in connection with U.S. Appl. No. 14/325,815.
Office Action, dated Sep. 6, 2018, in connection with U.S. Appl. No. 14/325,815.
Office Action and Applicant Initiated Interview Summary, dated May 6, 2019, in connection with U.S. Appl. No. 14/325,815.
Requirement for Restriction/Election, dated Nov. 13, 2014, in connection with U.S. Appl. No. 14/326,109.
Office Action, dated Apr. 24, 2015, in connection with U.S. Appl. No. 14/326,109.
Office Action, dated Nov. 13, 2015, in connection with U.S. Appl. No. 14/326,109.
Office Action, dated Jul. 11, 2016, in connection with U.S. Appl. No. 14/326,109.
Advisory Action, dated Nov. 26, 2016, in connection with U.S. Appl. No. 14/326,109.
Office Action, dated Feb. 16, 2017, in connection with U.S. Appl. No. 14/326,109.
Applicant Initiated Interview Summary, dated May 22, 2017, in connection with U.S. Appl. No. 14/326,109.
Examiner Initiated Interview Summary, dated Aug. 17, 2017 in connection with U.S. Appl. No. 14/326,109.
Notice of Allowance, dated Aug. 17, 2017 in connection with U.S. Appl. No. 14/326,109.
Requirement for Restriction/Election, dated Nov. 25, 2014, in connection with U.S. Appl. No. 14/326,140.
Office Action, dated Feb. 10, 2015, in connection with U.S. Appl. No. 14/326,140.
Office Action, dated Jun. 1, 2015, in connection with U.S. Appl. No. 14/326,140.

(56) References Cited

OTHER PUBLICATIONS

Advisory Action, dated Sep. 15, 2015, in connection with U.S. Appl. No. 14/326,140.
Requirement for Restriction/Election, dated Jan. 20, 2016, in connection with U.S. Appl. No. 14/326,140.
Office Action, dated May 5, 2016, in connection with U.S. Appl. No. 14/326,140.
Office Action, dated Sep. 7, 2016, in connection with U.S. Appl. No. 14/326,140.
Applicant Initiated Interview Summary, dated Dec. 5, 2016, in connection with U.S. Appl. No. 14/326,140.
Office Action, dated Nov. 21, 2014, in connection with U.S. Appl. No. 14/326,269.
Notice of Allowance, dated Apr. 3, 2015, in connection with U.S. Appl. No. 14/326,269
Requirement for Restriction/Election, dated Nov. 26, 2014, in connection with U.S. Appl. No. 14/326,290.
Office Action, dated May 1, 2015, in connection with U.S. Appl. No. 14/326,290.
Office Action, dated Oct. 16, 2015, in connection with U.S. Appl. No. 14/326,290.
Advisory Action, dated Feb. 5, 2016, in connection with U.S. Appl. No. 14/326,290.
Office Action, dated Mar. 10, 2016, in connection with U.S. Appl. No. 14/326,290.
Office Action, dated Sep. 22, 2016, in connection with U.S. Appl. No. 14/326,290.
Applicant Initiated Interview Summary, dated Dec. 6, 2016, in connection with U.S. Appl. No. 14/326,290.
Office Action, dated Jun. 1, 2017, in connection with U.S. Appl. No. 14/326,290.
Office Action, dated Jan. 16, 2018, in connection with U.S. Appl. No. 14/326,290.
Advisory Action, dated Jul. 6, 2018, in connection with U.S. Appl. No. 14/326,290.
Requirement for Restriction/Election, dated Nov. 24, 2014, in connection with U.S. Appl. No. 14/326,318.
Office Action, dated Feb. 26, 2015, in connection with U.S. Appl. No. 14/326,318.
Office Action, dated Jun. 15, 2015, in connection with U.S. Appl. No. 14/326,318.
Advisory Action, dated Sep. 23, 2015, in connection with U.S. Appl. No. 14/326,318.
Requirement for Restriction/Election, dated Jan. 22, 2016, in connection with U.S. Appl. No. 14/326,318.
Office Action, dated Feb. 7, 2017, in connection with U.S. Appl. No. 14/326,318.
Advisory Action, dated Jun. 16, 2017, in connection with U.S. Appl. No. 14/326,318.
Office Action, dated Jun. 27, 2016, in connection with U.S. Appl. No. 14/326,318.
Office Action, dated Oct. 11, 2017, in connection with U.S. Appl. No. 14/326,318.
Office Action, dated Oct. 26, 2018, in connection with U.S. Appl. No. 14/326,318.
Requirement for Restriction/Election, dated Nov. 25, 2014, in connection with U.S. Appl. No. 14/326,303.
Office Action, dated Apr. 9, 2015, in connection with U.S. Appl. No. 14/326,303.
Office Action, dated Sep. 11, 2015, in connection with U.S. Appl. No. 14/326,303.
Advisory Action, dated Dec. 21, 2015, in connection with U.S. Appl. No. 14/326,303.
Office Action, dated Mar. 18, 2016, in connection with U.S. Appl. No. 14/326,303.
Office Action, dated Oct. 5, 2016, in connection with U.S. Appl. No. 14/326,303.
Interview Summary, dated Jan. 27, 2017, in connection with U.S. Appl. No. 14/326,303.

\* cited by examiner

CAS VARIANTS FOR GENE EDITING

RELATED APPLICATIONS

This application is a national stage filing under 35 U.S.C. § 371 of international PCT application, PCT/US2014/070038, filed Dec. 12, 2014, which claims priority under 35 U.S.C. § 119(e) to U.S. provisional patent application, U.S. Ser. No. 61/915,386 filed Dec. 12, 2013, and U.S. provisional patent application, U.S. Ser. No. 61/980,333 filed Apr. 16, 2014; and also claims priority under 35 U.S.C. § 120 to U.S. patent applications, U.S. Ser. Nos. 14/325,815, 14/326,109, 14/326,140, 14/326,269, 14/326,290, 14/326,318, and 14/326,303, all filed on Jul. 8, 2014; each of which is incorporated herein by reference. This application is a continuation of and claims priority under 35 U.S.C. § 120 to U.S. patent applications, U.S. Ser. Nos. 14/325,815, 14/326,109, 14/326,140, 14/326,290, 14/326,318, and 14/326,303, all filed on Jul. 8, 2014, all of which claim priority under 35 U.S.C. § 119(e) to U.S. provisional patent application, U.S. Ser. No. 61/915,386, filed Dec. 12, 2013, and U.S. provisional patent application, U.S. Ser. No. 61/980,333 filed Apr. 16, 2014, each of which is incorporated herein by reference.

GOVERNMENT SUPPORT

This invention was made with Government support under HR0011-11-2-0003 and N66001-12-C-4207 awarded by the Department of Defense, and under GM095501 awarded by the National Institutes of Health. The Government has certain rights in this invention.

BACKGROUND OF THE INVENTION

Targeted editing of nucleic acid sequences, for example, the introduction of a specific modification into genomic DNA, is a highly promising approach for the study of gene function and also has the potential to provide new therapies for human genetic diseases.[1] An ideal nucleic acid editing technology possesses three characteristics: (1) high efficiency of installing the desired modification; (2) minimal off-target activity; and (3) the ability to be programmed to edit precisely any site in a given nucleic acid, e.g., any site within the human genome.[2] Current genome engineering tools, including engineered zinc finger nucleases (ZFNs),[3] transcription activator like effector nucleases (TALENs),[4] and most recently, the RNA-guided DNA endonuclease Cas9,[5] effect sequence-specific DNA cleavage in a genome. This programmable cleavage can result in mutation of the DNA at the cleavage site via non-homologous end joining (NHEJ) or replacement of the DNA surrounding the cleavage site via homology-directed repair (HDR).[6,7]

One drawback to the current technologies is that both NHEJ and HDR are stochastic processes that typically result in modest gene editing efficiencies as well as unwanted gene alterations that can compete with the desired alteration.[8] Since many genetic diseases in principle can be treated by effecting a specific nucleotide change at a specific location in the genome (for example, a C to T change in a specific codon of a gene associated with a disease),[9] the development of a programmable way to achieve such precision gene editing would represent both a powerful new research tool, as well as a potential new approach to gene editing-based human therapeutics.

SUMMARY OF THE INVENTION

The clustered regularly interspaced short palindromic repeat (CRISPR) system is a recently discovered prokaryotic adaptive immune system[10] that has been modified to enable robust and general genome engineering in a variety of organisms and cell lines.[11] CRISPR-Cas (CRISPR associated) systems are protein-RNA complexes that use an RNA molecule (sgRNA) as a guide to localize the complex to a target DNA sequence via base-pairing.[12] In the natural systems, a Cas protein then acts as an endonuclease to cleave the targeted DNA sequence.[13] The target DNA sequence must be both complementary to the sgRNA, and also contain a "protospacer-adjacent motif" (PAM) dinucleotide at the 3'-end of the complementary region in order for the system to function (FIG. 1).[14] Among the known Cas proteins, S. pyogenes Cas9 has been mostly widely used as a tool for genome engineering.[15] This Cas9 protein is a large, multi-domain protein containing two distinct nuclease domains. Point mutations can be introduced into Cas9 to abolish nuclease activity, resulting in a dead Cas9 (dCas9) that still retains its ability to bind DNA in a sgRNA-programmed manner.[16] In principle, when fused to another protein or domain, dCas9 can target that protein to virtually any DNA sequence simply by co-expression with an appropriate sgRNA.

The potential of the dCas9 complex for genome engineering purposes is immense. Its unique ability to bring proteins to specific sites in a genome programmed by the sgRNA in theory can be developed into a variety of site-specific genome engineering tools beyond nucleases, including transcriptional activators, transcriptional repressors, histone-modifying proteins, integrases, and recombinases.[11] Some of these potential applications have recently been implemented through dCas9 fusions with transcriptional activators to afford RNA-guided transcriptional activators,[17,18] transcriptional repressors,[16,19,20] and chromatin modification enzymes.[21] Simple co-expression of these fusions with a variety of sgRNAs results in specific expression of the target genes. These seminal studies have paved the way for the design and construction of readily programmable sequence-specific effectors for the precise manipulation of genomes.

Significantly, 80-90% of protein mutations responsible for human disease arise from the substitution, deletion, or insertion of only a single nucleotide.[6] No genome engineering tools, however, have yet been developed that enable the manipulation of a single nucleotide in a general and direct manner. Current strategies for single-base gene correction include engineered nucleases (which rely on the creation of double-strand breaks, DSBs, followed by stochastic, inefficient homology-directed repair, HDR), and DNA-RNA chimeric oligonucleotides.[22] The latter strategy involves the design of a RNA/DNA sequence to base pair with a specific sequence in genomic DNA except at the nucleotide to be edited. The resulting mismatch is recognized by the cell's endogenous repair system and fixed, leading to a change in the sequence of either the chimera or the genome. Both of these strategies suffer from low gene editing efficiencies and unwanted gene alterations, as they are subject to both the stochasticity of HDR and the competition between HDR and non-homologous end-joining, NHEJ.[23-25] HDR efficiencies vary according to the location of the target gene within the genome,[26] the state of the cell cycle,[27] and the type of cell/tissue.[28] The development of a direct, programmable way to install a specific type of base modification at a precise location in genomic DNA with enzyme-like efficiency and no stochasticity would therefore represent a powerful new approach to gene editing-based research tools and human therapeutics.

Some aspects of this disclosure provide strategies, systems, reagents, methods, and kits that are useful for the targeted editing of nucleic acids, including editing a single site within a subject's genome, e.g., the human genome. In some embodiments, fusion proteins of Cas9 and nucleic acid editing enzymes or enzyme domains, e.g., deaminase domains, are provided. In some embodiments, methods for targeted nucleic acid editing are provided. In some embodiments, reagents and kits for the generation of targeted nucleic acid editing proteins, e.g., fusion proteins of Cas9 and nucleic acid editing enzymes or domains, are provided.

Some aspects of this disclosure provide fusion proteins comprising (i) a nuclease-inactive CAS9 domain; and (ii) a nucleic acid-editing domain. In some embodiments, the nucleic acid-editing domain is a DNA-editing domain. In some embodiments, the nucleic-acid-editing domain is a deaminase domain. In some embodiments, the deaminase is a cytidine deaminase. In some embodiments, the deaminase is an apolipoprotein B mRNA-editing complex (APOBEC) family deaminase. In some embodiments, the deaminase is an APOBEC1 family deaminase. In some embodiments, the deaminase is an activation-induced cytidine deaminase (AID). In some embodiments, the deaminase is an ACF1/ASE deaminase. In some embodiments, the deaminase is an adenosine deaminase. In some embodiments, the deaminase is an ADAT family deaminase. In some embodiments, the nucleic-acid-editing domain is fused to the N-terminus of the CAS9 domain. In some embodiments, the nucleic-acid-editing domain is fused to the C-terminus of the CAS9 domain. In some embodiments, the CAS9 domain and the nucleic-acid-editing domain are fused via a linker. In some embodiments, the linker comprises a $(GGGGS)_n$ (SEQ ID NO: 91), a $(G)_n$, an $(EAAAK)_n$ (SEQ ID NO: 5), a $(GGS)_n$, an SGSETPGTSESATPES (SEQ ID NO: 93) motif (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference), or an $(XP)_n$ motif, or a combination of any of these, wherein n is independently an integer between 1 and 30.

Some aspects of this disclosure provide methods for DNA editing. In some embodiments, the methods comprise contacting a DNA molecule with (a) a fusion protein comprising a nuclease-inactive Cas9 domain and a deaminase domain; and (b) an sgRNA targeting the fusion protein of (a) to a target nucleotide sequence of the DNA strand; wherein the DNA molecule is contacted with the fusion protein and the sgRNA in an amount effective and under conditions suitable for the deamination of a nucleotide base. In some embodiments, the target DNA sequence comprises a sequence associated with a disease or disorder, and wherein the deamination of the nucleotide base results in a sequence that is not associated with a disease or disorder. In some embodiments, the DNA sequence comprises a T>C or A>G point mutation associated with a disease or disorder, and wherein the deamination of the mutant C or G base results in a sequence that is not associated with a disease or disorder. In some embodiments, the deamination corrects a point mutation in the sequence associated with the disease or disorder. In some embodiments, the sequence associated with the disease or disorder encodes a protein, and wherein the deamination introduces a stop codon into the sequence associated with the disease or disorder, resulting in a truncation of the encoded protein. In some embodiments, the deamination corrects a point mutation in the PI3KCA gene, thus correcting an H1047R and/or a A3140G mutation. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

Some aspects of this disclosure provide a reporter construct for detecting nucleic-acid-editing activity of a Cas9: DNA-editing domain fusion protein. In some embodiments, the construct comprises (a) a reporter gene comprising a target site for the Cas9 DNA-editing protein, wherein targeted DNA editing results in an increase in expression of the reporter gene; and (b) a promoter sequence that controls expression of the reporter gene. In some embodiments, the construct further comprises (c) a sequence encoding an sgRNA targeting the Cas9 DNA-editing protein to the target site of the reporter gene, wherein expression of the sgRNA is independent of the expression of the reporter gene. In some embodiments, the target site of the reporter gene comprises a premature stop codon, and wherein targeted DNA editing of the template strand by the Cas9 DNA-editing protein results in a conversion of the premature stop codon to a codon encoding an amino acid residue. In some embodiments, the reporter gene encodes a luciferase, a fluorescent protein, or an antibiotic resistance marker.

Some aspects of this disclosure provide kits comprising a nucleic acid construct that comprises a sequence encoding a nuclease-inactive Cas9 sequence, a sequence comprising a cloning site positioned to allow cloning of a sequence encoding a nucleic acid-editing enzyme or enzyme domain in-frame with the Cas9-encoding sequence, and, optionally, a sequence encoding a linker positioned between the Cas9 encoding sequence and the cloning site. In addition, in some embodiments, the kit comprises suitable reagents, buffers, and/or instructions for in-frame cloning of a sequence encoding a nucleic acid-editing enzyme or enzyme domain into the nucleic acid construct to generate a Cas9 nucleic acid editing fusion protein. In some embodiments, the sequence comprising the cloning site is N-terminal of the Cas9 sequence. In some embodiments, the sequence comprising the cloning site is C-terminal of the Cas9 sequence. In some embodiments, the encoded linker comprises a $(GGGGS)_n$ (SEQ ID NO: 91), a $(G)_n$, an $(EAAAK)_n$ (SEQ ID NO: 5), a $(GGS)_n$, an SGSETPGTSESATPES (SEQ ID NO: 93) motif (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference), or an $(XP)_n$ motif, or a combination of any of these, wherein n is independently an integer between 1 and 30.

Some aspects of this disclosure provide kits comprising a fusion protein comprising a nuclease-inactive Cas9 domain and a nucleic acid-editing enzyme or enzyme domain, and, optionally, a linker positioned between the Cas9 domain and the nucleic acid-editing enzyme or enzyme domain. In addition, in some embodiments, the kit comprises suitable reagents, buffers, and/or instructions for using the fusion protein, e.g., for in vitro or in vivo DNA or RNA editing. In some embodiments, the kit comprises instructions regarding the design and use of suitable sgRNAs for targeted editing of a nucleic acid sequence.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

DEFINITIONS

Figure 1:
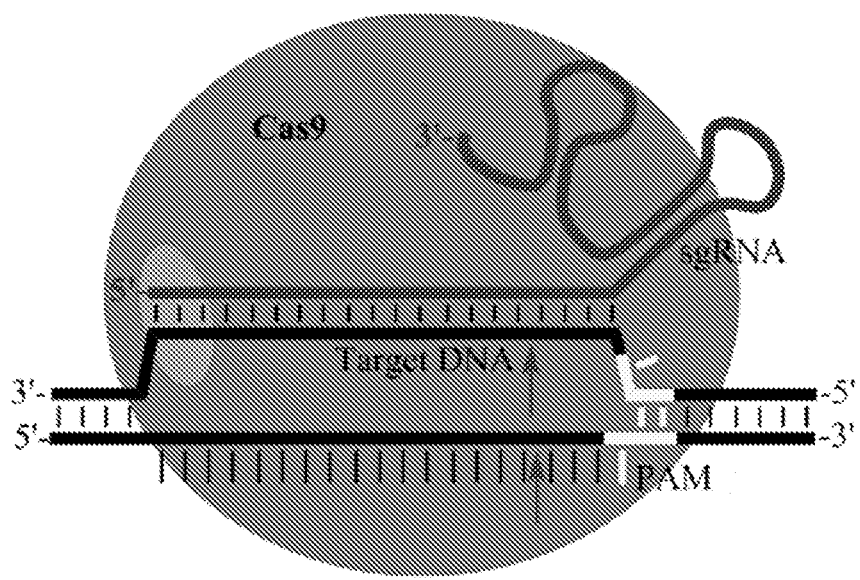
FIG. 1. The Cas9/sgRNA-DNA complex. The 3' end of the sgRNA forms a ribonucleoprotein complex with the Cas9 nuclease, while the 20 nt 5' end of the sgRNA recognizes its complementary stretch of DNA. DNA binding requires the 3-nt PAM sequence 5' to the target DNA. In the case of wtCas9, double-strand DNA cleavage occurs 3 nt from the PAM to produce blunt ends (shown by the arrows). It should be noted that the size of the bubble is unknown.

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof (e.g., a protein comprising an active or inactive DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain.

A nuclease-inactivated Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., *Science*. 337:816-821(2012); Qi et al., "Repurposing CRISPR as an RNA-Guided Platform for Sequence-Specific Control of Gene Expression" (2013) *Cell*. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H841A completely inactivate the nuclease activity of *S. pyogenes* Cas9 (Jinek et al., *Science*. 337:816-821(2012); Qi et al., *Cell*. 28; 152(5):1173-83 (2013). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

```
                                           (SEQ ID NO: 1)
ATGGATAAGAAATACTCAATAGGCTTAGATATCGGCACAAATAGCGTCGG

ATGGGCGGTGATCACTGATGATTATAAGGTTCCGTCTAAAAAGTTCAAGG

TTCTGGGAAATACAGACCGCCACAGTATCAAAAAAAATCTTATAGGGGCT

CTTTTATTTGGCAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGCAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAATCTACAATCAATTATTTGAAGAAAACCCT

ATTAACGCAAGTAGAGTAGATGCTAAAGCGATTCTTTCTGCACGATTGAG

TAAATCAAGACGATTAGAAAATCTCATTGCTCAGCTCCCCGGTGAGAAGA

GAAATGGCTTGTTTGGGAATCTCATTGCTTTGTCATTGGGATTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATAGTGAAATAACTAAGGCTCCCCT

ATCAGCTTCAATGATTAAGCGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAAGTACTACCAAAACATAGTTTGCTTTATGAGTA

TTTTACGGTTTATAACGAATTGACAAAGGTCAAATATGTTACTGAGGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGCGCCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGGGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGATATTCAAAAAGCACAGGTGTCTGGACAAGG

CCATAGTTTACATGAACAGATTGCTAACTTAGCTGGCAGTCCTGCTATTA

AAAAAGGTATTTTACAGACTGTAAAAATTGTTGATGAACTGGTCAAAGTA

ATGGGGCATAAGCCAGAAAATATCGTTATTGAAATGGCACGTGAAAATCA

GACAACTCAAAAGGGCCAGAAAAATTCGCGAGAGCGTATGAAACGAATCG

AAGAAGGTATCAAAGAATTAGGAAGTCAGATTCTTAAAGAGCATCCTGTT

GAAAATACTCAATTGCAAAATGAAAAGCTCTATCTCTATTATCTACAAAA

TGGAAGAGACATGTATGTGGACCAAGAATTAGATATTAATCGTTTAAGTG

ATTATGATGTCGATCACATTGTTCCACAAAGTTTCATTAAAGACGATTCA

ATAGACAATAAGGTACTAACGCGTTCTGATAAAAATCGTGGTAAATCGGA

TAACGTTCCAAGTGAAGAAGTAGTCAAAAAGATGAAAAACTATTGGAGAC

AACTTCTAAACGCCAAGTTAATCACTCAACGTAAGTTTGATAATTTAACG

AAAGCTGAACGTGGAGGTTTGAGTGAACTTGATAAAGCTGGTTTTATCAA

ACGCCAATTGGTTGAAACTCGCCAAATCACTAAGCATGTGGCACAAATTT

TGGATAGTCGCATGAATACTAAATACGATGAAAATGATAAACTTATTCGA

GAGGTTAAAGTGATTACCTTAAAATCTAAATTAGTTTCTGACTTCCGAAA

AGATTTCCAATTCTATAAAGTACGTGAGATTAACAATTACCATCATGCCC

ATGATGCGTATCTAAATGCCGTCGTTGGAACTGCTTTGATTAAGAAATAT

CCAAAACTTGAATCGGAGTTTGTCTATGGTGATTATAAAGTTTATGATGT

TCGTAAAATGATTGCTAAGTCTGAGCAAGAAATAGGCAAAGCAACCGCAA

AATATTTCTTTTACTCTAATATCATGAACTTCTTCAAAACAGAAATTACA

CTTGCAAATGGAGAGATTCGCAAACGCCCCTCTAATCGAAACTAATGGGA

AACTGGAGAAATTGTCTGGGATAAAGGGCGAGATTTTGCCACAGTGCGCA

AAGTATTGTCCATGCCCCAAGTCAATATTGTCAAGAAAACAGAAGTACAG

ACAGGCGGATTCTCCAAGGAGTCAATTTTACCAAAAAGAAATTCGGACAA

GCTTATTGCTCGTAAAAAAGACTGGGATCCAAAAAAATATGGTGGTTTTG

ATAGTCCAACGGTAGCTTATTCAGTCCTAGTGGTTGCTAAGGTGGAAAAA

GGGAAATCGAAGAAGTTAAAATCCGTTAAAGAGTTACTAGGGATCACAAT

TATGGAAAGAAGTTCCTTTGAAAAAAATCCGATTGACTTTTTAGAAGCTA

AAGGATATAAGGAAGTTAAAAAAGACTTAATCATTAAACTACCTAAATAT
```

-continued

```
AGTCTTTTTGAGTTAGAAAACGGTCGTAAACGGATGCTGGCTAGTGCCGG

AGAATTACAAAAAGGAAATGAGCTGGCTCTGCCAAGCAAATATGTGAATT

TTTTATATTTAGCTAGTCATTATGAAAAGTTGAAGGGTAGTCCAGAAGAT

AACGAACAAAAACAATTGTTTGTGGAGCAGCATAAGCATTATTTAGATGA

GATTATTGAGCAAATCAGTGAATTTTCTAAGCGTGTTATTTTAGCAGATG

CCAATTTAGATAAAGTTCTTAGTGCATATAACAAACATAGAGACAAACCA

ATACGTGAACAAGCAGAAAATATTATTCATTTATTTACGTTGACGAATCT

TGGAGCTCCCGCTGCTTTTAAATATTTTGATACAACAATTGATCGTAAAC

GATATACGTCTACAAAAGAAGTTTTAGATGCCACTCTTATCCATCAATCC

ATCACTGGTCTTTATGAAACACGCATTGATTTGAGTCAGCTAGGAGGTGA

CTGA
```

(SEQ ID NO: 2)
MDKK<u>YSIGLDIGTNSVGWAVITDDYKVPSKKFKVLGNTDRHSIKKNLIGA
LLFGSGET</u>AEATRLKRTARRRYTRRKNRICYLQEIFSNEMAKVDDSFFHR
LEESFLVEEDKKHERHPIFGNIVDEVAYHEKYPTIYHLRKKLADSTDKAD
LRLIYLALAHMIKFRGHFLIEGDLNPDNSDVDKLFIQLVQIYNQLFEENP
INASRVDAKAILSARLSKSRRLENLIAQLPGEKRNGLFGNLIALSLGLTP
NFKSNFDLAEDAKLQLSKDTYDDDLDNLLAQIGDQYADLFLAAKNLSDAI
LLSDILRVNSEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGAYHDLLKI
IKDKDFLDNEENEDILEDIVLTLTLFEDRGMIEERLKTYAHLFDDKVMKQ
LKRRRYTGWGRLSRKLINGIRDKQSGKTILDFLKSDGFANRNFMQLIHDD
SLTFKEDIQKAQVSGQ<u>GHSLHEQIANLAGSPAIKKGILQTVKIVDELVKV
MGHKPENIVIEMAR</u>ENQTTQK<u>GQKNSRERMKRIEEGIKELGSQILKEHPV
ENTQLQNEKLYLYYLQNGRDMYVDQELDINRLSDYDVDHIVPQSFIKDDS
IDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIR
EVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQ
T</u>GGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKY
SLFELENGRKRMLASAGELQKGNELALPSKYVNFLYLASHYEKLKGSPED
NEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQS
ITGLYETRIDLSQLGGD
(single underline: HNH domain; double
underline: RuvC domain)

In some embodiments, wild type Cas9 corresponds to, or comprises SEQ ID NO:3 (nucleotide) and/or SEQ ID NO: 4 (amino acid):

(SEQ ID NO: 3)
ATGGATAAAAAGTATTCTATTGGTTTAGACATCGGCACTAATTCCGTTGG

ATGGGCTGTCATAACCGATGAATACAAAGTACCTTCAAAGAAATTTAAGG

TGTTGGGGAACACAGACCGTCATTCGATTAAAAAGAATCTTATCGGTGCC

CTCCTATTCGATAGTGGCGAAACGGCAGAGGCGACTCGCCTGAAACGAAC

CGCTCGGAGAAGGTATACACGTCGCAAGAACCGAATATGTTACTTACAAG

AAATTTTTAGCAATGAGATGGCCAAAGTTGACGATTCTTTCTTTCACCGT

TTGGAAGAGTCCTTCCTTGTCGAAGAGGACAAGAAACATGAACGGCACCC

CATCTTTGGAAACATAGTAGATGAGGTGGCATATCATGAAAGTACCCAA

CGATTTATCACCTCAGAAAAAGCTAGTTGACTCAACTGATAAAGCGGAC

CTGAGGTTAATCTACTTGGCTCTTGCCCATATGATAAAGTTCCGTGGGCA

CTTTCTCATTGAGGGTGATCTAAATCCGGACAACTCGGATGTCGACAAAC

TGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTC

TAAATCCCGACGGCTAGAAAACCTGATCGCACAATTACCCGGAGAGAAGA

AAAATGGGTTGTTCGGTAACCTTATAGCGCTCTCACTAGGCCTGACACCA

AATTTTAAGTCGAACTTCGACTTAGCTGAAGATGCCAAATTGCAGCTTAG

TAAGGACACGTACGATGACGATCTCGACAATCTACTGGCACAAATTGGAG

ATCAGTATGCGGACTTATTTTTGGCTGCCAAAAACCTTAGCGATGCAATC

CTCCTATCTGACATACTGAGAGTTAATACTGAGATTACCAAGGCGCCGTT

ATCCGCTTCAATGATCAAAAGGTACGATGAACATCACCAAGACTTGACAC

TTCTCAAGGCCCTAGTCCGTCAGCAACTGCCTGAGAAATATAAGGAAATA

TTCTTTGATCAGTCGAAAAACGGGTACGCAGGTTATATTGACGGCGGAGC

GAGTCAAGAGGAATTCTACAAGTTTATCAAACCCATATTAGAGAAGATGG

ATGGGACGGAAGAGTTGCTTGTAAAACTCAATCGCGAAGATCTACTGCGA

AAGCAGCGGACTTTCGACAACGGTAGCATTCCACATCAAATCCACTTAGG

CGAATTGCATGCTATACTTAGAAGGCAGGAGGATTTTTATCCGTTCCTCA

AAGACAATCGTGAAAAGATTGAGAAAATCCTAACCTTTCGCATACCTTAC

TATGTGGGACCCCTGGCCCGAGGGAACTCTCGGTTCGCATGGATGACAAG

AAAGTCCGAAGAAACGATTACTCCATGGAATTTTGAGGAAGTTGTCGATA

AAGGTGCGTCAGCTCAATCGTTCATCGAGAGGATGACCAACTTTGACAAG

AATTTACCGAACGAAAAGTATTGCCTAAGCACAGTTTACTTTACGAGTA

TTTCACAGTGTACAATGAACTCACGAAAGTTAAGTATGTCACTGAGGGCA

TGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGA

CTACTTTAAGAAAATTGAATGCTTCGATTCTGTCGAGATCTCCGGGGTAG

AAGATCGATTTAATGCGTCACTTGGTACGTATCATGACCTCCTAAAGATA

ATTAAAGATAAGGACTTCCTGGATAACGAAGAGAATGAAGATATCTTAGA

AGATATAGTGTTGACTCTTACCCTCTTTGAAGATCGGGAAATGATTGAGG
```

-continued

```
AAAGACTAAAAACATACGCTCACCTGTTCGACGATAAGGTTATGAAACAG

TTAAAGAGGCGTCGCTATACGGGCTGGGGACGATTGTCGCGGAAACTTAT

CAACGGGATAAGAGACAAGCAAAGTGGTAAAACTATTCTCGATTTTCTAA

AGAGCGACGGCTTCGCCAATAGGAACTTTATGCAGCTGATCCATGATGAC

TCTTTAACCTTCAAAGAGGATATACAAAAGGCACAGGTTTCCGGACAAGG

GGACTCATTGCACGAACATATTGCGAATCTTGCTGGTTCGCCAGCCATCA

AAAAGGGCATACTCCAGACAGTCAAAGTAGTGGATGAGCTAGTTAAGGTC

ATGGGACGTCACAAACCGGAAAACATTGTAATCGAGATGGCACGCGAAAA

TCAAACGACTCAGAAGGGGCAAAAAAACAGTCGAGAGCGGATGAAGAGAA

TAGAAGAGGGTATTAAAGAACTGGGCAGCCAGATCTTAAAGGAGCATCCT

GTGGAAAATACCCAATTGCAGAACGAGAAACTTTACCTCTATTACCTACA

AAATGGAAGGGACATGTATGTTGATCAGGAACTGGACATAAACCGTTTAT

CTGATTACGACGTCGATCACATTGTACCCCAATCCTTTTTGAAGGACGAT

TCAATCGACAATAAAGTGCTTACACGCTCGGATAAGAACCGAGGGAAAAG

TGACAATGTTCCAAGCGAGGAAGTCGTAAAGAAAATGAAGAACTATTGGC

GGCAGCTCCTAAATGCGAAACTGATAACGCAAAGAAAGTTCGATAACTTA

ACTAAAGCTGAGAGGGGTGGCTTGTCTGAACTTGACAAGGCCGGATTTAT

TAAACGTCAGCTCGTGGAAACCCGCCAAATCACAAAGCATGTTGCACAGA

TACTAGATTCCCGAATGAATACGAAATACGACGAGAACGATAAGCTGATT

CGGGAAGTCAAAGTAATCACTTTAAAGTCAAAATTGGTGTCGGACTTCAG

AAAGGATTTTCAATTCTATAAAGTTAGGGAGATAAATAACTACCACCATG

CGCACGACGCTTATCTTAATGCCGTCGTAGGGACCGCACTCATTAAGAAA

TACCCGAAGCTAGAAAGTGAGTTTGTGTATGGTGATTACAAAGTTTATGA

CGTCCGTAAGATGATCGCGAAAAGCGAACAGGAGATAGGCAAGGCTACAG

CCAAATACTTCTTTTATTCTAACATTATGAATTTCTTTAAGACGGAAATC

ACTCTGGCAAACGGAGAGATACGCAAACGACCTTTAATTGAAACCAATGG

GGAGACAGGTGAAATCGTATGGGATAAGGGCCGGGACTTCGCGACGGTGA

GAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGA

TAAGCTCATCGCTCGTAAAAAGGACTGGGACCCGAAAAAGTACGGTGGCT

TCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAAC

GATTATGGAGCGCTCGTCTTTTGAAAAGAACCCCATCGACTTCCTTGAGG

CGAAAGGTTACAAGGAAGTAAAAAAGGATCTCATAATTAAACTACCAAAG

TATAGTCTGTTTGAGTTAGAAAATGGCCGAAAACGGATGTTGGCTAGCGC

CGGAGAGCTTCAAAAGGGGAACGAACTCGCACTACCGTCTAAATACGTGA

ATTTCCTGTATTTAGCGTCCCATTACGAGAAGTTGAAAGGTTCACCTGAA

GATAACGAACAGAAGCAACTTTTTGTTGAGCAGCACAAACATTATCTCGA

CGAAATCATAGAGCAAATTTCGGAATTCAGTAAGAGAGTCATCCTAGCTG

ATGCCAATCTGGACAAAGTATTAAGCGCATACAACAAGCACAGGGATAAA

CCCATACGTGAGCAGGCGGAAAATATTATCCATTTGTTTACTCTTACCAA

CCTCGGCGCTCCAGCCGCATTCAAGTATTTTGACACAACGATAGATCGCA

AACGATACACTTCTACCAAGGAGGTGCTAGACGCGACACTGATTCACCAA

TCCATCACGGGATTATATGAAACTCGGATAGATTTGTCACAGCTTGGGGG

TGACGGATCCCCCAAGAAGAAGAGGAAAGTCTCGAGCGACTACAAAGACC

ATGACGGTGATTATAAAGATCATGACATCGATTACAAGGATGACGATGAC

AAGGCTGCAGGA
```

(SEQ ID NO: 4)
MDKK<u>YSIGLAIGTNSVGWAVITDEYKVPSKKFKVLGNTDRHSIKKNLIGA</u>

<u>LLFDSGET</u>AEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQG<u>DSLHEHIANLAGSPAIKKGILQTVKVVDELVKV</u>

<u>MGRHKPENIVIEMAR</u>ENQTTQKG<u>QKNSRERMKRIEEGIKELGSQILKEHP</u>

<u>VENTQLQNEKLYLYYLQNGRDMYVDQELDINRLSDYDVDHIVPQSFLKDD</u>

<u>SIDNKVLTRSDKNRGKSDNVPSEEVVKKMKNYWRQLLNAKLITQRKFDNL</u>

<u>TKAERG</u><u><u>GLSELDKAGFIKRQLVETRQITKHVAQILDSRMNTKYDENDKLI</u></u>

<u><u>REVKVITLKSKLVSDFRKDFQFYKVREINNYHHAHDAYLNAVVGTALIKK</u></u>

<u><u>YPKLESEFVYGDYKVYDVRKMIAKSEQEIGKATAKYFFYSNIMNFFKTEI</u></u>

<u><u>TLANGEIRKRPLIETNGETGEIVWDKGRDFATVRKVLSMPQVNIVKKTEV</u></u>

<u><u>QT</u></u>GGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
(single underline: HNH domain; double
underline: RuvC domain)

In some embodiments, dCas9 corresponds to, or comprises in part or in whole, a Cas9 amino acid sequence having one or more mutations that inactivate the Cas9 nuclease activity. For example, in some embodiments, a dCas9 domain comprises D10A and/or H820A mutation.

dCas9 (D10A and H840A):
(SEQ ID NO: 34)
MDKK<u>YSIGLAIGTNSVGWAVITDEYKVPSKKFKVLGNTDRHSIKKNLIGA</u>
<u>LLFDSGETA</u>EATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQG<u>DSLHEHIANLAGSPAIKKGILQTVKVVDELVKV</u>
<u>MGRHKPENIVIEMA</u>RENQTTQKGQKNSRERMKRIEEGIKELGSQILKEHP
VENTQLQNEKLYLYYLQNGRDMYVDQELDINRLSDYDVDAIVPQSFLKDD
SIDNKVLTRSDKNRGKSDNVPSEEVVKKMKNYWRQLLNAKLITQRKFDNL
TKAERG<u>GLSELDKAGFIKRQLVETRQITKHVAQILDSRMNTKYDENDKLI</u>
<u>REVKVITLKSKLVSDFRKDFQFYKVREINNYHHAHDAYLNAVVGTALIKK</u>
<u>YPKLESEFVYGDYKVYDVRKMIAKSEQEIGKATAKYFFYSNIMNFFKTEI</u>
<u>TLANGEIRKRPLIETNGETGEIVWDKGRDFATVRKVLSMPQVNIVKKTEV</u>
<u>QT</u>GGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGD
(single underline: HNH domain; double
underline: RuvC domain)

In other embodiments, dCas9 variants having mutations other than D10A and H820A are provided, which e.g., result in nuclease inactivated Cas9 (dCas9). Such mutations, by way of example, include other amino acid substitutions at D10 and H820, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 34) are provided which are at least about 70% identical, at least about 80% identical, at least about 90% identical, at least about 95% identical, at least about 98% identical, at least about 99% identical, at least about 99.5% identical, or at least about 99.9% to SEQ ID NO: 34. In some embodiments, variants of dCas9 (e.g., variants of SEQ ID NO: 34) are provided having amino acid sequences which are shorter, or longer than SEQ ID NO: 34, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some embodiments, Cas9 fusion proteins as provided herein comprise the full-length amino acid of a Cas9 protein, e.g., one of the sequences provided above. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all. Exemplary amino acid sequences of suitable Cas9 domains and Cas9 fragments are provided herein, and additional suitable sequences of Cas9 domains and fragments will be apparent to those of skill in the art.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

The term "deaminase" refers to an enzyme that catalyzes a deamination reaction. In some embodiments, the deaminase is a cytidine deaminase, catalyzing the hydrolytic deamination of cytidine or deoxycytidine to uracil or deoxyuracil, respectively.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a fusion protein provided herein, e.g., of a fusion protein comprising a nuclease-inactive Cas9 domain and a nucleic acid-editing domain (e.g., a deaminase domain) may refer to the amount of the fusion protein that is sufficient to induce editing of a target site specifically bound and edited by the fusion protein. As will be appreciated by the skilled artisan, the effective amount of an agent, e.g., a fusion protein, a nuclease, a deaminase, a recombinase, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

The term "linker," as used herein, refers to a chemical group or a molecule linking two molecules or moieties, e.g., two domains of a fusion protein, such as, for example, a nuclease-inactive Cas9 domain and a nucleic acid-editing domain (e.g., a deaminase domain). In some embodiments, a linker joins a gRNA binding domain of an RNA-programmable nuclease, including a Cas9 nuclease domain, and the catalytic domain of anucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4$^{th}$ ed., Cold Spring Harbor Laboratory Press, Cold Spring Harbor, N.Y. (2012)), the entire contents of which are incorporated herein by reference.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is homologous to a tracrRNA as depicted in FIG. 1E of Jinek et al., *Science* 337:816-821(2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof," and U.S. Provisional Patent Application, U.S. Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2), and may be referred to as an "extended gRNA." For example, an extended gRNA will, e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to target DNA cleavage sites, these proteins are able to be targeted, in principle, to any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The term "target site" refers to a sequence within a nucleic acid molecule that is deaminated by a deaminase or a fusion protein comprising a deaminase, (e.g., a dCas9-deaminase fusion protein provided herein).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

DETAILED DESCRIPTION OF CERTAIN
EMBODIMENTS OF THE INVENTION

Some aspects of this disclosure provide fusion proteins that comprise a Cas9 domain that binds to a guide RNA (also referred to as gRNA or sgRNA), which, in turn, binds a target nucleic acid sequence via strand hybridization; and a DNA-editing domain, for example, a deaminase domain that can deaminate a nucleobase, such as, for example, cytidine. The deamination of a nucleobase by a deaminase can lead to a point mutation at the respective residue, which is referred to herein as nucleic acid editing. Fusion proteins comprising a Cas9 variant or domain and a DNA editing domain can thus be used for the targeted editing of nucleic acid sequences. Such fusion proteins are useful for targeted editing of DNA in vitro, e.g., for the generation of mutant cells or animals; for the introduction of targeted mutations, e.g., for the correction of genetic defects in cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a subject. Typically, the Cas9 domain of the fusion proteins described herein does not have any nuclease activity but instead is a Cas9 fragment or a dCas9 protein or domain. Methods for the use of Cas9 fusion proteins as described herein are also provided.

Non-limiting, exemplary nuclease-inactive Cas9 domains are provided herein. One exemplary suitable nuclease-inactive Cas9 domain is the D10A/H840A Cas9 domain mutant:

```
(SEQ ID NO: 37; see, e.g., Qi et al., Repurposing
   CRISPR as an RNA-guided platform for sequence-
   specific control of gene expression. Cell. 2013;
   152(5): 1173-83, the entire contents of which are
                 incorporated herein by reference).
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

Additional suitable nuclease-inactive Cas9 domains will be apparent to those of skill in the art based on this disclosure. Such additional exemplary suitable nuclease-inactive Cas9 domains include, but are not limited to, D10A, D10A/D839A/H840A, and D10A/D839A/H840A/N863A mutant domains (See, e.g., Prashant et al., CAS9 transcriptional activators for target specificity screening and paired nickases for cooperative genome engineering. Nature Biotechnology. 2013; 31(9): 833-838, the entire contents of which are incorporated herein by reference).

Fusion Proteins Between Cas9 and Nucleic Acid Editing Enzymes or Domains

Some aspects of this disclosure provide fusion proteins comprising (i) a nuclease-inactive Cas9 enzyme or domain; and (ii) a nucleic acid-editing enzyme or domain. In some embodiments, the nucleic acid-editing enzyme or domain is a DNA-editing enzyme or domain. In some embodiments, the nucleic acid-editing enzyme possesses deaminase activity. In some embodiments, the nucleic acid-editing enzyme or domain comprises or is a deaminase domain. In some embodiments, the deaminase is a cytidine deaminase. In some embodiments, the deaminase is an apolipoprotein B mRNA-editing complex (APOBEC) family deaminase. In some embodiments, the deaminase is an APOBEC1 family deaminase. In some embodiments, the deaminase is an activation-induced cytidine deaminase (AID). In some embodiments, the deaminase is an ACF1/ASE deaminase. In some embodiments, the deaminase is an adenosine deaminase. In some embodiments, the deaminase is an ADAT family deaminase. Some nucleic-acid editing enzymes and domains as well as Cas9 fusion proteins including such enzymes or domains are described in detail herein. Additional suitable nucleic acid-editing enzymes or domains will be apparent to the skilled artisan based on this disclosure.

The instant disclosure provides Cas9:nucleic acid-editing enzyme/domain fusion proteins of various configurations. In some embodiments, the nucleic acid-editing enzyme or domain is fused to the N-terminus of the Cas9 domain. In some embodiments, the nucleic acid-editing enzyme or domain is fused to the C-terminus of the Cas9 domain. In some embodiments, the Cas9 domain and the nucleic acid-editing-editing enzyme or domain are fused via a linker. In some embodiments, the linker comprises a $(GGGGS)_n$ (SEQ ID NO: 91), a $(G)_n$, an $(EAAAK)_n$ (SEQ ID NO: 5), a $(GGS)_n$, an SGSETPGTSESATPES (SEQ ID NO: 93) motif (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference), or an $(XP)_n$ motif, or a combination of any of these, wherein n is independently an integer between 1 and 30. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. Additional suitable linker motifs and linker configurations will be apparent to those of skill in the art. In some embodiments, suitable linker motifs and configurations include those described in Chen et al., Fusion protein linkers: property, design and functionality. Adv Drug Deliv Rev. 2013; 65(10):1357-69, the entire contents of which are incorporated herein by reference. Additional suitable linker sequences will be apparent to those of skill in the art based on the instant disclosure.

In some embodiments, the general architecture of exemplary Cas9 fusion proteins provided herein comprises the structure:

[NH$_2$]-[nucleic acid-editing enzyme or domain]-[Cas9]-[COOH] or

[NH$_2$]-[Cas9]-[nucleic acid-editing enzyme or domain]-[COOH], wherein NH$_2$ is the N-terminus of the fusion protein, and COOH is the C-terminus of the fusion protein.

Additional features may be present, for example, one or more linker sequences between the NLS and the rest of the fusion protein and/or between the nucleic acid-editing enzyme or domain and the Cas9. Other exemplary features that may be present are localization sequences, such as nuclear localization sequences, cytoplasmic localization sequences, export sequences, such as nuclear export sequences, or other localization sequences, as well as sequence tags that are useful for solubilization, purification, or detection of the fusion proteins. Suitable localization signal sequences and sequences of protein tags are provided herein, and include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art.

In some embodiments, the nucleic acid-editing enzyme or domain is a deaminase. For example, in some embodiments, the general architecture of exemplary Cas9 fusion proteins with a deaminase enzyme or domain comprises the structure:

[NH$_2$]-[NLS]-[Cas9]-[deaminase]-[COOH],

[NH$_2$]-[NLS]-[deaminase]-[Cas9]-[COOH],

[NH$_2$]-[Cas9]-[deaminase]-[COOH], or

Figure 2:
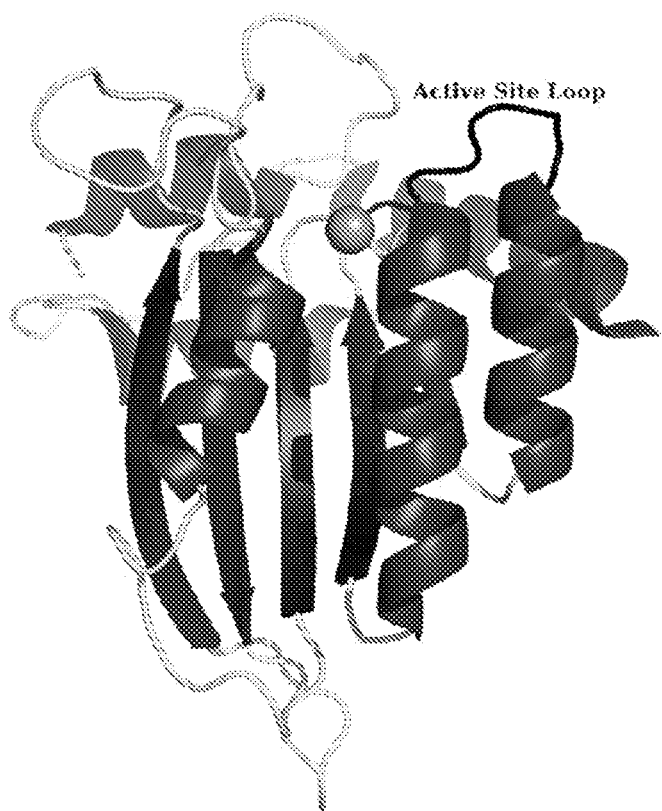
FIG. 2. Crystal structure of the catalytic domain of APOBEC3G (PDB ID 3E1U). The core secondary structure, which is believed to be conserved among the entire family, consists of a five-stranded β-sheet (arrows) flanked by six α-helices. The active center loop (active site loop), is believed to be responsible for determining deamination specificity. The $Zn^{2+}$ responsible for catalytic activity is shown as a sphere. Sequences correspond, from top to bottom, to SEQ ID NOs: 97-98.

[NH$_2$]-[deaminase]-[Cas9]-[COOH]

wherein NLS is a nuclear localization signal, NH$_2$ is the N-terminus of the fusion protein, and COOH is the C-terminus of the fusion protein. In some embodiments, a linker is inserted between the Cas9 and the deaminase. In some embodiments, the NLS is located C-terminal of the deaminase and/or the Cas9 domain. In some embodiments, the NLS is located between the deaminase and the Cas9 domain. Additional features, such as sequence tags, may also be present One exemplary suitable type of nucleic acid-editing enzymes and domains are cytosine deaminases, for example, of the APOBEC family. The apolipoprotein B mRNA-editing complex (APOBEC) family of cytosine deaminase enzymes encompasses eleven proteins that serve to initiate mutagenesis in a controlled and beneficial manner.[29] One family member, activation-induced cytidine deaminase (AID), is responsible for the maturation of antibodies by converting cytosines in ssDNA to uracils in a transcription-dependent, strand-biased fashion.[30] The apolipoprotein B editing complex 3 (APOBEC3) enzyme provides protection to human cells against a certain HIV-1 strain via the deamination of cytosines in reverse-transcribed viral ssDNA.[31] These proteins all require a Zn$^{2+}$-coordinating motif (His-X-Glu-X$_{23-26}$-Pro-Cys-X$_{24}$-Cys) and bound water molecule for catalytic activity. The Glu residue acts to activate the water molecule to a zinc hydroxide for nucleophilic attack in the deamination reaction. Each family member preferentially deaminates at its own particular "hotspot", ranging from WRC (W is A or T, R is A or G) for hAID, to TTC for hAPOBEC3F.[32] A recent crystal structure of the catalytic domain of APOBEC3G (FIG. 2) revealed a secondary structure comprised of a five-stranded β-sheet core flanked by six α-helices, which is believed to be conserved across the entire family.[33] The active center loops have been shown to be responsible for both ssDNA binding and in determining "hotspot" identity.[34] Overexpression of these enzymes has been linked to genomic instability and cancer, thus highlighting the importance of sequence-specific targeting.[35]

Another exemplary suitable type of nucleic acid-editing enzymes and domains are adenosine deaminases. For example, an ADAT family adenosine deaminase can be fused to a Cas9 domain, e.g., a nuclease-inactive Cas9 domain, thus yielding a Cas9-ADAT fusion protein.

Some aspects of this disclosure provide a systematic series of fusions between Cas9 and deaminase enzymes, e.g., cytosine deaminase enzymes such as APOBEC enzymes, or adenosine deaminase enzymes such as ADAT enzymes, that has been generated in order to direct the enzymatic activities of these deaminases to a specific site in genomic DNA. The advantages of using Cas9 as the recognition agent are twofold: (1) the sequence specificity of Cas9 can be easily altered by simply changing the sgRNA sequence; and (2) Cas9 binds to its target sequence by denaturing the dsDNA, resulting in a stretch of DNA that is single-stranded and therefore a viable substrate for the deaminase. Successful fusion proteins have been generated with human and mouse deaminase domains, e.g., AID domains. A variety of other fusion proteins between the catalytic domains of human and mouse AID and Cas9 are also contemplated. It will be understood that other catalytic domains, or catalytic domains from other deaminases, can also be used to generate fusion proteins with Cas9, and that the disclosure is not limited in this regard.

In some embodiments, fusion proteins of Cas9 and AID are provided. In an effort to engineer Cas9 fusion proteins to increase mutation rates in ssDNA, both mouse and human AID were tethered to gene V of filamentous phage (a nonspecific ssDNA binding protein). The resulting fusion proteins exhibited enhanced mutagenic activities compared to the wild type enzymes in a cell-based assay. This work demonstrates that the enzymatic activity of these proteins is maintained in and can be successfully targeted to genetic sequences with fusion proteins.[36]

While several crystal structures of Cas9 (and even Cas9 in complex with its sgRNA and target DNA) have been reported, (see, e.g., Jinek M, Jiang F, Taylor D W, Sternberg S H, Kaya E, Ma E, Anders C, Hauer M, Zhou K, Lin S, Kaplan M, lavarone A T, Charpentier E, Nogales E, Doudna J A. Structures of Cas9 endonucleases reveal RNA-mediated conformational activation. *Science.* 2014; 343(6176): 1247997. PMID: 24505130; and Nishimasu H, Ran F A, Hsu P D, Konermann S, Shehata S I, Dohmae N, Ishitani R, Zhang F, Nureki O. Crystal structure of Cas9 in complex with guide RNA and target DNA. *Cell.* 2014; 156(5):935-49. PMID: 24529477, the entire contents of each of which are incorporated herein by reference), the portion of DNA that is single stranded in the Cas9-DNA complex is unknown (the size of the Cas9-DNA bubble). However, it has been shown in a dCas9 system with a sgRNA specifically designed for the complex to interfere with transcription that transcriptional interference only occurs when the sgRNA binds to the non-template strand. This result suggests that certain portions of the DNA in the DNA-Cas9 complex are unguarded by Cas9, and could potentially be targeted by a deaminase in the fusion protein (see Qi L S, Larson M H, Gilbert L A, Doudna J A, Weissman J S, Arkin A P, Lim W A. Repurposing CRISPR as an RNA-guided platform for sequence-specific control of gene expression. *Cell.* 2013; 152(5):1173-83. PMID: 23452860, the entire contents of which are incorporated herein by reference). Further supporting this notion, footprinting experiments with exonuclease III and nuclease P1 (which only acts on ssDNA as a substrate) have revealed that at least 26 bases on the non-template strand are susceptible to digestion by these enzymes (see Jinek M, Jiang F, Taylor D W, Sternberg S H, Kaya E, Ma E, Anders C, Hauer M, Zhou K, Lin S, Kaplan M, Iavarone A T, Charpentier E, Nogales E, Doudna J A. Structures of Cas9 endonucleases reveal RNA-mediated conformational activation. *Science.* 2014; 343(6176): 1247997. PMID: 24505130). It has also been reported that in certain cases, Cas9 induces single base-substitution mutations in this susceptible stretch of DNA at frequencies as high as 15% (see Tsai S Q, Wyvekens N, Khayter C, Foden J A, Thapar V, Reyon D, Goodwin M J, Aryee M J, Joung J K. Dimeric CRISPR RNA-guided FokI nucleases for highly specific genome editing. *Nat Biotechnol.* 2014; 32(6): 569-76. PMID: 24770325, the entire contents of which are incorporated herein by reference). While the mechanism of introduction of these mutations is unknown, in all cases, the base that is mutated is a cytosine, which could possibly indicate the involvement of a cytosine deaminase enzyme. Taken together, these data are clearly consistent with a portion of the target DNA being single stranded and susceptible to other enzymes. It has been shown in a dCas9 system with a sgRNA specifically designed for the complex to interfere with transcription that transcriptional interference only occurs when the sgRNA binds to the non-template strand. This result suggests that certain portions of the DNA in the DNA-Cas9 complex are unguarded by Cas9, and could potentially be targeted by AID in the fusion protein.[16] Accordingly, both N-terminal and C-terminal fusions of Cas9 with a deaminase domain are useful according to aspects of this disclosure.

In some embodiments, the deaminase domain and the Cas9 domain are fused to each other via a linker. Various linker lengths and flexibilities between the deaminase domain (e.g., AID) and the Cas9 domain can be employed (e.g., ranging from very flexible linkers of the form (GGGGS)$_n$ (SEQ ID NO: 91), (GGS)$_n$, and (G)$_n$ to more rigid linkers of the form (EAAAK)$_n$ (SEQ ID NO: 5), SGSETPGTSESATPES (SEQ ID NO: 93) (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference) and (XP)$_n$)[37] in order to achieve the optimal length for deaminase activity for the specific application.

Some exemplary suitable nucleic-acid editing enzymes and domains, e.g., deaminases and deaminase domains, that can be fused to Cas9 domains according to aspects of this disclosure are provided below. It will be understood that, in some embodiments, the active domain of the respective sequence can be used, e.g., the domain without a localizing signal (nuclear localizing signal, without nuclear export signal, cytoplasmic localizing signal).

Human AID:
(SEQ ID NO: 6)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPNLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGL
(underline: nuclear localization signal; double underline: nuclear export signal)

Mouse AID:
(SEQ ID NO: 7)
MDSLLMKQKKFLYHFKNVRWAKGRHETYLCYVVKRRDSATSCSLDFGHLR

NKSGCHVELLFLRYISDWDLDPGRCYRVTWFTSWSPCYDCARHVAEFLRW

NPNLSLRIFTARLYFCEDRKAEPEGLRRLHRAGVQIGIMTFKDYFYCWNT

FVENRERTFKAWEGLHENSVRLTRQLRRILLPLYEVDDLRDAFRMLGF
(underline: nuclear localization signal; double underline: nuclear export signal)

Dog AID:
(SEQ ID NO: 8)
MDSLLMKQRKFLYHFKNVRWAKGRHETYLCYVVKRRDSATSFSLDFGHLR

NKSGCHVELLFLRYISDWDLDPGRCYRVTWFTSWSPCYDCARHVADFLRG

YPNLSLRIFAARLYFCEDRKAEPEGLRRLHRAGVQIAIMTFKDYFYCWNT

FVENREKTFKAWEGLHENSVRLSRQLRRILLPLYEVDDLRDAFRTLGL
(underline: nuclear localization signal; double underline: nuclear export signal)

Bovine AID:
(SEQ ID NO: 9)
MDSLLKKQRQFLYQFKNVRWAKGRHETYLCYVVKRRDSPTSFSLDFGHLR

NKAGCHVELLFLRYISDWDLDPGRCYRVTWFTSWSPCYDCARHVADFLRG

YPNLSLRIFTARLYFCDKERKAEPEGLRRLHRAGVQIAIMTFKDYFYCWN

TFVENHERTFKAWEGLHENSVRLSRQLRRILLPLYEVDDLRDAFRTLGL
(underline: nuclear localization signal; double underline: nuclear export signal)

Mouse APOBEC-3:
(SEQ ID NO: 10)
MGPFCLGCSHRKCYSPIRNLISQETFKFHFKNLGYAKGRKDTFLCYEVTR

KDCDSPVSLHHGVFKNKDNI*HAEICFLYWFHDKVLKVLSPREEFKITWYM*

*SWSPCFEC*AEQIVRFLATHHNLSLDIFSSRLYNVQDPETQQNLCRLVQEG

AQVAAMDLYEFKKCWKKFVDNGGRRFRPWKRLLTNFRYQDSKLQEILRPC

YIPVPSSSSSTLSNICLTKGLPETRFCVEGRRMDPLSEEEFYSQFYNQRV

KHLCYYHRMKPYLCYQLEQFNGQAPLKGCLLSEKGK*QHAEILFLDKIRSM*

*ELSQVTITCYLTWSPCPNC*AWQLAAFKRDRPDLILHIYTSRLYFHWKRPF

QKGLCSLWQSGILVDVMDLPQFTDCWTNFVNPKRPFWPWKGLEIISRRTQ

RRLRRIKESWGLQDLVNDFGNLQLGPPMS
(italic: nucleic acid editing domain)

Rat APOBEC-3:
(SEQ ID NO: 11)
MGPFCLGCSHRKCYSPIRNLISQETFKFHFKNLRYAIDRKDTFLCYEVTR

KDCDSPVSLHHGVFKNKDNI*HAEICFLYWFHDKVLKVLSPREEFKITWYM*

*SWSPCFEC*AEQVLRFLATHHNLSLDIFSSRLYNIRDPENQQNLCRLVQEG

AQVAAMDLYEFKKCWKKFVDNGGRRFRPWKKLLTNFRYQDSKLQEILRPC

YIPVPSSSSSTLSNICLTKGLPETRFCVERRRVHLLSEEEFYSQFYNQRV

KHLCYYHGVKPYLCYQLEQFNGQAPLKGCLLSEKGK*QHAEILFLDKIRSM*

*ELSQVIITCYLTWSPCPNC*AWQLAAFKRDRPDLILHIYTSRLYFHWKRPF

QKGLCSLWQSGILVDVMDLPQFTDCWTNFVNPKRPFWPWKGLEIISRRTQ

RRLHRIKESWGLQDLVNDFGNLQLGPPMS
(italic: nucleic acid editing domain)

Rhesus macaque APOBEC-3G:
(SEQ ID NO: 12)
MVEPMDPRTFVSNFNNRPILSGLNTVWLCCEVKTKDPSGPPLDAKIFQGK
VYSKAKYHPEMRFLRWFHKWRQLHHDQEYKVTWYVSWSPCTRCANSVATF
LAKDPKVTLTIFVARLYYFWKPDYQQALRILCQKRGGPHATMKIMNYNEF
QDCWNKFVDGRGKPFKPRNNLPKHYTLLQATLGELLRHLMDPGTFTSNFN
NKPWVSGQHETYLCYKVERLHNDTWVPLNQHRGFLRNQAPNIHGFPKGRH
AELCFLDLIPFWKLDGQQYRVTCFTSWSPCFSCAQEMAKFISNNEHVSLC
IFAARIYDDQGRYQEGLRALHRDGAKIAMMNYSEFEYCWDTFVDRQGRPF
QPWDGLDEHSQALSGRLRAI
(italic: nucleic acid editing domain;
underline: cytoplasmic localization signal)

Chimpanzee APOBEC-3G:
(SEQ ID NO: 13)
MKPHFRNPVERMYQDTFSDNFYNRPILSHRNTVWLCYEVKTKGPSRPPLD
AKIFRGQVYSKLKYHPEMRFFHWFSKWRKLHRDQEYEVTWYISWSPCTKC
TRDVATFLAEDPKVTLTIFVARLYYFWDPDYQEALRSLCQKRDGPRATMK
IMNYDEFQHCWSKFVYSQRELFEPWNNLPKYYILLHIMLGEILRHSMDPP
TFTSNFNNELWVRGRHETYLCYEVERLHNDTWVLLNQRRGFLCNQAPHKH
GFLEGRHAELCFLDVIPFWKLDLHQDYRVTCFTSWSPCFSCAQEMAKFIS
NNKHVSLCIFAARIYDDQGRCQEGLRTLAKAGAKISIMTYSEFKHCWDTF
VDHQGCPFQPWDGLEEHSQALSGRLRAILQNQGN
(italic: nucleic acid editing domain;
underline: cytoplasmic localization signal)

Green monkey APOBEC-3G:
(SEQ ID NO: 14)
MNPQIRNMVEQMEPDIFVYYFNNRPILSGRNTVWLCYEVKTKDPSGPPLD
ANIFQGKLYPEAKDHPEMKFLHWFRKWRQLHRDQEYEVTWYVSWSPCTRC
ANSVATFLAEDPKVTLTIFVARLYYFWKPDYQQALRILCQERGGPHATMK
IMNYNEFQHCWNEFVDGQGKPFKPRKNLPKHYTLLHATLGELLRHVMDPG
TFTSNFNNKPWVSGQRETYLCYKVERSHNDTWVLLNQHRGFLRNQAPDRH
GFPKGRHAELCFLDLIPFWKLDDQQYRVTCFTSWSPCFSCAQKMAKFISN
NKHVSLCIFAARIYDDQGRCQEGLRTLHRDGAKIAVMNYSEFEYCWDTFV
DRQGRPFQPWDGLDEHSQALSGRLRAI
(italic: nucleic acid editing domain;
underline: cytoplasmic localization signal)

Human APOBEC-3G:
(SEQ ID NO: 15)
MKPHFRNTVERMYRDTFSYNFYNRPILSRRNTVWLCYEVKTKGPSRPPLD
AKIFRGQVYSELKYHPEMRFFHWFSKWRKLHRDQEYEVTWYISWSPCTKC
TRDMATFLAEDPKVTLTIFVARLYYFWDPDYQEALRSLCQKRDGPRATMK
IMNYDEFQHCWSKFVYSQRELFEPWNNLPKYYILLHIMLGEILRHSMDPP
TFTFNFNNEPWVRGRHETYLCYEVERMHNDTWVLLNQRRGFLCNQAPHKH
GFLEGRHAELCFLDVIPFWKLDLDQDYRVTCFTSWSPCFSCAQEMAKFIS
KNKHVSLCIFTARIYDDQGRCQEGLRTLAEAGAKISIMTYSEFKHCWDTF
VDHQGCPFQPWDGLDEHSQDLSGRLRAILQNQEN
(italic: nucleic acid editing domain;
underline: cytoplasmic localization signal)

Human APOBEC-3F:
(SEQ ID NO: 16)
MKPHFRNTVERMYRDTFSYNFYNRPILSRRNTVWLCYEVKTKGPSRPRLD
AKIFRGQVYSQPEHHAEMCFLSWFCGNQLPAYKCFQITWFVSWTPCPDCV
AKLAEFLAEHPNVTLTISAARLYYYWERDYRRALCRLSQAGARVKIMDDE
EFAYCWENFVYSEGQPFMPWYKFDDNYAFLHRTLKEILRNPMEAMYPHIF
YFHFKNLRKAYGRNESWLCFTMEVVKHHSPVSWKRGVFRNQVDPETHCHA
ERCFLSWFCDDILSPNTNYEVTWYTSWSPCPECAGEVAEFLARHSNVNLT
IFTARLYYFWDTDYQEGLRSLSQEGASVEIMGYKDFKYCWENFVYNDDEP
FKPWKGLKYNFLFLDSKLQEILE
(italic: nucleic acid editing domain)

Human APOBEC-3B:
(SEQ ID NO: 17)
MNPQIRNPMERMYRDTFYDNFENEPILYGRSYTWLCYEVKIKRGRSNLLW
DTGVFRGQVYFKPQYHAEMCFLSWFCGNQLPAYKCFQITWFVSWTPCPDC
VAKLAEFLSEHPNVTLTISAARLYYYWERDYRRALCRLSQAGARVTIMDY
EEFAYCWENFVYNEGQQFMPWYKFDENYAFLHRTLKEILRYLMDPDTFTF
NFNNDPLVLRRRQTYLCYEVERLDNGTWVLMDQHMGFLCNEAKNLLCGFY
GRHAELRFLDLVPSLQLDPAQIYRVTWFISWSPCFSWGCAGEVRAFLQEN
THVRLRIFAARIYDYDPLYKEALQMLRDAGAQVSIMTYDEFEYCWDTFVY
RQGCPFQPWDGLEEHSQALSGRLRAILQNQGN
(italic: nucleic acid editing domain)

Human APOBEC-3C:
(SEQ ID NO: 18)
MNPQIRNPMKAMYPGTFYFQFKNLWEANDRNETWLCFTVEGIKRRSVVSW
KTGVFRNQVDSETHCHAERCFLSWFCDDILSPNTKYQVTWYTSWSPCPDC
AGEVAEFLARHSNVNLTIFTARLYYFQYPCYQEGLRSLSQEGVAVEIMDY
EDFKYCWENFVYNDNEPFKPWKGLKTNFRLLKRRLRESLQ
(italic: nucleic acid editing domain)

Human APOBEC-3A:
(SEQ ID NO: 19)
MEASPASGPRHLMDPHIFTSNFNNGIGRHKTYLCYEVERLDNGTSVKMDQ
HRGFLHNQAKNLLCGFYGRHAELRFLDLVPSLQLDPAQIYRVTWFISWSP
CFSWGCAGEVRAFLQENTHVRLRIFAARIYDYDPLYKEALQMLRDAGAQV
SIMTYDEFKHCWDTFVDHQGCPFQPWDGLDEHSQALSGRLRAILQNQGN
(italic: nucleic acid editing domain)

Human APOBEC-3H:
(SEQ ID NO: 20)
MALLTAETFRLQFNNKRRLRRPYYPRKALLCYQLTPQNGSTPTRGYFENK
KKCHAEICFINEIKSMGLDETQCYQVTCYLTWSPCSSCAWELVDFIKAHD
HLNLGIFASRLYYHWCKPQQKGLRLLCGSQVPVEVMGFPKFADCWENFVD
HEKPLSFNPYKMLEELDKNSRAIKRRLERIKIPGVRAQGRYMDILCDAEV
(italic: nucleic acid editing domain)

Human APOBEC-3D:
(SEQ ID NO: 21)
MNPQIRNPMERMYRDTFYDNFENEPILYGRSYTWLCYEVKIKRGRSNLLW
DTGVFRGPVLPKRQSNHRQEVYFRFENHAEMCFLSWFCGNRLPANRRFQI
TWFVSWNPCLPCVVKVTKFLAEHPNVTLTISAARLYYYRDRDWRWVLLRL
HKAGARVKIMDYEDFAYCWENFVCNEGQPFMPWYKFDDNYASLHRTLKEI -continued
LRNPMEAMYPHIFYFHFKNLLKACGRNESWLCFTMEVTKHHSAVFRKRGV

FRNQVDPETHCHAERCFLSWFCDDILSPNTNYEVTWYTSWSPCPECAGEV

AEFLARHSNVNLTIFTARLCYFWDTDYQEGLCSLSQEGASVKIMGYKDFV

SCWKNFVYSDDEPFKPWKGLQTNFRLLKRRLREILQ
(italic: nucleic acid editing domain)

Human APOBEC-1:
(SEQ ID NO: 22)
MTSEKGPSTGDPTLRRRIEPWEFDVFYDPRELRKEACLLYEIKWGMSRKI

WRSSGKNTTNHVEVNFIKKFTSERDFHPSMSCSITWFLSWSPCWECSQAI

REFLSRHPGVTLVIYVARLFWHMDQQNRQGLRDLVNSGVTIQIMRASEYY

HCWRNFVNYPPGDEAHWPQYPPLWMMLYALELHCIILSLPPCLKISRRWQ

NHLTFFRLHLQNCHYQTIPPHILLATGLIHPSVAWR

Mouse APOBEC-1:
(SEQ ID NO: 23)
MSSETGPVAVDPTLRRRIEPHEFEVFFDPRELRKETCLLYEINWGGRHSV

WRHTSQNTSNHVEVNFLEKFTTERYFRPNTRCSITWFLSWSPCGECSRAI

TEFLSRHPYVTLFIYIARLYHHTDQRNRQGLRDLISSGVTIQIMTEQEYC

YCWRNFVNYPPSNEAYWPRYPHLWVKLYVLELYCIILGLPPCLKILRRKQ

PQLTFFTITLQTCHYQRIPPHLLWATGLK

Rat APOBEC-1:
(SEQ ID NO: 24)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLK

Human ADAT-2:
(SEQ ID NO: 25)
MEAKAAPKPAASGACSVSAEETEKWMEEAMHMAKEALENTEVPVGCLMVY

NNEVVGKGRNEVNQTKNATRHAEMVAIDQVLDWCRQSGKSPSEVFEHTVL

YVTVEPCIMCAAALRLMKIPLVVYGCQNERFGGCGSVLNIASADLPNTGR

PFQCIPGYRAEEAVEMLKTFYKQENPNAPKSKVRKKECQKS

Mouse ADAT-2:
(SEQ ID NO: 26)
MEEKVESTTTPDGPCVVSVQETEKWMEEAMRMAKEALENIEVPVGCLMVY

NNEVVGKGRNEVNQTKNATRHAEMVAIDQVLDWCHQHGQSPSTVFEHTVL

YVTVEPCIMCAAALRLMKIPLVVYGCQNERFGGCGSVLNIASADLPNTGR

PFQCIPGYRAEEAVELLKTFYKQENPNAPKSKVRKKDCQKS

Mouse ADAT-1:
(SEQ ID NO: 27)
MWTADEIAQLCYAHYNVRLPKQGKPEPNREWTLLAAVVKIQASANQACDI

PEKEVQVTKEVV*SMGTGTKCIGQSKMRESGDILNDSHAEIIARRSFQRYL*

*LHQLHLAAVLKEDSIFVPGTQRGLWRLRPDLSFVFFSSHTPCGDASIIPM*

*LEFEEQPCCPVIRSWANNSPVQETENLEDSKDKRNCEDPASPVAKKMRLG*

*TPARSLSNCVAHHGTQESGPVKPDVSSSDLTKEEPDAANGIASGSFRVVD*

*VYRTGAKCVPGETGDLREPGAAYHQVGLLRVKPGRGDRTCSMSCSDKMAR*

*WNVLGCQGALLMHFLEKPIYLSAVVIGKCPYSQEAMRRALTGRCEETLVL*

-continued
*PRGFGVQELEIQQSGLLFEQSRCAVHRKRGDSPGRLVPCGAAISWSAVPQ*

*QPLDVTANGFPQGTTKKEIGSPRARSRISKVELFRSFQKLLSSIADDEQP*

*DSIRVTKKLDTYQEYKDAASAYQEAWGALRRIQPFASWIRNPPDYHQFK*
(italic: nucleic acid editing domain)

Human ADAT-1:
(SEQ ID NO: 28)
MWTADEIAQLCYEHYGIRLPKKGKPEPNHEWTLLAAVVKIQSPADKACDT

PDKPVQVTKEVV*SMGTGTKCIGQSKMRKNGDILNDSHAEVIARRSFQRYL*

*LHQLQLAATLKEDSIFVPGTQKGVWKLRRDLIFVFFSSHTPCGDASIIPM*

*LEFEDQPCCPVFRNWAHNSSVEASSNLEAPGNERKCEDPDSPVTKKMRLE*

*PGTAAREVTNGAAHHQSFGKQKSGPISPGIHSCDLTVEGLATVTRIAPGS*

*AKVIDVYRTGAKCVPGEAGDSGKPGAAFHQVGLLRVKPGRGDRTRSMSCS*

*DKMARWNVLGCQGALLMHLLEEPIYLSAVVIGKCPYSQEAMQRALIGRCQ*

*NVSALPKGFGVQELKILQSDLLFEQSRSAVQAKRADSPGRLVPCGAAISW*

*SAVPEQPLDVTANGFPQGTTKKTIGSLQARSQISKVELFRSFQKLLSRIA*

*RDKWPHSLRVQKLDTYQEYKEAASSYQEAWSTLRKQVFGSWIRNPPDYHQ*

*FK*
(italic: nucleic acid editing domain)

In some embodiments, fusion proteins as provided herein comprise the full-length amino acid of a nucleic acid-editing enzyme, e.g., one of the sequences provided above. In other embodiments, however, fusion proteins as provided herein do not comprise a full-length sequence of a nucleic acid-editing enzyme, but only a fragment thereof. For example, in some embodiments, a fusion protein provided herein comprises a Cas9 domain and a fragment of a nucleic acid-editing enzyme, e.g., wherein the fragment comprises a nucleic acid-editing domain. Exemplary amino acid sequences of nucleic acid-editing domains are shown in the sequences above as italicized letters, and additional suitable sequences of such domains will be apparent to those of skill in the art.

Additional suitable nucleic-acid editing enzyme sequences, e.g., deaminase enzyme and domain sequences, that can be used according to aspects of this invention, e.g., that can be fused to a nuclease-inactive Cas9 domain, will be apparent to those of skill in the art based on this disclosure. In some embodiments, such additional enzyme sequences include deaminase enzyme or deaminase domain sequences that are at least 70%, at least 75%, at least 80%, at least 85%, at least 90%, at least 95%, at least 96%, at least 97%, at least 98%, or at least 99% similar to the sequences provided herein. Additional suitable Cas9 domains, variants, and sequences will also be apparent to those of skill in the art. Examples of such additional suitable Cas9 domains include, but are not limited to, D10A, D10A/D839A/H840A, and D10A/D839A/H840A/N863A mutant domains (See, e.g., Prashant et al., CAS9 transcriptional activators for target specificity screening and paired nickases for cooperative genome engineering. Nature Biotechnology. 2013; 31(9): 833-838 the entire contents of which are incorporated herein by reference).

Additional suitable strategies for generating fusion proteins comprising a Cas9 domain and a deaminase domain will be apparent to those of skill in the art based on this disclosure in combination with the general knowledge in the art. Suitable strategies for generating fusion proteins according to aspects of this disclosure using linkers or without the use of linkers will also be apparent to those of skill in the art in view of the instant disclosure and the knowledge in the art. For example, Gilbert et al., CRISPR-mediated modular RNA-guided regulation of transcription in eukaryotes. *Cell.* 2013; 154(2):442-51, showed that C-terminal fusions of Cas9 with VP64 using 2 NLS's as a linker (SPKKKRK-VEAS, SEQ ID NO: 29), can be employed for transcriptional activation. Mali et al., CAS9 transcriptional activators for target specificity screening and paired nickases for cooperative genome engineering. *Nat Biotechnol.* 2013; 31(9):833-8, reported that C-terminal fusions with VP64 without linker can be employed for transcriptional activation. And Maeder et al., CRISPR RNA-guided activation of endogenous human genes. *Nat Methods.* 2013; 10: 977-979, reported that C-terminal fusions with VP64 using a Gly$_4$Ser (SEQ ID NO: 91) linker can be used as transcriptional activators. Recently, dCas9-FokI nuclease fusions have successfully been generated and exhibit improved enzymatic specificity as compared to the parental Cas9 enzyme (In Guilinger J P, Thompson D B, Liu D R. Fusion of catalytically inactive Cas9 to FokI nuclease improves the specificity of genome modification. *Nat. Biotechnol.* 2014; 32(6): 577-82, and in Tsai S Q, Wyvekens N, Khayter C, Foden J A, Thapar V, Reyon D, Goodwin M J, Aryee M J, Joung J K. Dimeric CRISPR RNA-guided FokI nucleases for highly specific genome editing. *Nat Biotechnol.* 2014; 32(6):569-76. PMID: 24770325 a SGSETPGTSESATPES (SEQ ID NO: 93) or a GGGGS (SEQ ID NO: 91) linker was used in FokI-dCas9 fusion proteins, respectively).

Use of Cas9 DNA Editing Fusion Proteins for Correcting Disease-Associated Mutations Some embodiments provide methods for using the Cas9 DNA editing fusion proteins provided herein. In some embodiments, the fusion protein is used to introduce a point mutation into a nucleic acid by deaminating a target nucleobase, e.g., a C residue. In some embodiments, the deamination of the target nucleobase results in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ a Cas9 DNA editing fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provide herein is to restore the function of a dysfunctional gene via genome editing. The Cas9 deaminase fusion proteins provided herein can be validated for gene editing-based human therapeutics in vitro, e.g., by correcting a disease-associated mutation in human cell culture. It will be understood by the skilled artisan that the fusion proteins provided herein, e.g., the fusion proteins comprising a Cas9 domain and a nucleic acid deaminase domain can be used to correct any single point T→C or A→G mutation. In the first case, deamination of the mutant C back to U corrects the mutation, and in the latter case, deamination of the C that is base-paired with the mutant G, followed by a round of replication, corrects the mutation.

An exemplary disease-relevant mutation that can be corrected by the provided fusion proteins in vitro or in vivo is the H1047R (A3140G) polymorphism in the PI3KCA protein. The phosphoinositide-3-kinase, catalytic alpha subunit (PI3KCA) protein acts to phosphorylate the 3-OH group of the inositol ring of phosphatidylinositol. The PI3KCA gene has been found to be mutated in many different carcinomas, and thus it is considered to be a potent oncogene.[50] In fact, the A3140G mutation is present in several NCI-60 cancer cell lines, such as, for example, the HCT116, SKOV3, and T47D cell lines, which are readily available from the American Type Culture Collection (ATCC).[51]

In some embodiments, a cell carrying a mutation to be corrected, e.g., a cell carrying a point mutation, e.g., an A3140G point mutation in exon 20 of the PI3KCA gene, resulting in a H1047R substitution in the PI3KCA protein, is contacted with an expression construct encoding a Cas9 deaminase fusion protein and an appropriately designed sgRNA targeting the fusion protein to the respective mutation site in the encoding PI3KCA gene. Control experiments can be performed where the sgRNAs are designed to target the fusion enzymes to non-C residues that are within the PI3KCA gene. Genomic DNA of the treated cells can be extracted, and the relevant sequence of the PI3KCA genes PCR amplified and sequenced to assess the activities of the fusion proteins in human cell culture.

It will be understood that the example of correcting point mutations in PI3KCA is provided for illustration purposes and is not meant to limit the instant disclosure. The skilled artisan will understand that the instantly disclosed DNA-editing fusion proteins can be used to correct other point mutations and mutations associated with other cancers and with diseases other than cancer including other proliferative diseases.

The successful correction of point mutations in disease-associated genes and alleles opens up new strategies for gene correction with applications in therapeutics and basic research. Site-specific single-base modification systems like the disclosed fusions of Cas9 and deaminase enzymes or domains also have applications in "reverse" gene therapy, where certain gene functions are purposely suppressed or abolished. In these cases, site-specifically mutating Trp (TGG), Gln (CAA and CAG), or Arg (CGA) residues to premature stop codons (TAA, TAG, TGA) can be used to abolish protein function in vitro, ex vivo, or in vivo.

The instant disclosure provides methods for the treatment of a subject diagnosed with a disease associated with or caused by a point mutation that can be corrected by a Cas9 DNA editing fusion protein provided herein. For example, in some embodiments, a method is provided that comprises administering to a subject having such a disease, e.g., a cancer associated with a PI3KCA point mutation as described above, an effective amount of a Cas9 deaminase fusion protein that corrects the point mutation or introduces a deactivating mutation into the disease-associated gene. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting a point mutation or introducing a deactivating mutation into a disease-associated gene will be known to those of skill in the art, and the disclosure is not limited in this respect.

The instant disclosure provides methods for the treatment of additional diseases or disorders, e.g., diseases or disorders that are associated or caused by a point mutation that can be corrected by deaminase-mediated gene editing. Some such diseases are described herein, and additional suitable diseases that can be treated with the strategies and fusion proteins provided herein will be apparent to those of skill in the art based on the instant disclosure. Exemplary suitable diseases and disorders are listed below. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment and determination of homologous residues. Exemplary suitable diseases and disorders include, without limitation, cystic fibrosis (see, e.g., Schwank et al., Functional repair of CFTR by CRISPR/Cas9 in intestinal stem cell organoids of cystic fibrosis patients. Cell stem cell. 2013; 13: 653-658; and Wu et. al., Correction of a genetic disease in mouse via use of CRISPR-Cas9. Cell stem cell. 2013; 13: 659-662, neither of which uses a deaminase fusion protein to correct the genetic defect); phenylketonuria—e.g., phenylalanine to serine mutation at position 835 (mouse) or 240 (human) or a homologous residue in phenylalanine hydroxylase gene (T>C mutation)—see, e.g., McDonald et al., Genomics. 1997; 39:402-405; Bernard-Soulier syndrome (BSS)—e.g., phenylalanine to serine mutation at position 55 or a homologous residue, or cysteine to arginine at residue 24 or a homologous residue in the platelet membrane glycoprotein IX (T>C mutation)—see, e.g., Noris et al., British Journal of Haematology. 1997; 97: 312-320, and Ali et al., Hematol. 2014; 93: 381-384; epidermolytic hyperkeratosis (EHK)—e.g., leucine to proline mutation at position 160 or 161 (if counting the initiator methionine) or a homologous residue in keratin 1 (T>C mutation)—see, e.g., Chipev et al., Cell. 1992; 70: 821-828, see also accession number P04264 in the UNIPROT database at www[dot]uniprot[dot]org; chronic obstructive pulmonary disease (COPD)—e.g., leucine to proline mutation at position 54 or 55 (if counting the initiator methionine) or a homologous residue in the processed form of $\alpha_1$-antitrypsin or residue 78 in the unprocessed form or a homologous residue (T>C mutation)—see, e.g., Poller et al., Genomics. 1993; 17: 740-743, see also accession number P01011 in the UNIPROT database; Charcot-Marie-Toot disease type 4J—e.g., isoleucine to threonine mutation at position 41 or a homologous residue in FIG. 4 (T>C mutation)—see, e.g., Lenk et al., PLoS Genetics. 2011; 7: e1002104; neuroblastoma (NB)—e.g., leucine to proline mutation at position 197 or a homologous residue in Caspase-9 (T>C mutation)—see, e.g., Kundu et al., 3 Biotech. 2013, 3:225-234; von Willebrand disease (vWD)—e.g., cysteine to arginine mutation at position 509 or a homologous residue in the processed form of von Willebrand factor, or at position 1272 or a homologous residue in the unprocessed form of von Willebrand factor (T>C mutation)—see, e.g., Lavergne et al., Br. J. Haematol. 1992, see also accession number P04275 in the UNIPROT database; 82: 66-72; myotonia congenital—e.g., cysteine to arginine mutation at position 277 or a homologous residue in the muscle chloride channel gene CLCN1 (T>C mutation)—see, e.g., Weinberger et al., The J. of Physiology. 2012; 590: 3449-3464; hereditary renal amyloidosis—e.g., stop codon to arginine mutation at position 78 or a homologous residue in the processed form of apolipoprotein AII or at position 101 or a homologous residue in the unprocessed form (T>C mutation)—see, e.g., Yazaki et al., Kidney Int. 2003; 64: 11-16; dilated cardiomyopathy (DCM)—e.g., tryptophan to Arginine mutation at position 148 or a homologous residue in the FOXD4 gene (T>C mutation), see, e.g., Minoretti et. al., Int. J. of Mol. Med. 2007; 19: 369-372; hereditary lymphedema—e.g., histidine to arginine mutation at position 1035 or a homologous residue in VEGFR3 tyrosine kinase (A>G mutation), see, e.g., Irrthum et al., Am. J. Hum. Genet. 2000; 67: 295-301; familial Alzheimer's disease—e.g., isoleucine to valine mutation at position 143 or a homologous residue in presenilin1 (A>G mutation), see, e.g., Gallo et. al., J. Alzheimer's disease. 2011; 25: 425-431; Prion disease—e.g., methionine to valine mutation at position 129 or a homologous residue in prion protein (A>G mutation)—see, e.g., Lewis et. al., J. of General Virology. 2006; 87: 2443-2449; chronic infantile neurologic cutaneous articular syndrome (CINCA)—e.g., Tyrosine to Cysteine mutation at position 570 or a homologous residue in cryopyrin (A>G mutation)—see, e.g., Fujisawa et. al. Blood. 2007; 109: 2903-2911; and desmin-related myopathy (DRM)—e.g., arginine to glycine mutation at position 120 or a homologous residue in αB crystallin (A>G mutation)—see, e.g., Kumar et al., J. Biol. Chem. 1999; 274: 24137-24141. The entire contents of all references and database entries is incorporated herein by reference.

It will be apparent to those of skill in the art that in order to target a Cas9:nucleic acid-editing enzyme/domain fusion protein as disclosed herein to a target site, e.g., a site comprising a point mutation to be edited, it is typically necessary to co-express the Cas9:nucleic acid-editing enzyme/domain fusion protein together with a guide RNA, e.g., an sgRNA. As explained in more detail elsewhere herein, a guide RNA typically comprises a tracrRNA framework allowing for Cas9 binding, and a guide sequence, which confers sequence specificity to the Cas9:nucleic acid-editing enzyme/domain fusion protein. In some embodiments, the guide RNA comprises a structure 5'-[guide sequence]-guuuuagagcuagaaauagcaaguuaaaauaaggcuaguc-cguuaucaacuugaaaaaguggcaccgagucggugcuuuuu-3' (SEQ ID NO: 38), wherein the guide sequence comprises a sequence that is complementary to the target sequence. The guide sequence is typically 20 nucleotides long. The sequences of suitable guide RNAs for targeting Cas9:nucleic acid-editing enzyme/domain fusion proteins to specific genomic target sites will be apparent to those of skill in the art based on the instant disclosure. Such suitable guide RNA sequences typically comprise guide sequences that are complementary to a nucleic sequence within 50 nucleotides upstream or downstream of the target nucleotide to be edited. Some exemplary guide RNA sequences suitable for targeting Cas9:nucleic acid-editing enzyme/domain fusion proteins to specific target sequences are provided below.

H1047R (A3140G) polymorphism in the phosphoinositide-3-kinase catalytic alpha subunit (PI3KCA or PIK3CA) (the position of the mutated nucleotide and the respective codon are underlined):

```
gatgacattgcatacattcgaaagaccctagccttagataaaactgagca
 D   D   I   A   Y   I   R   K   T   L   A   L   D   K   T   E   Q agaggctttggagtatttcatgaaacaaatgaatgatgcacgtcatggtg
 E   A   L   E   Y   F   M   K   Q   M   N   D   A   R   H   G
```

```
gctggacaacaaaaatggattggatcttccacacaattaaacagcatgca
 G  W  T  T  K  M  D  W  I  F  H  T  I  K  Q  H  A ttgaactgaaagataactgagaaaatgaaa
 L  N  -  K  I  T  E  K  M  K
(Nucleotide sequence - SEQ ID NO: 39; protein
sequence - SEQ ID NO: 40).
```

Exemplary suitable guide sequences for targeting a Cas9:nucleic acid-editing enzyme/domain fusion proteins to the mutant A3140G residue include, without limitation: 5'-aucggaauctauuuugacuc-3' (SEQ ID NO: 41); 5'-ucggaaucuauuuugacucg-3' (SEQ ID NO: 42); 5'-cuuagauaaaacugagcaag-3' (SEQ ID NO: 43); 5'-aucuauuuugacucguucuc-3' (SEQ ID NO: 44); 5'-uaaaacugagcaagaggcuu-3' (SEQ ID NO: 45); 5'-ugguggcuggacaacaaaaa-3' (SEQ ID NO: 46); 5'-gcuggacaacaaaaauggau-3' (SEQ ID NO: 47); 5'-guguuaauuugucguacgua-3' (SEQ ID NO: 48). Additional suitable guide sequences for targeting a Cas9:nucleic acid-editing enzyme/domain fusion protein to a mutant PI3KCA sequence, to any of the additional sequences provided below, or to additional mutant sequences associated with a disease will be apparent to those of skill in the art based on the instant disclosure.

Phenylketonuria phenylalanine to serine mutation at residue 240 in phenylalanine hydroxylase gene (T>C mutation) (the position of the mutated nucleotide and the respective codon are underlined):

```
aatcacattttccacttcttgaaaagtactgtggcttccatgaagataa
 N  H  I  F  P  L  L  E  K  Y  C  G  F  H  E  D  N cattccccagctggaagacgtttctcaattcctgcagacttgcactggtc
 I  P  Q  L  E  D  V  S  Q  F  L  Q  T  C  T  G tccgcctccgacctgtggctggcctgctttcctctcgggatttcttgggt
 S  R  L  R  P  V  A  G  L  L  S  S  R  D  F  L  G ggcctggccttccgagtcttccactgcaca
 G  L  A  F  R  V  F  H  C  T
(Nucleotide sequence - SEQ ID NO: 49; protein
sequence - SEQ ID NO: 50).
```

Bernard-Soulier syndrome (BSS)—cysteine to arginine at residue 24 in the platelet membrane glycoprotein IX (T>C mutation):

```
atgcctgcctggggagccctgttcctgctctgggccacagcagaggccac
 M  P  A  W  G  A  L  F  L  L  W  A  T  A  E  A  T caaggactgcccagcccacgtacctgccgcgccctggaaaccatggggc
 K  D  C  P  S  P  R  T  C  R  A  L  E  T  M  G tgtgggtggactgcaggggccacggactcacggccctgcctgccctgccg
 L  W  V  D  C  R  G  H  G  L  T  A  L  P  A  L  P gcccgcacccgccaccttctgctggccaac
 A  R  T  R  H  L  L  L  A  N
(Nucleotide sequence - SEQ ID NO: 51; protein
sequence - SEQ ID NO: 52).
```

Epidermolytic hyperkeratosis (EHK)—leucine to proline mutation at residue 161 in keratin 1 (T>C mutation):

```
ggttatggtcctgtctgccctcctggtggcatacaagaagtcactatcaa
 G  Y  G  P  V  C  P  P  G  G  I  Q  E  V  T  I  N ccagagccctcttcagcccctcaatgtggagattgacctgagatccaaa
 Q  S  P  L  Q  P  L  N  V  E  I  D  P  E  I  Q aggtgaagtctcgagaaagg
 K  V  K  S  R  E  R
(Nucleotide sequence - SEQ ID NO: 53; protein
sequence - SEQ ID NO: 54).
```

Chronic obstructive pulmonary disease (COPD)—leucine to proline mutation at residue 54 in α₁-antitrypsin (T>C mutation):

```
gtctccctggctgaggatccccagggagatgctgcccagaagacagatac
 V  S  L  A  E  D  P  Q  G  D  A  A  Q  K  T  D  T atcccaccatgatcaggatcacccaaccttcaacaagatcaccccaacc
 S  H  H  D  Q  D  H  P  T  F  N  K  I  T  P  N cggctgagttcgccttcagcctataccgccagctggcacaccagtccaac
 P  A  E  F  A  F  S  L  Y  R  Q  L  A  H  Q  S  N agcaccaatatcttcttctccccagtgagc
 S  T  N  I  F  F  S  P  V  S
(Nucleotide sequence - SEQ ID NO: 55; protein
sequence - SEQ ID NO: 56).
```

Chronic obstructive pulmonary disease (COPD)—leucine to proline mutation at residue 78 in α1-antichymotrypsin (T>C mutation):

```
gcctccgccaacgtggacttcgctttcagcctgtacaagcagttagtcct
 A  S  A  N  V  D  F  A  F  S  L  Y  K  Q  L  V  L gaaggcccctgataagaatgtcatcttctccccaccgagcatctccaccg
 K  A  P  D  K  N  V  I  F  S  P  P  S  I  S  T ccttggccttcctgtctctgggggccataataccaccctgacagagatt
 A  L  A  F  L  S  L  G  A  H  N  T  T  L  T  E  I ctcaaaggcctcaagttctacctcacggag
 L  K  G  L  K  F  Y  L  T  E
(Nucleotide sequence - SEQ ID NO: 89; protein
sequence - SEQ ID NO: 90).
```

Neuroblastoma (NB)—leucine to proline mutation at residue 197 in Caspase-9 (T>C mutation):

```
ggccactgcctcattatcaacaatgtgaacttctgccgtgagtccgggct
 G  H  C  L  I  I  N  N  V  N  F  C  R  E  S  G  L ccgcacccgcactggctccaacatcgactgtgagaagttgcggcgtcgct
 R  T  R  T  G  S  N  I  D  C  E  K  L  R  R  R tctcctcgccgcatttcatggtggaggtgaagggcgacctgactgccaag
 F  S  S  P  H  F  M  V  E  V  K  G  D  L  T  A  K aaaatggtgctggctttgctggagctggcg
 K  M  V  L  A  L  L  E  L  A
(Nucleotide sequence - SEQ ID NO: 57; protein
sequence - SEQ ID NO: 58).
```

Figure 4:
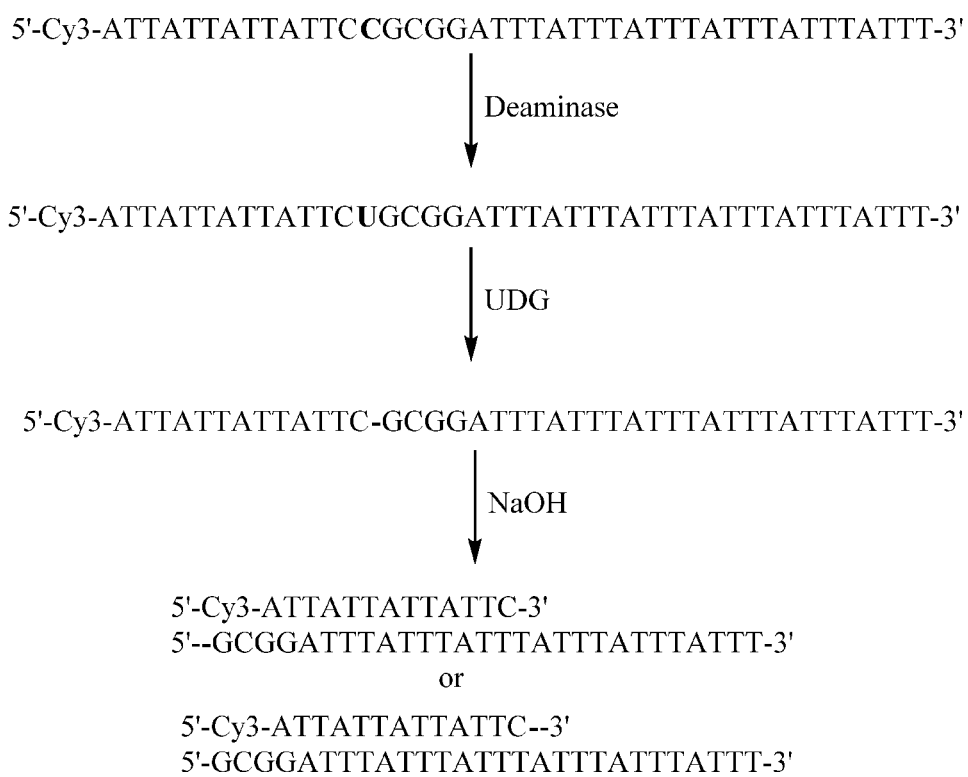
FIG. 4. Deaminase assay. Sequences correspond, from top to bottom, to SEQ ID NOs: 99-105.

Charcot-Marie-Tooth disease type 4J—isoleucine to threonine mutation at residue 41 in FIG. 4 (T>C mutation):

```
actagagctagatactttctagttgggagcaataatgcagaaacgaaata
 T  R  A  R  Y  F  L  V  H  D  N  N  A  R  T  K  Y tcgtgtcttgaagactgatagaacagaaccaaaagatttggtcataattg
 R  V  L  K  T  D  R  T  E  P  K  D  L  V  I  I atgacaggcatgtctatactcaacaagaagtaagggaacttcttggccgc
 D  D  R  H  V  Y  T  Q  Q  E  V  R  E  L  L  G  R
```

-continued
```
ttggatcttggaaatagaacaaagatggga
 L  D  L  G  N  R  T  K  M  G
(Nucleotide sequence - SEQ ID NO: 59; protein
sequence - SEQ ID NO: 60).
``` von Willebrand disease (vWD)—cysteine to arginine mutation at residue 1272 in von Willebrand factor (T>C mutation):

```
acagatgccccggtgagccccaccactctgtatgtggaggacatctcgg
 T  D  A  P  V  S  P  T  T  L  Y  V  E  D  I  S aaccgccgttgcacgatttctaccgcagcaggctactggacctggtctt
 E  P  P  L  H  D  F  Y  R  S  R  L  L  D  L  V  F cctgctggatggctcctccaggctgtccgaggctgagtttgaagtgctg
 L  L  D  G  S  S  R  L  S  E  A  E  F  E  V  L aaggcctttgtggtggacatgatggagcggctg
 K  A  F  V  V  D  M  M  E  R  L
(Nucleotide sequence - SEQ ID NO: 61; protein
sequence - SEQ ID NO: 62).
```

Myotonia congenital—cysteine to arginine mutation at position 277 in the muscle chloride channel gene CLCN1 (T>C mutation):

```
atctgtgctgctgtcctcagcaaattcatgtctgtgttctgcggggtat
 I  C  A  A  V  L  S  K  F  M  S  V  F  C  G  V atgagcagccatactactactctgatatcctgacggtgggctgtgctgt
 Y  E  Q  P  Y  Y  Y  S  D  I  L  T  V  G  C  A  V gggagtcggccgttgttttgggacaccacttggaggagtgctatttagc
 G  V  G  R  C  F  G  T  P  L  G  G  V  L  F  S atcgaggtcacctccacctactttgctgttcgg
 I  E  V  T  S  T  Y  F  A  V  R
(Nucleotide sequence - SEQ ID NO: 63; protein
sequence - SEQ ID NO: 64).
```

Hereditary renal amyloidosis—stop codon to arginine mutation at residue 111 in apolipoprotein AII (T>C mutation):

```
tactttgaaaagtcaaaggagcagctgacaccctgatcaagaaggctg
 Y  F  E  K  S  K  E  Q  L  T  P  L  I  K  K  A gaacggaactggttaacttcttgagctatttcgtggaacttggaacaca
 G  T  E  L  V  N  F  L  S  Y  F  V  E  L  G  T  Q gcctgccacccagcgaagtgtccagcaccattgtcttccaaccccagct
 P  A  T  Q  R  S  V  Q  H  H  C  L  P  T  P  A ggcctctagaacacccactggccagtcctagag
 G  L  -  N  T  H  W  P  V  L  E
(Nucleotide sequence - SEQ ID NO: 65; protein
sequence - SEQ ID NO: 66).
```

Dilated cardiomyopathy (DCM)—tryptophan to Arginine mutation at position 148 in the FOXD4 gene (T>C mutation):

```
ccgcacaagcgcctcacgctcagcggcatctgcgccttcattagtgacc
 P  H  K  R  L  T  L  S  G  I  C  A  F  I  S  D gcttcccctactaccgccgcaagttccccgcccggcagaacagcatccg
 R  F  P  Y  Y  R  R  K  F  P  A  R  Q  N  S  I  R ccacaacctctcgctgaacgactgcttcgtcaagatccccgcgagccg
 H  N  L  S  L  N  D  C  F  V  K  I  P  R  E  P
```

-continued
```
ggccgcccaggcaagggcaactactggagcctg
 G  R  P  G  K  G  N  Y  W  S  L
(Nucleotide sequence - SEQ ID NO: 67; protein
sequence - SEQ ID NO: 68).
```

Hereditary lymphedema—histidine to arginine mutation at residue 1035 in VEGFR3 tyrosine kinase (A>G mutation):

```
gctgaggacctgtggctgagcccgctgaccatggaagatcttgtctgct
 A  E  D  L  W  L  S  P  L  T  M  E  D  L  V  C acagcttccaggtggccagagggatggagttcctggcttcccgaaagtg
 Y  S  F  Q  V  A  R  G  M  E  F  L  A  S  R  K  C catccgcagagacctggctgctcggaacattctgctgtcggaaagcgac
 I  R  R  D  L  A  A  R  N  I  L  L  S  E  S  D gtggtgaagatctgtgactttggccttgcccgg
 V  V  K  I  C  D  F  G  L  A  R
(Nucleotide sequence - SEQ ID NO: 69; protein
sequence - SEQ ID NO: 70).
```

Familial Alzheimer's disease—isoleucine to valine mutation at residue 143 in presenilin1 (A>G mutation):

```
gataccgagactgtgggccagagagccctgcactcaattctgaatgctg
 D  T  E  T  V  G  Q  R  A  L  H  S  I  L  N  A ccatcatgatcagtgtcgttgttgtcatgactatcctcctggtggttct
 A  I  M  I  S  V  V  V  V  M  T  I  L  L  V  V  L gtataaatacaggtgctataaggtcatccatgcctggcttattatatca
 Y  K  Y  R  C  Y  K  V  I  H  A  W  L  I  I  S tctctattgttgctgttctttttttcattcatt
 S  L  L  L  L  F  F  F  S  F  I
(Nucleotide sequence - SEQ ID NO: 71; protein
sequence - SEQ ID NO: 72).
```

Prion disease—methionine to valine mutation at residue 129 in prion protein (A>G mutation):

```
aagccgagtaagccaaaaaccaacatgaagcacatggctggtgctgcag
 K  P  S  K  P  K  T  N  M  K  H  M  A  G  A  A cagctggggcagtggtggggggccttggcggctacgtgctgggaagtgc
 A  A  G  A  V  V  G  G  L  G  G  Y  V  L  G  S  A catgagcaggcccatcatacatttcggcagtgactatgaggaccgttac
 M  S  R  P  I  I  H  F  G  S  D  Y  E  D  R  Y tatcgtgaaaacatgcaccgttaccccaaccaa
 Y  R  E  N  M  H  R  Y  P  N  Q
(Nucleotide sequence - SEQ ID NO: 73; protein
sequence - SEQ ID NO: 74).
```

Chronic infantile neurologic cutaneous articular syndrome (CINCA)—Tyrosine to Cysteine mutation at residue 570 in cryopyrin (A>G mutation):

```
cttcccagccgagacgtgacagtccttctggaaaactatggcaaattcg
 L  P  S  R  D  V  T  V  L  L  E  N  Y  G  K  F aaaaggggtgtttgatttttgttgtacgtttcctcttttggcctggtaaa
 E  K  G  C  L  I  F  V  V  R  F  L  F  G  L  V  N ccaggagaggacctcctacttg
 Q  E  R  T  S  Y  L
(Nucleotide sequence - SEQ ID NO: 75; protein
sequence - SEQ ID NO: 76).
```

Desmin-related myopathy (DRM)—arginine to glycine mutation at residue 120 in αB crystallin (A>G mutation):

```
gtgaagcacttctccccagaggaactcaaagttaaggtgttgggagatg
 V   K   H   F   S   P   E   E   L   K   V   K   V   L   G   D tgattgaggtgcatggaaaacatgaagagcgccaggatgaacatggttt
 V   I   E   V   H   G   K   H   E   E   R   Q   D   E   H   G   F catctccagggagttccacgggaaataccggatcccagctgatgtagac
 I   S   R   E   F   H   G   K   Y   R   I   P   A   D   V   D cctctcaccattacttcatccctgtcatctgat
 P   L   T   I   T   S   S   L   S   S   D
(Nucleotide sequence - SEQ ID NO: 77; protein
sequence - SEQ ID NO: 78).
```

Beta-thalassemia-one example is leucine to proline mutation at residue 115 in Hemoglobin B.

```
gagctgcactgtgacaagctgcacgtggatcctgagaacttcaggctcc
 E   L   H   C   D   K   L   H   V   D   P   E   N   F   R   L tgggcaacgtgctggtctgtgtgccggcccatcactttggcaaagaatt
 L   G   N   V   L   V   C   V   P   A   H   H   F   G   K   E   F cacccaccagtgcaggctgcctatcagaaagtggtggctggtgtggct
 T   P   P   V   Q   A   A   Y   Q   K   V   V   A   G   V   A aatgccctggcccacaagtatcactaagctcgc
 N   A   L   A   H   K   Y   H   -   A   R
(Nucleotide sequence - SEQ ID NO: 79; protein
sequence - SEQ ID NO: 80).
```

It is to be understood that the sequences provided above are exemplary and not meant to be limiting the scope of the instant disclosure. Additional suitable sequences of point mutations that are associated with disease and amenable to correction by Cas9:nucleic acid-editing enzyme/domain fusion proteins as well as suitable guide RNA sequences will be apparent to those of skill in the art based on this disclosure.

Reporter Systems

Some aspects of this disclosure provide a reporter system that can be used for detecting deaminase activity of the fusion proteins described herein. In some embodiments, the reporter system is a luciferase-based assay in which deaminase activity leads to expression of luciferase. To minimize the impact of potential substrate promiscuity of the deaminase domain (e.g., the AID domain), the number of residues that could unintentionally be targeted for deamination (e.g., off-target C residues that could potentially reside on ssDNA within the reporter system) is minimized. In some embodiments, an intended target residue is be located in an ACG mutated start codon of the luciferase gene that is unable to initiate translation. Desired deaminase activity results in a ACG>AUG modification, thus enabling translation of luciferase and detection and quantification of the deaminase activity.

In some embodiments, in order to minimize single-stranded C residues, a leader sequence is inserted between the mutated start codon and the beginning of the luciferase gene which consists of a stretch of Lys (AAA), Asn (AAT), Leu (TTA), Ile (ATT, ATA), Tyr (TAT), or Phe (TTT) residues. The resulting mutants can be tested to ensure that the leader sequence does not adversely affect luciferase expression or activity. Background luciferase activity with the mutated start codon can be determined as well.

Figure 3:
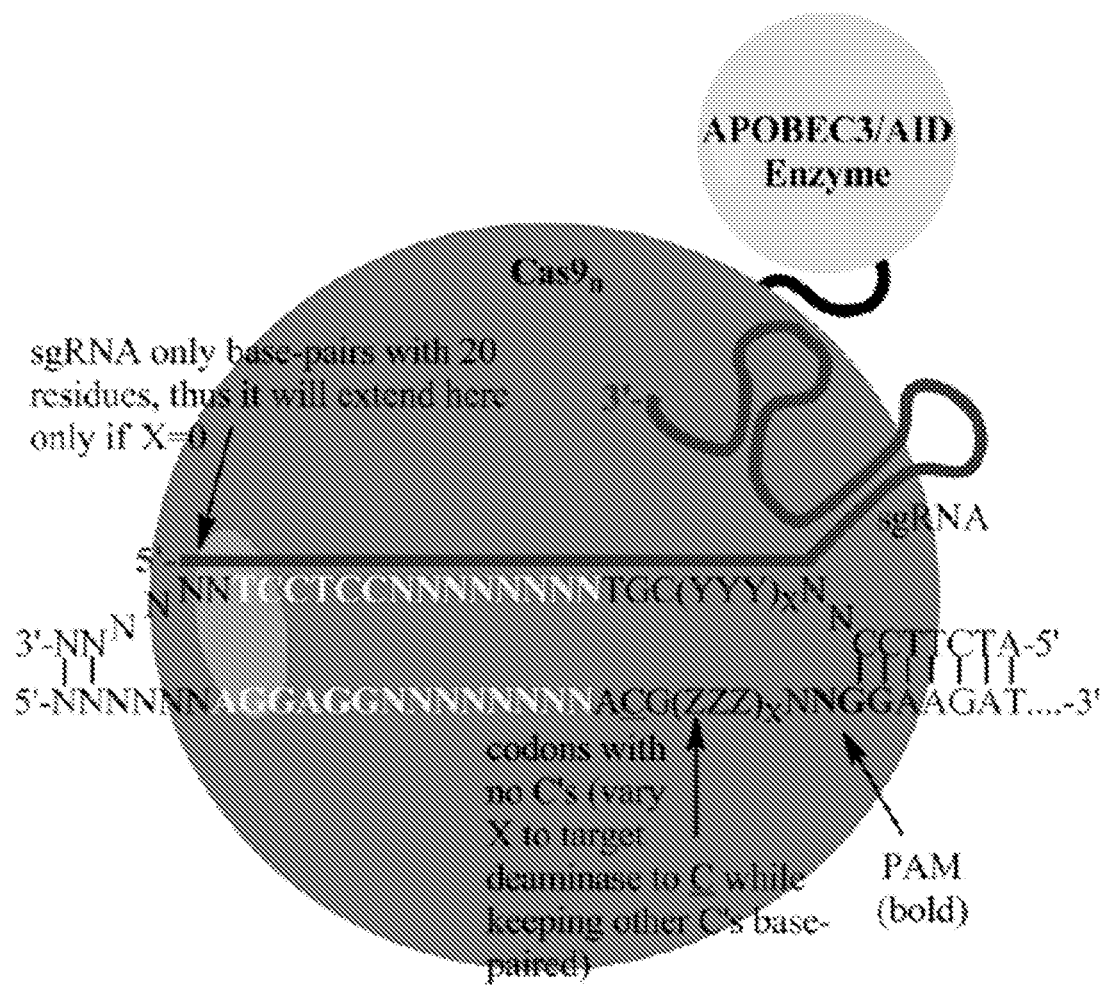
FIG. 3. Design of luciferase-based reporter assay. The sgRNA will be varied to target numerous sequences that correspond to regions prior to and including the luciferase gene in order to target the mutated start codon (C residue underlined). A "buffer" region will be added between the start codon and the luciferase gene to include codons of only A's and T's (shown as $(ZZZ)_x$). The Shine-Dalgarno sequence is indicated. In some embodiments, it is preferable to keep all C's base-paired to prevent off-target effects.

The reporter system can be used to test many different sgRNAs, e.g., in order to determine which residue(s) with respect to the target DNA sequence the respective deaminase (e.g., AID enzyme) will target (FIG. 3). Because the size of the Cas9-DNA bubble is not known, sgRNAs that target non-template strand can also be tested in order to assess off-target effects of a specific Cas9 deaminase fusion protein. In some embodiments, such sgRNAs are designed such that the mutated start codon will not be base-paired with the sgRNA.

Once fusion proteins that are capable of programmable site-specific C to U modifications have been identified, their activities can be further characterized. The data from the luciferase assays can, for example, be integrated into heat maps that describe which nucleotides, with respect to the sgRNA target DNA, are being targeted for deamination by a specific fusion protein. In some embodiments, the position that results in the highest activity in the luciferase assay for each fusion is considered the "target" position, while all others are considered off-target positions.

In some embodiments, Cas9 fusions with various APOBEC3 enzymes, or deaminase domains thereof, are provided. In some embodiments, Cas9 fusion proteins with other nucleic acid editing enzymes or catalytic domains are provided, including, for example, ssRNA editing enzymes, such as the cytidine deaminases APOBEC1 and ACF1/ASF, as well as the ADAT family of adenosine deaminases,[38] that can be used for ssDNA editing activity when fused to Cas9. The activity of such fusion proteins can be tested using the same reporter systems and assays described above.

In some embodiments, a reporter system is provided herein that includes a reporter gene comprising a deactivated start codon, e.g., a mutation on the template strand from 3'-TAC-5' to 3'-CAC-5'. Upon successful deamination of the target C, the corresponding mRNA will be transcribed as 5'-AUG-3' instead of 5'-GUG-3', enabling the translation of the reporter gene. Suitable reporter genes will be apparent to those of skill in the art.

The description of exemplary embodiments of the reporter systems above is provided for illustration purposes only and not meant to be limiting. Additional reporter systems, e.g., variations of the exemplary systems described in detail above, are also embraced by this disclosure.

EXAMPLES

Example 1: Fusion Proteins

Exemplary Cas9:deaminase fusion proteins are provided below:

```
Cas9: human AID fusion (C-terminal)
                                            (SEQ ID NO: 30)
MDSLLMNRRKFLYQFKNVRWAKGRRETYLCDKKYSIGLAIGTNSVGWAVITDEYKVPSKKFK

VLGNTDRHSIKKNLIGALLFDSGETAEATRLKRTARRRYTRRKNRICYLQEIFSNEMAKVDD

SFFHRLEESFLVEEDKKHERHPIFGNIVDEVAYHEKYPTIYHLRKKLVDSTDKADLRLIYLA

LAHMIKFRGHFLIEGDLNPDNSDVDKLFIQLVQTYNQLFEENPINASGVDAKAILSARLSKS
```

-continued

RRLENLIAQLPGEKKNGLFGNLIALSLGLTPNFKSNFDLAEDAKLQLSKDTYDDDLDNLLAQ

IGDQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAWMTR

KSEETITPWNFEEVVDKGASAQSFIERMTNFDKNLPNEKVLPKHSLLYEYFTVYNELTKVKY

VTEGMRKPAFLSGEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAHLFDDKVMKQLKR

RRYTGWGRLSRKLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARENQTTQKGQKNS

RERMKRIEEGIKELGSQILKEHPVENTQLQNEKLYLYYLQNGRDMYVDQELDINRLSDYDVD

AIVPQSFLKDDSIDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIREVKVITLKSKLV

SDFRKDFQFYKVREINNYHHAHDAYLNAVVGTALIKKYPKLESEFVYGDYKVYDVRKMIAKS

EQEIGKATAKYFFYSNIMNFFKTEITLANGEIRKRPLIETNGETGEIVWDKGRDFATVRKVL

SMPQVNIVKKTEVQTGGFSKESILPKRNSDKLIARKKDWDPKKYGGFDSPTVAYSVLVVAKV

EKGKSKKLKSVKELLGITIMERSSFEKNPIDFLEAKGYKEVKKDLIIKLPKYSLFELENGRK

RMLASAGELQKGNELALPSKYVNFLYLASHYEKLKGSPEDNEQKQLFVEQHKHYLDEIIEQI

SEFSKRVILADANLDKVLSAYNKHRDKPIREQAENIIHLFTLTNLGAPAAFKYFDTTIDRKR

YTSTKEVLDATLIHQSITGLYETRIDLSQLGGDGGGGSGGGGSGGGGSYVVKRRDSATSFSL

DFGYLRNKNGCHVELLFLRYISDWDLDPGRCYRVTWFTSWSPCYDCARHVADFLRGNPNLSL

RIFTARLYFCEDRKAEPEGLRRLHRAGVQIAIMTFKDYFYCWNTFVENHERTFKAWEGLHEN

SVRLSRQLRRILLP<u>LYEVDDLRDAFRTLGL</u>
(underline: nuclear localization signal; double underline:
nuclear export signal, bold: linker
sequence)

Cas9: human AID fusion (N-terminal)
(SEQ ID NO: 31)

<u>MDSLLMNRRKFLYQFKNVRWAKGRRETYLC</u>YVVKRRDSATSFSLDFGYLRNKNGCHVELLFL

RYISDWDLDPGRCYRVTWFTSWSPCYDCARHVADFLRGNPNLSLRIFTARLYFCEDRKAEPE

GLRRLHRAGVQIAIMTFKDYFYCWNTFVENHERTFKAWEGLHENSVRLSRQLRRILLPGGGG

SGGGGSGGGGSDKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEGDLNP

DNSDVDKLFIQLVQTYNQLFEENPINASGVDAKAILSARLSKSRRLENLIAQLPGEKKNGLF

GNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGY

IDGGASQEEFYKFIKPILEKMDGTEELLVKLNREDLLRKQRTFDNGSIPHQIHLGELHAILR

RQEDFYPFLKDNREKIEKILTFRIPYYVGPLARGNSRFAWMTRKSEETITPWNFEEVVDKGA

SAQSFIERMTNFDKNLPNEKVLPKHSLLYEYFTVYNELTKVKYVTEGMRKPAFLSGEQKKAI

VDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRD

KQSGKTILDFLKSDGFANRNFMQLIHDDSLTFKEDIQKAQVSGQGDSLHEHIANLAGSPAIK

KGILQTVKVVDELVKVMGRHKPENIVIEMARENQTTQKGQKNSRERMKRIEEGIKELGSQIL

-continued

KEHPVENTQLQNEKLYLYYLQNGRDMYVDQELDINRLSDYDVDAIVPQSFLKDDSIDNKVLT

RSDKNRGKSDNVPSEEVVKKMKNYWRQLLNAKLITQRKFDNLTKAERGGLSELDKAGFIKRQ

LVETRQITKHVAQILDSRMNTKYDENDKLIREVKVITLKSKLVSDFRKDFQFYKVREINNYH

HAHDAYLNAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQTGGFS

KESILPKRNSDKLIARKKDWDPKKYGGFDSPTVAYSVLVVAKVEKGKSKKLKSVKELLGITI

MERSSFEKNPIDFLEAKGYKEVKKDLIIKLPKYSLFELENGRKRMLASAGELQKGNELALPS

KYVNFLYLASHYEKLKGSPEDNEQKQLFVEQHKHYLDEIIEQISEFSKRVILADANLDKVLS

AYNKHRDKPIREQAENIIHLFTLTNLGAPAAFKYFDTTIDRKRYTSTKEVLDATLIHQSITG

LYETRIDLSQLGGD
(underline: nuclear localization signal; bold: linker
sequence)

Cas9: mouse AID fusion (C-terminal)
(SEQ ID NO: 32)

<u>MDSLLMNRRKFLYQFKNVRWAKGRRETYLC</u>DKKYSIGLAIGTNSVGWAVITDEYKVPSKKFK

VLGNTDRHSIKKNLIGALLFDSGETAEATRLKRTARRRYTRRKNRICYLQEIFSNEMAKVDD

SFFHRLEESFLVEEDKKHERHPIFGNIVDEVAYHEKYPTIYHLRKKLVDSTDKADLRLIYLA

LAHMIKFRGHFLIEGDLNPDNSDVDKLFIQLVQTYNQLFEENPINASGVDAKAILSARLSKS

RRLENLIAQLPGEKKNGLFGNLIALSLGLTPNFKSNFDLAEDAKLQLSKDTYDDDLDNLLAQ

IGDQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAWMTR

KSEETITPWNFEEVVDKGASAQSFIERMTNFDKNLPNEKVLPKHSLLYEYFTVYNELTKVKY

VTEGMRKPAFLSGEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAHLFDDKVMKQLKR

RRYTGWGRLSRKLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARENQTTQKGQKNS

RERMKRIEEGIKELGSQILKEHPVENTQLQNEKLYLYYLQNGRDMYVDQELDINRLSDYDVD

AIVPQSFLKDDSIDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIREVKVITLKSKLV

SDFRKDFQFYKVREINNYHHAHDAYLNAVVGTALIKKYPKLESEFVYGDYKVYDVRKMIAKS

EQEIGKATAKYFFYSNIMNFFKTEITLANGEIRKRPLIETNGETGEIVWDKGRDFATVRKVL

SMPQVNIVKKTEVQTGGFSKESILPKRNSDKLIARKKDWDPKKYGGFDSPTVAYSVLVVAKV

EKGKSKKLKSVKELLGITIMERSSFEKNPIDFLEAKGYKEVKKDLIIKLPKYSLFELENGRK

RMLASAGELQKGNELALPSKYVNFLYLASHYEKLKGSPEDNEQKQLFVEQHKHYLDEIIEQI

SEFSKRVILADANLDKVLSAYNKHRDKPIREQAENIIHLFTLTNLGAPAAFKYFDTTIDRKR

YTSTKEVLDATLIHQSITGLYETRIDLSQLGGDGGGGSGGGGSGGGGSYVVKRRDSATSCSL

DFGHLRNKSGCHVELLFLRYISDWDLDPGRCYRVTWFTSWSPCYDCARHVAEFLRWNPNLSL

RIFTARLYFCEDRKAEPEGLRRLHRAGVQIGIMTFKDYFYCWNTFVENRERTFKAWEGLHEN

SVRLTRQLRRILLP<u><u>LYEVDDLRDAFRMLGF</u></u>
(underline: nuclear localization signal; bod: linker
sequence; double underline: nuclear export signal)

-continued

Cas9: human APOBEC-3G fusion (N-terminal)
(SEQ ID NO: 33)
<u>SPKKKRKVEAS</u>MELKYHPEMRFFHWFSKWRKLHRDQEYEVTWYISWSPCTKCTRDMATFLAE

DPKVTLTIFVARLYYFWDPDYQEALRSLCQKRDGPRATMKIMNYDEFQHCWSKFVYSQRELF

EPWNNLPKYYILLHIMLGEILRHSMDPPTFTFNFNNEPWVRGRHETYLCYEVERMHNDTWVL

LNQRRGFLCNQAPHKHGFLEGRHAELCFLDVIPFWKLDLDQDYRVTCFTSWSPCFSCAQEMA

KFISKNKHVSLCIFTARIYDDQGRCQEGLRTLAEAGAKISIMTYSEFKHCWDTFVDHQGCPF

QPWDGLDEHSQDLSGRLRAILQNQENSPKKKRKVEASSPKKKRKVEASKKYSIGLAIGTNSV

GWAVITDEYKVPSKKFKVLGNTDRHSIKKNLIGALLFDSGETAEATRLKRTARRRYTRRKNR

ICYLQEIFSNEMAKVDDSFFHRLEESFLVEEDKKHERHPIFGNIVDEVAYHEKYPTIYHLRK

KLVDSTDKADLRLIYLALAHMIKFRGHFLIEGDLNPDNSDVDKLFIQLVQTYNQLFEENPIN

ASGVDAKAILSARLSKSRRLENLIAQLPGEKKNGLFGNLIALSLGLTPNFKSNFDLAEDAKL

QLSKDTYDDDLDNLLAQIGDQYADLFLAAKNLSDAILLSDILRVNTEITKAPLSASMIKRYD

EHHQDLTLLKALVRQQLPEKYKEIFFDQSKNGYAGYIDGGASQEEFYKFIKPILEKMDGTEE

LLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHS

LLYEYFTVYNELTKVKYVTEGMRKPAFLSGEQKKAIVDLLFKTNRKVTVKQLKEDYFKKIEC

FDSVEISGVEDRFNASLGTYHDLLKIIKDKDFLDNEENEDILEDIVLTLTLFEDREMIEERL

KTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIV

IEMARENQTTQKGQKNSRERMKRIEEGIKELGSQILKEHPVENTQLQNEKLYLYYLQNGRDM

YVDQELDINRLSDYDVDAIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDEN

DKLIREVKVITLKSKLVSDFRKDFQFYKVREINNYHHAHDAYLNAVVGTALIKKYPKLESEF

VYGDYKVYDVRKMIAKSEQEIGKATAKYFFYSNIMNFFKTEITLANGEIRKRPLIETNGETG

EIVWDKGRDFATVRKVLSMPQVNIVKKTEVQTGGFSKESILPKRNSDKLIARKKDWDPKKYG

GFDSPTVAYSVLVVAKVEKGKSKKLKSVKELLGITIMERSSFEKNPIDFLEAKGYKEVKKDL

IIKLPKYSLFELENGRKRMLASAGELQKGNELALPSKYVNFLYLASHYEKLKGSPEDNEQKQ

LFVEQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD
(underline: nuclear localization signal; bold: linker
(1 NLS), Cas9: human APOBEC-1 fusion (N-terminal)
(SEQ ID NO: 92)
<u>SPKKKRKVEAS</u>MTSEKGPSTGDPTLRRRIEPWEFDVFYDPRELRKEACLLYEIKWGMSRKIW

RSSGKNTTNHVEVNFIKKFTSERDFHPSMSCSITWFLSWSPCWECSQAIREFLSRHPGVTLV

IYVARLFWHMDQQNRQGLRDLVNSGVTIQIMRASEYYHCWRNFVNYPPGDEAHWPQYPPLWM

MLYALELHCIILSLPPCLKISRRWQNHLTFFRLHLQNCHYQTIPPHILLATGLIHPSVAWRS

PKKKRKVEASSPKKKRKVEASDKKYSIGLAIGTNSVGWAVITDEYKVPSKKFKVLGNTDRHS

IKKNLIGALLFDSGETAEATRLKRTARRRYTRRKNRICYLQEIFSNEMAKVDDSFFHRLEES

FLVEEDKKHERHPIFGNIVDEVAYHEKYPTIYHLRKKLVDSTDKADLRLIYLALAHMIKFRG

HFLIEGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQYADLF

LAAKNLSDAILLSDILRVNTEITKAPLSASMIKRYDEHHQDLTLLKALVRQQLPEKYKEIFF

-continued

DQSKNGYAGYIDGGASQEEFYKFIKPILEKMDGTEELLVKLNREDLLRKQRTFDNGSIPHQI

HLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRL

SRKLINGIRDKQSGKTILDFLKSDGFANRNFMQLIHDDSLTFKEDIQKAQVSGQGDSLHEHI

ANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDAIVPQSFLK

DDSIDNKVLTRSDKNRGKSDNVPSEEVVKKMKNYWRQLLNAKLITQRKFDNLTKAERGGLSE

LDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATA

KYFFYSNIMNFFKTEITLANGEIRKRPLIETNGETGEIVWDKGRDFATVRKVLSMPQVNIVK

KTEVQTGGFSKESILPKRNSDKLIARKKDWDPKKYGGFDSPTVAYSVLVVAKVEKGKSKKLK

SVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEVLD

ATLIHQSITGLYETRIDLSQLGGD
(underline: nuclear localization signal; bold: linker
(1 NLS), Cas9: human ADAT1 fusion (N-terminal)
(SEQ ID NO: 35)
<u>MDSLLMNRRKFLYQFKNVRWAKGRRETYLC</u>SMGTGTKCIGQSKMRKNGDILNDSHAEVIARR

SFQRYLLHQLQLAATLKEDSIFVPGTQKGVWKLRRDLIFVFFSSHTPCGDASIIPMLEFEDQ

PCCPVFRNWAHNSSVEASSNLEAPGNERKCEDPDSPVTKKMRLEPGTAAREVTNGAAHHQSF

GKQKSGPISPGIHSCDLTVEGLATVTRIAPGSAKVIDVYRTGAKCVPGEAGDSGKPGAAFHQ

VGLLRVKPGRGDRTRSMSCSDKMARWNVLGCQGALLMHLLEEPIYLSAVVIGKCPYSQEAMQ

RALIGRCQNVSALPKGFGVQELKILQSDLLFEQSRSAVQAKRADSPGRLVPCGAAISWSAVP

EQPLDVTANGFPQGTTKKTIGSLQARSQISKVELFRSFQKLLSRIARDKWPHSLRVQKLDTY

QEYKEAASSYQEAWSTLRKQVFGSWIRNPPDYHQFGGGGSGGGGSGGGGSDKKYSIGLAIGT

NSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYH

LRKKLVDSTDKADLRLIYLALAHMIKFRGHFLIEGDLNPDNSDVDKLFIQLVQTYNQLFEEN

PINASGVDAKAILSARLSKSRRLENLIAQLPGEKKNGLFGNLIALSLGLTPNFKSNFDLAED

AKLQLSKDTYDDDLDNLLAQIGDQYADLFLAAKNLSDAILLSDILRVNTEITKAPLSASMIK

RYDEHHQDLTLLKALVRQQLPEKYKEIFFDQSKNGYAGYIDGGASQEEFYKFIKPILEKMDG

TEELLVKLNREDLLRKQRTFDNGSIPHQIHLGELHAILRRQEDFYPFLKDNREKIEKILTFR

IPYYVGPLARGNSRFAWMTRKSEETITPWNFEEVVDKGASAQSFIERMTNFDKNLPNEKVLP

KHSLLYEYFTVYNELTKVKYVTEGMRKPAFLSGEQKKAIVDLLFKTNRKVTVKQLKEDYFKK

IECFDSVEISGVEDRFNASLGTYHDLLKIIKDKDFLDNEENEDILEDIVLTLTLFEDREMIE

ERLKTYAHLFDDKVMKQLKRRRYTGWGRLSRKLINGIRDKQSGKTILDFLKSDGFANRNFMQ

LIHDDSLTFKEDIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQNEKLYLYYLQNG

-continued

RDMYVDQELDINRLSDYDVDAIVPQSFLKDDSIDNKVLTRSDKNRGKSDNVPSEEVVKKMKN

YWRQLLNAKLITQRKFDNLTKAERGGLSELDKAGFIKRQLVETRQITKHVAQILDSRMNTKY

DENDKLIREVKVITLKSKLVSDFRKDFQFYKVREINNYHHAHDAYLNAVVGTALIKKYPKLE

SEFVYGDYKVYDVRKMIAKSEQEIGKATAKYFFYSNIMNFFKTEITLANGEIRKRPLIETNG

ETGEIVWDKGRDFATVRKVLSMPQVNIVKKTEVQTGGFSKESILPKRNSDKLIARKKDWDPK

KYGGFDSPTVAYSVLVVAKVEKGKSKKLKSVKELLGITIMERSSFEKNPIDFLEAKGYKEVK

KDLIIKLPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHLFTL

TNLGAPAAFKYFDTTIDRKRYTSTKEVLDATLIHQSITGLYETRIDLSQLGGD
(underline: nuclear localization signal; bold: linker
sequence)

Cas9: human ADAT1 fusion (-terminal)

(SEQ ID NO: 36)

<u>MDSLLMNRRKFLYQFKNVRWAKGRRETYLC</u>DKKYSIGLAIGTNSVGWAVITDEYKVPSKKFK

VLGNTDRHSIKKNLIGALLFDSGETAEATRLKRTARRRYTRRKNRICYLQEIFSNEMAKVDD

SFFHRLEESFLVEEDKKHERHPIFGNIVDEVAYHEKYPTIYHLRKKLVDSTDKADLRLIYLA

LAHMIKFRGHFLIEGDLNPDNSDVDKLFIQLVQTYNQLFEENPINASGVDAKAILSARLSKS

RRLENLIAQLPGEKKNGLFGNLIALSLGLTPNFKSNFDLAEDAKLQLSKDTYDDDLDNLLAQ

IGDQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAWMTR

KSEETITPWNFEEVVDKGASAQSFIERMTNFDKNLPNEKVLPKHSLLYEYFTVYNELTKVKY

VTEGMRKPAFLSGEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAHLFDDKVMKQLKR

RRYTGWGRLSRKLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARENQTTQKGQKNS

RERMKRIEEGIKELGSQILKEHPVENTQLQNEKLYLYYLQNGRDMYVDQELDINRLSDYDVD

AIVPQSFLKDDSIDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIREVKVITLKSKLV

SDFRKDFQFYKVREINNYHHAHDAYLNAVVGTALIKKYPKLESEFVYGDYKVYDVRKMIAKS

EQEIGKATAKYFFYSNIMNFFKTEITLANGEIRKRPLIETNGETGEIVWDKGRDFATVRKVL

SMPQVNIVKKTEVQTGGFSKESILPKRNSDKLIARKKDWDPKKYGGFDSPTVAYSVLVVAKV

EKGKSKKLKSVKELLGITIMERSSFEKNPIDFLEAKGYKEVKKDLIIKLPKYSLFELENGRK

RMLASAGELQKGNELALPSKYVNFLYLASHYEKLKGSPEDNEQKQLFVEQHKHYLDEIIEQI

SEFSKRVILADANLDKVLSAYNKHRDKPIREQAENIIHLFTLTNLGAPAAFKYFDTTIDRKR

YTSTKEVLDATLIHQSITGLYETRIDLSQLGGDGGGGSGGGGS*SMGTGTKCIGQSKMRKNGD*

*ILNDSHAEVIARRSFQRYLLHQLQLAATLKEDSIFVPGTQKGVWKLRRDLIFVFFSSHTPCG*

*DASIIPMLEFEDQPCCPVFRNWAHNSSVEASSNLEAPGNERKCEDPDSPVTKKMRLEPGTAA*

*REVTNGAAHHQSFGKQKSGPISPGIHSCDLTVEGLATVTRIAPGSAKVIDVYRTGAKCVPGE*

*AGDSGKPGAAFHQVGLLRVKPGRGDRTRSMSCSDKMARWNVLGCQGALLMHLLEEPIYLSAV*

*VIGKCPYSQEAMQRALIGRCQNVSALPKGFGVQELKILQSDLLFEQSRSAVQAKRADSPGRL*

```
-continued
VPCGAAISWSAVPEQPLDVTANGFPQGTTKKTIGSLQARSQISKVELFRSFQKLLSRIARDK

WPHSLRVQKLDTYQEYKEAASSYQEAWSTLRKQVFGSWIRNPPDYHQF
(underline: nuclear localization signal; bold: linker
sequence)
```

Example 2: Correction of a PI3K Point Mutation by a Cas9 Fusion Protein

An A3140G point mutation in exon 20 of the PI3KCA gene, resulting in an H1047R amino acid substitution in the PI3K protein is corrected by contacting a nucleic acid encoding the mutant protein with a Cas9:AID (SEQ ID NO: 30) or a Cas9:APOBEC1 (SEQ ID NO: 92) fusion protein and an appropriately designed sgRNA targeting the fusion protein to the mutation site in the encoding PI3KCA gene. The A3140G point mutation is confirmed via genomic PCR of the respective exon 20 sequence, e.g., generation of a PCR amplicon of nucleotides 3000-3250, and subsequent sequencing of the PCT amplicon.

Cells expressing a mutant PI3K protein comprising an A3140G point mutation in exon 20 are contacted with an expression construct encoding the Cas9:AID (SEQ ID NO: 30) or a Cas9:APOBEC1 (SEQ ID NO: 92) fusion protein and an appropriately designed sgRNA targeting the fusion protein to the mutation site in the antisense strand of the encoding PI3KCA gene. The sgRNA is of the sequence

```
                                          (SEQ ID NO: 81)
5'-
aucggaauctauuuugacucguuuuagagcuagaaauagcaaguuaaaau aaaggcuaguccguuaucaacuugaaaaaguggcaccgagucggugcuuu uu 3';

(SEQ ID NO: 82)
5'-
ucggaaucuauuuugacucgguuuuagagcuagaaauagcaaguuaaaau aaaggcuaguccguuaucaacuugaaaaaguggcaccgagucggugcuuu uu-3';

(SEQ ID NO: 83)
5'-
cuuagauaaaacugagcaagguuuuagagcuagaaauagcaaguuaaaau aaaggcuaguccguuaucaacuugaaaaaguggcaccgagucggugcuuu uu-3';

(SEQ ID NO: 84)
5'-
aucuauuuugacucguucucguuuuagagcuagaaauagcaaguuaaaau aaaggcuaguccguuaucaacuugaaaaaguggcaccgagucggugcuuu uu-3';

(SEQ ID NO: 85)
5'-
uaaaacugagcaagaggcuuguuuuagagcuagaaauagcaaguuaaaau aaaggcuaguccguuaucaacuugaaaaaguggcaccgagucggugcuuu uu-3';

(SEQ ID NO: 86)
5'-
ugguggcuggacaacaaaaaguuuuagagcuagaaauagcaaguuaaaau aaaggcuaguccguuaucaacuugaaaaaguggcaccgagucggugcuuu uu-3';

(SEQ ID NO: 87)
5'-
gcuggacaacaaaaauggauguuuuagagcuagaaauagcaaguuaaaau aaaggcuaguccguuaucaacuugaaaaaguggcaccgagucggugcuuu uu-3';

or (SEQ ID NO: 88)
5'-
guguuaauuugucguacguaguuuuagagcuagaaauagcaaguuaaaau aaaggcuaguccguuaucaacuugaaaaaguggcaccgagucggugcuuu uu.
```

The cytosine deaminase activity of the Cas9:AID or the Cas9:APOBEC1 fusion protein results in deamination of the cytosine that is base-paired with the mutant G3140 to uridine. After one round of replication, the wild type A3140 is restored. Genomic DNA of the treated cells is extracted and a PCR amplicon of nucleotides 3000-3250 is amplified with suitable PCR primers. The correction of the A3140G point mutation after treatment of the cells with the fusion protein is confirmed by sequencing the PCR amplicon.

Example 3: Correction of a Presenilin 1 Point Mutation by a Cas9 Fusion Protein An A→G point mutation in codon 143 of the presenilin1 (PSEN1) gene, resulting in an I143V amino acid substitution in the PSEN1 protein is corrected by contacting a nucleic acid encoding the mutant PSEN1 protein with a Cas9:AID (SEQ ID NO: 30) or a Cas9:APOBEC1 (SEQ ID NO: 92) fusion protein and an appropriately designed sgRNA targeting the fusion protein to the mutation site in the encoding PSEN1 gene. See, e.g., Gallo et. al., *J. Alzheimer's disease.* 2011; 25: 425-431 for a description of an exemplary PSEN1 I143V mutation associated with familial Alzheimer's Disease. The A→G point mutation is confirmed via genomic PCR of the respective PSEN1 sequence, e.g., generation of a PCR amplicon of about 100-250 nucleotides around exon 143, and subsequent sequencing of the PCT amplicon.

Cells expressing the mutant PSEN1 protein are contacted with an expression construct encoding the Cas9:AID (SEQ ID NO: 30) or a Cas9:APOBEC1 (SEQ ID NO: 92) fusion protein and an appropriately designed sgRNA targeting the fusion protein to the mutation site in the antisense strand of the encoding PSEN1 gene. The cytosine deaminase activity of the Cas9:AID or the Cas9:APOBEC1 fusion protein results in deamination of the cytosine that is base-paired with the mutant G in codon 143 to uridine. After one round of replication, the wild type A is restored. Genomic DNA of the treated cells is extracted and a PCR amplicon of 100-250 nucleotides is amplified with suitable PCR primers. The correction of the A→G point mutation after treatment of the cells with the fusion protein is confirmed by sequencing the PCR amplicon.

Example 4: Correction of an Ac-Antitrypsin Point Mutation by a Cas9 Fusion Protein A T→C point mutation in codon 55 of the $\alpha_1$-antitrypsin gene, resulting in an L55P amino acid substitution in the $\alpha_1$-antitrypsin protein is corrected by contacting a nucleic acid encoding the mutant $\alpha_1$-antitrypsin protein with a Cas9:ADAT1 fusion protein (SEQ ID NO: 35 or 36) and an appropriately designed sgRNA targeting the fusion protein to the mutation site in the encoding $\alpha_1$-antitrypsin gene. See, e.g., Poller et al., *Genomics*. 1993; 17: 740-743 for a more detailed description of an exemplary codon 55 T→C mutation associated with chronic obstructive pulmonary disease (COPD). The T→C point mutation is confirmed via genomic PCR of the respective $\alpha_1$-antitrypsin sequence encoding codon 55, e.g., generation of a PCR amplicon of about 100-250 nucleotides, and subsequent sequencing of the PCT amplicon.

Cells expressing the mutant $\alpha_1$-antitrypsin protein are contacted with an expression construct encoding the Cas9: AID (SEQ ID NO: 30) or a Cas9:APOBEC1 (SEQ ID NO: 92) fusion protein and an appropriately designed sgRNA targeting the fusion protein to the mutated nucleotide in codon 55 on the sense strand in the encoding $\alpha_1$-antitrypsin gene. The cytosine deaminase activity of the Cas9:ADAT1 fusion protein results in deamination of the mutant cytosine to uridine thus correcting the mutation. Genomic DNA of the treated cells is extracted and a PCR amplicon of 100-250 nucleotides is amplified with suitable PCR primers. The correction of the T→C point mutation in codon 55 of the $\alpha_1$-antitrypsin gene after treatment of the cells with the fusion protein is confirmed by sequencing the PCR amplicon

Example 5: Correction of a Von Willebrand Factor Point Mutation by a Cas9 Fusion Protein A T→C point mutation in codon 509 of the von Willebrand factor gene, resulting in a C509A amino acid substitution in the von Willebrand factor protein is corrected by contacting a nucleic acid encoding the mutant von Willebrand factor protein with a Cas9:ADAT1 fusion protein (SEQ ID NO: 35 or 36) and an appropriately designed sgRNA targeting the fusion protein to the mutation site in the sense strand of the encoding von Willebrand factor gene. See, e.g., Lavergne et al., *Br. J. Haematol*. 1992; 82: 66-7, for a description of an exemplary von Willebrand factor C509A mutation associated with von Willebrand disease (vWD). The T→C point mutation is confirmed via genomic PCR of the respective von Willebrand factor genomic sequence, e.g., generation of a PCR amplicon of about 100-250 nucleotides around exon 509, and subsequent sequencing of the PCT amplicon.

Cells expressing the mutant von Willebrand factor protein are contacted with an expression construct encoding the Cas9:ADAT1 fusion protein (SEQ ID NO: 35 or 36) and an appropriately designed sgRNA targeting the fusion protein to the mutation site in the sense strand of the encoding von Willebrand factor gene. The cytosine deaminase activity of the Cas9:ADAT1 fusion protein results in deamination of the mutant cytosine in codon 509 to uridine, thus correcting the mutation. Genomic DNA of the treated cells is extracted and a PCR amplicon of 100-250 nucleotides is amplified with suitable PCR primers. The correction of the T→C point mutation in codon 509 of the von Willebrand factor gene after treatment of the cells with the fusion protein is confirmed by sequencing the PCR amplicon.

Example 6: Correction of a Caspase 9 Point Mutation by a Cas9 Fusion Protein-Neuroblastoma A T→C point mutation in codon 197 of the Caspase-9 gene, resulting in an L197P amino acid substitution in the Caspase-9 protein is corrected by contacting a nucleic acid encoding the mutant Caspase-9 protein with a Cas9:ADAT1 fusion protein (SEQ ID NO: 35 or 36) and an appropriately designed sgRNA targeting the fusion protein to the mutation site in the sense strand of the encoding Caspase-9 gene. See, e.g., Lenk et al., *PLoS Genetics*. 2011; 7: e1002104, for a description of an exemplary Caspase-9 L197P mutation associated with neuroblastoma (NB). The T→C point mutation is confirmed via genomic PCR of the respective Caspase-9 genomic sequence, e.g., generation of a PCR amplicon of about 100-250 nucleotides around exon 197, and subsequent sequencing of the PCT amplicon.

Cells expressing the mutant Caspase-9 protein are contacted with an expression construct encoding the Cas9: ADAT1 fusion protein (SEQ ID NO: 35 or 36) and an appropriately designed sgRNA targeting the fusion protein to the mutation site in the sense strand of the encoding Caspase-9 gene. The cytosine deaminase activity of the Cas9:ADAT1 fusion protein results in deamination of the mutant cytosine in codon 197 to uridine, thus correcting the mutation. Genomic DNA of the treated cells is extracted and a PCR amplicon of 100-250 nucleotides is amplified with suitable PCR primers. The correction of the T→C point mutation in codon 197 of the Caspase-9 gene after treatment of the cells with the fusion protein is confirmed by sequencing the PCR amplicon.

Example 7: Deaminase Activity of Two dCas9-APOBEC1 Fusion Proteins

Two dCas9-APOBEC1 fusion proteins with different linkers were generated:

rAPOBEC1_GGS_dCas9:

(SEQ ID NO: 94)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKGGSMDKKYSIGLAIGTNSVGW

AVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPI

FGNIVDEVAYHEKYPTIYHLRKKLVDSTDKADLRLIYLALAHMIKFRGHF

LIEGDLNPDNSDVDKLFIQLVQTYNQLFEENPINASGVDAKAILSARLSK

SRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLS

ASMIKRYDEHHQDLTLLKALVRQQLPEKYKEIFFDQSKNGYAGYIDGGAS

-continued
QEEFYKFIKPILEKMDGTEELLVKLNREDLLRKQRTFDNGSIPHQIHLGE

LHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKEDY

FKKIECFDSVEISGVEDRFNASLGTYHDLLKIIKDKDFLDNEENEDILED

IVLTLTLFEDREMIEERLKTYAHLFDDKVMKQLKRRRYTGWGRLSRKLIN

GIRDKQSGKTILDFLKSDGFANRNFMQLIHDDSLTFKEDIQKAQVSGQGD

SLHEHIANLAGSPAIKKGILQTVKVVDELVKVMGRHKPENIVIEMARENQ

TTQKGQKNSRERMKRIEEGIKELGSQILKEHPVENTQLQNEKLYLYYLQN

GRDMYVDQELDINRLSDYDVDAIVPQSFLKDDSIDNKVLTRSDKNRGKSD

NVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRK

DFQFYKVREINNYHHAHDAYLNAVVGTALIKKYPKLESEFVYGDYKVYDV

RKMIAKSEQEIGKATAKYFFYSNIMNFFKTEITLANGEIRKRPLIETNGE

TGEIVWDKGRDFATVRKVLSMPQVNIVKKTEVQTGGFSKESILPKRNSDK

LIARKKDWDPKKYGGFDSPTVAYSVLVVAKVEKGKSKKLKSVKELLGITI

MERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNL

GAPAAFKYFDTTIDRKRYTSTKEVLDATLIHQSITGLYETRIDLSQLGG

D;
underline = rAPOBEC1; double underline = dCas9.

rAPOBEC1_(GGS)₃_dCas9:
(SEQ ID NO: 95)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKGGSGGSGGSMDKKYSIGLAIG

TNSVGWAVITDEYKVPSKKFKVLGNTDRHSIKKNLIGALLFDSGETAEAT

RLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAIL

SARLSKSRRLENLIAQLPGEKKNGLFGNLIALSLGLTPNFKSNFDLAEDA

KLQLSKDTYDDDLDNLLAQIGDQYADLFLAAKNLSDAILLSDILRVNTEI

TKAPLSASMIKRYDEHHQDLTLLKALVRQQLPEKYKEIFFDQSKNGYAGY

IDGGASQEEFYKFIKPILEKMDGTEELLVKLNREDLLRKQRTFDNGSIPH

QIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHS

LLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRL

-continued
SRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIE

MARENQTTQKGQKNSRERMKRIEEGIKELGSQILKEHPVENTQLQNEKLY

LYYLQNGRDMYVDQELDINRLSDYDVDAIVPQSFLKDDSIDNKVLTRSDK

NRGKSDNVPSEEVVKKMKNYWRQLLNAKLITQRKFDNLTKAERGGLSELD

KAGFIKRQLVETRQITKHVAQILDSRMNTKYDENDKLIREVKVITLKSKL

VSDFRKDFQFYKVREINNYHHAHDAYLNAVVGTALIKKYPKLESEFVYGD

YKVYDVRKMIAKSEQEIGKATAKYFFYSNIMNFFKTEITLANGEIRKRPL

IETNGETGEIVWDKGRDFATVRKVLSMPQVNIVKKTEVQTGGFSKESILP

KRNSDKLIARKKDWDPKKYGGFDSPTVAYSVLVVAKVEKGKSKKLKSVKE

LLGITIMERSSFEKNPIDFLEAKGYKEVKKDLIIKLPKYSLFELENGRKR

MLASAGELQKGNELALPSKYVNFLYLASHYEKLKGSPEDNEQKQLFVEQH

KHYLDEIIEQISEFSKRVILADANLDKVLSAYNKHRDKPIREQAENIIHL

FTLTNLGAPAAFKYFDTTIDRKRYTSTKEVLDATLIHQSITGLYETRIDL

SQLGGD;
underline = rAPOBEC1; double underline = dCas9.

Deaminase activity of both fusion proteins were examined. A deaminase assay was adapted from Nuc. Acids Res. 2014, 42, p. 1095; J. Biol. Chem. 2004, 279, p 53379; J. Virology 2014, 88, p. 3850; and J. Virology 2006, 80, p. 5992, the entire contents of each of which are incorporated by reference.

Figure 5:
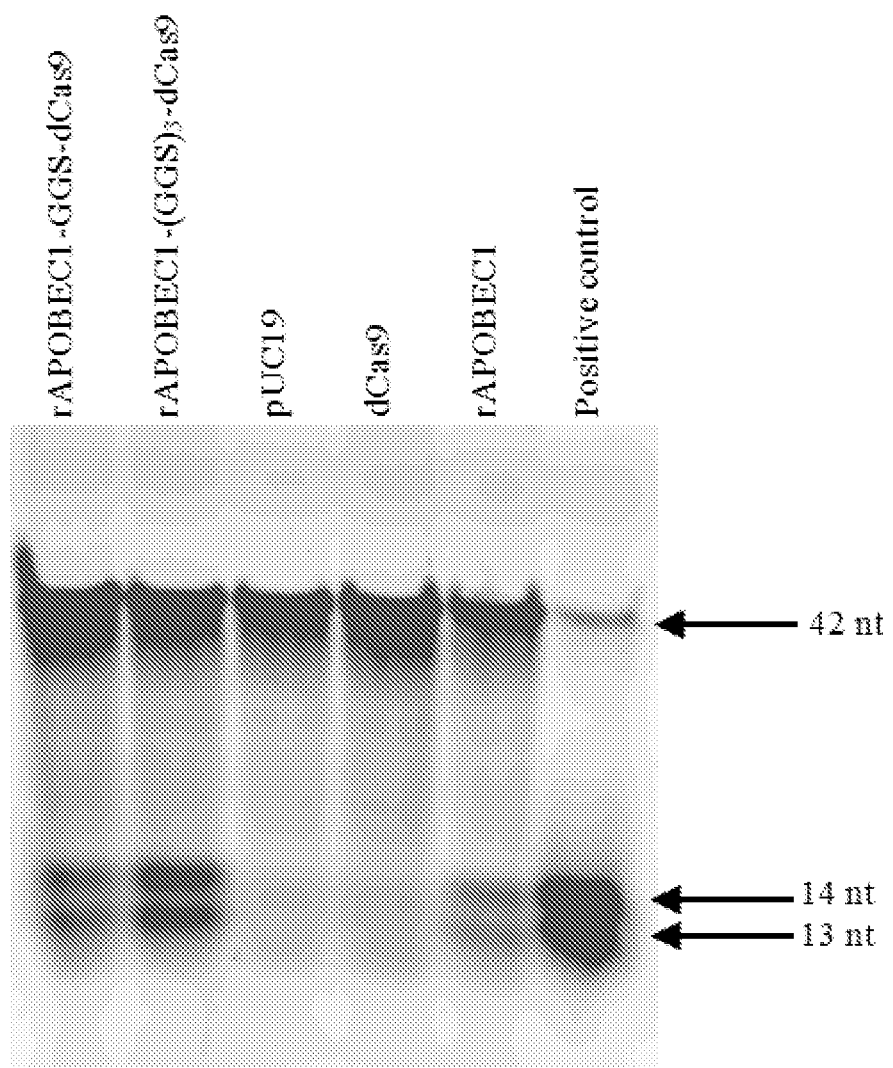
FIG. 5. SDS PAGE gel of ssDNA edited by Cas9-APOBEC1 fusion proteins.

Expression constructs encoding the fusion proteins were inserted into a CMV backbone plasmid (Addgene plasmid 52970; see Guilinger J P, Thompson D B, Liu D R. Fusion of catalytically inactive Cas9 to FokI nuclease improves the specificity of genome modification. *Nat. Biotechnol.* 2014; 32(6): 577-82). The fusion proteins were expressed using a TNT Quick Coupled Transcription/Translation System (Promega). After 90 min, 5 µL of lysate was incubated with 5'-labeled ssDNA substrate (Cy3-ATTATTATTATTC-CGCGGATTTATT TATTTATTTATTTATTT, SEQ ID NO: 96) and UDG (Uracil DNA Glycosylase) at 37° C. for 3 hr. A 1M solution of NaOH (10 µL) was then added to cleave the DNA at the abasic site. See FIG. 4. The DNA was resolved on a 10% TBE PAGE gel (FIG. 5). A negative control, where pUC19 was incubated in the TNT system, and a positive control, where the DNA has been synthesized with a "U" in place of the target C, were also included. FIG. 5 illustrates that both fusion proteins exhibit cytosine deaminase activity.

REFERENCES

1. Humbert O, Davis L, Maizels N. Targeted gene therapies: tools, applications, optimization. *Crit Rev Biochem Mol.* 2012; 47(3):264-81. PMID: 22530743.
2. Perez-Pinera P, Ousterout D G, Gersbach C A. Advances in targeted genome editing. *Curr Opin Chem Biol.* 2012; 16(3-4):268-77. PMID: 22819644.
3. Urnov F D, Rebar E J, Holmes M C, Zhang H S, Gregory P D. Genome editing with engineered zinc finger nucleases. *Nat Rev Genet.* 2010; 11(9):636-46. PMID: 20717154.
4. Joung J K, Sander J D. TALENs: a widely applicable technology for targeted genome editing. *Nat Rev Mol Cell Biol.* 2013; 14(1):49-55. PMID: 23169466.

5. Charpentier E, Doudna J A. Biotechnology: Rewriting a genome. *Nature.* 2013; 495, (7439):50-1. PMID: 23467164.
6. Pan Y, Xia L, Li A S, Zhang X, Sirois P, Zhang J, Li K. Biological and biomedical applications of engineered nucleases. *Mol Biotechnol.* 2013; 55(1):54-62. PMID: 23089945.
7. De Souza, N. Primer: genome editing with engineered nucleases. *Nat Methods.* 2012; 9(1):27. PMID: 22312638.
8. Santiago Y, Chan E, Liu P Q, Orlando S, Zhang L, Urnov F D, Holmes M C, Guschin D, Waite A, Miller J C, Rebar E J, Gregory P D, Klug A, Collingwood T N. Targeted gene knockout in mammalian cells by using engineered zinc-finger nucleases. *Proc Natl Acad Sci USA.* 2008; 105(15):5809-14. PMID: 18359850.
9. Cargill M, Altshuler D, Ireland J, Sklar P, Ardlie K, Patil N, Lane C R, Lim E P, Kalyanaraman N, Nemesh J, Ziaugra L, Friedland L, Rolfe A, Warrington J, Lipshutz R, Daley G Q, Lander E S. Characterization of single-nucleotide polymorphisms in coding regions of human genes. *Nat Genet.* 1999; 22(3):231-8. PMID: 10391209.
10. Jansen R, van Embden J D, Gaastra W, Schouls L M. Identification of genes that are associated with DNA repeats in prokaryotes. *Mol Microbiol.* 2002; 43(6):1565-75. PMID: 11952905.
11. Mali P, Esvelt K M, Church G M. Cas9 as a versatile tool for engineering biology. *Nat Methods.* 2013; 10(10):957-63. PMID: 24076990.
12. Jore M M, Lundgren M, van Duijin E, Bultema J B, Westra E R, Waghmare S P, Wiedenheft B, Pul U, Wurm R, Wagner R, Beijer M R, Barendregt A, Shou K, Snijders A P, Dickman M J, Doudna J A, Boekema E J, Heck A J, van der Oost J, Brouns S J. Structural basis for CRISPR RNA-guided DNA recognition by Cascade. *Nat Struct Mol Biol.* 2011; 18(5):529-36. PMID: 21460843.
13. Horvath P, Barrangou R. CRISPR/Cas, the immune system of bacteria and archaea. *Science.* 2010; 327(5962): 167-70. PMID: 20056882.
14. Wiedenheft B, Sternberg S H, Doudna J A. RNA-guided genetic silencing systems in bacteria and archaea. *Nature.* 2012; 482(7385):331-8. PMID: 22337052.
15. Gasiunas G, Siksnys V. RNA-dependent DNA endonuclease Cas9 of the CRISPR system: Holy Grail of genome editing? *Trends Microbiol.* 2013; 21(11):562-7. PMID: 24095303.
16. Qi L S, Larson M H, Gilbert L A, Doudna J A, Weissman J S, Arkin A P, Lim W A. Repurposing CRISPR as an RNA-guided platform for sequence-specific control of gene expression. *Cell.* 2013; 152(5):1173-83. PMID: 23452860.
17. Perez-Pinera P, Kocak D D, Vockley C M, Adler A F, Kabadi A M, Polstein L R, Thakore P I, Glass K A, Ousterout D G, Leong K W, Guilak F, Crawford G E, Reddy T E, Gersbach C A. RNA-guided gene activation by CRISPR-Cas9-based transcription factors. *Nat Methods.* 2013; 10(10):973-6. PMID: 23892895.
18. Mali P, Aach J, Stranges P B, Esvelt K M, Moosburner M, Kosuri S, Yang L, Church G M. CAS9 transcriptional activators for target specificity screening and paired nickases for cooperative genome engineering. *Nat Biotechnol.* 2013; 31(9):833-8. PMID: 23907171.
19. Gilbert L A, Larson M H, Morsut L, Liu Z, Brar G A, Torres S E, Stern-Ginossar N, Brandman O, Whitehead E H, Doudna J A, Lim W A, Weissman J S, Qi L S. CRISPR-mediated modular RNA-guided regulation of transcription in eukaryotes. *Cell.* 2013; 154(2):442-51. PMID: 23849981.
20. Larson M H, Gilbert L A, Wang X, Lim W A, Weissman J S, Qi L S. CRISPR interference (CRISPRi) for sequence-specific control of gene expression. *Nat Protoc.* 2013; 8(11):2180-96. PMID: 24136345.
21. Mali P, Yang L, Esvelt K M, Aach J, Guell M, DiCarlo J E, Norville J E, Church G M. RNA-guided human genome engineering via Cas9. *Science.* 2013; 339(6121): 823-6. PMID: 23287722.
22. Cole-Strauss A, Yoon K, Xiang Y, Byrne B C, Rice M C, Gryn J, Holloman W K, Kmiec E B. Correction of the mutation responsible for sickle cell anemia by an RNA-DNA oligonucleotide. *Science.* 1996; 273(5280):1386-9. PMID: 8703073.
23. Tagalakis A D, Owen J S, Simons J P. Lack of RNA-DNA oligonucleotide (chimeraplast) mutagenic activity in mouse embryos. *Mol Reprod Dev.* 2005; 71(2):140-4. PMID: 15791601.
24. Ray A, Langer M. Homologous recombination: ends as the means. *Trends Plant Sci.* 2002; 7(10):435-40. PMID 12399177.
25. Britt A B, May G D. Re-engineering plant gene targeting. *Trends Plant Sci.* 2003; 8(2):90-5. PMID: 12597876.
26. Vagner V, Ehrlich S D. Efficiency of homologous DNA recombination varies along the *Bacillus subtilis* chromosome. *J Bacteriol.* 1988; 170(9):3978-82. PMID: 3137211.
27. Saleh-Gohari N, Helleday T. Conservative homologous recombination preferentially repairs DNA double-strand breaks in the S phase of the cell cycle in human cells. *Nucleic Acids Res.* 2004; 32(12):3683-8. PMID: 15252152.
28. Lombardo A, Genovese P, Beausejour C M, Colleoni S, Lee Y L, Kim K A, Ando D, Urnov F D, Galli C, Gregory P D, Holmes M C, Naldini L. Gene editing in human stem cells using zince finger nucleases and integrase-defective lentiviral vector delivery. *Nat Biotechnol.* 2007; 25(11): 1298-306. PMID: 17965707.
29. Conticello S G. The AID/APOBEC family of nucleic acid mutators. *Genome Biol.* 2008; 9(6):229. PMID: 18598372.
30. Reynaud C A, Aoufouchi S, Faili A, Weill J C. What role for AID: mutator, or assembler of the immunoglobulin mutasome? *Nat Immunol.* 2003; 4(7):631-8.
31. Bhagwat A S. DNA-cytosine deaminases: from antibody maturation to antiviral defense. *DNA Repair (Amst).* 2004; 3(1):85-9. PMID: 14697763.
32. Navaratnam N, Sarwar R. An overview of cytidine deaminases. *Int J Hematol.* 2006; 83(3):195-200. PMID: 16720547.
33. Holden L G, Prochnow C, Chang Y P, Bransteitter R, Chelico L, Sen U, Stevens R C, Goodman M F, Chen X S. Crystal structure of the anti-viral APOBEC3G catalytic domain and functional implications. *Nature.* 2008; 456 (7218):121-4. PMID: 18849968.
34. Chelico L, Pham P, Petruska J, Goodman M F. Biochemical basis of immunological and retroviral responses to DNA-targeted cytosine deamination by activation-induced cytidine deaminase and APOBEC3G. *J Biol Chem.* 2009; 284(41). 27761-5. PMID: 19684020.
35. Pham P, Bransteitter R, Goodman M F. Reward versus risk: DNA cytidine deaminases triggering immunity and disease. *Biochemistry.* 2005; 44(8):2703-15. PMID 15723516.
36. Barbas C F, Kim D H. Cytidine deaminase fusions and related methods. PCT Int Appl. 2010; WO 2010132092 A2 20101118.

37. Chen X, Zaro J L, Shen W C. Fusion protein linkers: property, design and functionality. *Adv Drug Deliv Rev.* 2013; 65(10):1357-69. PMID: 23026637.
38. Gerber A P, Keller W. RNA editing by base deamination: more enzymes, more targets, new mysteries. *Trends Biochem Sci.* 2001; 26(6):376-84. PMID: 11406411.
39. Yuan L, Kurek I, English J, Keenan R. Laboratory-directed protein evolution. *Microbiol Mol Biol Rev.* 2005; 69(3):373-92. PMID: 16148303.
40. Cobb R E, Sun N, Zhao H. Directed evolution as a powerful synthetic biology tool. *Methods.* 2013; 60(1): 81-90. PMID: 22465795.
41. Bershtein S, Tawfik D S. Advances in laboratory evolution of enzymes. *Curr Opin Chem Biol.* 2008; 12(2): 151-8. PMID: 18284924.
42. Hida K, Hanes J, Ostermeier M. Directed evolution for drug and nucleic acid delivery. *Adv Drug Deliv Rev.* 2007; 59(15):1562-78. PMID: 17933418.
43. Esvelt K M, Carlson J C, Liu D R. A system for the continuous directed evolution of biomolecules. *Nature.* 2011; 472(7344):499-503. PMID: 21478873.
44. Husimi Y. Selection and evolution of bacteriophages in cellstat. *Adv Biophys.* 1989; 25:1-43. PMID: 2696338.
45. Riechmann L, Holliger P. The C-terminal domain of TolA is the coreceptor for filamentous phage infection of *E. coli. Cell.* 1997; 90(2):351-60. PMID: 9244308.
46. Nelson F K, Friedman S M, Smith G P. Filamentous phage DNA cloning vectors: a noninfective mutant with a nonpolar deletion in gene III. *Virology.* 1981; 108(2):338-50. PMID: 6258292.
47. Rakonjac J, Model P. Roles of pIII in filamentous phage assembly. *J Mol Biol.* 1998; 282(1):25-41.
48. Smith G P. Filamentous fusion phage: novel expression vectors that display cloned antigens on the virion surface. *Science.* 1985; 228(4705):1315-7. PMID: 4001944.
49. Sheridan C. Gene therapy finds its niche. *Nat Biotechnol.* 2011; 29(2):121-8. PMID: 21301435.
50. Lee J W, Soung Y H, Kim S Y, Lee H W, Park W S, Nam S W, Kim S H, Lee J Y, Yoo N J, Lee S H. PIK3CA gene is frequently mutated in breast carcinomas and hepatocellular carcinomas. *Oncogene.* 2005; 24(8):1477-80. PMID: 15608678.
51. Ikediobi O N, Davies H, Bignell G, Edkins S, Stevens C, O'Meara S, Santarius T, Avis T, Barthorpe S, Brackenbury L, Buck G, Butler A, Clements J, Cole J, Dicks E, Forbes S, Gray K, Halliday K, Harrison R, Hills K, Hinton J, Hunter C, Jenkinson A, Jones D, Kosmidou V, Lugg R, Menzies A, Mironenko T, Parker A, Perry J, Raine K, Richardson D, Shepherd R, Small A, Smith R, Solomon H, Stephens P, Teague J, Tofts C, Varian J, Webb T, West S, Widaa S, Yates A, Reinhold W, Weinstein J N, Stratton M R, Futreal P A, Wooster R. Mutation analysis of 24 known cancer genes in the NCI-60 cell line set. *Mol Cancer Ther.* 2006; 5(11):2606-12. PMID: 17088437.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

SEQUENCE LISTING

<160> NUMBER OF SEQ ID NOS: 106

<210> SEQ ID NO 1
<211> LENGTH: 4104
<212> TYPE: DNA
<213> ORGANISM: Streptococcus pyogenes

<400> SEQUENCE: 1

| | | | | | |
|---|---|---|---|---|---|
| atggataaga | aatactcaat | aggcttagat | atcggcacaa | atagcgtcgg | atgggcggtg | 60 |
| atcactgatg | attataaggt | tccgtctaaa | aagttcaagg | ttctgggaaa | tacagaccgc | 120 |
| cacagtatca | aaaaaatct | tatagggct | cttttatttg | gcagtggaga | gacagcggaa | 180 |
| gcgactcgtc | tcaaacggac | agctcgtaga | aggtatacac | gtcggaagaa | tcgtatttgt | 240 |
| tatctacagg | agattttttc | aaatgagatg | gcgaaagtag | atgatagttt | ctttcatcga | 300 |
| cttgaagagt | cttttttggt | ggaagaagac | aagaagcatg | aacgtcatcc | tattttga | 360 |
| aatatagtag | atgaagttgc | ttatcatgag | aaatatccaa | ctatctatca | tctgcgaaaa | 420 |
| aaattggcag | attctactga | taaagcggat | ttgcgcttaa | tctatttggc | cttagcgcat | 480 |
| atgattaagt | ttcgtggtca | ttttttgatt | gagggagatt | taaatcctga | taatagtgat | 540 |
| gtggacaaac | tatttatcca | gttggtacaa | atctacaatc | aattatttga | agaaaaccct | 600 |
| attaacgcaa | gtagagtaga | tgctaaagcg | attctttctg | cacgattgag | taaatcaaga | 660 |
| cgattagaaa | atctcattgc | tcagctcccc | ggtgagaaga | gaaatggctt | gtttgggaat | 720 |
| ctcattgctt | tgtcattggg | attgaccct | aattttaaat | caaattttga | tttggcagaa | 780 |
| gatgctaaat | tacagctttc | aaaagatact | tacgatgatg | atttagataa | tttattggcg | 840 |
| caaattggag | atcaatatgc | tgatttgttt | ttggcagcta | agaatttatc | agatgctatt | 900 |
| ttactttcag | atatcctaag | agtaaatagt | gaaataacta | aggctcccct | atcagcttca | 960 |
| atgattaagc | gctacgatga | acatcatcaa | gacttgactc | tttaaaagc | tttagttcga | 1020 |
| caacaacttc | cagaaaagta | taaagaaatc | tttttgatc | aatcaaaaaa | cggatatgca | 1080 |
| ggttatattg | atgggggagc | tagccaagaa | gaatttata | aatttatcaa | accaatttta | 1140 |
| gaaaaaatgg | atggtactga | ggaattattg | gtgaaactaa | atcgtgaaga | tttgctgcgc | 1200 |
| aagcaacgga | cctttgacaa | cggctctatt | ccccatcaaa | ttcacttggg | tgagctgcat | 1260 |
| gctattttga | gaagacaaga | agactttat | ccattttaa | aagacaatcg | tgagaagatt | 1320 |
| gaaaaaatct | tgacttttcg | aattccttat | tatgttggtc | cattggcgcg | tggcaatagt | 1380 |
| cgttttgcat | ggatgactcg | gaagtctgaa | gaaacaatta | ccccatggaa | ttttgaagaa | 1440 |
| gttgtcgata | aaggtgcttc | agctcaatca | tttattgaac | gcatgacaaa | ctttgataaa | 1500 |
| aatcttccaa | atgaaaaagt | actaccaaaa | catagtttgc | tttatgagta | ttttacggtt | 1560 |
| tataacgaat | tgacaaaggt | caaatatgtt | actgagggaa | tgcgaaaacc | agcatttctt | 1620 |
| tcaggtgaac | agaagaaagc | cattgttgat | ttactcttca | aaacaaatcg | aaaagtaacc | 1680 |
| gttaagcaat | taaagaaga | ttatttcaaa | aaatagaat | gttttgatag | tgttgaaatt | 1740 |
| tcaggagttg | aagatagatt | taatgcttca | ttaggcgcct | accatgattt | gctaaaaatt | 1800 |

```
attaaagata aagattttt  ggataatgaa gaaaatgaag atatcttaga ggatattgtt   1860
ttaacattga ccttatttga agataggggg atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gattttttga aatcagatgg ttttgccaat cgcaatttta tgcagctgat ccatgatgat   2100
agtttgacat ttaaagaaga tattcaaaaa gcacaggtgt ctggacaagg ccatagttta   2160
catgaacaga ttgctaactt agctggcagt cctgctatta aaaaaggtat tttacagact   2220
gtaaaaattg ttgatgaact ggtcaaagta atggggcata agccagaaaa tatcgttatt   2280
gaaatggcac gtgaaaatca gacaactcaa aagggccaga aaaattcgcg agagcgtatg   2340
aaacgaatcg aagaaggtat caagaaatta ggaagtcaga ttcttaaaga gcatcctgtt   2400
gaaaatactc aattgcaaaa tgaaaagctc tatctctatt atctacaaaa tggaagagac   2460
atgtatgtgg accaagaatt agatattaat cgtttaagtg attatgatgt cgatcacatt   2520
gttccacaaa gtttcattaa agacgattca atagacaata aggtactaac gcgttctgat   2580
aaaaatcgtg gtaaatcgga taacgttcca agtgaagaag tagtcaaaaa gatgaaaaac   2640
tattggagac aacttctaaa cgccaagtta atcactcaac gtaagtttga taatttaacg   2700
aaagctgaac gtggaggttt gagtgaactt gataaagctg gttttatcaa cgccaattg   2760
gttgaaactc gccaaatcac taagcatgtg gcacaaattt tggatagtcg catgaatact   2820
aaaatacgat aaaatgataa acttattcga gaggttaaag tgattacctt aaaatctaaa   2880
ttagtttctg acttccgaaa agatttccaa ttctataaag tacgtgagat taacaattac   2940
catcatgccc atgatgcgta tctaaatgcc gtcgttggaa ctgctttgat taagaaatat   3000
ccaaaacttg aatcggagtt tgtctatggt gattataaag tttatgatgt tcgtaaaatg   3060
attgctaagt ctgagcaaga aataggcaaa gcaaccgcaa atatttctt ttactctaat   3120
atcatgaact tcttcaaaac agaaattaca cttgcaaatg gagagattcg caaacgccct   3180
ctaatcgaaa ctaatgggga aactggagaa attgtctggg ataaagggcg agattttgcc   3240
acagtgcgca aagtattgtc catgccccaa gtcaatattg tcaagaaaac agaagtacag   3300
acaggcggat tctccaagga gtcaatttta ccaaaaagaa attcggacaa gcttattgct   3360
cgtaaaaaag actgggatcc aaaaaaatat ggtggttttg atagtccaac ggtagcttat   3420
tcagtcctag tggttgctaa ggtggaaaaa gggaaatcga agaagttaaa atccgttaaa   3480
gagttactag ggatcacaat tatggaaaga agttcctttg aaaaaaatcc gattgacttt   3540
ttagaagcta aaggatataa ggaagttaaa aaagacttaa tcattaaact acctaaatat   3600
agtcttttg agttagaaaa cggtcgtaaa cggatgctgg ctagtgccgg agaattacaa   3660
aaaggaaatg agctggctct gccaagcaaa tatgtgaatt ttttatattt agctagtcat   3720
tatgaaaagt tgaagggtag tccagaagat aacgaacaaa aacaattgtt tgtggagcag   3780
cataagcatt atttagatga gattattgag caaatcagtg aattttctaa gcgtgttatt   3840
ttagcagatg ccaatttaga taaagttctt agtgcatata acaaacatag agacaaacca   3900
atacgtgaac aagcagaaaa tattattcat ttatttacgt tgacgaatct ggagctccc    3960
gctgctttta atatttttga tacaacaatt gatcgtaaac gatatacgtc tacaaaagaa   4020
gttttagatg ccactcttat ccatcaatcc atcactggtc tttatgaaac acgcattgat   4080
ttgagtcagc taggaggtga ctga                                          4104
```

<210> SEQ ID NO 2
<211> LENGTH: 1367
<212> TYPE: PRT
<213> ORGANISM: Streptococcus pyogenes

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380
```

```
Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800
```

Glu Asn Thr Gln Leu Gln Asn Glu Lys Leu Tyr Leu Tyr Leu Gln
                    805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                    885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                    965                 970                 975

Ile Asn Asn Tyr His His Ala His Asp Ala Tyr Leu Asn Ala Val Val
                    980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050

Gly Glu Ile Arg Lys Arg Pro Leu Ile Glu Thr Asn Gly Glu Thr
            1055                1060                1065

Gly Glu Ile Val Trp Asp Lys Gly Arg Asp Phe Ala Thr Val Arg
            1070                1075                1080

Lys Val Leu Ser Met Pro Gln Val Asn Ile Val Lys Lys Thr Glu
            1085                1090                1095

Val Gln Thr Gly Gly Phe Ser Lys Glu Ser Ile Leu Pro Lys Arg
            1100                1105                1110

Asn Ser Asp Lys Leu Ile Ala Arg Lys Lys Asp Trp Asp Pro Lys
            1115                1120                1125

Lys Tyr Gly Gly Phe Asp Ser Pro Thr Val Ala Tyr Ser Val Leu
            1130                1135                1140

Val Val Ala Lys Val Glu Lys Gly Lys Ser Lys Lys Leu Lys Ser
            1145                1150                1155

Val Lys Glu Leu Leu Gly Ile Thr Ile Met Glu Arg Ser Ser Phe
            1160                1165                1170

Glu Lys Asn Pro Ile Asp Phe Leu Glu Ala Lys Gly Tyr Lys Glu
            1175                1180                1185

Val Lys Lys Asp Leu Ile Ile Lys Leu Pro Lys Tyr Ser Leu Phe
            1190                1195                1200

Glu Leu Glu Asn Gly Arg Lys Arg Met Leu Ala Ser Ala Gly Glu

```
                 1205                1210                1215
Leu Gln Lys Gly Asn Glu Leu  Ala Leu Pro Ser Lys  Tyr Val Asn
         1220                1225                1230

Phe Leu Tyr Leu Ala Ser His  Tyr Glu Lys Leu Lys  Gly Ser Pro
         1235                1240                1245

Glu Asp Asn Glu Gln Lys Gln  Leu Phe Val Glu Gln  His Lys His
         1250                1255                1260

Tyr Leu Asp Glu Ile Ile Glu  Gln Ile Ser Glu Phe  Ser Lys Arg
         1265                1270                1275

Val Ile Leu Ala Asp Ala Asn  Leu Asp Lys Val Leu  Ser Ala Tyr
         1280                1285                1290

Asn Lys His Arg Asp Lys Pro  Ile Arg Glu Gln Ala  Glu Asn Ile
         1295                1300                1305

Ile His Leu Phe Thr Leu Thr  Asn Leu Gly Ala Pro  Ala Ala Phe
         1310                1315                1320

Lys Tyr Phe Asp Thr Thr Ile  Asp Arg Lys Arg Tyr  Thr Ser Thr
         1325                1330                1335

Lys Glu Val Leu Asp Ala Thr  Leu Ile His Gln Ser  Ile Thr Gly
         1340                1345                1350

Leu Tyr Glu Thr Arg Ile Asp  Leu Ser Gln Leu Gly  Gly Asp
         1355                1360                1365

<210> SEQ ID NO 3
<211> LENGTH: 4212
<212> TYPE: DNA
<213> ORGANISM: Streptococcus pyogenes

<400> SEQUENCE: 3
atggataaaa agtattctat tggtttagac atcggcacta attccgttgg atgggctgtc      60
ataaccgatg aatacaaagt accttcaaag aaatttaagg tgttggggaa cacagaccgt     120
cattcgatta aaaagaatct tatcggtgcc ctcctattcg atagtggcga aacggcagag     180
gcgactcgcc tgaaacgaac cgctcggaga aggtatacac gtcgcaagaa ccgaatatgt     240
tacttacaag aaattttag caatgagatg gccaaagttg acgattcttt ctttcaccgt     300
ttggaagagt ccttccttgt cgaagaggac aagaaacatg aacggcaccc catctttgga     360
aacatagtag atgaggtggc atatcatgaa agtacccaa cgatttatca cctcagaaaa     420
aagctagttg actcaactga taaagcggac ctgaggttaa tctacttggc tcttgcccat     480
atgataaagt tccgtgggca ctttctcatt gagggtgatc taaatccgga caactcggat     540
gtcgacaaac tgttcatcca gttagtacaa acctataatc agttgtttga agagaaccct     600
ataaatgcaa gtggcgtgga tgcgaaggct attcttagcg cccgcctctc taaatcccga     660
cggctagaaa acctgatcgc acaattaccc ggagagaaga aaaatgggtt gttcggtaac     720
cttatagcgc tctcactagg cctgacacca aattttaagt cgaacttcga cttagctgaa     780
gatgccaaat tgcagcttag taaggacacg tacgatgacg atctcgacaa tctactggca     840
caaattggag atcagtatgc ggacttattt ttggctgcca aaaaccttag cgatgcaatc     900
ctcctatctg acatactgag agttaatact gagattacca aggcgccgtt atccgcttca     960
atgatcaaaa ggtacgatga acatcaccaa gacttgacac ttctcaaggc cctagtccgt    1020
cagcaactgc ctgagaaata taaggaaata ttctttgatc agtcgaaaaa cgggtacgca    1080
ggttatattg acggcggagc gagtcaagag gaattctaca gtttatcaa acccatatta    1140 gagaagatgg atgggacgga agagttgctt gtaaaactca atcgcgaaga tctactgcga    1200
```

```
aagcagcgga ctttcgacaa cggtagcatt ccacatcaaa tccacttagg cgaattgcat    1260
gctatactta gaaggcagga ggattttat  ccgttcctca aagacaatcg tgaaaagatt    1320
gagaaaatcc taacctttcg cataccttac tatgtgggac ccctggcccg agggaactct    1380
cggttcgcat ggatgacaag aaagtccgaa gaaacgatta ctccatggaa ttttgaggaa    1440
gttgtcgata aggtgcgtc  agctcaatcg ttcatcgaga ggatgaccaa ctttgacaag    1500
aatttaccga acgaaaaagt attgcctaag cacagtttac tttacgagta tttcacagtg    1560
tacaatgaac tcacgaaagt taagtatgtc actgagggca tgcgtaaacc cgccttctta    1620
agcggagaac agaagaaagc aatagtagat ctgttattca agaccaaccg caaagtgaca    1680
gttaagcaat tgaaagagga ctactttaag aaaattgaat gcttcgattc tgtcgagatc    1740
tccggggtag aagatcgatt taatgcgtca cttggtacgt atcatgacct cctaaagata    1800
attaaagata aggacttcct ggataacgaa gagaatgaag atatcttaga agatatagtg    1860
ttgactctta ccctctttga agatcggaa  atgattgagg aaagactaaa acatacgct     1920 cacctgttcg acgataaggt tatgaaacag ttaaagaggc gtcgctatac gggctgggga    1980
cgattgtcgc ggaaacttat caacgggata agagacaagc aaagtggtaa aactattctc    2040
gattttctaa agagcgacgg cttcgccaat aggaacttta tgcagctgat ccatgatgac    2100
tctttaacct tcaaagagga tatacaaaag gcacaggttt ccggacaagg ggactcattg    2160
cacgaacata ttgcgaatct tgctggttcg ccagccatca aaagggcat  actccagaca    2220 gtcaaagtag tggatgagct agttaaggtc atgggacgtc acaaaccgga aaacattgta    2280
atcgagatgg cacgcgaaaa tcaaacgact cagaagggc  aaaaaaacag tcgagagcgg    2340
atgaagagaa tagaagaggg tattaaagaa ctgggcagcc agatcttaaa ggagcatcct    2400
gtggaaaata cccaattgca gaacgagaaa ctttacctct attacctaca aatggaagg     2460 gacatgtatg ttgatcagga actggacata aaccgtttat ctgattacga cgtcgatcac    2520
attgtacccc aatcctttt  gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agaggggtgg cttgtctgaa cttgacaagg ccggatttat taaacgtcag    2760
ctcgtggaaa cccgccaaat cacaaagcat gttgcacaga tactagattc ccgaatgaat    2820
acgaaatacg acgagaacga taagctgatt cgggaagtca agtaatcac  tttaaagtca    2880 aaattggtgt cggacttcag aaaggatttt caattctata agttaggga  gataaataac    2940 taccaccatg cgcacgacgc ttatcttaat gccgtcgtag ggaccgcact cattaagaaa    3000
tacccgaagc tagaaagtga gtttgtgtat ggtgattaca aagtttatga cgtccgtaag    3060
atgatcgcga aaagcgaaca ggagataggc aaggctacag ccaaatactt ctttttattct   3120 aacattatga atttctttaa gacggaaatc actctggcaa acggagagat acgcaaacga    3180
cctttaattg aaaccaatgg ggagacaggt gaaatcgtat gggataaggg ccgggacttc    3240
gcgacggtga gaaaagtttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgatagccc tacagttgcc    3420
tattctgtcc tagtagtggc aaaagttgag aagggaaaat ccaagaaact gaagtcagtc    3480
aaagaattat tggggataac gattatggag cgctcgtctt ttgaaaagaa ccccatcgac    3540
```

-continued

```
ttccttgagg cgaaaggtta caaggaagta aaaaggatc tcataattaa actaccaaag    3600
tatagtctgt ttgagttaga aaatggccga aaacggatgt tggctagcgc cggagagctt    3660
caaaagggga acgaactcgc actaccgtct aaatacgtga atttcctgta tttagcgtcc    3720
cattacgaga agttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
ccagccgcat tcaagtattt tgacacaacg atagatcgca aacgatacac ttctaccaag    4020
gaggtgctag acgcgacact gattcaccaa tccatcacgg gattatatga aactcggata    4080
gatttgtcac agcttggggg tgacggatcc cccaagaaga agaggaaagt ctcgagcgac    4140
tacaaagacc atgacggtga ttataaagat catgacatcg attacaagga tgacgatgac    4200
aaggctgcag ga                                                       4212
```

<210> SEQ ID NO 4
<211> LENGTH: 1368
<212> TYPE: PRT
<213> ORGANISM: Streptococcus pyogenes

<400> SEQUENCE: 4

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255
```

-continued

```
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
```

```
Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
```

```
                  1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

Glu Ala Ala Ala Lys
1               5

<210> SEQ ID NO 6
<211> LENGTH: 198
<212> TYPE: PRT
<213> ORGANISM: Homo sapiens

<400> SEQUENCE: 6

Met Asp Ser Leu Leu Met Asn Arg Arg Lys Phe Leu Tyr Gln Phe Lys
1               5                   10                  15
```

```
Asn Val Arg Trp Ala Lys Gly Arg Arg Glu Thr Tyr Leu Cys Tyr Val
             20                  25                  30

Val Lys Arg Arg Asp Ser Ala Thr Ser Phe Ser Leu Asp Phe Gly Tyr
         35                  40                  45

Leu Arg Asn Lys Asn Gly Cys His Val Glu Leu Leu Phe Leu Arg Tyr
     50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 7
<211> LENGTH: 198
<212> TYPE: PRT
<213> ORGANISM: Mus musculus

<400> SEQUENCE: 7

Met Asp Ser Leu Leu Met Lys Gln Lys Lys Phe Leu Tyr His Phe Lys
 1               5                  10                  15

Asn Val Arg Trp Ala Lys Gly Arg His Glu Thr Tyr Leu Cys Tyr Val
             20                  25                  30

Val Lys Arg Arg Asp Ser Ala Thr Ser Cys Ser Leu Asp Phe Gly His
         35                  40                  45

Leu Arg Asn Lys Ser Gly Cys His Val Glu Leu Leu Phe Leu Arg Tyr
     50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Glu
                 85                  90                  95

Phe Leu Arg Trp Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Gly Ile Met Thr Phe Lys Asp Tyr
    130                 135                 140

Phe Tyr Cys Trp Asn Thr Phe Val Glu Asn Arg Glu Arg Thr Phe Lys
145                 150                 155                 160

Ala Trp Glu Gly Leu His Glu Asn Ser Val Arg Leu Thr Arg Gln Leu
                165                 170                 175

Arg Arg Ile Leu Leu Pro Leu Tyr Glu Val Asp Asp Leu Arg Asp Ala
```

```
                    180                 185                 190

Phe Arg Met Leu Gly Phe
            195

<210> SEQ ID NO 8
<211> LENGTH: 198
<212> TYPE: PRT
<213> ORGANISM: Canis lupus

<400> SEQUENCE: 8

Met Asp Ser Leu Leu Met Lys Gln Arg Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Ala Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Lys Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 9
<211> LENGTH: 199
<212> TYPE: PRT
<213> ORGANISM: Bos taurus

<400> SEQUENCE: 9

Met Asp Ser Leu Leu Lys Lys Gln Arg Gln Phe Leu Tyr Gln Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Pro Thr Ser Phe Ser Leu Asp Phe Gly His
        35                  40                  45

Leu Arg Asn Lys Ala Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Thr Ala Arg
```

-continued

```
              100                 105                 110
Leu Tyr Phe Cys Asp Lys Glu Arg Lys Ala Glu Pro Glu Gly Leu Arg
            115                 120                 125

Arg Leu His Arg Ala Gly Val Gln Ile Ala Ile Met Thr Phe Lys Asp
        130                 135                 140

Tyr Phe Tyr Cys Trp Asn Thr Phe Val Glu Asn His Glu Arg Thr Phe
145                 150                 155                 160

Lys Ala Trp Glu Gly Leu His Glu Asn Ser Val Arg Leu Ser Arg Gln
                165                 170                 175

Leu Arg Arg Ile Leu Leu Pro Leu Tyr Glu Val Asp Asp Leu Arg Asp
            180                 185                 190

Ala Phe Arg Thr Leu Gly Leu
            195

<210> SEQ ID NO 10
<211> LENGTH: 429
<212> TYPE: PRT
<213> ORGANISM: Mus musculus

<400> SEQUENCE: 10

Met Gly Pro Phe Cys Leu Gly Cys Ser His Arg Lys Cys Tyr Ser Pro
1               5                   10                  15

Ile Arg Asn Leu Ile Ser Gln Glu Thr Phe Lys Phe His Phe Lys Asn
            20                  25                  30

Leu Gly Tyr Ala Lys Gly Arg Lys Asp Thr Phe Leu Cys Tyr Glu Val
        35                  40                  45

Thr Arg Lys Asp Cys Asp Ser Pro Val Ser Leu His His Gly Val Phe
    50                  55                  60

Lys Asn Lys Asp Asn Ile His Ala Glu Ile Cys Phe Leu Tyr Trp Phe
65                  70                  75                  80

His Asp Lys Val Leu Lys Val Leu Ser Pro Arg Glu Glu Phe Lys Ile
                85                  90                  95

Thr Trp Tyr Met Ser Trp Ser Pro Cys Phe Glu Cys Ala Glu Gln Ile
            100                 105                 110

Val Arg Phe Leu Ala Thr His His Asn Leu Ser Leu Asp Ile Phe Ser
        115                 120                 125

Ser Arg Leu Tyr Asn Val Gln Asp Pro Glu Thr Gln Gln Asn Leu Cys
    130                 135                 140

Arg Leu Val Gln Glu Gly Ala Gln Val Ala Ala Met Asp Leu Tyr Glu
145                 150                 155                 160

Phe Lys Lys Cys Trp Lys Lys Phe Val Asp Asn Gly Gly Arg Arg Phe
                165                 170                 175

Arg Pro Trp Lys Arg Leu Leu Thr Asn Phe Arg Tyr Gln Asp Ser Lys
            180                 185                 190

Leu Gln Glu Ile Leu Arg Pro Cys Tyr Ile Pro Val Pro Ser Ser Ser
        195                 200                 205

Ser Ser Thr Leu Ser Asn Ile Cys Leu Thr Lys Gly Leu Pro Glu Thr
    210                 215                 220

Arg Phe Cys Val Glu Gly Arg Arg Met Asp Pro Leu Ser Glu Glu Glu
225                 230                 235                 240

Phe Tyr Ser Gln Phe Tyr Asn Gln Arg Val Lys His Leu Cys Tyr Tyr
                245                 250                 255

His Arg Met Lys Pro Tyr Leu Cys Tyr Gln Leu Glu Gln Phe Asn Gly
            260                 265                 270
```

```
Gln Ala Pro Leu Lys Gly Cys Leu Ser Glu Lys Gly Lys Gln His
            275                 280                 285

Ala Glu Ile Leu Phe Leu Asp Lys Ile Arg Ser Met Glu Leu Ser Gln
290                 295                 300

Val Thr Ile Thr Cys Tyr Leu Thr Trp Ser Pro Cys Pro Asn Cys Ala
305                 310                 315                 320

Trp Gln Leu Ala Ala Phe Lys Arg Asp Arg Pro Asp Leu Ile Leu His
                325                 330                 335

Ile Tyr Thr Ser Arg Leu Tyr Phe His Trp Lys Arg Pro Phe Gln Lys
                340                 345                 350

Gly Leu Cys Ser Leu Trp Gln Ser Gly Ile Leu Val Asp Val Met Asp
                355                 360                 365

Leu Pro Gln Phe Thr Asp Cys Trp Thr Asn Phe Val Asn Pro Lys Arg
370                 375                 380

Pro Phe Trp Pro Trp Lys Gly Leu Glu Ile Ile Ser Arg Arg Thr Gln
385                 390                 395                 400

Arg Arg Leu Arg Arg Ile Lys Glu Ser Trp Gly Leu Gln Asp Leu Val
                405                 410                 415

Asn Asp Phe Gly Asn Leu Gln Leu Gly Pro Pro Met Ser
                420                 425
```

<210> SEQ ID NO 11
<211> LENGTH: 429
<212> TYPE: PRT
<213> ORGANISM: Rattus norvegicus

<400> SEQUENCE: 11

```
Met Gly Pro Phe Cys Leu Gly Cys Ser His Arg Lys Cys Tyr Ser Pro
1               5                   10                  15

Ile Arg Asn Leu Ile Ser Gln Glu Thr Phe Lys Phe His Phe Lys Asn
                20                  25                  30

Leu Arg Tyr Ala Ile Asp Arg Lys Asp Thr Phe Leu Cys Tyr Glu Val
            35                  40                  45

Thr Arg Lys Asp Cys Asp Ser Pro Val Ser Leu His His Gly Val Phe
50                  55                  60

Lys Asn Lys Asp Asn Ile His Ala Glu Ile Cys Phe Leu Tyr Trp Phe
65                  70                  75                  80

His Asp Lys Val Leu Lys Val Leu Ser Pro Arg Glu Glu Phe Lys Ile
                85                  90                  95

Thr Trp Tyr Met Ser Trp Ser Pro Cys Phe Glu Cys Ala Glu Gln Val
                100                 105                 110

Leu Arg Phe Leu Ala Thr His His Asn Leu Ser Leu Asp Ile Phe Ser
            115                 120                 125

Ser Arg Leu Tyr Asn Ile Arg Asp Pro Glu Asn Gln Gln Asn Leu Cys
130                 135                 140

Arg Leu Val Gln Glu Gly Ala Gln Val Ala Ala Met Asp Leu Tyr Glu
145                 150                 155                 160

Phe Lys Lys Cys Trp Lys Lys Phe Val Asp Asn Gly Gly Arg Arg Phe
                165                 170                 175

Arg Pro Trp Lys Lys Leu Leu Thr Asn Phe Arg Tyr Gln Asp Ser Lys
            180                 185                 190

Leu Gln Glu Ile Leu Arg Pro Cys Tyr Ile Pro Val Pro Ser Ser Ser
                195                 200                 205

Ser Ser Thr Leu Ser Asn Ile Cys Leu Thr Lys Gly Leu Pro Glu Thr
210                 215                 220
```

-continued

Arg Phe Cys Val Glu Arg Arg Val His Leu Leu Ser Glu Glu Glu
225                 230                 235                 240

Phe Tyr Ser Gln Phe Tyr Asn Gln Arg Val Lys His Leu Cys Tyr Tyr
                245                 250                 255

His Gly Val Lys Pro Tyr Leu Cys Tyr Gln Leu Glu Gln Phe Asn Gly
            260                 265                 270

Gln Ala Pro Leu Lys Gly Cys Leu Leu Ser Glu Lys Gly Lys Gln His
        275                 280                 285

Ala Glu Ile Leu Phe Leu Asp Lys Ile Arg Ser Met Glu Leu Ser Gln
    290                 295                 300

Val Ile Ile Thr Cys Tyr Leu Thr Trp Ser Pro Cys Pro Asn Cys Ala
305                 310                 315                 320

Trp Gln Leu Ala Ala Phe Lys Arg Asp Arg Pro Asp Leu Ile Leu His
                325                 330                 335

Ile Tyr Thr Ser Arg Leu Tyr Phe His Trp Lys Arg Pro Phe Gln Lys
            340                 345                 350

Gly Leu Cys Ser Leu Trp Gln Ser Gly Ile Leu Val Asp Val Met Asp
        355                 360                 365

Leu Pro Gln Phe Thr Asp Cys Trp Thr Asn Phe Val Asn Pro Lys Arg
    370                 375                 380

Pro Phe Trp Pro Trp Lys Gly Leu Glu Ile Ile Ser Arg Arg Thr Gln
385                 390                 395                 400

Arg Arg Leu His Arg Ile Lys Glu Ser Trp Gly Leu Gln Asp Leu Val
                405                 410                 415

Asn Asp Phe Gly Asn Leu Gln Leu Gly Pro Pro Met Ser
            420                 425

<210> SEQ ID NO 12
<211> LENGTH: 370
<212> TYPE: PRT
<213> ORGANISM: Macaca fascicularis

<400> SEQUENCE: 12

Met Val Glu Pro Met Asp Pro Arg Thr Phe Val Ser Asn Phe Asn Asn
1               5                   10                  15

Arg Pro Ile Leu Ser Gly Leu Asn Thr Val Trp Leu Cys Cys Glu Val
                20                  25                  30

Lys Thr Lys Asp Pro Ser Gly Pro Pro Leu Asp Ala Lys Ile Phe Gln
            35                  40                  45

Gly Lys Val Tyr Ser Lys Ala Lys Tyr His Pro Glu Met Arg Phe Leu
        50                  55                  60

Arg Trp Phe His Lys Trp Arg Gln Leu His His Asp Gln Glu Tyr Lys
65                  70                  75                  80

Val Thr Trp Tyr Val Ser Trp Ser Pro Cys Thr Arg Cys Ala Asn Ser
                85                  90                  95

Val Ala Thr Phe Leu Ala Lys Asp Pro Lys Val Thr Leu Thr Ile Phe
            100                 105                 110

Val Ala Arg Leu Tyr Tyr Phe Trp Lys Pro Asp Tyr Gln Gln Ala Leu
        115                 120                 125

Arg Ile Leu Cys Gln Lys Arg Gly Gly Pro His Ala Thr Met Lys Ile
    130                 135                 140

Met Asn Tyr Asn Glu Phe Gln Asp Cys Trp Asn Lys Phe Val Asp Gly
145                 150                 155                 160

Arg Gly Lys Pro Phe Lys Pro Arg Asn Asn Leu Pro Lys His Tyr Thr

```
                    165                 170                 175
Leu Leu Gln Ala Thr Leu Gly Glu Leu Leu Arg His Leu Met Asp Pro
                180                 185                 190

Gly Thr Phe Thr Ser Asn Phe Asn Asn Lys Pro Trp Val Ser Gly Gln
                195                 200                 205

His Glu Thr Tyr Leu Cys Tyr Lys Val Glu Arg Leu His Asn Asp Thr
            210                 215                 220

Trp Val Pro Leu Asn Gln His Arg Gly Phe Leu Arg Asn Gln Ala Pro
225                 230                 235                 240

Asn Ile His Gly Phe Pro Lys Gly Arg His Ala Glu Leu Cys Phe Leu
                245                 250                 255

Asp Leu Ile Pro Phe Trp Lys Leu Asp Gly Gln Gln Tyr Arg Val Thr
                260                 265                 270

Cys Phe Thr Ser Trp Ser Pro Cys Phe Ser Cys Ala Gln Glu Met Ala
            275                 280                 285

Lys Phe Ile Ser Asn Asn Glu His Val Ser Leu Cys Ile Phe Ala Ala
            290                 295                 300

Arg Ile Tyr Asp Asp Gln Gly Arg Tyr Gln Glu Gly Leu Arg Ala Leu
305                 310                 315                 320

His Arg Asp Gly Ala Lys Ile Ala Met Met Asn Tyr Ser Glu Phe Glu
                325                 330                 335

Tyr Cys Trp Asp Thr Phe Val Asp Arg Gln Gly Arg Pro Phe Gln Pro
                340                 345                 350

Trp Asp Gly Leu Asp Glu His Ser Gln Ala Leu Ser Gly Arg Leu Arg
                355                 360                 365

Ala Ile
370

<210> SEQ ID NO 13
<211> LENGTH: 384
<212> TYPE: PRT
<213> ORGANISM: Pan troglodytes

<400> SEQUENCE: 13

Met Lys Pro His Phe Arg Asn Pro Val Glu Arg Met Tyr Gln Asp Thr
1               5                   10                  15

Phe Ser Asp Asn Phe Tyr Asn Arg Pro Ile Leu Ser His Arg Asn Thr
                20                  25                  30

Val Trp Leu Cys Tyr Glu Val Lys Thr Lys Gly Pro Ser Arg Pro Pro
            35                  40                  45

Leu Asp Ala Lys Ile Phe Arg Gly Gln Val Tyr Ser Lys Leu Lys Tyr
50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Val Ala Thr Phe Leu Ala Glu Asp Pro
            100                 105                 110

Lys Val Thr Leu Thr Ile Phe Val Ala Arg Leu Tyr Tyr Phe Trp Asp
            115                 120                 125

Pro Asp Tyr Gln Glu Ala Leu Arg Ser Leu Cys Gln Lys Arg Asp Gly
            130                 135                 140

Pro Arg Ala Thr Met Lys Ile Met Asn Tyr Asp Glu Phe Gln His Cys
145                 150                 155                 160
```

```
Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Ser Asn Phe Asn Asn
        195                 200                 205

Glu Leu Trp Val Arg Gly Arg His Glu Thr Tyr Leu Cys Tyr Glu Val
    210                 215                 220

Glu Arg Leu His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu His Gln Asp Tyr Arg Val Thr Cys Phe Thr Ser Trp Ser Pro Cys
        275                 280                 285

Phe Ser Cys Ala Gln Glu Met Ala Lys Phe Ile Ser Asn Asn Lys His
    290                 295                 300

Val Ser Leu Cys Ile Phe Ala Ala Arg Ile Tyr Asp Asp Gln Gly Arg
305                 310                 315                 320

Cys Gln Glu Gly Leu Arg Thr Leu Ala Lys Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Glu Glu His Ser
        355                 360                 365

Gln Ala Leu Ser Gly Arg Leu Arg Ala Ile Leu Gln Asn Gln Gly Asn
    370                 375                 380

<210> SEQ ID NO 14
<211> LENGTH: 377
<212> TYPE: PRT
<213> ORGANISM: Chlorocebus aethiops

<400> SEQUENCE: 14

Met Asn Pro Gln Ile Arg Asn Met Val Glu Gln Met Glu Pro Asp Ile
1               5                   10                  15

Phe Val Tyr Tyr Phe Asn Asn Arg Pro Ile Leu Ser Gly Arg Asn Thr
            20                  25                  30

Val Trp Leu Cys Tyr Glu Val Lys Thr Lys Asp Pro Ser Gly Pro Pro
        35                  40                  45

Leu Asp Ala Asn Ile Phe Gln Gly Lys Leu Tyr Pro Glu Ala Lys Asp
    50                  55                  60

His Pro Glu Met Lys Phe Leu His Trp Phe Arg Lys Trp Arg Gln Leu
65                  70                  75                  80

His Arg Asp Gln Glu Tyr Glu Val Thr Trp Tyr Val Ser Trp Ser Pro
                85                  90                  95

Cys Thr Arg Cys Ala Asn Ser Val Ala Thr Phe Leu Ala Glu Asp Pro
            100                 105                 110

Lys Val Thr Leu Thr Ile Phe Val Ala Arg Leu Tyr Tyr Phe Trp Lys
        115                 120                 125

Pro Asp Tyr Gln Gln Ala Leu Arg Ile Leu Cys Gln Glu Arg Gly Gly
    130                 135                 140

Pro His Ala Thr Met Lys Ile Met Asn Tyr Asn Glu Phe Gln His Cys
145                 150                 155                 160
```

```
Trp Asn Glu Phe Val Asp Gly Gln Gly Lys Pro Phe Lys Pro Arg Lys
                165                 170                 175

Asn Leu Pro Lys His Tyr Thr Leu Leu His Ala Thr Leu Gly Glu Leu
            180                 185                 190

Leu Arg His Val Met Asp Pro Gly Thr Phe Thr Ser Asn Phe Asn Asn
        195                 200                 205

Lys Pro Trp Val Ser Gly Gln Arg Glu Thr Tyr Leu Cys Tyr Lys Val
    210                 215                 220

Glu Arg Ser His Asn Asp Thr Trp Val Leu Leu Asn Gln His Arg Gly
225                 230                 235                 240

Phe Leu Arg Asn Gln Ala Pro Asp Arg His Gly Phe Pro Lys Gly Arg
                245                 250                 255

His Ala Glu Leu Cys Phe Leu Asp Leu Ile Pro Phe Trp Lys Leu Asp
            260                 265                 270

Asp Gln Gln Tyr Arg Val Thr Cys Phe Thr Ser Trp Ser Pro Cys Phe
        275                 280                 285

Ser Cys Ala Gln Lys Met Ala Lys Phe Ile Ser Asn Asn Lys His Val
    290                 295                 300

Ser Leu Cys Ile Phe Ala Ala Arg Ile Tyr Asp Asp Gln Gly Arg Cys
305                 310                 315                 320

Gln Glu Gly Leu Arg Thr Leu His Arg Asp Gly Ala Lys Ile Ala Val
                325                 330                 335

Met Asn Tyr Ser Glu Phe Glu Tyr Cys Trp Asp Thr Phe Val Asp Arg
            340                 345                 350

Gln Gly Arg Pro Phe Gln Pro Trp Asp Gly Leu Asp Glu His Ser Gln
        355                 360                 365

Ala Leu Ser Gly Arg Leu Arg Ala Ile
    370                 375

<210> SEQ ID NO 15
<211> LENGTH: 384
<212> TYPE: PRT
<213> ORGANISM: Homo sapiens

<400> SEQUENCE: 15

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
```

```
145                 150                 155                 160
Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
                180                 185                 190

Leu Arg His Ser Met Asp Pro Thr Phe Thr Phe Asn Phe Asn Asn
                195                 200                 205

Glu Pro Trp Val Arg Gly Arg His Glu Thr Tyr Leu Cys Tyr Glu Val
            210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
                260                 265                 270

Leu Asp Gln Asp Tyr Arg Val Thr Cys Phe Thr Ser Trp Ser Pro Cys
                275                 280                 285

Phe Ser Cys Ala Gln Glu Met Ala Lys Phe Ile Ser Lys Asn Lys His
        290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
                340                 345                 350

His Gln Gly Cys Pro Phe Gln Pro Trp Asp Gly Leu Asp Glu His Ser
                355                 360                 365

Gln Asp Leu Ser Gly Arg Leu Arg Ala Ile Leu Gln Asn Gln Glu Asn
            370                 375                 380

<210> SEQ ID NO 16
<211> LENGTH: 373
<212> TYPE: PRT
<213> ORGANISM: Homo sapiens

<400> SEQUENCE: 16

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
                20                  25                  30

Val Trp Leu Cys Tyr Glu Val Lys Thr Lys Gly Pro Ser Arg Pro Arg
            35                  40                  45

Leu Asp Ala Lys Ile Phe Arg Gly Gln Val Tyr Ser Gln Pro Glu His
        50                  55                  60

His Ala Glu Met Cys Phe Leu Ser Trp Phe Cys Gly Asn Gln Leu Pro
65                  70                  75                  80

Ala Tyr Lys Cys Phe Gln Ile Thr Trp Phe Val Ser Trp Thr Pro Cys
                85                  90                  95

Pro Asp Cys Val Ala Lys Leu Ala Glu Phe Leu Ala Glu His Pro Asn
                100                 105                 110

Val Thr Leu Thr Ile Ser Ala Ala Arg Leu Tyr Tyr Tyr Trp Glu Arg
            115                 120                 125

Asp Tyr Arg Arg Ala Leu Cys Arg Leu Ser Gln Ala Gly Ala Arg Val
        130                 135                 140
```

```
Lys Ile Met Asp Asp Glu Phe Ala Tyr Cys Trp Glu Asn Phe Val
145                 150                 155                 160

Tyr Ser Glu Gly Gln Pro Phe Met Pro Trp Tyr Lys Phe Asp Asp Asn
                165                 170                 175

Tyr Ala Phe Leu His Arg Thr Leu Lys Glu Ile Leu Arg Asn Pro Met
            180                 185                 190

Glu Ala Met Tyr Pro His Ile Phe Tyr Phe His Phe Lys Asn Leu Arg
        195                 200                 205

Lys Ala Tyr Gly Arg Asn Glu Ser Trp Leu Cys Phe Thr Met Glu Val
    210                 215                 220

Val Lys His His Ser Pro Val Ser Trp Lys Arg Gly Val Phe Arg Asn
225                 230                 235                 240

Gln Val Asp Pro Glu Thr His Cys His Ala Glu Arg Cys Phe Leu Ser
                245                 250                 255

Trp Phe Cys Asp Asp Ile Leu Ser Pro Asn Thr Asn Tyr Glu Val Thr
            260                 265                 270

Trp Tyr Thr Ser Trp Ser Pro Cys Pro Glu Cys Ala Gly Glu Val Ala
        275                 280                 285

Glu Phe Leu Ala Arg His Ser Asn Val Asn Leu Thr Ile Phe Thr Ala
    290                 295                 300

Arg Leu Tyr Tyr Phe Trp Asp Thr Asp Tyr Gln Glu Gly Leu Arg Ser
305                 310                 315                 320

Leu Ser Gln Glu Gly Ala Ser Val Glu Ile Met Gly Tyr Lys Asp Phe
                325                 330                 335

Lys Tyr Cys Trp Glu Asn Phe Val Tyr Asn Asp Asp Gly Pro Phe Lys
            340                 345                 350

Pro Trp Lys Gly Leu Lys Tyr Asn Phe Leu Phe Leu Asp Ser Lys Leu
        355                 360                 365

Gln Glu Ile Leu Glu
        370

<210> SEQ ID NO 17
<211> LENGTH: 382
<212> TYPE: PRT
<213> ORGANISM: Homo sapiens

<400> SEQUENCE: 17

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
            35                  40                  45

Leu Trp Asp Thr Gly Val Phe Arg Gly Gln Val Tyr Phe Lys Pro Gln
        50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140
```

```
Val Thr Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
            165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
            195                 200                 205

Leu Arg Arg Arg Gln Thr Tyr Leu Cys Tyr Glu Val Glu Arg Leu Asp
            210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
            245                 250                 255

Arg Phe Leu Asp Leu Val Pro Ser Leu Gln Leu Asp Pro Ala Gln Ile
            260                 265                 270

Tyr Arg Val Thr Trp Phe Ile Ser Trp Ser Pro Cys Phe Ser Trp Gly
            275                 280                 285

Cys Ala Gly Glu Val Arg Ala Phe Leu Gln Glu Asn Thr His Val Arg
290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
            325                 330                 335

Thr Tyr Asp Glu Phe Glu Tyr Cys Trp Asp Thr Phe Val Tyr Arg Gln
            340                 345                 350

Gly Cys Pro Phe Gln Pro Trp Asp Gly Leu Glu Glu His Ser Gln Ala
            355                 360                 365

Leu Ser Gly Arg Leu Arg Ala Ile Leu Gln Asn Gln Gly Asn
            370                 375                 380

<210> SEQ ID NO 18
<211> LENGTH: 190
<212> TYPE: PRT
<213> ORGANISM: Homo sapiens

<400> SEQUENCE: 18

Met Asn Pro Gln Ile Arg Asn Pro Met Lys Ala Met Tyr Pro Gly Thr
1               5                   10                  15

Phe Tyr Phe Gln Phe Lys Asn Leu Trp Glu Ala Asn Asp Arg Asn Glu
            20                  25                  30

Thr Trp Leu Cys Phe Thr Val Glu Gly Ile Lys Arg Arg Ser Val Val
            35                  40                  45

Ser Trp Lys Thr Gly Val Phe Arg Asn Gln Val Asp Ser Glu Thr His
50                  55                  60

Cys His Ala Glu Arg Cys Phe Leu Ser Trp Phe Cys Asp Asp Ile Leu
65                  70                  75                  80

Ser Pro Asn Thr Lys Tyr Gln Val Thr Trp Tyr Thr Ser Trp Ser Pro
            85                  90                  95

Cys Pro Asp Cys Ala Gly Glu Val Ala Glu Phe Leu Ala Arg His Ser
            100                 105                 110

Asn Val Asn Leu Thr Ile Phe Thr Ala Arg Leu Tyr Tyr Phe Gln Tyr
            115                 120                 125

Pro Cys Tyr Gln Glu Gly Leu Arg Ser Leu Ser Gln Glu Gly Val Ala
```

```
            130                 135                 140
Val Glu Ile Met Asp Tyr Glu Asp Phe Lys Tyr Cys Trp Glu Asn Phe
145                 150                 155                 160

Val Tyr Asn Asp Asn Glu Pro Phe Lys Pro Trp Lys Gly Leu Lys Thr
                165                 170                 175

Asn Phe Arg Leu Leu Lys Arg Arg Leu Arg Glu Ser Leu Gln
            180                 185                 190

<210> SEQ ID NO 19
<211> LENGTH: 199
<212> TYPE: PRT
<213> ORGANISM: Homo sapiens

<400> SEQUENCE: 19

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 20
<211> LENGTH: 200
<212> TYPE: PRT
<213> ORGANISM: Homo sapiens

<400> SEQUENCE: 20

Met Ala Leu Leu Thr Ala Glu Thr Phe Arg Leu Gln Phe Asn Asn Lys
1               5                   10                  15

Arg Arg Leu Arg Arg Pro Tyr Tyr Pro Arg Lys Ala Leu Leu Cys Tyr
                20                  25                  30

Gln Leu Thr Pro Gln Asn Gly Ser Thr Pro Thr Arg Gly Tyr Phe Glu
            35                  40                  45

Asn Lys Lys Lys Cys His Ala Glu Ile Cys Phe Ile Asn Glu Ile Lys
50                  55                  60

Ser Met Gly Leu Asp Glu Thr Gln Cys Tyr Gln Val Thr Cys Tyr Leu
```

```
                65                  70                  75                  80
Thr Trp Ser Pro Cys Ser Ser Cys Ala Trp Glu Leu Val Asp Phe Ile
                85                  90                  95

Lys Ala His Asp His Leu Asn Leu Gly Ile Phe Ala Ser Arg Leu Tyr
                100                 105                 110

Tyr His Trp Cys Lys Pro Gln Gln Lys Gly Leu Arg Leu Leu Cys Gly
                115                 120                 125

Ser Gln Val Pro Val Glu Val Met Gly Phe Pro Lys Phe Ala Asp Cys
130                 135                 140

Trp Glu Asn Phe Val Asp His Glu Lys Pro Leu Ser Phe Asn Pro Tyr
145                 150                 155                 160

Lys Met Leu Glu Glu Leu Asp Lys Asn Ser Arg Ala Ile Lys Arg Arg
                165                 170                 175

Leu Glu Arg Ile Lys Ile Pro Gly Val Arg Ala Gln Gly Arg Tyr Met
                180                 185                 190

Asp Ile Leu Cys Asp Ala Glu Val
                195                 200

<210> SEQ ID NO 21
<211> LENGTH: 386
<212> TYPE: PRT
<213> ORGANISM: Homo sapiens

<400> SEQUENCE: 21

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
            35                  40                  45

Leu Trp Asp Thr Gly Val Phe Arg Gly Pro Val Leu Pro Lys Arg Gln
        50                  55                  60

Ser Asn His Arg Gln Glu Val Tyr Phe Arg Phe Glu Asn His Ala Glu
65                  70                  75                  80

Met Cys Phe Leu Ser Trp Phe Cys Gly Asn Arg Leu Pro Ala Asn Arg
                85                  90                  95

Arg Phe Gln Ile Thr Trp Phe Val Ser Trp Asn Pro Cys Leu Pro Cys
                100                 105                 110

Val Val Lys Val Thr Lys Phe Leu Ala Glu His Pro Asn Val Thr Leu
            115                 120                 125

Thr Ile Ser Ala Ala Arg Leu Tyr Tyr Tyr Arg Asp Arg Asp Trp Arg
130                 135                 140

Trp Val Leu Leu Arg Leu His Lys Ala Gly Ala Arg Val Lys Ile Met
145                 150                 155                 160

Asp Tyr Glu Asp Phe Ala Tyr Cys Trp Glu Asn Phe Val Cys Asn Glu
                165                 170                 175

Gly Gln Pro Phe Met Pro Trp Tyr Lys Phe Asp Asp Asn Tyr Ala Ser
                180                 185                 190

Leu His Arg Thr Leu Lys Glu Ile Leu Arg Asn Pro Met Glu Ala Met
            195                 200                 205

Tyr Pro His Ile Phe Tyr Phe His Phe Lys Asn Leu Leu Lys Ala Cys
        210                 215                 220

Gly Arg Asn Glu Ser Trp Leu Cys Phe Thr Met Glu Val Thr Lys His
225                 230                 235                 240
```

```
His Ser Ala Val Phe Arg Lys Arg Gly Val Phe Arg Asn Gln Val Asp
            245                 250                 255

Pro Glu Thr His Cys His Ala Glu Arg Cys Phe Leu Ser Trp Phe Cys
        260                 265                 270

Asp Asp Ile Leu Ser Pro Asn Thr Asn Tyr Glu Val Thr Trp Tyr Thr
            275                 280                 285

Ser Trp Ser Pro Cys Pro Glu Cys Ala Gly Glu Val Ala Glu Phe Leu
        290                 295                 300

Ala Arg His Ser Asn Val Asn Leu Thr Ile Phe Thr Ala Arg Leu Cys
305                 310                 315                 320

Tyr Phe Trp Asp Thr Asp Tyr Gln Glu Gly Leu Cys Ser Leu Ser Gln
            325                 330                 335

Glu Gly Ala Ser Val Lys Ile Met Gly Tyr Lys Asp Phe Val Ser Cys
        340                 345                 350

Trp Lys Asn Phe Val Tyr Ser Asp Asp Glu Pro Phe Lys Pro Trp Lys
            355                 360                 365

Gly Leu Gln Thr Asn Phe Arg Leu Leu Lys Arg Leu Arg Glu Ile
        370                 375                 380

Leu Gln
385

<210> SEQ ID NO 22
<211> LENGTH: 236
<212> TYPE: PRT
<213> ORGANISM: Homo sapiens

<400> SEQUENCE: 22

Met Thr Ser Glu Lys Gly Pro Ser Thr Gly Asp Pro Thr Leu Arg Arg
1               5                   10                  15

Arg Ile Glu Pro Trp Glu Phe Asp Val Phe Tyr Asp Pro Arg Glu Leu
            20                  25                  30

Arg Lys Glu Ala Cys Leu Leu Tyr Glu Ile Lys Trp Gly Met Ser Arg
        35                  40                  45

Lys Ile Trp Arg Ser Ser Gly Lys Asn Thr Thr Asn His Val Glu Val
    50                  55                  60

Asn Phe Ile Lys Lys Phe Thr Ser Glu Arg Asp Phe His Pro Ser Met
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
            100                 105                 110

Val Ile Tyr Val Ala Arg Leu Phe Trp His Met Asp Gln Gln Asn Arg
        115                 120                 125

Gln Gly Leu Arg Asp Leu Val Asn Ser Gly Val Thr Ile Gln Ile Met
    130                 135                 140

Arg Ala Ser Glu Tyr Tyr His Cys Trp Arg Asn Phe Val Asn Tyr Pro
145                 150                 155                 160

Pro Gly Asp Glu Ala His Trp Pro Gln Tyr Pro Pro Leu Trp Met Met
                165                 170                 175

Leu Tyr Ala Leu Glu Leu His Cys Ile Ile Leu Ser Leu Pro Pro Cys
            180                 185                 190

Leu Lys Ile Ser Arg Arg Trp Gln Asn His Leu Thr Phe Phe Arg Leu
        195                 200                 205

His Leu Gln Asn Cys His Tyr Gln Thr Ile Pro Pro His Ile Leu Leu
    210                 215                 220
```

```
Ala Thr Gly Leu Ile His Pro Ser Val Ala Trp Arg
225                 230                 235

<210> SEQ ID NO 23
<211> LENGTH: 229
<212> TYPE: PRT
<213> ORGANISM: Mus musculus

<400> SEQUENCE: 23

Met Ser Ser Glu Thr Gly Pro Val Ala Val Asp Pro Thr Leu Arg Arg
1               5                   10                  15

Arg Ile Glu Pro His Glu Phe Glu Val Phe Asp Pro Arg Glu Leu
            20                  25                  30

Arg Lys Glu Thr Cys Leu Leu Tyr Glu Ile Asn Trp Gly Gly Arg His
        35                  40                  45

Ser Val Trp Arg His Thr Ser Gln Asn Thr Ser Asn His Val Glu Val
    50                  55                  60

Asn Phe Leu Glu Lys Phe Thr Thr Glu Arg Tyr Phe Arg Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg His Pro Tyr Val Thr Leu
            100                 105                 110

Phe Ile Tyr Ile Ala Arg Leu Tyr His His Thr Asp Gln Arg Asn Arg
        115                 120                 125

Gln Gly Leu Arg Asp Leu Ile Ser Ser Gly Val Thr Ile Gln Ile Met
    130                 135                 140

Thr Glu Gln Glu Tyr Cys Tyr Cys Trp Arg Asn Phe Val Asn Tyr Pro
145                 150                 155                 160

Pro Ser Asn Glu Ala Tyr Trp Pro Arg Tyr Pro His Leu Trp Val Lys
                165                 170                 175

Leu Tyr Val Leu Glu Leu Tyr Cys Ile Ile Leu Gly Leu Pro Pro Cys
            180                 185                 190

Leu Lys Ile Leu Arg Arg Lys Gln Pro Gln Leu Thr Phe Phe Thr Ile
        195                 200                 205

Thr Leu Gln Thr Cys His Tyr Gln Arg Ile Pro Pro His Leu Leu Trp
    210                 215                 220

Ala Thr Gly Leu Lys
225

<210> SEQ ID NO 24
<211> LENGTH: 229
<212> TYPE: PRT
<213> ORGANISM: Rattus norvegicus

<400> SEQUENCE: 24

Met Ser Ser Glu Thr Gly Pro Val Ala Val Asp Pro Thr Leu Arg Arg
1               5                   10                  15

Arg Ile Glu Pro His Glu Phe Glu Val Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80
```

-continued

```
Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 25
<211> LENGTH: 191
<212> TYPE: PRT
<213> ORGANISM: Homo sapiens

<400> SEQUENCE: 25

Met Glu Ala Lys Ala Ala Pro Lys Pro Ala Ala Ser Gly Ala Cys Ser
1               5                   10                  15

Val Ser Ala Glu Glu Thr Glu Lys Trp Met Glu Ala Met His Met
            20                  25                  30

Ala Lys Glu Ala Leu Glu Asn Thr Glu Val Pro Val Gly Cys Leu Met
        35                  40                  45

Val Tyr Asn Asn Glu Val Val Gly Lys Gly Arg Asn Glu Val Asn Gln
50                  55                  60

Thr Lys Asn Ala Thr Arg His Ala Glu Met Val Ala Ile Asp Gln Val
65                  70                  75                  80

Leu Asp Trp Cys Arg Gln Ser Gly Lys Ser Pro Ser Glu Val Phe Glu
            85                  90                  95

His Thr Val Leu Tyr Val Thr Val Glu Pro Cys Ile Met Cys Ala Ala
            100                 105                 110

Ala Leu Arg Leu Met Lys Ile Pro Leu Val Val Tyr Gly Cys Gln Asn
        115                 120                 125

Glu Arg Phe Gly Gly Cys Gly Ser Val Leu Asn Ile Ala Ser Ala Asp
130                 135                 140

Leu Pro Asn Thr Gly Arg Pro Phe Gln Cys Ile Pro Gly Tyr Arg Ala
145                 150                 155                 160

Glu Glu Ala Val Glu Met Leu Lys Thr Phe Tyr Lys Gln Glu Asn Pro
                165                 170                 175

Asn Ala Pro Lys Ser Lys Val Arg Lys Lys Glu Cys Gln Lys Ser
            180                 185                 190

<210> SEQ ID NO 26
<211> LENGTH: 191
<212> TYPE: PRT
```

<213> ORGANISM: Mus musculus

<400> SEQUENCE: 26

Met Glu Glu Lys Val Glu Ser Thr Thr Thr Pro Asp Gly Pro Cys Val
1               5                   10                  15

Val Ser Val Gln Glu Thr Glu Lys Trp Met Glu Ala Met Arg Met
        20                  25                  30

Ala Lys Glu Ala Leu Glu Asn Ile Glu Val Pro Val Gly Cys Leu Met
        35                  40                  45

Val Tyr Asn Asn Glu Val Val Gly Lys Gly Arg Asn Glu Val Asn Gln
    50                  55                  60

Thr Lys Asn Ala Thr Arg His Ala Glu Met Val Ala Ile Asp Gln Val
65                  70                  75                  80

Leu Asp Trp Cys His Gln His Gly Gln Ser Pro Ser Thr Val Phe Glu
                85                  90                  95

His Thr Val Leu Tyr Val Thr Val Glu Pro Cys Ile Met Cys Ala Ala
                100                 105                 110

Ala Leu Arg Leu Met Lys Ile Pro Leu Val Val Tyr Gly Cys Gln Asn
            115                 120                 125

Glu Arg Phe Gly Gly Cys Gly Ser Val Leu Asn Ile Ala Ser Ala Asp
130                 135                 140

Leu Pro Asn Thr Gly Arg Pro Phe Gln Cys Ile Pro Gly Tyr Arg Ala
145                 150                 155                 160

Glu Glu Ala Val Glu Leu Leu Lys Thr Phe Tyr Lys Gln Glu Asn Pro
                165                 170                 175

Asn Ala Pro Lys Ser Lys Val Arg Lys Asp Cys Gln Lys Ser
            180                 185                 190

<210> SEQ ID NO 27
<211> LENGTH: 499
<212> TYPE: PRT
<213> ORGANISM: Mus musculus

<400> SEQUENCE: 27

Met Trp Thr Ala Asp Glu Ile Ala Gln Leu Cys Tyr Ala His Tyr Asn
1               5                   10                  15

Val Arg Leu Pro Lys Gln Gly Lys Pro Glu Pro Asn Arg Glu Trp Thr
            20                  25                  30

Leu Leu Ala Ala Val Val Lys Ile Gln Ala Ser Ala Asn Gln Ala Cys
            35                  40                  45

Asp Ile Pro Glu Lys Val Gln Val Thr Lys Glu Val Val Ser Met
    50                  55                  60

Gly Thr Gly Thr Lys Cys Ile Gly Gln Ser Lys Met Arg Glu Ser Gly
65                  70                  75                  80

Asp Ile Leu Asn Asp Ser His Ala Glu Ile Ile Ala Arg Arg Ser Phe
                85                  90                  95

Gln Arg Tyr Leu Leu His Gln Leu His Leu Ala Ala Val Leu Lys Glu
            100                 105                 110

Asp Ser Ile Phe Val Pro Gly Thr Gln Arg Gly Leu Trp Arg Leu Arg
            115                 120                 125

Pro Asp Leu Ser Phe Val Phe Phe Ser Ser His Thr Pro Cys Gly Asp
            130                 135                 140

Ala Ser Ile Ile Pro Met Leu Glu Phe Glu Glu Gln Pro Cys Cys Pro
145                 150                 155                 160

Val Ile Arg Ser Trp Ala Asn Asn Ser Pro Val Gln Glu Thr Glu Asn

```
                165                 170                 175
Leu Glu Asp Ser Lys Asp Lys Arg Asn Cys Glu Asp Pro Ala Ser Pro
            180                 185                 190

Val Ala Lys Lys Met Arg Leu Gly Thr Pro Ala Arg Ser Leu Ser Asn
            195                 200                 205

Cys Val Ala His His Gly Thr Gln Glu Ser Gly Pro Val Lys Pro Asp
            210                 215                 220

Val Ser Ser Ser Asp Leu Thr Lys Glu Pro Asp Ala Ala Asn Gly
225                 230                 235                 240

Ile Ala Ser Gly Ser Phe Arg Val Val Asp Val Tyr Arg Thr Gly Ala
                245                 250                 255

Lys Cys Val Pro Gly Glu Thr Gly Asp Leu Arg Glu Pro Gly Ala Ala
                260                 265                 270

Tyr His Gln Val Gly Leu Leu Arg Val Lys Pro Gly Arg Gly Asp Arg
                275                 280                 285

Thr Cys Ser Met Ser Cys Ser Asp Lys Met Ala Arg Trp Asn Val Leu
            290                 295                 300

Gly Cys Gln Gly Ala Leu Leu Met His Phe Leu Glu Lys Pro Ile Tyr
305                 310                 315                 320

Leu Ser Ala Val Val Ile Gly Lys Cys Pro Tyr Ser Gln Glu Ala Met
                325                 330                 335

Arg Arg Ala Leu Thr Gly Arg Cys Glu Glu Thr Leu Val Leu Pro Arg
            340                 345                 350

Gly Phe Gly Val Gln Glu Leu Glu Ile Gln Gln Ser Gly Leu Leu Phe
            355                 360                 365

Glu Gln Ser Arg Cys Ala Val His Arg Lys Arg Gly Asp Ser Pro Gly
            370                 375                 380

Arg Leu Val Pro Cys Gly Ala Ala Ile Ser Trp Ser Ala Val Pro Gln
385                 390                 395                 400

Gln Pro Leu Asp Val Thr Ala Asn Gly Phe Pro Gln Gly Thr Thr Lys
                405                 410                 415

Lys Glu Ile Gly Ser Pro Arg Ala Arg Ser Arg Ile Ser Lys Val Glu
                420                 425                 430

Leu Phe Arg Ser Phe Gln Lys Leu Leu Ser Ser Ile Ala Asp Asp Glu
            435                 440                 445

Gln Pro Asp Ser Ile Arg Val Thr Lys Lys Leu Asp Thr Tyr Gln Glu
            450                 455                 460

Tyr Lys Asp Ala Ala Ser Ala Tyr Gln Glu Ala Trp Gly Ala Leu Arg
465                 470                 475                 480

Arg Ile Gln Pro Phe Ala Ser Trp Ile Arg Asn Pro Pro Asp Tyr His
                485                 490                 495

Gln Phe Lys

<210> SEQ ID NO 28
<211> LENGTH: 502
<212> TYPE: PRT
<213> ORGANISM: Homo sapiens

<400> SEQUENCE: 28

Met Trp Thr Ala Asp Glu Ile Ala Gln Leu Cys Tyr Glu His Tyr Gly
1               5                   10                  15

Ile Arg Leu Pro Lys Lys Gly Lys Pro Glu Pro Asn His Glu Trp Thr
            20                  25                  30

Leu Leu Ala Ala Val Val Lys Ile Gln Ser Pro Ala Asp Lys Ala Cys
```

```
                35                  40                  45
Asp Thr Pro Asp Lys Pro Val Gln Val Thr Lys Glu Val Val Ser Met
 50                  55                  60

Gly Thr Gly Thr Lys Cys Ile Gly Gln Ser Lys Met Arg Lys Asn Gly
 65                  70                  75                  80

Asp Ile Leu Asn Asp Ser His Ala Glu Val Ile Ala Arg Arg Ser Phe
                 85                  90                  95

Gln Arg Tyr Leu Leu His Gln Leu Gln Leu Ala Ala Thr Leu Lys Glu
                100                 105                 110

Asp Ser Ile Phe Val Pro Gly Thr Gln Lys Gly Val Trp Lys Leu Arg
                115                 120                 125

Arg Asp Leu Ile Phe Val Phe Phe Ser Ser His Thr Pro Cys Gly Asp
                130                 135                 140

Ala Ser Ile Ile Pro Met Leu Glu Phe Glu Asp Gln Pro Cys Cys Pro
145                 150                 155                 160

Val Phe Arg Asn Trp Ala His Asn Ser Ser Val Glu Ala Ser Ser Asn
                165                 170                 175

Leu Glu Ala Pro Gly Asn Glu Arg Lys Cys Glu Asp Pro Asp Ser Pro
                180                 185                 190

Val Thr Lys Lys Met Arg Leu Glu Pro Gly Thr Ala Ala Arg Glu Val
                195                 200                 205

Thr Asn Gly Ala Ala His His Gln Ser Phe Gly Lys Gln Lys Ser Gly
                210                 215                 220

Pro Ile Ser Pro Gly Ile His Ser Cys Asp Leu Thr Val Glu Gly Leu
225                 230                 235                 240

Ala Thr Val Thr Arg Ile Ala Pro Gly Ser Ala Lys Val Ile Asp Val
                245                 250                 255

Tyr Arg Thr Gly Ala Lys Cys Val Pro Gly Glu Ala Gly Asp Ser Gly
                260                 265                 270

Lys Pro Gly Ala Ala Phe His Gln Val Gly Leu Leu Arg Val Lys Pro
                275                 280                 285

Gly Arg Gly Asp Arg Thr Arg Ser Met Ser Cys Ser Asp Lys Met Ala
                290                 295                 300

Arg Trp Asn Val Leu Gly Cys Gln Gly Ala Leu Leu Met His Leu Leu
305                 310                 315                 320

Glu Glu Pro Ile Tyr Leu Ser Ala Val Val Ile Gly Lys Cys Pro Tyr
                325                 330                 335

Ser Gln Glu Ala Met Gln Arg Ala Leu Ile Gly Arg Cys Gln Asn Val
                340                 345                 350

Ser Ala Leu Pro Lys Gly Phe Gly Val Gln Glu Leu Lys Ile Leu Gln
                355                 360                 365

Ser Asp Leu Leu Phe Glu Gln Ser Arg Ser Ala Val Gln Ala Lys Arg
                370                 375                 380

Ala Asp Ser Pro Gly Arg Leu Val Pro Cys Gly Ala Ala Ile Ser Trp
385                 390                 395                 400

Ser Ala Val Pro Glu Gln Pro Leu Asp Val Thr Ala Asn Gly Phe Pro
                405                 410                 415

Gln Gly Thr Thr Lys Lys Thr Ile Gly Ser Leu Gln Ala Arg Ser Gln
                420                 425                 430

Ile Ser Lys Val Glu Leu Phe Arg Ser Phe Gln Lys Leu Leu Ser Arg
                435                 440                 445

Ile Ala Arg Asp Lys Trp Pro His Ser Leu Arg Val Gln Lys Leu Asp
450                 455                 460
```

```
Thr Tyr Gln Glu Tyr Lys Glu Ala Ala Ser Ser Tyr Gln Glu Ala Trp
465                 470                 475                 480

Ser Thr Leu Arg Lys Gln Val Phe Gly Ser Trp Ile Arg Asn Pro Pro
                485                 490                 495

Asp Tyr His Gln Phe Lys
            500

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 29

Ser Pro Lys Lys Lys Arg Lys Val Glu Ala Ser
1               5                   10

<210> SEQ ID NO 30
<211> LENGTH: 1580
<212> TYPE: PRT
<213> ORGANISM: Artificial Sequence
<220> FEATURE:
<223> OTHER INFORMATION: Synthetic Polypeptide

<400> SEQUENCE: 30

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Asp Lys
            20                  25                  30

Lys Tyr Ser Ile Gly Leu Ala Ile Gly Thr Asn Ser Val Gly Trp Ala
        35                  40                  45

Val Ile Thr Asp Glu Tyr Lys Val Pro Ser Lys Lys Phe Lys Val Leu
    50                  55                  60

Gly Asn Thr Asp Arg His Ser Ile Lys Lys Asn Leu Ile Gly Ala Leu
65                  70                  75                  80

Leu Phe Asp Ser Gly Glu Thr Ala Glu Ala Thr Arg Leu Lys Arg Thr
                85                  90                  95

Ala Arg Arg Arg Tyr Thr Arg Arg Lys Asn Arg Ile Cys Tyr Leu Gln
            100                 105                 110

Glu Ile Phe Ser Asn Glu Met Ala Lys Val Asp Asp Ser Phe Phe His
        115                 120                 125

Arg Leu Glu Glu Ser Phe Leu Val Glu Glu Asp Lys Lys His Glu Arg
    130                 135                 140

His Pro Ile Phe Gly Asn Ile Val Asp Glu Val Ala Tyr His Glu Lys
145                 150                 155                 160

Tyr Pro Thr Ile Tyr His Leu Arg Lys Lys Leu Val Asp Ser Thr Asp
                165                 170                 175

Lys Ala Asp Leu Arg Leu Ile Tyr Leu Ala Leu Ala His Met Ile Lys
            180                 185                 190

Phe Arg Gly His Phe Leu Ile Glu Gly Asp Leu Asn Pro Asp Asn Ser
        195                 200                 205

Asp Val Asp Lys Leu Phe Ile Gln Leu Val Gln Thr Tyr Asn Gln Leu
    210                 215                 220

Phe Glu Glu Asn Pro Ile Asn Ala Ser Gly Val Asp Ala Lys Ala Ile
225                 230                 235                 240

Leu Ser Ala Arg Leu Ser Lys Ser Arg Arg Leu Glu Asn Leu Ile Ala
```

```
                245                 250                 255
Gln Leu Pro Gly Glu Lys Lys Asn Gly Leu Phe Gly Asn Leu Ile Ala
            260                 265                 270
Leu Ser Leu Gly Leu Thr Pro Asn Phe Lys Ser Asn Phe Asp Leu Ala
            275                 280                 285
Glu Asp Ala Lys Leu Gln Leu Ser Lys Asp Thr Tyr Asp Asp Asp Leu
            290                 295                 300
Asp Asn Leu Leu Ala Gln Ile Gly Asp Gln Tyr Ala Asp Leu Phe Leu
305                 310                 315                 320
Ala Ala Lys Asn Leu Ser Asp Ala Ile Leu Leu Ser Asp Ile Leu Arg
                325                 330                 335
Val Asn Thr Glu Ile Thr Lys Ala Pro Leu Ser Ala Ser Met Ile Lys
            340                 345                 350
Arg Tyr Asp Glu His His Gln Asp Leu Thr Leu Leu Lys Ala Leu Val
            355                 360                 365
Arg Gln Gln Leu Pro Glu Lys Tyr Lys Glu Ile Phe Phe Asp Gln Ser
            370                 375                 380
Lys Asn Gly Tyr Ala Gly Tyr Ile Asp Gly Gly Ala Ser Gln Glu Glu
385                 390                 395                 400
Phe Tyr Lys Phe Ile Lys Pro Ile Leu Glu Lys Met Asp Gly Thr Glu
                405                 410                 415
Glu Leu Leu Val Lys Leu Asn Arg Glu Asp Leu Leu Arg Lys Gln Arg
            420                 425                 430
Thr Phe Asp Asn Gly Ser Ile Pro His Gln Ile His Leu Gly Glu Leu
            435                 440                 445
His Ala Ile Leu Arg Arg Gln Glu Asp Phe Tyr Pro Phe Leu Lys Asp
            450                 455                 460
Asn Arg Glu Lys Ile Glu Lys Ile Leu Thr Phe Arg Ile Pro Tyr Tyr
465                 470                 475                 480
Val Gly Pro Leu Ala Arg Gly Asn Ser Arg Phe Ala Trp Met Thr Arg
                485                 490                 495
Lys Ser Glu Glu Thr Ile Thr Pro Trp Asn Phe Glu Glu Val Val Asp
            500                 505                 510
Lys Gly Ala Ser Ala Gln Ser Phe Ile Glu Arg Met Thr Asn Phe Asp
            515                 520                 525
Lys Asn Leu Pro Asn Glu Lys Val Leu Pro Lys His Ser Leu Leu Tyr
            530                 535                 540
Glu Tyr Phe Thr Val Tyr Asn Glu Leu Thr Lys Val Lys Tyr Val Thr
545                 550                 555                 560
Glu Gly Met Arg Lys Pro Ala Phe Leu Ser Gly Glu Gln Lys Lys Ala
                565                 570                 575
Ile Val Asp Leu Leu Phe Lys Thr Asn Arg Lys Val Thr Val Lys Gln
            580                 585                 590
Leu Lys Glu Asp Tyr Phe Lys Lys Ile Glu Cys Phe Asp Ser Val Glu
            595                 600                 605
Ile Ser Gly Val Glu Asp Arg Phe Asn Ala Ser Leu Gly Thr Tyr His
            610                 615                 620
Asp Leu Leu Lys Ile Ile Lys Asp Lys Asp Phe Leu Asp Asn Glu Glu
625                 630                 635                 640
Asn Glu Asp Ile Leu Glu Asp Ile Val Leu Thr Leu Thr Leu Phe Glu
                645                 650                 655
Asp Arg Glu Met Ile Glu Glu Arg Leu Lys Thr Tyr Ala His Leu Phe
            660                 665                 670
```

```
Asp Asp Lys Val Met Lys Gln Leu Lys Arg Arg Tyr Thr Gly Trp
        675                 680                 685
Gly Arg Leu Ser Arg Lys Leu Ile Asn Gly Ile Arg Asp Lys Gln Ser
690                 695                 700
Gly Lys Thr Ile Leu Asp Phe Leu Lys Ser Asp Gly Phe Ala Asn Arg
705                 710                 715                 720
Asn Phe Met Gln Leu Ile His Asp Asp Ser Leu Thr Phe Lys Glu Asp
                725                 730                 735
Ile Gln Lys Ala Gln Val Ser Gly Gln Gly Asp Ser Leu His Glu His
            740                 745                 750
Ile Ala Asn Leu Ala Gly Ser Pro Ala Ile Lys Lys Gly Ile Leu Gln
            755                 760                 765
Thr Val Lys Val Val Asp Glu Leu Val Lys Val Met Gly Arg His Lys
770                 775                 780
Pro Glu Asn Ile Val Ile Glu Met Ala Arg Glu Asn Gln Thr Thr Gln
785                 790                 795                 800
Lys Gly Gln Lys Asn Ser Arg Glu Arg Met Lys Arg Ile Glu Glu Gly
                805                 810                 815
Ile Lys Glu Leu Gly Ser Gln Ile Leu Lys Glu His Pro Val Glu Asn
            820                 825                 830
Thr Gln Leu Gln Asn Glu Lys Leu Tyr Leu Tyr Tyr Leu Gln Asn Gly
            835                 840                 845
Arg Asp Met Tyr Val Asp Gln Glu Leu Asp Ile Asn Arg Leu Ser Asp
        850                 855                 860
Tyr Asp Val Asp Ala Ile Val Pro Gln Ser Phe Leu Lys Asp Asp Ser
865                 870                 875                 880
Ile Asp Asn Lys Val Leu Thr Arg Ser Asp Lys Asn Arg Gly Lys Ser
                885                 890                 895
Asp Asn Val Pro Ser Glu Glu Val Val Lys Lys Met Lys Asn Tyr Trp
            900                 905                 910
Arg Gln Leu Leu Asn Ala Lys Leu Ile Thr Gln Arg Lys Phe Asp Asn
            915                 920                 925
Leu Thr Lys Ala Glu Arg Gly Gly Leu Ser Glu Leu Asp Lys Ala Gly
930                 935                 940
Phe Ile Lys Arg Gln Leu Val Glu Thr Arg Gln Ile Thr Lys His Val
945                 950                 955                 960
Ala Gln Ile Leu Asp Ser Arg Met Asn Thr Lys Tyr Asp Glu Asn Asp
                965                 970                 975
Lys Leu Ile Arg Glu Val Lys Val Ile Thr Leu Lys Ser Lys Leu Val
            980                 985                 990
Ser Asp Phe Arg Lys Asp Phe Gln Phe Tyr Lys Val Arg Glu Ile Asn
        995                 1000                1005
Asn Tyr His His Ala His Asp Ala Tyr Leu Asn Ala Val Val Gly
    1010                1015                1020
Thr Ala Leu Ile Lys Lys Tyr Pro Lys Leu Glu Ser Glu Phe Val
    1025                1030                1035
Tyr Gly Asp Tyr Lys Val Tyr Asp Val Arg Lys Met Ile Ala Lys
    1040                1045                1050
Ser Glu Gln Glu Ile Gly Lys Ala Thr Ala Lys Tyr Phe Phe Tyr
    1055                1060                1065
Ser Asn Ile Met Asn Phe Phe Lys Thr Glu Ile Thr Leu Ala Asn
    1070                1075                1080
```

```
Gly Glu Ile Arg Lys Arg Pro Leu Ile Glu Thr Asn Gly Glu Thr
    1085                1090                1095

Gly Glu Ile Val Trp Asp Lys Gly Arg Asp Phe Ala Thr Val Arg
    1100                1105                1110

Lys Val Leu Ser Met Pro Gln Val Asn Ile Val Lys Lys Thr Glu
    1115                1120                1125

Val Gln Thr Gly Gly Phe Ser Lys Glu Ser Ile Leu Pro Lys Arg
    1130                1135                1140

Asn Ser Asp Lys Leu Ile Ala Arg Lys Lys Asp Trp Asp Pro Lys
    1145                1150                1155

Lys Tyr Gly Gly Phe Asp Ser Pro Thr Val Ala Tyr Ser Val Leu
    1160                1165                1170

Val Val Ala Lys Val Glu Lys Gly Lys Ser Lys Lys Leu Lys Ser
    1175                1180                1185

Val Lys Glu Leu Leu Gly Ile Thr Ile Met Glu Arg Ser Ser Phe
    1190                1195                1200

Glu Lys Asn Pro Ile Asp Phe Leu Glu Ala Lys Gly Tyr Lys Glu
    1205                1210                1215

Val Lys Lys Asp Leu Ile Ile Lys Leu Pro Lys Tyr Ser Leu Phe
    1220                1225                1230

Glu Leu Glu Asn Gly Arg Lys Arg Met Leu Ala Ser Ala Gly Glu
    1235                1240                1245

Leu Gln Lys Gly Asn Glu Leu Ala Leu Pro Ser Lys Tyr Val Asn
    1250                1255                1260

Phe Leu Tyr Leu Ala Ser His Tyr Glu Lys Leu Lys Gly Ser Pro
    1265                1270                1275

Glu Asp Asn Glu Gln Lys Gln Leu Phe Val Glu Gln His Lys His
    1280                1285                1290

Tyr Leu Asp Glu Ile Ile Glu Gln Ile Ser Glu Phe Ser Lys Arg
    1295                1300                1305

Val Ile Leu Ala Asp Ala Asn Leu Asp Lys Val Leu Ser Ala Tyr
    1310                1315                1320

Asn Lys His Arg Asp Lys Pro Ile Arg Glu Gln Ala Glu Asn Ile
    1325                1330                1335

Ile His Leu Phe Thr Leu Thr Asn Leu Gly Ala Pro Ala Ala Phe
    1340                1345                1350

Lys Tyr Phe Asp Thr Thr Ile Asp Arg Lys Arg Tyr Thr Ser Thr
    1355                1360                1365

Lys Glu Val Leu Asp Ala Thr Leu Ile His Gln Ser Ile Thr Gly
    1370                1375                1380

Leu Tyr Glu Thr Arg Ile Asp Leu Ser Gln Leu Gly Gly Asp Gly
    1385                1390                1395

Gly Gly Gly Ser Gly Gly Gly Ser Gly Gly Gly Ser Tyr
    1400                1405                1410

Val Val Lys Arg Arg Asp Ser Ala Thr Ser Phe Ser Leu Asp Phe
    1415                1420                1425

Gly Tyr Leu Arg Asn Lys Asn Gly Cys His Val Glu Leu Leu Phe
    1430                1435                1440

Leu Arg Tyr Ile Ser Asp Trp Asp Leu Asp Pro Gly Arg Cys Tyr
    1445                1450                1455

Arg Val Thr Trp Phe Thr Ser Trp Ser Pro Cys Tyr Asp Cys Ala
    1460                1465                1470

Arg His Val Ala Asp Phe Leu Arg Gly Asn Pro Asn Leu Ser Leu
```

```
                    1475                1480                1485
Arg Ile Phe Thr Ala Arg Leu Tyr Phe Cys Glu Asp Arg Lys Ala
            1490                1495                1500

Glu Pro Glu Gly Leu Arg Arg Leu His Arg Ala Gly Val Gln Ile
        1505                1510                1515

Ala Ile Met Thr Phe Lys Asp Tyr Phe Tyr Cys Trp Asn Thr Phe
    1520                1525                1530

Val Glu Asn His Glu Arg Thr Phe Lys Ala Trp Glu Gly Leu His
1535                1540                1545

Glu Asn Ser Val Arg Leu Ser Arg Gln Leu Arg Ile Leu Leu
        1550                1555                1560

Pro Leu Tyr Glu Val Asp Asp Leu Arg Asp Ala Phe Arg Thr Leu
    1565                1570                1575

Gly Leu
    1580

<210> SEQ ID NO 31
<211> LENGTH: 1564
<212> TYPE: PRT
<213> ORGANISM: Artificial Sequence
<220> FEATURE:
<223> OTHER INFORMATION: Synthetic Polypeptide

<400> SEQUENCE: 31

Met Asp Ser Leu Leu Met Asn Arg Arg Lys Phe Leu Tyr Gln Phe Lys
1               5                   10                  15

Asn Val Arg Trp Ala Lys Gly Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Gly Gly Gly Ser Gly Gly Gly Gly Ser
            180                 185                 190

Gly Gly Gly Gly Ser Asp Lys Lys Tyr Ser Ile Gly Leu Ala Ile Gly
        195                 200                 205

Thr Asn Ser Val Gly Trp Ala Val Ile Thr Asp Glu Tyr Lys Val Pro
    210                 215                 220

Ser Lys Lys Phe Lys Val Leu Gly Asn Thr Asp Arg His Ser Ile Lys
225                 230                 235                 240

Lys Asn Leu Ile Gly Ala Leu Leu Phe Asp Ser Gly Glu Thr Ala Glu
```

-continued

```
                    245                 250                 255
Ala Thr Arg Leu Lys Arg Thr Ala Arg Arg Tyr Thr Arg Arg Lys
                260                 265                 270

Asn Arg Ile Cys Tyr Leu Gln Glu Ile Phe Ser Asn Glu Met Ala Lys
                275                 280                 285

Val Asp Asp Ser Phe Phe His Arg Leu Glu Glu Ser Phe Leu Val Glu
    290                 295                 300

Glu Asp Lys Lys His Glu Arg His Pro Ile Phe Gly Asn Ile Val Asp
305                 310                 315                 320

Glu Val Ala Tyr His Glu Lys Tyr Pro Thr Ile Tyr His Leu Arg Lys
                325                 330                 335

Lys Leu Val Asp Ser Thr Asp Lys Ala Asp Leu Arg Leu Ile Tyr Leu
                340                 345                 350

Ala Leu Ala His Met Ile Lys Phe Arg Gly His Phe Leu Ile Glu Gly
                355                 360                 365

Asp Leu Asn Pro Asp Asn Ser Asp Val Asp Lys Leu Phe Ile Gln Leu
            370                 375                 380

Val Gln Thr Tyr Asn Gln Leu Phe Glu Glu Asn Pro Ile Asn Ala Ser
385                 390                 395                 400

Gly Val Asp Ala Lys Ala Ile Leu Ser Ala Arg Leu Ser Lys Ser Arg
                405                 410                 415

Arg Leu Glu Asn Leu Ile Ala Gln Leu Pro Gly Glu Lys Lys Asn Gly
                420                 425                 430

Leu Phe Gly Asn Leu Ile Ala Leu Ser Leu Gly Leu Thr Pro Asn Phe
            435                 440                 445

Lys Ser Asn Phe Asp Leu Ala Glu Asp Ala Lys Leu Gln Leu Ser Lys
        450                 455                 460

Asp Thr Tyr Asp Asp Asp Leu Asp Asn Leu Leu Ala Gln Ile Gly Asp
465                 470                 475                 480

Gln Tyr Ala Asp Leu Phe Leu Ala Ala Lys Asn Leu Ser Asp Ala Ile
                485                 490                 495

Leu Leu Ser Asp Ile Leu Arg Val Asn Thr Glu Ile Thr Lys Ala Pro
                500                 505                 510

Leu Ser Ala Ser Met Ile Lys Arg Tyr Asp Glu His His Gln Asp Leu
            515                 520                 525

Thr Leu Leu Lys Ala Leu Val Arg Gln Gln Leu Pro Glu Lys Tyr Lys
        530                 535                 540

Glu Ile Phe Phe Asp Gln Ser Lys Asn Gly Tyr Ala Gly Tyr Ile Asp
545                 550                 555                 560

Gly Gly Ala Ser Gln Glu Glu Phe Tyr Lys Phe Ile Lys Pro Ile Leu
                565                 570                 575

Glu Lys Met Asp Gly Thr Glu Glu Leu Leu Val Lys Leu Asn Arg Glu
            580                 585                 590

Asp Leu Leu Arg Lys Gln Arg Thr Phe Asp Asn Gly Ser Ile Pro His
        595                 600                 605

Gln Ile His Leu Gly Glu Leu His Ala Ile Leu Arg Arg Gln Glu Asp
    610                 615                 620

Phe Tyr Pro Phe Leu Lys Asp Asn Arg Glu Lys Ile Glu Lys Ile Leu
625                 630                 635                 640

Thr Phe Arg Ile Pro Tyr Tyr Val Gly Pro Leu Ala Arg Gly Asn Ser
                645                 650                 655

Arg Phe Ala Trp Met Thr Arg Lys Ser Glu Glu Thr Ile Thr Pro Trp
            660                 665                 670
```

```
Asn Phe Glu Glu Val Val Asp Lys Gly Ala Ser Ala Gln Ser Phe Ile
            675                 680                 685

Glu Arg Met Thr Asn Phe Asp Lys Asn Leu Pro Asn Glu Lys Val Leu
        690                 695                 700

Pro Lys His Ser Leu Leu Tyr Glu Tyr Phe Thr Val Tyr Asn Glu Leu
705                 710                 715                 720

Thr Lys Val Lys Tyr Val Thr Glu Gly Met Arg Lys Pro Ala Phe Leu
                725                 730                 735

Ser Gly Glu Gln Lys Lys Ala Ile Val Asp Leu Leu Phe Lys Thr Asn
            740                 745                 750

Arg Lys Val Thr Val Lys Gln Leu Lys Glu Asp Tyr Phe Lys Lys Ile
        755                 760                 765

Glu Cys Phe Asp Ser Val Glu Ile Ser Gly Val Glu Asp Arg Phe Asn
770                 775                 780

Ala Ser Leu Gly Thr Tyr His Asp Leu Leu Lys Ile Ile Lys Asp Lys
785                 790                 795                 800

Asp Phe Leu Asp Asn Glu Glu Asn Glu Asp Ile Leu Glu Asp Ile Val
                805                 810                 815

Leu Thr Leu Thr Leu Phe Glu Asp Arg Glu Met Ile Glu Glu Arg Leu
            820                 825                 830

Lys Thr Tyr Ala His Leu Phe Asp Asp Lys Val Met Lys Gln Leu Lys
        835                 840                 845

Arg Arg Arg Tyr Thr Gly Trp Gly Arg Leu Ser Arg Lys Leu Ile Asn
850                 855                 860

Gly Ile Arg Asp Lys Gln Ser Gly Lys Thr Ile Leu Asp Phe Leu Lys
865                 870                 875                 880

Ser Asp Gly Phe Ala Asn Arg Asn Phe Met Gln Leu Ile His Asp Asp
                885                 890                 895

Ser Leu Thr Phe Lys Glu Asp Ile Gln Lys Ala Gln Val Ser Gly Gln
            900                 905                 910

Gly Asp Ser Leu His Glu His Ile Ala Asn Leu Ala Gly Ser Pro Ala
        915                 920                 925

Ile Lys Lys Gly Ile Leu Gln Thr Val Lys Val Val Asp Glu Leu Val
930                 935                 940

Lys Val Met Gly Arg His Lys Pro Glu Asn Ile Val Ile Glu Met Ala
945                 950                 955                 960

Arg Glu Asn Gln Thr Thr Gln Lys Gly Gln Lys Asn Ser Arg Glu Arg
                965                 970                 975

Met Lys Arg Ile Glu Glu Gly Ile Lys Glu Leu Gly Ser Gln Ile Leu
            980                 985                 990

Lys Glu His Pro Val Glu Asn Thr Gln Leu Gln Asn Glu Lys Leu Tyr
        995                 1000                1005

Leu Tyr Tyr Leu Gln Asn Gly Arg Asp Met Tyr Val Asp Gln Glu
    1010                1015                1020

Leu Asp Ile Asn Arg Leu Ser Asp Tyr Asp Val Asp Ala Ile Val
    1025                1030                1035

Pro Gln Ser Phe Leu Lys Asp Asp Ser Ile Asp Asn Lys Val Leu
    1040                1045                1050

Thr Arg Ser Asp Lys Asn Arg Gly Lys Ser Asp Asn Val Pro Ser
    1055                1060                1065

Glu Glu Val Val Lys Lys Met Lys Asn Tyr Trp Arg Gln Leu Leu
    1070                1075                1080
```

-continued

| | | | | | | | | | | | |
|---|---|---|---|---|---|---|---|---|---|---|---|
| Asn | Ala | Lys | Leu | Ile | Thr | Gln | Arg | Lys | Phe | Asp | Asn | Leu | Thr | Lys |
| | 1085 | | | | | 1090 | | | | | 1095 | | | |
| Ala | Glu | Arg | Gly | Gly | Leu | Ser | Glu | Leu | Asp | Lys | Ala | Gly | Phe | Ile |
| | 1100 | | | | | 1105 | | | | | 1110 | | | |
| Lys | Arg | Gln | Leu | Val | Glu | Thr | Arg | Gln | Ile | Thr | Lys | His | Val | Ala |
| | 1115 | | | | | 1120 | | | | | 1125 | | | |
| Gln | Ile | Leu | Asp | Ser | Arg | Met | Asn | Thr | Lys | Tyr | Asp | Glu | Asn | Asp |
| | 1130 | | | | | 1135 | | | | | 1140 | | | |
| Lys | Leu | Ile | Arg | Glu | Val | Lys | Val | Ile | Thr | Leu | Lys | Ser | Lys | Leu |
| | 1145 | | | | | 1150 | | | | | 1155 | | | |
| Val | Ser | Asp | Phe | Arg | Lys | Asp | Phe | Gln | Phe | Tyr | Lys | Val | Arg | Glu |
| | 1160 | | | | | 1165 | | | | | 1170 | | | |
| Ile | Asn | Asn | Tyr | His | His | Ala | His | Asp | Ala | Tyr | Leu | Asn | Ala | Val |
| | 1175 | | | | | 1180 | | | | | 1185 | | | |
| Val | Gly | Thr | Ala | Leu | Ile | Lys | Lys | Tyr | Pro | Lys | Leu | Glu | Ser | Glu |
| | 1190 | | | | | 1195 | | | | | 1200 | | | |
| Phe | Val | Tyr | Gly | Asp | Tyr | Lys | Val | Tyr | Asp | Val | Arg | Lys | Met | Ile |
| | 1205 | | | | | 1210 | | | | | 1215 | | | |
| Ala | Lys | Ser | Glu | Gln | Glu | Ile | Gly | Lys | Ala | Thr | Ala | Lys | Tyr | Phe |
| | 1220 | | | | | 1225 | | | | | 1230 | | | |
| Phe | Tyr | Ser | Asn | Ile | Met | Asn | Phe | Phe | Lys | Thr | Glu | Ile | Thr | Leu |
| | 1235 | | | | | 1240 | | | | | 1245 | | | |
| Ala | Asn | Gly | Glu | Ile | Arg | Lys | Arg | Pro | Leu | Ile | Glu | Thr | Asn | Gly |
| | 1250 | | | | | 1255 | | | | | 1260 | | | |
| Glu | Thr | Gly | Glu | Ile | Val | Trp | Asp | Lys | Gly | Arg | Asp | Phe | Ala | Thr |
| | 1265 | | | | | 1270 | | | | | 1275 | | | |
| Val | Arg | Lys | Val | Leu | Ser | Met | Pro | Gln | Val | Asn | Ile | Val | Lys | Lys |
| | 1280 | | | | | 1285 | | | | | 1290 | | | |
| Thr | Glu | Val | Gln | Thr | Gly | Gly | Phe | Ser | Lys | Glu | Ser | Ile | Leu | Pro |
| | 1295 | | | | | 1300 | | | | | 1305 | | | |
| Lys | Arg | Asn | Ser | Asp | Lys | Leu | Ile | Ala | Arg | Lys | Lys | Asp | Trp | Asp |
| | 1310 | | | | | 1315 | | | | | 1320 | | | |
| Pro | Lys | Lys | Tyr | Gly | Gly | Phe | Asp | Ser | Pro | Thr | Val | Ala | Tyr | Ser |
| | 1325 | | | | | 1330 | | | | | 1335 | | | |
| Val | Leu | Val | Val | Ala | Lys | Val | Glu | Lys | Gly | Lys | Ser | Lys | Lys | Leu |
| | 1340 | | | | | 1345 | | | | | 1350 | | | |
| Lys | Ser | Val | Lys | Glu | Leu | Leu | Gly | Ile | Thr | Ile | Met | Glu | Arg | Ser |
| | 1355 | | | | | 1360 | | | | | 1365 | | | |
| Ser | Phe | Glu | Lys | Asn | Pro | Ile | Asp | Phe | Leu | Glu | Ala | Lys | Gly | Tyr |
| | 1370 | | | | | 1375 | | | | | 1380 | | | |
| Lys | Glu | Val | Lys | Lys | Asp | Leu | Ile | Ile | Lys | Leu | Pro | Lys | Tyr | Ser |
| | 1385 | | | | | 1390 | | | | | 1395 | | | |
| Leu | Phe | Glu | Leu | Glu | Asn | Gly | Arg | Lys | Arg | Met | Leu | Ala | Ser | Ala |
| | 1400 | | | | | 1405 | | | | | 1410 | | | |
| Gly | Glu | Leu | Gln | Lys | Gly | Asn | Glu | Leu | Ala | Leu | Pro | Ser | Lys | Tyr |
| | 1415 | | | | | 1420 | | | | | 1425 | | | |
| Val | Asn | Phe | Leu | Tyr | Leu | Ala | Ser | His | Tyr | Glu | Lys | Leu | Lys | Gly |
| | 1430 | | | | | 1435 | | | | | 1440 | | | |
| Ser | Pro | Glu | Asp | Asn | Glu | Gln | Lys | Gln | Leu | Phe | Val | Glu | Gln | His |
| | 1445 | | | | | 1450 | | | | | 1455 | | | |
| Lys | His | Tyr | Leu | Asp | Glu | Ile | Ile | Glu | Gln | Ile | Ser | Glu | Phe | Ser |
| | 1460 | | | | | 1465 | | | | | 1470 | | | |
| Lys | Arg | Val | Ile | Leu | Ala | Asp | Ala | Asn | Leu | Asp | Lys | Val | Leu | Ser |

-continued

```
                1475                1480                1485

Ala Tyr Asn Lys His Arg Asp Lys Pro Ile Arg Glu Gln Ala Glu
        1490                1495                1500

Asn Ile Ile His Leu Phe Thr Leu Thr Asn Leu Gly Ala Pro Ala
        1505                1510                1515

Ala Phe Lys Tyr Phe Asp Thr Thr Ile Asp Arg Lys Arg Tyr Thr
        1520                1525                1530

Ser Thr Lys Glu Val Leu Asp Ala Thr Leu Ile His Gln Ser Ile
        1535                1540                1545

Thr Gly Leu Tyr Glu Thr Arg Ile Asp Leu Ser Gln Leu Gly Gly
        1550                1555                1560

Asp

<210> SEQ ID NO 32
<211> LENGTH: 1580
<212> TYPE: PRT
<213> ORGANISM: Artificial Sequence
<220> FEATURE:
<223> OTHER INFORMATION: Synthetic Polypeptide

<400> SEQUENCE: 32

Met Asp Ser Leu Leu Met Asn Arg Arg Lys Phe Leu Tyr Gln Phe Lys
1               5                   10                  15

Asn Val Arg Trp Ala Lys Gly Arg Glu Thr Tyr Leu Cys Asp Lys
            20                  25                  30

Lys Tyr Ser Ile Gly Leu Ala Ile Gly Thr Asn Ser Val Gly Trp Ala
                35                  40                  45

Val Ile Thr Asp Glu Tyr Lys Val Pro Ser Lys Lys Phe Lys Val Leu
    50                  55                  60

Gly Asn Thr Asp Arg His Ser Ile Lys Lys Asn Leu Ile Gly Ala Leu
65                  70                  75                  80

Leu Phe Asp Ser Gly Glu Thr Ala Glu Ala Thr Arg Leu Lys Arg Thr
                85                  90                  95

Ala Arg Arg Arg Tyr Thr Arg Arg Lys Asn Arg Ile Cys Tyr Leu Gln
            100                 105                 110

Glu Ile Phe Ser Asn Glu Met Ala Lys Val Asp Asp Ser Phe Phe His
        115                 120                 125

Arg Leu Glu Glu Ser Phe Leu Val Glu Glu Asp Lys Lys His Glu Arg
        130                 135                 140

His Pro Ile Phe Gly Asn Ile Val Asp Glu Val Ala Tyr His Glu Lys
145                 150                 155                 160

Tyr Pro Thr Ile Tyr His Leu Arg Lys Lys Leu Val Asp Ser Thr Asp
                165                 170                 175

Lys Ala Asp Leu Arg Leu Ile Tyr Leu Ala Leu Ala His Met Ile Lys
            180                 185                 190

Phe Arg Gly His Phe Leu Ile Glu Gly Asp Leu Asn Pro Asp Asn Ser
        195                 200                 205

Asp Val Asp Lys Leu Phe Ile Gln Leu Val Gln Thr Tyr Asn Gln Leu
        210                 215                 220

Phe Glu Glu Asn Pro Ile Asn Ala Ser Gly Val Asp Ala Lys Ala Ile
225                 230                 235                 240

Leu Ser Ala Arg Leu Ser Lys Ser Arg Arg Leu Glu Asn Leu Ile Ala
                245                 250                 255

Gln Leu Pro Gly Glu Lys Lys Asn Gly Leu Phe Gly Asn Leu Ile Ala
            260                 265                 270
```

-continued

```
Leu Ser Leu Gly Leu Thr Pro Asn Phe Lys Ser Asn Phe Asp Leu Ala
        275                 280                 285

Glu Asp Ala Lys Leu Gln Leu Ser Lys Asp Thr Tyr Asp Asp Asp Leu
    290                 295                 300

Asp Asn Leu Leu Ala Gln Ile Gly Asp Gln Tyr Ala Asp Leu Phe Leu
305                 310                 315                 320

Ala Ala Lys Asn Leu Ser Asp Ala Ile Leu Leu Ser Asp Ile Leu Arg
            325                 330                 335

Val Asn Thr Glu Ile Thr Lys Ala Pro Leu Ser Ala Ser Met Ile Lys
            340                 345                 350

Arg Tyr Asp Glu His His Gln Asp Leu Thr Leu Leu Lys Ala Leu Val
        355                 360                 365

Arg Gln Gln Leu Pro Glu Lys Tyr Lys Glu Ile Phe Phe Asp Gln Ser
    370                 375                 380

Lys Asn Gly Tyr Ala Gly Tyr Ile Asp Gly Gly Ala Ser Gln Glu Glu
385                 390                 395                 400

Phe Tyr Lys Phe Ile Lys Pro Ile Leu Glu Lys Met Asp Gly Thr Glu
            405                 410                 415

Glu Leu Leu Val Lys Leu Asn Arg Glu Asp Leu Leu Arg Lys Gln Arg
            420                 425                 430

Thr Phe Asp Asn Gly Ser Ile Pro His Gln Ile His Leu Gly Glu Leu
        435                 440                 445

His Ala Ile Leu Arg Arg Gln Glu Asp Phe Tyr Pro Phe Leu Lys Asp
    450                 455                 460

Asn Arg Glu Lys Ile Glu Lys Ile Leu Thr Phe Arg Ile Pro Tyr Tyr
465                 470                 475                 480

Val Gly Pro Leu Ala Arg Gly Asn Ser Arg Phe Ala Trp Met Thr Arg
            485                 490                 495

Lys Ser Glu Glu Thr Ile Thr Pro Trp Asn Phe Glu Glu Val Val Asp
            500                 505                 510

Lys Gly Ala Ser Ala Gln Ser Phe Ile Glu Arg Met Thr Asn Phe Asp
        515                 520                 525

Lys Asn Leu Pro Asn Glu Lys Val Leu Pro Lys His Ser Leu Leu Tyr
    530                 535                 540

Glu Tyr Phe Thr Val Tyr Asn Glu Leu Thr Lys Val Lys Tyr Val Thr
545                 550                 555                 560

Glu Gly Met Arg Lys Pro Ala Phe Leu Ser Gly Glu Gln Lys Lys Ala
            565                 570                 575

Ile Val Asp Leu Leu Phe Lys Thr Asn Arg Lys Val Thr Val Lys Gln
            580                 585                 590

Leu Lys Glu Asp Tyr Phe Lys Lys Ile Glu Cys Phe Asp Ser Val Glu
        595                 600                 605

Ile Ser Gly Val Glu Asp Arg Phe Asn Ala Ser Leu Gly Thr Tyr His
    610                 615                 620

Asp Leu Leu Lys Ile Ile Lys Asp Lys Asp Phe Leu Asp Asn Glu Glu
625                 630                 635                 640

Asn Glu Asp Ile Leu Glu Asp Ile Val Leu Thr Leu Thr Leu Phe Glu
            645                 650                 655

Asp Arg Glu Met Ile Glu Glu Arg Leu Lys Thr Tyr Ala His Leu Phe
            660                 665                 670

Asp Asp Lys Val Met Lys Gln Leu Lys Arg Arg Arg Tyr Thr Gly Trp
        675                 680                 685
```

```
Gly Arg Leu Ser Arg Lys Leu Ile Asn Gly Ile Arg Asp Lys Gln Ser
    690             695             700

Gly Lys Thr Ile Leu Asp Phe Leu Lys Ser Asp Gly Phe Ala Asn Arg
705             710             715             720

Asn Phe Met Gln Leu Ile His Asp Asp Ser Leu Thr Phe Lys Glu Asp
                725             730             735

Ile Gln Lys Ala Gln Val Ser Gly Gln Gly Asp Ser Leu His Glu His
            740             745             750

Ile Ala Asn Leu Ala Gly Ser Pro Ala Ile Lys Lys Gly Ile Leu Gln
            755             760             765

Thr Val Lys Val Val Asp Glu Leu Val Lys Val Met Gly Arg His Lys
    770             775             780

Pro Glu Asn Ile Val Ile Glu Met Ala Arg Glu Asn Gln Thr Thr Gln
785             790             795             800

Lys Gly Gln Lys Asn Ser Arg Glu Arg Met Lys Arg Ile Glu Glu Gly
                805             810             815

Ile Lys Glu Leu Gly Ser Gln Ile Leu Lys Glu His Pro Val Glu Asn
            820             825             830

Thr Gln Leu Gln Asn Glu Lys Leu Tyr Leu Tyr Tyr Leu Gln Asn Gly
            835             840             845

Arg Asp Met Tyr Val Asp Gln Glu Leu Asp Ile Asn Arg Leu Ser Asp
    850             855             860

Tyr Asp Val Asp Ala Ile Val Pro Gln Ser Phe Leu Lys Asp Asp Ser
865             870             875             880

Ile Asp Asn Lys Val Leu Thr Arg Ser Asp Lys Asn Arg Gly Lys Ser
                885             890             895

Asp Asn Val Pro Ser Glu Glu Val Val Lys Lys Met Lys Asn Tyr Trp
            900             905             910

Arg Gln Leu Leu Asn Ala Lys Leu Ile Thr Gln Arg Lys Phe Asp Asn
            915             920             925

Leu Thr Lys Ala Glu Arg Gly Gly Leu Ser Glu Leu Asp Lys Ala Gly
    930             935             940

Phe Ile Lys Arg Gln Leu Val Glu Thr Arg Gln Ile Thr Lys His Val
945             950             955             960

Ala Gln Ile Leu Asp Ser Arg Met Asn Thr Lys Tyr Asp Glu Asn Asp
                965             970             975

Lys Leu Ile Arg Glu Val Lys Val Ile Thr Leu Lys Ser Lys Leu Val
            980             985             990

Ser Asp Phe Arg Lys Asp Phe Gln Phe Tyr Lys Val Arg Glu Ile Asn
            995             1000            1005

Asn Tyr His His Ala His Asp Ala Tyr Leu Asn Ala Val Val Gly
    1010            1015            1020

Thr Ala Leu Ile Lys Lys Tyr Pro Lys Leu Glu Ser Glu Phe Val
    1025            1030            1035

Tyr Gly Asp Tyr Lys Val Tyr Asp Val Arg Lys Met Ile Ala Lys
    1040            1045            1050

Ser Glu Gln Glu Ile Gly Lys Ala Thr Ala Lys Tyr Phe Phe Tyr
    1055            1060            1065

Ser Asn Ile Met Asn Phe Phe Lys Thr Glu Ile Thr Leu Ala Asn
    1070            1075            1080

Gly Glu Ile Arg Lys Arg Pro Leu Ile Glu Thr Asn Gly Glu Thr
    1085            1090            1095

Gly Glu Ile Val Trp Asp Lys Gly Arg Asp Phe Ala Thr Val Arg
```

```
            1100                1105                1110
Lys Val Leu Ser Met Pro Gln Val Asn Ile Val Lys Lys Thr Glu
            1115                1120                1125
Val Gln Thr Gly Gly Phe Ser Lys Glu Ser Ile Leu Pro Lys Arg
            1130                1135                1140
Asn Ser Asp Lys Leu Ile Ala Arg Lys Lys Asp Trp Asp Pro Lys
            1145                1150                1155
Lys Tyr Gly Gly Phe Asp Ser Pro Thr Val Ala Tyr Ser Val Leu
            1160                1165                1170
Val Val Ala Lys Val Glu Lys Gly Lys Ser Lys Lys Leu Lys Ser
            1175                1180                1185
Val Lys Glu Leu Leu Gly Ile Thr Ile Met Glu Arg Ser Ser Phe
            1190                1195                1200
Glu Lys Asn Pro Ile Asp Phe Leu Glu Ala Lys Gly Tyr Lys Glu
            1205                1210                1215
Val Lys Lys Asp Leu Ile Ile Lys Leu Pro Lys Tyr Ser Leu Phe
            1220                1225                1230
Glu Leu Glu Asn Gly Arg Lys Arg Met Leu Ala Ser Ala Gly Glu
            1235                1240                1245
Leu Gln Lys Gly Asn Glu Leu Ala Leu Pro Ser Lys Tyr Val Asn
            1250                1255                1260
Phe Leu Tyr Leu Ala Ser His Tyr Glu Lys Leu Lys Gly Ser Pro
            1265                1270                1275
Glu Asp Asn Glu Gln Lys Gln Leu Phe Val Glu Gln His Lys His
            1280                1285                1290
Tyr Leu Asp Glu Ile Ile Glu Gln Ile Ser Glu Phe Ser Lys Arg
            1295                1300                1305
Val Ile Leu Ala Asp Ala Asn Leu Asp Lys Val Leu Ser Ala Tyr
            1310                1315                1320
Asn Lys His Arg Asp Lys Pro Ile Arg Glu Gln Ala Glu Asn Ile
            1325                1330                1335
Ile His Leu Phe Thr Leu Thr Asn Leu Gly Ala Pro Ala Ala Phe
            1340                1345                1350
Lys Tyr Phe Asp Thr Thr Ile Asp Arg Lys Arg Tyr Thr Ser Thr
            1355                1360                1365
Lys Glu Val Leu Asp Ala Thr Leu Ile His Gln Ser Ile Thr Gly
            1370                1375                1380
Leu Tyr Glu Thr Arg Ile Asp Leu Ser Gln Leu Gly Gly Asp Gly
            1385                1390                1395
Gly Gly Gly Ser Gly Gly Gly Gly Ser Gly Gly Gly Gly Ser Tyr
            1400                1405                1410
Val Val Lys Arg Arg Asp Ser Ala Thr Ser Cys Ser Leu Asp Phe
            1415                1420                1425
Gly His Leu Arg Asn Lys Ser Gly Cys His Val Glu Leu Leu Phe
            1430                1435                1440
Leu Arg Tyr Ile Ser Asp Trp Asp Leu Asp Pro Gly Arg Cys Tyr
            1445                1450                1455
Arg Val Thr Trp Phe Thr Ser Trp Ser Pro Cys Tyr Asp Cys Ala
            1460                1465                1470
Arg His Val Ala Glu Phe Leu Arg Trp Asn Pro Asn Leu Ser Leu
            1475                1480                1485
Arg Ile Phe Thr Ala Arg Leu Tyr Phe Cys Glu Asp Arg Lys Ala
            1490                1495                1500
```

```
Glu Pro Glu Gly Leu Arg Arg Leu His Arg Ala Gly Val Gln Ile
    1505                1510                1515

Gly Ile Met Thr Phe Lys Asp Tyr Phe Tyr Cys Trp Asn Thr Phe
    1520                1525                1530

Val Glu Asn Arg Glu Arg Thr Phe Lys Ala Trp Glu Gly Leu His
    1535                1540                1545

Glu Asn Ser Val Arg Leu Thr Arg Gln Leu Arg Arg Ile Leu Leu
    1550                1555                1560

Pro Leu Tyr Glu Val Asp Asp Leu Arg Asp Ala Phe Arg Met Leu
    1565                1570                1575

Gly Phe
    1580

<210> SEQ ID NO 33
<211> LENGTH: 1724
<212> TYPE: PRT
<213> ORGANISM: Artificial Sequence
<220> FEATURE:
<223> OTHER INFORMATION: Synthetic Polypeptide

<400> SEQUENCE: 33

Ser Pro Lys Lys Lys Arg Lys Val Glu Ala Ser Met Glu Leu Lys Tyr
1               5                   10                  15

His Pro Glu Met Arg Phe Phe His Trp Phe Ser Lys Trp Arg Lys Leu
            20                  25                  30

His Arg Asp Gln Glu Tyr Glu Val Thr Trp Tyr Ile Ser Trp Ser Pro
        35                  40                  45

Cys Thr Lys Cys Thr Arg Asp Met Ala Thr Phe Leu Ala Glu Asp Pro
    50                  55                  60

Lys Val Thr Leu Thr Ile Phe Val Ala Arg Leu Tyr Tyr Phe Trp Asp
65                  70                  75                  80

Pro Asp Tyr Gln Glu Ala Leu Arg Ser Leu Cys Gln Lys Arg Asp Gly
                85                  90                  95

Pro Arg Ala Thr Met Lys Ile Met Asn Tyr Asp Glu Phe Gln His Cys
            100                 105                 110

Trp Ser Lys Phe Val Tyr Ser Gln Arg Glu Leu Phe Glu Pro Trp Asn
        115                 120                 125

Asn Leu Pro Lys Tyr Tyr Ile Leu Leu His Ile Met Leu Gly Glu Ile
    130                 135                 140

Leu Arg His Ser Met Asp Pro Pro Thr Phe Thr Phe Asn Phe Asn Asn
145                 150                 155                 160

Glu Pro Trp Val Arg Gly Arg His Glu Thr Tyr Leu Cys Tyr Glu Val
                165                 170                 175

Glu Arg Met His Asn Asp Thr Trp Val Leu Leu Asn Gln Arg Arg Gly
            180                 185                 190

Phe Leu Cys Asn Gln Ala Pro His Lys His Gly Phe Leu Glu Gly Arg
        195                 200                 205

His Ala Glu Leu Cys Phe Leu Asp Val Ile Pro Phe Trp Lys Leu Asp
    210                 215                 220

Leu Asp Gln Asp Tyr Arg Val Thr Cys Phe Thr Ser Trp Ser Pro Cys
225                 230                 235                 240

Phe Ser Cys Ala Gln Glu Met Ala Lys Phe Ile Ser Lys Asn Lys His
                245                 250                 255

Val Ser Leu Cys Ile Phe Thr Ala Arg Ile Tyr Asp Asp Gln Gly Arg
            260                 265                 270
```

```
Cys Gln Glu Gly Leu Arg Thr Leu Ala Glu Ala Gly Ala Lys Ile Ser
        275                 280                 285

Ile Met Thr Tyr Ser Glu Phe Lys His Cys Trp Asp Thr Phe Val Asp
    290                 295                 300

His Gln Gly Cys Pro Phe Gln Pro Trp Asp Gly Leu Asp Glu His Ser
305                 310                 315                 320

Gln Asp Leu Ser Gly Arg Leu Arg Ala Ile Leu Gln Asn Gln Glu Asn
                325                 330                 335

Ser Pro Lys Lys Arg Lys Val Glu Ala Ser Ser Pro Lys Lys Lys
                340                 345                 350

Arg Lys Val Glu Ala Ser Lys Lys Tyr Ser Ile Gly Leu Ala Ile Gly
        355                 360                 365

Thr Asn Ser Val Gly Trp Ala Val Ile Thr Asp Glu Tyr Lys Val Pro
    370                 375                 380

Ser Lys Lys Phe Lys Val Leu Gly Asn Thr Asp Arg His Ser Ile Lys
385                 390                 395                 400

Lys Asn Leu Ile Gly Ala Leu Leu Phe Asp Ser Gly Glu Thr Ala Glu
                405                 410                 415

Ala Thr Arg Leu Lys Arg Thr Ala Arg Arg Arg Tyr Thr Arg Arg Lys
        420                 425                 430

Asn Arg Ile Cys Tyr Leu Gln Glu Ile Phe Ser Asn Glu Met Ala Lys
    435                 440                 445

Val Asp Asp Ser Phe Phe His Arg Leu Glu Glu Ser Phe Leu Val Glu
    450                 455                 460

Glu Asp Lys Lys His Glu Arg His Pro Ile Phe Gly Asn Ile Val Asp
465                 470                 475                 480

Glu Val Ala Tyr His Glu Lys Tyr Pro Thr Ile Tyr His Leu Arg Lys
                485                 490                 495

Lys Leu Val Asp Ser Thr Asp Lys Ala Asp Leu Arg Leu Ile Tyr Leu
        500                 505                 510

Ala Leu Ala His Met Ile Lys Phe Arg Gly His Phe Leu Ile Glu Gly
        515                 520                 525

Asp Leu Asn Pro Asp Asn Ser Asp Val Asp Lys Leu Phe Ile Gln Leu
        530                 535                 540

Val Gln Thr Tyr Asn Gln Leu Phe Glu Glu Asn Pro Ile Asn Ala Ser
545                 550                 555                 560

Gly Val Asp Ala Lys Ala Ile Leu Ser Ala Arg Leu Ser Lys Ser Arg
                565                 570                 575

Arg Leu Glu Asn Leu Ile Ala Gln Leu Pro Gly Glu Lys Lys Asn Gly
        580                 585                 590

Leu Phe Gly Asn Leu Ile Ala Leu Ser Leu Gly Leu Thr Pro Asn Phe
        595                 600                 605

Lys Ser Asn Phe Asp Leu Ala Glu Asp Ala Lys Leu Gln Leu Ser Lys
        610                 615                 620

Asp Thr Tyr Asp Asp Asp Leu Asp Asn Leu Leu Ala Gln Ile Gly Asp
625                 630                 635                 640

Gln Tyr Ala Asp Leu Phe Leu Ala Ala Lys Asn Leu Ser Asp Ala Ile
                645                 650                 655

Leu Leu Ser Asp Ile Leu Arg Val Asn Thr Glu Ile Thr Lys Ala Pro
        660                 665                 670

Leu Ser Ala Ser Met Ile Lys Arg Tyr Asp Glu His His Gln Asp Leu
        675                 680                 685
```

```
Thr Leu Leu Lys Ala Leu Val Arg Gln Gln Leu Pro Glu Lys Tyr Lys
        690                 695                 700

Glu Ile Phe Phe Asp Gln Ser Lys Asn Gly Tyr Ala Gly Tyr Ile Asp
705                 710                 715                 720

Gly Gly Ala Ser Gln Glu Glu Phe Tyr Lys Phe Ile Lys Pro Ile Leu
                725                 730                 735

Glu Lys Met Asp Gly Thr Glu Glu Leu Leu Val Lys Leu Asn Arg Glu
            740                 745                 750

Asp Leu Leu Arg Lys Gln Arg Thr Phe Asp Asn Gly Ser Ile Pro His
        755                 760                 765

Gln Ile His Leu Gly Glu Leu His Ala Ile Leu Arg Arg Gln Glu Asp
    770                 775                 780

Phe Tyr Pro Phe Leu Lys Asp Asn Arg Glu Lys Ile Glu Lys Ile Leu
785                 790                 795                 800

Thr Phe Arg Ile Pro Tyr Tyr Val Gly Pro Leu Ala Arg Gly Asn Ser
                805                 810                 815

Arg Phe Ala Trp Met Thr Arg Lys Ser Glu Glu Thr Ile Thr Pro Trp
            820                 825                 830

Asn Phe Glu Glu Val Val Asp Lys Gly Ala Ser Ala Gln Ser Phe Ile
        835                 840                 845

Glu Arg Met Thr Asn Phe Asp Lys Asn Leu Pro Asn Glu Lys Val Leu
    850                 855                 860

Pro Lys His Ser Leu Leu Tyr Glu Tyr Phe Thr Val Tyr Asn Glu Leu
865                 870                 875                 880

Thr Lys Val Lys Tyr Val Thr Glu Gly Met Arg Lys Pro Ala Phe Leu
                885                 890                 895

Ser Gly Glu Gln Lys Lys Ala Ile Val Asp Leu Leu Phe Lys Thr Asn
            900                 905                 910

Arg Lys Val Thr Val Lys Gln Leu Lys Glu Asp Tyr Phe Lys Lys Ile
        915                 920                 925

Glu Cys Phe Asp Ser Val Glu Ile Ser Gly Val Glu Asp Arg Phe Asn
    930                 935                 940

Ala Ser Leu Gly Thr Tyr His Asp Leu Leu Lys Ile Ile Lys Asp Lys
945                 950                 955                 960

Asp Phe Leu Asp Asn Glu Glu Asn Glu Asp Ile Leu Glu Asp Ile Val
                965                 970                 975

Leu Thr Leu Thr Leu Phe Glu Asp Arg Glu Met Ile Glu Glu Arg Leu
            980                 985                 990

Lys Thr Tyr Ala His Leu Phe Asp Asp Lys Val Met Lys Gln Leu Lys
        995                 1000                1005

Arg Arg Arg Tyr Thr Gly Trp Gly Arg Leu Ser Arg Lys Leu Ile
    1010                1015                1020

Asn Gly Ile Arg Asp Lys Gln Ser Gly Lys Thr Ile Leu Asp Phe
    1025                1030                1035

Leu Lys Ser Asp Gly Phe Ala Asn Arg Asn Phe Met Gln Leu Ile
    1040                1045                1050

His Asp Asp Ser Leu Thr Phe Lys Glu Asp Ile Gln Lys Ala Gln
    1055                1060                1065

Val Ser Gly Gln Gly Asp Ser Leu His Glu His Ile Ala Asn Leu
    1070                1075                1080

Ala Gly Ser Pro Ala Ile Lys Lys Gly Ile Leu Gln Thr Val Lys
    1085                1090                1095

Val Val Asp Glu Leu Val Lys Val Met Gly Arg His Lys Pro Glu
```

-continued

|      | 1100 |      |      | 1105 |      |      | 1110 |      |      |
|------|------|------|------|------|------|------|------|------|------|
| Asn  | Ile  | Val  | Ile  | Glu  | Met  | Ala  | Arg  | Glu  | Asn  | Gln  | Thr  | Thr  | Gln  | Lys  |
|      | 1115 |      |      |      | 1120 |      |      |      | 1125 |

Gly Gln Lys Asn Ser Arg Glu Arg Met Lys Arg Ile Glu Glu Gly
    1130                1135                1140

Ile Lys Glu Leu Gly Ser Gln Ile Leu Lys Glu His Pro Val Glu
    1145                1150                1155

Asn Thr Gln Leu Gln Asn Glu Lys Leu Tyr Leu Tyr Tyr Leu Gln
    1160                1165                1170

Asn Gly Arg Asp Met Tyr Val Asp Gln Glu Leu Asp Ile Asn Arg
    1175                1180                1185

Leu Ser Asp Tyr Asp Val Asp Ala Ile Val Pro Gln Ser Phe Leu
    1190                1195                1200

Lys Asp Asp Ser Ile Asp Asn Lys Val Leu Thr Arg Ser Asp Lys
    1205                1210                1215

Asn Arg Gly Lys Ser Asp Asn Val Pro Ser Glu Glu Val Val Lys
    1220                1225                1230

Lys Met Lys Asn Tyr Trp Arg Gln Leu Leu Asn Ala Lys Leu Ile
    1235                1240                1245

Thr Gln Arg Lys Phe Asp Asn Leu Thr Lys Ala Glu Arg Gly Gly
    1250                1255                1260

Leu Ser Glu Leu Asp Lys Ala Gly Phe Ile Lys Arg Gln Leu Val
    1265                1270                1275

Glu Thr Arg Gln Ile Thr Lys His Val Ala Gln Ile Leu Asp Ser
    1280                1285                1290

Arg Met Asn Thr Lys Tyr Asp Glu Asn Asp Lys Leu Ile Arg Glu
    1295                1300                1305

Val Lys Val Ile Thr Leu Lys Ser Lys Leu Val Ser Asp Phe Arg
    1310                1315                1320

Lys Asp Phe Gln Phe Tyr Lys Val Arg Glu Ile Asn Asn Tyr His
    1325                1330                1335

His Ala His Asp Ala Tyr Leu Asn Ala Val Val Gly Thr Ala Leu
    1340                1345                1350

Ile Lys Lys Tyr Pro Lys Leu Glu Ser Glu Phe Val Tyr Gly Asp
    1355                1360                1365

Tyr Lys Val Tyr Asp Val Arg Lys Met Ile Ala Lys Ser Glu Gln
    1370                1375                1380

Glu Ile Gly Lys Ala Thr Ala Lys Tyr Phe Phe Tyr Ser Asn Ile
    1385                1390                1395

Met Asn Phe Phe Lys Thr Glu Ile Thr Leu Ala Asn Gly Glu Ile
    1400                1405                1410

Arg Lys Arg Pro Leu Ile Glu Thr Asn Gly Glu Thr Gly Glu Ile
    1415                1420                1425

Val Trp Asp Lys Gly Arg Asp Phe Ala Thr Val Arg Lys Val Leu
    1430                1435                1440

Ser Met Pro Gln Val Asn Ile Val Lys Lys Thr Glu Val Gln Thr
    1445                1450                1455

Gly Gly Phe Ser Lys Glu Ser Ile Leu Pro Lys Arg Asn Ser Asp
    1460                1465                1470

Lys Leu Ile Ala Arg Lys Lys Asp Trp Asp Pro Lys Lys Tyr Gly
    1475                1480                1485

Gly Phe Asp Ser Pro Thr Val Ala Tyr Ser Val Leu Val Val Ala
    1490                1495                1500

Lys Val Glu Lys Gly Lys Ser Lys Leu Lys Ser Val Lys Glu
1505                1510                1515

Leu Leu Gly Ile Thr Ile Met Glu Arg Ser Ser Phe Glu Lys Asn
1520                1525                1530

Pro Ile Asp Phe Leu Glu Ala Lys Gly Tyr Lys Glu Val Lys Lys
1535                1540                1545

Asp Leu Ile Ile Lys Leu Pro Lys Tyr Ser Leu Phe Glu Leu Glu
1550                1555                1560

Asn Gly Arg Lys Arg Met Leu Ala Ser Ala Gly Glu Leu Gln Lys
1565                1570                1575

Gly Asn Glu Leu Ala Leu Pro Ser Lys Tyr Val Asn Phe Leu Tyr
1580                1585                1590

Leu Ala Ser His Tyr Glu Lys Leu Lys Gly Ser Pro Glu Asp Asn
1595                1600                1605

Glu Gln Lys Gln Leu Phe Val Glu Gln His Lys His Tyr Leu Asp
1610                1615                1620

Glu Ile Ile Glu Gln Ile Ser Glu Phe Ser Lys Arg Val Ile Leu
1625                1630                1635

Ala Asp Ala Asn Leu Asp Lys Val Leu Ser Ala Tyr Asn Lys His
1640                1645                1650

Arg Asp Lys Pro Ile Arg Glu Gln Ala Glu Asn Ile Ile His Leu
1655                1660                1665

Phe Thr Leu Thr Asn Leu Gly Ala Pro Ala Ala Phe Lys Tyr Phe
1670                1675                1680

Asp Thr Thr Ile Asp Arg Lys Arg Tyr Thr Ser Thr Lys Glu Val
1685                1690                1695

Leu Asp Ala Thr Leu Ile His Gln Ser Ile Thr Gly Leu Tyr Glu
1700                1705                1710

Thr Arg Ile Asp Leu Ser Gln Leu Gly Gly Asp
1715                1720

<210> SEQ ID NO 34
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 34

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

```
His Glu Lys Tyr Pro Thr Ile Tyr His Leu Arg Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540
```

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
```

-continued

Glu Ile Asn Asn Tyr His His Ala His Asp Ala Tyr Leu Asn Ala Val
965                 970                 975
Val Gly Thr Ala Leu Ile Lys Lys Tyr Pro Lys Leu Glu Ser Glu Phe
    980                 985                 990
Val Tyr Gly Asp Tyr Lys Val Tyr Asp Val Arg Lys Met Ile Ala
    995                 1000                1005
Lys Ser Glu Gln Glu Ile Gly Lys Ala Thr Ala Lys Tyr Phe Phe
1010            1015                1020
Tyr Ser Asn Ile Met Asn Phe Phe Lys Thr Glu Ile Thr Leu Ala
1025            1030                1035
Asn Gly Glu Ile Arg Lys Arg Pro Leu Ile Glu Thr Asn Gly Glu
1040            1045                1050
Thr Gly Glu Ile Val Trp Asp Lys Gly Arg Asp Phe Ala Thr Val
1055            1060                1065
Arg Lys Val Leu Ser Met Pro Gln Val Asn Ile Val Lys Lys Thr
1070            1075                1080
Glu Val Gln Thr Gly Gly Phe Ser Lys Glu Ser Ile Leu Pro Lys
1085            1090                1095
Arg Asn Ser Asp Lys Leu Ile Ala Arg Lys Lys Asp Trp Asp Pro
1100            1105                1110
Lys Lys Tyr Gly Gly Phe Asp Ser Pro Thr Val Ala Tyr Ser Val
1115            1120                1125
Leu Val Val Ala Lys Val Glu Lys Gly Lys Ser Lys Lys Leu Lys
1130            1135                1140
Ser Val Lys Glu Leu Leu Gly Ile Thr Ile Met Glu Arg Ser Ser
1145            1150                1155
Phe Glu Lys Asn Pro Ile Asp Phe Leu Glu Ala Lys Gly Tyr Lys
1160            1165                1170
Glu Val Lys Lys Asp Leu Ile Ile Lys Leu Pro Lys Tyr Ser Leu
1175            1180                1185
Phe Glu Leu Glu Asn Gly Arg Lys Arg Met Leu Ala Ser Ala Gly
1190            1195                1200
Glu Leu Gln Lys Gly Asn Glu Leu Ala Leu Pro Ser Lys Tyr Val
1205            1210                1215
Asn Phe Leu Tyr Leu Ala Ser His Tyr Glu Lys Leu Lys Gly Ser
1220            1225                1230
Pro Glu Asp Asn Glu Gln Lys Gln Leu Phe Val Glu Gln His Lys
1235            1240                1245
His Tyr Leu Asp Glu Ile Ile Glu Gln Ile Ser Glu Phe Ser Lys
1250            1255                1260
Arg Val Ile Leu Ala Asp Ala Asn Leu Asp Lys Val Leu Ser Ala
1265            1270                1275
Tyr Asn Lys His Arg Asp Lys Pro Ile Arg Glu Gln Ala Glu Asn
1280            1285                1290
Ile Ile His Leu Phe Thr Leu Thr Asn Leu Gly Ala Pro Ala Ala
1295            1300                1305
Phe Lys Tyr Phe Asp Thr Thr Ile Asp Arg Lys Arg Tyr Thr Ser
1310            1315                1320
Thr Lys Glu Val Leu Asp Ala Thr Leu Ile His Gln Ser Ile Thr
1325            1330                1335
Gly Leu Tyr Glu Thr Arg Ile Asp Leu Ser Gln Leu Gly Gly Asp
1340            1345                1350
                1355            1360                1365

<210> SEQ ID NO 35
<211> LENGTH: 1851
<212> TYPE: PRT
<213> ORGANISM: Artificial Sequence
<220> FEATURE:
<223> OTHER INFORMATION: Synthetic Polypeptide

<400> SEQUENCE: 35

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Ser Met
                20                  25                  30

Gly Thr Gly Thr Lys Cys Ile Gly Gln Ser Lys Met Arg Lys Asn Gly
            35                  40                  45

Asp Ile Leu Asn Asp Ser His Ala Glu Val Ile Ala Arg Arg Ser Phe
50                  55                  60

Gln Arg Tyr Leu Leu His Gln Leu Gln Leu Ala Ala Thr Leu Lys Glu
65                  70                  75                  80

Asp Ser Ile Phe Val Pro Gly Thr Gln Lys Gly Val Trp Lys Leu Arg
                85                  90                  95

Arg Asp Leu Ile Phe Val Phe Phe Ser Ser His Thr Pro Cys Gly Asp
                100                 105                 110

Ala Ser Ile Ile Pro Met Leu Glu Phe Glu Asp Gln Pro Cys Cys Pro
            115                 120                 125

Val Phe Arg Asn Trp Ala His Asn Ser Ser Val Glu Ala Ser Ser Asn
130                 135                 140

Leu Glu Ala Pro Gly Asn Glu Arg Lys Cys Glu Asp Pro Asp Ser Pro
145                 150                 155                 160

Val Thr Lys Lys Met Arg Leu Glu Pro Gly Thr Ala Ala Arg Glu Val
                165                 170                 175

Thr Asn Gly Ala Ala His His Gln Ser Phe Gly Lys Gln Lys Ser Gly
            180                 185                 190

Pro Ile Ser Pro Gly Ile His Ser Cys Asp Leu Thr Val Glu Gly Leu
        195                 200                 205

Ala Thr Val Thr Arg Ile Ala Pro Gly Ser Ala Lys Val Ile Asp Val
210                 215                 220

Tyr Arg Thr Gly Ala Lys Cys Val Pro Gly Glu Ala Gly Asp Ser Gly
225                 230                 235                 240

Lys Pro Gly Ala Ala Phe His Gln Val Gly Leu Leu Arg Val Lys Pro
                245                 250                 255

Gly Arg Gly Asp Arg Thr Arg Ser Met Ser Cys Ser Asp Lys Met Ala
            260                 265                 270

Arg Trp Asn Val Leu Gly Cys Gln Gly Ala Leu Leu Met His Leu Leu
        275                 280                 285

Glu Glu Pro Ile Tyr Leu Ser Ala Val Val Ile Gly Lys Cys Pro Tyr
290                 295                 300

Ser Gln Glu Ala Met Gln Arg Ala Leu Ile Gly Arg Cys Gln Asn Val
305                 310                 315                 320

Ser Ala Leu Pro Lys Gly Phe Val Gln Glu Leu Lys Ile Leu Gln
                325                 330                 335

Ser Asp Leu Leu Phe Glu Gln Ser Arg Ser Ala Val Gln Ala Lys Arg
            340                 345                 350

Ala Asp Ser Pro Gly Arg Leu Val Pro Cys Gly Ala Ala Ile Ser Trp
        355                 360                 365
```

```
Ser Ala Val Pro Glu Gln Pro Leu Asp Val Thr Ala Asn Gly Phe Pro
    370                 375                 380

Gln Gly Thr Thr Lys Lys Thr Ile Gly Ser Leu Gln Ala Arg Ser Gln
385                 390                 395                 400

Ile Ser Lys Val Glu Leu Phe Arg Ser Phe Gln Lys Leu Leu Ser Arg
                405                 410                 415

Ile Ala Arg Asp Lys Trp Pro His Ser Leu Arg Val Gln Lys Leu Asp
            420                 425                 430

Thr Tyr Gln Glu Tyr Lys Glu Ala Ala Ser Ser Tyr Gln Glu Ala Trp
        435                 440                 445

Ser Thr Leu Arg Lys Gln Val Phe Gly Ser Trp Ile Arg Asn Pro Pro
450                 455                 460

Asp Tyr His Gln Phe Gly Gly Gly Ser Gly Gly Gly Gly Ser Gly
465                 470                 475                 480

Gly Gly Gly Ser Asp Lys Lys Tyr Ser Ile Gly Leu Ala Ile Gly Thr
                485                 490                 495

Asn Ser Val Gly Trp Ala Val Ile Thr Asp Glu Tyr Lys Val Pro Ser
                500                 505                 510

Lys Lys Phe Lys Val Leu Gly Asn Thr Asp Arg His Ser Ile Lys Lys
            515                 520                 525

Asn Leu Ile Gly Ala Leu Leu Phe Asp Ser Gly Glu Thr Ala Glu Ala
530                 535                 540

Thr Arg Leu Lys Arg Thr Ala Arg Arg Arg Tyr Thr Arg Arg Lys Asn
545                 550                 555                 560

Arg Ile Cys Tyr Leu Gln Glu Ile Phe Ser Asn Glu Met Ala Lys Val
                565                 570                 575

Asp Asp Ser Phe Phe His Arg Leu Glu Glu Ser Phe Leu Val Glu Glu
            580                 585                 590

Asp Lys Lys His Glu Arg His Pro Ile Phe Gly Asn Ile Val Asp Glu
        595                 600                 605

Val Ala Tyr His Glu Lys Tyr Pro Thr Ile Tyr His Leu Arg Lys Lys
    610                 615                 620

Leu Val Asp Ser Thr Asp Lys Ala Asp Leu Arg Leu Ile Tyr Leu Ala
625                 630                 635                 640

Leu Ala His Met Ile Lys Phe Arg Gly His Phe Leu Ile Glu Gly Asp
                645                 650                 655

Leu Asn Pro Asp Asn Ser Asp Val Asp Lys Leu Phe Ile Gln Leu Val
            660                 665                 670

Gln Thr Tyr Asn Gln Leu Phe Glu Glu Asn Pro Ile Asn Ala Ser Gly
        675                 680                 685

Val Asp Ala Lys Ala Ile Leu Ser Ala Arg Leu Ser Lys Ser Arg Arg
    690                 695                 700

Leu Glu Asn Leu Ile Ala Gln Leu Pro Gly Glu Lys Lys Asn Gly Leu
705                 710                 715                 720

Phe Gly Asn Leu Ile Ala Leu Ser Leu Gly Leu Thr Pro Asn Phe Lys
                725                 730                 735

Ser Asn Phe Asp Leu Ala Glu Asp Ala Lys Leu Gln Leu Ser Lys Asp
            740                 745                 750

Thr Tyr Asp Asp Asp Leu Asp Asn Leu Leu Ala Gln Ile Gly Asp Gln
        755                 760                 765

Tyr Ala Asp Leu Phe Leu Ala Ala Lys Asn Leu Ser Asp Ala Ile Leu
    770                 775                 780
```

```
Leu Ser Asp Ile Leu Arg Val Asn Thr Glu Ile Thr Lys Ala Pro Leu
785                 790                 795                 800

Ser Ala Ser Met Ile Lys Arg Tyr Asp Glu His His Gln Asp Leu Thr
                805                 810                 815

Leu Leu Lys Ala Leu Val Arg Gln Gln Leu Pro Glu Lys Tyr Lys Glu
            820                 825                 830

Ile Phe Phe Asp Gln Ser Lys Asn Gly Tyr Ala Gly Tyr Ile Asp Gly
        835                 840                 845

Gly Ala Ser Gln Glu Glu Phe Tyr Lys Phe Ile Lys Pro Ile Leu Glu
850                 855                 860

Lys Met Asp Gly Thr Glu Glu Leu Leu Val Lys Leu Asn Arg Glu Asp
865                 870                 875                 880

Leu Leu Arg Lys Gln Arg Thr Phe Asp Asn Gly Ser Ile Pro His Gln
                885                 890                 895

Ile His Leu Gly Glu Leu His Ala Ile Leu Arg Arg Gln Glu Asp Phe
            900                 905                 910

Tyr Pro Phe Leu Lys Asp Asn Arg Glu Lys Ile Glu Lys Ile Leu Thr
        915                 920                 925

Phe Arg Ile Pro Tyr Tyr Val Gly Pro Leu Ala Arg Gly Asn Ser Arg
930                 935                 940

Phe Ala Trp Met Thr Arg Lys Ser Glu Glu Thr Ile Thr Pro Trp Asn
945                 950                 955                 960

Phe Glu Glu Val Val Asp Lys Gly Ala Ser Ala Gln Ser Phe Ile Glu
                965                 970                 975

Arg Met Thr Asn Phe Asp Lys Asn Leu Pro Asn Glu Lys Val Leu Pro
            980                 985                 990

Lys His Ser Leu Leu Tyr Glu Tyr Phe Thr Val Tyr Asn Glu Leu Thr
        995                 1000                1005

Lys Val Lys Tyr Val Thr Glu Gly Met Arg Lys Pro Ala Phe Leu
1010                1015                1020

Ser Gly Glu Gln Lys Lys Ala Ile Val Asp Leu Leu Phe Lys Thr
1025                1030                1035

Asn Arg Lys Val Thr Val Lys Gln Leu Lys Glu Asp Tyr Phe Lys
1040                1045                1050

Lys Ile Glu Cys Phe Asp Ser Val Glu Ile Ser Gly Val Glu Asp
1055                1060                1065

Arg Phe Asn Ala Ser Leu Gly Thr Tyr His Asp Leu Leu Lys Ile
1070                1075                1080

Ile Lys Asp Lys Asp Phe Leu Asp Asn Glu Glu Asn Glu Asp Ile
1085                1090                1095

Leu Glu Asp Ile Val Leu Thr Leu Thr Leu Phe Glu Asp Arg Glu
1100                1105                1110

Met Ile Glu Glu Arg Leu Lys Thr Tyr Ala His Leu Phe Asp Asp
1115                1120                1125

Lys Val Met Lys Gln Leu Lys Arg Arg Arg Tyr Thr Gly Trp Gly
1130                1135                1140

Arg Leu Ser Arg Lys Leu Ile Asn Gly Ile Arg Asp Lys Gln Ser
1145                1150                1155

Gly Lys Thr Ile Leu Asp Phe Leu Lys Ser Asp Gly Phe Ala Asn
1160                1165                1170

Arg Asn Phe Met Gln Leu Ile His Asp Asp Ser Leu Thr Phe Lys
1175                1180                1185

Glu Asp Ile Gln Lys Ala Gln Val Ser Gly Gln Gly Asp Ser Leu
```

```
              1190                1195              1200
His Glu His Ile Ala Asn Leu Ala Gly Ser Pro Ala Ile Lys Lys
     1205                1210              1215

Gly Ile Leu Gln Thr Val Lys Val Val Asp Glu Leu Val Lys Val
     1220                1225              1230

Met Gly Arg His Lys Pro Glu Asn Ile Val Ile Glu Met Ala Arg
     1235                1240              1245

Glu Asn Gln Thr Thr Gln Lys Gly Gln Lys Asn Ser Arg Glu Arg
     1250                1255              1260

Met Lys Arg Ile Glu Glu Gly Ile Lys Glu Leu Gly Ser Gln Ile
     1265                1270              1275

Leu Lys Glu His Pro Val Glu Asn Thr Gln Leu Gln Asn Glu Lys
     1280                1285              1290

Leu Tyr Leu Tyr Tyr Leu Gln Asn Gly Arg Asp Met Tyr Val Asp
     1295                1300              1305

Gln Glu Leu Asp Ile Asn Arg Leu Ser Asp Tyr Asp Val Asp Ala
     1310                1315              1320

Ile Val Pro Gln Ser Phe Leu Lys Asp Asp Ser Ile Asp Asn Lys
     1325                1330              1335

Val Leu Thr Arg Ser Asp Lys Asn Arg Gly Lys Ser Asp Asn Val
     1340                1345              1350

Pro Ser Glu Glu Val Val Lys Lys Met Lys Asn Tyr Trp Arg Gln
     1355                1360              1365

Leu Leu Asn Ala Lys Leu Ile Thr Gln Arg Lys Phe Asp Asn Leu
     1370                1375              1380

Thr Lys Ala Glu Arg Gly Gly Leu Ser Glu Leu Asp Lys Ala Gly
     1385                1390              1395

Phe Ile Lys Arg Gln Leu Val Glu Thr Arg Gln Ile Thr Lys His
     1400                1405              1410

Val Ala Gln Ile Leu Asp Ser Arg Met Asn Thr Lys Tyr Asp Glu
     1415                1420              1425

Asn Asp Lys Leu Ile Arg Glu Val Lys Val Ile Thr Leu Lys Ser
     1430                1435              1440

Lys Leu Val Ser Asp Phe Arg Lys Asp Phe Gln Phe Tyr Lys Val
     1445                1450              1455

Arg Glu Ile Asn Asn Tyr His His Ala His Asp Ala Tyr Leu Asn
     1460                1465              1470

Ala Val Val Gly Thr Ala Leu Ile Lys Lys Tyr Pro Lys Leu Glu
     1475                1480              1485

Ser Glu Phe Val Tyr Gly Asp Tyr Lys Val Tyr Asp Val Arg Lys
     1490                1495              1500

Met Ile Ala Lys Ser Glu Gln Glu Ile Gly Lys Ala Thr Ala Lys
     1505                1510              1515

Tyr Phe Phe Tyr Ser Asn Ile Met Asn Phe Phe Lys Thr Glu Ile
     1520                1525              1530

Thr Leu Ala Asn Gly Glu Ile Arg Lys Arg Pro Leu Ile Glu Thr
     1535                1540              1545

Asn Gly Glu Thr Gly Glu Ile Val Trp Asp Lys Gly Arg Asp Phe
     1550                1555              1560

Ala Thr Val Arg Lys Val Leu Ser Met Pro Gln Val Asn Ile Val
     1565                1570              1575

Lys Lys Thr Glu Val Gln Thr Gly Gly Phe Ser Lys Glu Ser Ile
     1580                1585              1590
```

```
Leu Pro Lys Arg Asn Ser Asp Lys Leu Ile Ala Arg Lys Lys Asp
1595                1600                1605

Trp Asp Pro Lys Lys Tyr Gly Gly Phe Asp Ser Pro Thr Val Ala
1610                1615                1620

Tyr Ser Val Leu Val Val Ala Lys Val Glu Lys Gly Lys Ser Lys
1625                1630                1635

Lys Leu Lys Ser Val Lys Glu Leu Leu Gly Ile Thr Ile Met Glu
1640                1645                1650

Arg Ser Ser Phe Glu Lys Asn Pro Ile Asp Phe Leu Glu Ala Lys
1655                1660                1665

Gly Tyr Lys Glu Val Lys Lys Asp Leu Ile Ile Lys Leu Pro Lys
1670                1675                1680

Tyr Ser Leu Phe Glu Leu Glu Asn Gly Arg Lys Arg Met Leu Ala
1685                1690                1695

Ser Ala Gly Glu Leu Gln Lys Gly Asn Glu Leu Ala Leu Pro Ser
1700                1705                1710

Lys Tyr Val Asn Phe Leu Tyr Leu Ala Ser His Tyr Glu Lys Leu
1715                1720                1725

Lys Gly Ser Pro Glu Asp Asn Glu Gln Lys Gln Leu Phe Val Glu
1730                1735                1740

Gln His Lys His Tyr Leu Asp Glu Ile Ile Glu Gln Ile Ser Glu
1745                1750                1755

Phe Ser Lys Arg Val Ile Leu Ala Asp Ala Asn Leu Asp Lys Val
1760                1765                1770

Leu Ser Ala Tyr Asn Lys His Arg Asp Lys Pro Ile Arg Glu Gln
1775                1780                1785

Ala Glu Asn Ile Ile His Leu Phe Thr Leu Thr Asn Leu Gly Ala
1790                1795                1800

Pro Ala Ala Phe Lys Tyr Phe Asp Thr Thr Ile Asp Arg Lys Arg
1805                1810                1815

Tyr Thr Ser Thr Lys Glu Val Leu Asp Ala Thr Leu Ile His Gln
1820                1825                1830

Ser Ile Thr Gly Leu Tyr Glu Thr Arg Ile Asp Leu Ser Gln Leu
1835                1840                1845

Gly Gly Asp
1850

<210> SEQ ID NO 36
<211> LENGTH: 1846
<212> TYPE: PRT
<213> ORGANISM: Artificial Sequence
<220> FEATURE:
<223> OTHER INFORMATION: Synthetic Polypeptide

<400> SEQUENCE: 36

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Asp Lys
                20                  25                  30

Lys Tyr Ser Ile Gly Leu Ala Ile Gly Thr Asn Ser Val Gly Trp Ala
            35                  40                  45

Val Ile Thr Asp Glu Tyr Lys Val Pro Ser Lys Lys Phe Lys Val Leu
        50                  55                  60

Gly Asn Thr Asp Arg His Ser Ile Lys Lys Asn Leu Ile Gly Ala Leu
65                  70                  75                  80
```

```
Leu Phe Asp Ser Gly Glu Thr Ala Glu Ala Thr Arg Leu Lys Arg Thr
                85                  90                  95

Ala Arg Arg Arg Tyr Thr Arg Arg Lys Asn Arg Ile Cys Tyr Leu Gln
            100                 105                 110

Glu Ile Phe Ser Asn Glu Met Ala Lys Val Asp Asp Ser Phe Phe His
        115                 120                 125

Arg Leu Glu Glu Ser Phe Leu Val Glu Glu Asp Lys Lys His Glu Arg
    130                 135                 140

His Pro Ile Phe Gly Asn Ile Val Asp Glu Val Ala Tyr His Glu Lys
145                 150                 155                 160

Tyr Pro Thr Ile Tyr His Leu Arg Lys Lys Leu Val Asp Ser Thr Asp
                165                 170                 175

Lys Ala Asp Leu Arg Leu Ile Tyr Leu Ala Leu Ala His Met Ile Lys
            180                 185                 190

Phe Arg Gly His Phe Leu Ile Glu Gly Asp Leu Asn Pro Asp Asn Ser
        195                 200                 205

Asp Val Asp Lys Leu Phe Ile Gln Leu Val Gln Thr Tyr Asn Gln Leu
    210                 215                 220

Phe Glu Glu Asn Pro Ile Asn Ala Ser Gly Val Asp Ala Lys Ala Ile
225                 230                 235                 240

Leu Ser Ala Arg Leu Ser Lys Ser Arg Arg Leu Glu Asn Leu Ile Ala
                245                 250                 255

Gln Leu Pro Gly Glu Lys Lys Asn Gly Leu Phe Gly Asn Leu Ile Ala
            260                 265                 270

Leu Ser Leu Gly Leu Thr Pro Asn Phe Lys Ser Asn Phe Asp Leu Ala
        275                 280                 285

Glu Asp Ala Lys Leu Gln Leu Ser Lys Asp Thr Tyr Asp Asp Asp Leu
    290                 295                 300

Asp Asn Leu Leu Ala Gln Ile Gly Asp Gln Tyr Ala Asp Leu Phe Leu
305                 310                 315                 320

Ala Ala Lys Asn Leu Ser Asp Ala Ile Leu Leu Ser Asp Ile Leu Arg
                325                 330                 335

Val Asn Thr Glu Ile Thr Lys Ala Pro Leu Ser Ala Ser Met Ile Lys
            340                 345                 350

Arg Tyr Asp Glu His His Gln Asp Leu Thr Leu Leu Lys Ala Leu Val
        355                 360                 365

Arg Gln Gln Leu Pro Glu Lys Tyr Lys Glu Ile Phe Phe Asp Gln Ser
    370                 375                 380

Lys Asn Gly Tyr Ala Gly Tyr Ile Asp Gly Gly Ala Ser Gln Glu Glu
385                 390                 395                 400

Phe Tyr Lys Phe Ile Lys Pro Ile Leu Glu Lys Met Asp Gly Thr Glu
                405                 410                 415

Glu Leu Leu Val Lys Leu Asn Arg Glu Asp Leu Leu Arg Lys Gln Arg
            420                 425                 430

Thr Phe Asp Asn Gly Ser Ile Pro His Gln Ile His Leu Gly Glu Leu
        435                 440                 445

His Ala Ile Leu Arg Arg Gln Glu Asp Phe Tyr Pro Phe Leu Lys Asp
450                 455                 460

Asn Arg Glu Lys Ile Glu Lys Ile Leu Thr Phe Arg Ile Pro Tyr Tyr
465                 470                 475                 480

Val Gly Pro Leu Ala Arg Gly Asn Ser Arg Phe Ala Trp Met Thr Arg
                485                 490                 495
```

```
Lys Ser Glu Glu Thr Ile Thr Pro Trp Asn Phe Glu Val Val Asp
                500             505             510
Lys Gly Ala Ser Ala Gln Ser Phe Ile Glu Arg Met Thr Asn Phe Asp
            515                 520                 525
Lys Asn Leu Pro Asn Glu Lys Val Leu Pro Lys His Ser Leu Leu Tyr
        530                 535                 540
Glu Tyr Phe Thr Val Tyr Asn Glu Leu Thr Lys Val Lys Tyr Val Thr
545                 550                 555                 560
Glu Gly Met Arg Lys Pro Ala Phe Leu Ser Gly Glu Gln Lys Lys Ala
                565                 570                 575
Ile Val Asp Leu Leu Phe Lys Thr Asn Arg Lys Val Thr Val Lys Gln
            580                 585                 590
Leu Lys Glu Asp Tyr Phe Lys Lys Ile Glu Cys Phe Asp Ser Val Glu
        595                 600                 605
Ile Ser Gly Val Glu Asp Arg Phe Asn Ala Ser Leu Gly Thr Tyr His
        610                 615                 620
Asp Leu Leu Lys Ile Ile Lys Asp Lys Asp Phe Leu Asp Asn Glu Glu
625                 630                 635                 640
Asn Glu Asp Ile Leu Glu Asp Ile Val Leu Thr Leu Thr Leu Phe Glu
                645                 650                 655
Asp Arg Glu Met Ile Glu Glu Arg Leu Lys Thr Tyr Ala His Leu Phe
            660                 665                 670
Asp Asp Lys Val Met Lys Gln Leu Lys Arg Arg Arg Tyr Thr Gly Trp
        675                 680                 685
Gly Arg Leu Ser Arg Lys Leu Ile Asn Gly Ile Arg Asp Lys Gln Ser
        690                 695                 700
Gly Lys Thr Ile Leu Asp Phe Leu Lys Ser Asp Gly Phe Ala Asn Arg
705                 710                 715                 720
Asn Phe Met Gln Leu Ile His Asp Asp Ser Leu Thr Phe Lys Glu Asp
                725                 730                 735
Ile Gln Lys Ala Gln Val Ser Gly Gln Gly Asp Ser Leu His Glu His
            740                 745                 750
Ile Ala Asn Leu Ala Gly Ser Pro Ala Ile Lys Lys Gly Ile Leu Gln
        755                 760                 765
Thr Val Lys Val Val Asp Glu Leu Val Lys Val Met Gly Arg His Lys
        770                 775                 780
Pro Glu Asn Ile Val Ile Glu Met Ala Arg Glu Asn Gln Thr Thr Gln
785                 790                 795                 800
Lys Gly Gln Lys Asn Ser Arg Glu Arg Met Lys Arg Ile Glu Glu Gly
                805                 810                 815
Ile Lys Glu Leu Gly Ser Gln Ile Leu Lys Glu His Pro Val Glu Asn
            820                 825                 830
Thr Gln Leu Gln Asn Glu Lys Leu Tyr Leu Tyr Leu Gln Asn Gly
        835                 840                 845
Arg Asp Met Tyr Val Asp Gln Glu Leu Asp Ile Asn Arg Leu Ser Asp
        850                 855                 860
Tyr Asp Val Asp Ala Ile Val Pro Gln Ser Phe Leu Lys Asp Asp Ser
865                 870                 875                 880
Ile Asp Asn Lys Val Leu Thr Arg Ser Asp Lys Asn Arg Gly Lys Ser
                885                 890                 895
Asp Asn Val Pro Ser Glu Glu Val Val Lys Lys Met Lys Asn Tyr Trp
            900                 905                 910
Arg Gln Leu Leu Asn Ala Lys Leu Ile Thr Gln Arg Lys Phe Asp Asn
```

```
                915                 920                 925
Leu Thr Lys Ala Glu Arg Gly Gly Leu Ser Glu Leu Asp Lys Ala Gly
    930                 935                 940
Phe Ile Lys Arg Gln Leu Val Glu Thr Arg Gln Ile Thr Lys His Val
945                 950                 955                 960
Ala Gln Ile Leu Asp Ser Arg Met Asn Thr Lys Tyr Asp Glu Asn Asp
                965                 970                 975
Lys Leu Ile Arg Glu Val Lys Val Ile Thr Leu Lys Ser Lys Leu Val
            980                 985                 990
Ser Asp Phe Arg Lys Asp Phe Gln Phe Tyr Lys Val Arg Glu Ile Asn
            995                 1000                1005
Asn Tyr His His Ala His Asp Ala Tyr Leu Asn Ala Val Val Gly
    1010                1015                1020
Thr Ala Leu Ile Lys Lys Tyr Pro Lys Leu Glu Ser Glu Phe Val
    1025                1030                1035
Tyr Gly Asp Tyr Lys Val Tyr Asp Val Arg Lys Met Ile Ala Lys
    1040                1045                1050
Ser Glu Gln Glu Ile Gly Lys Ala Thr Ala Lys Tyr Phe Phe Tyr
    1055                1060                1065
Ser Asn Ile Met Asn Phe Phe Lys Thr Glu Ile Thr Leu Ala Asn
    1070                1075                1080
Gly Glu Ile Arg Lys Arg Pro Leu Ile Glu Thr Asn Gly Glu Thr
    1085                1090                1095
Gly Glu Ile Val Trp Asp Lys Gly Arg Asp Phe Ala Thr Val Arg
    1100                1105                1110
Lys Val Leu Ser Met Pro Gln Val Asn Ile Val Lys Lys Thr Glu
    1115                1120                1125
Val Gln Thr Gly Gly Phe Ser Lys Glu Ser Ile Leu Pro Lys Arg
    1130                1135                1140
Asn Ser Asp Lys Leu Ile Ala Arg Lys Lys Asp Trp Asp Pro Lys
    1145                1150                1155
Lys Tyr Gly Gly Phe Asp Ser Pro Thr Val Ala Tyr Ser Val Leu
    1160                1165                1170
Val Val Ala Lys Val Glu Lys Gly Lys Ser Lys Lys Leu Lys Ser
    1175                1180                1185
Val Lys Glu Leu Leu Gly Ile Thr Ile Met Glu Arg Ser Ser Phe
    1190                1195                1200
Glu Lys Asn Pro Ile Asp Phe Leu Glu Ala Lys Gly Tyr Lys Glu
    1205                1210                1215
Val Lys Lys Asp Leu Ile Ile Lys Leu Pro Lys Tyr Ser Leu Phe
    1220                1225                1230
Glu Leu Glu Asn Gly Arg Lys Arg Met Leu Ala Ser Ala Gly Glu
    1235                1240                1245
Leu Gln Lys Gly Asn Glu Leu Ala Leu Pro Ser Lys Tyr Val Asn
    1250                1255                1260
Phe Leu Tyr Leu Ala Ser His Tyr Glu Lys Leu Lys Gly Ser Pro
    1265                1270                1275
Glu Asp Asn Glu Gln Lys Gln Leu Phe Val Glu Gln His Lys His
    1280                1285                1290
Tyr Leu Asp Glu Ile Ile Glu Gln Ile Ser Glu Phe Ser Lys Arg
    1295                1300                1305
Val Ile Leu Ala Asp Ala Asn Leu Asp Lys Val Leu Ser Ala Tyr
    1310                1315                1320
```

```
Asn Lys His Arg Asp Lys Pro Ile Arg Glu Gln Ala Glu Asn Ile
    1325            1330                1335
Ile His Leu Phe Thr Leu Thr Asn Leu Gly Ala Pro Ala Ala Phe
    1340            1345                1350
Lys Tyr Phe Asp Thr Thr Ile Asp Arg Lys Arg Tyr Thr Ser Thr
    1355            1360                1365
Lys Glu Val Leu Asp Ala Thr Leu Ile His Gln Ser Ile Thr Gly
    1370            1375                1380
Leu Tyr Glu Thr Arg Ile Asp Leu Ser Gln Leu Gly Gly Asp Gly
    1385            1390                1395
Gly Gly Gly Ser Gly Gly Gly Ser Ser Met Gly Thr Gly Thr
    1400            1405                1410
Lys Cys Ile Gly Gln Ser Lys Met Arg Lys Asn Gly Asp Ile Leu
    1415            1420                1425
Asn Asp Ser His Ala Glu Val Ile Ala Arg Arg Ser Phe Gln Arg
    1430            1435                1440
Tyr Leu Leu His Gln Leu Gln Leu Ala Ala Thr Leu Lys Glu Asp
    1445            1450                1455
Ser Ile Phe Val Pro Gly Thr Gln Lys Gly Val Trp Lys Leu Arg
    1460            1465                1470
Arg Asp Leu Ile Phe Val Phe Phe Ser Ser His Thr Pro Cys Gly
    1475            1480                1485
Asp Ala Ser Ile Ile Pro Met Leu Glu Phe Glu Asp Gln Pro Cys
    1490            1495                1500
Cys Pro Val Phe Arg Asn Trp Ala His Asn Ser Ser Val Glu Ala
    1505            1510                1515
Ser Ser Asn Leu Glu Ala Pro Gly Asn Glu Arg Lys Cys Glu Asp
    1520            1525                1530
Pro Asp Ser Pro Val Thr Lys Lys Met Arg Leu Glu Pro Gly Thr
    1535            1540                1545
Ala Ala Arg Glu Val Thr Asn Gly Ala Ala His His Gln Ser Phe
    1550            1555                1560
Gly Lys Gln Lys Ser Gly Pro Ile Ser Pro Gly Ile His Ser Cys
    1565            1570                1575
Asp Leu Thr Val Glu Gly Leu Ala Thr Val Thr Arg Ile Ala Pro
    1580            1585                1590
Gly Ser Ala Lys Val Ile Asp Val Tyr Arg Thr Gly Ala Lys Cys
    1595            1600                1605
Val Pro Gly Glu Ala Gly Asp Ser Gly Lys Pro Gly Ala Ala Phe
    1610            1615                1620
His Gln Val Gly Leu Leu Arg Val Lys Pro Gly Arg Gly Asp Arg
    1625            1630                1635
Thr Arg Ser Met Ser Cys Ser Asp Lys Met Ala Arg Trp Asn Val
    1640            1645                1650
Leu Gly Cys Gln Gly Ala Leu Leu Met His Leu Leu Glu Glu Pro
    1655            1660                1665
Ile Tyr Leu Ser Ala Val Val Ile Gly Lys Cys Pro Tyr Ser Gln
    1670            1675                1680
Glu Ala Met Gln Arg Ala Leu Ile Gly Arg Cys Gln Asn Val Ser
    1685            1690                1695
Ala Leu Pro Lys Gly Phe Gly Val Gln Glu Leu Lys Ile Leu Gln
    1700            1705                1710
```

```
Ser Asp Leu Leu Phe Glu Gln Ser Arg Ser Ala Val Gln Ala Lys
1715                1720                1725

Arg Ala Asp Ser Pro Gly Arg Leu Val Pro Cys Gly Ala Ala Ile
1730                1735                1740

Ser Trp Ser Ala Val Pro Glu Gln Pro Leu Asp Val Thr Ala Asn
1745                1750                1755

Gly Phe Pro Gln Gly Thr Thr Lys Lys Thr Ile Gly Ser Leu Gln
1760                1765                1770

Ala Arg Ser Gln Ile Ser Lys Val Glu Leu Phe Arg Ser Phe Gln
1775                1780                1785

Lys Leu Leu Ser Arg Ile Ala Arg Asp Lys Trp Pro His Ser Leu
1790                1795                1800

Arg Val Gln Lys Leu Asp Thr Tyr Gln Glu Tyr Lys Glu Ala Ala
1805                1810                1815

Ser Ser Tyr Gln Glu Ala Trp Ser Thr Leu Arg Lys Gln Val Phe
1820                1825                1830

Gly Ser Trp Ile Arg Asn Pro Pro Asp Tyr His Gln Phe
1835                1840                1845

<210> SEQ ID NO 37
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 37

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
        260                 265                 270

Asp Asp Leu Asp Asn Leu Leu Ala Gln Ile Gly Asp Gln Tyr Ala Asp
    275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
```

-continued

```
                645                 650                 655
Thr Gly Trp Gly Arg Leu Ser Arg Lys Leu Ile Asn Gly Ile Arg Asp
                    660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
        690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
        770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
            835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
```

```
Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 38
<211> LENGTH: 82
<212> TYPE: RNA
<213> ORGANISM: Artificial Sequence
<220> FEATURE:
<223> OTHER INFORMATION: Synthetic Polynucleotide

<400> SEQUENCE: 38
guuuuagagc uagaaauagc aaguuaaaau aaaggcuagu ccguuaucaa cuugaaaaag    60
uggcaccgag ucggugcuuu uu                                             82

<210> SEQ ID NO 39
<211> LENGTH: 180
<212> TYPE: DNA
```

<213> ORGANISM: Artificial Sequence
<220> FEATURE:
<223> OTHER INFORMATION: Synthetic Polynucleotide

<400> SEQUENCE: 39

```
gatgacattg catacattcg aaagaccta gccttagata aaactgagca agaggctttg      60
gagtatttca tgaaacaaat gaatgatgca cgtcatggtg gctggacaac aaaaatggat    120
tggatcttcc acacaattaa acagcatgca ttgaactgaa agataactga gaaaatgaaa    180
```

<210> SEQ ID NO 40
<211> LENGTH: 59
<212> TYPE: PRT
<213> ORGANISM: Artificial Sequence
<220> FEATURE:
<223> OTHER INFORMATION: Synthetic Polypeptide

<400> SEQUENCE: 40

```
Asp Asp Ile Ala Tyr Ile Arg Lys Thr Leu Ala Leu Asp Lys Thr Glu
1               5                   10                  15

Gln Glu Ala Leu Glu Tyr Phe Met Lys Gln Met Asn Asp Ala Arg His
            20                  25                  30

Gly Gly Trp Thr Thr Lys Met Asp Trp Ile Phe His Thr Ile Lys Gln
        35                  40                  45

His Ala Leu Asn Lys Ile Thr Glu Lys Met Lys
    50                  55
```

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 41

```
aucggaauct auuuugacuc                                                 20
```

<210> SEQ ID NO 42
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 42

```
ucggaaucua uuuugacucg                                                 20
```

<210> SEQ ID NO 43
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 43

```
cuuagauaaa acugagcaag                                                 20
```

<210> SEQ ID NO 44
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 44
aucuauuuug acucguucuc                                              20

<210> SEQ ID NO 45
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 45
uaaaacugag caagaggcuu                                              20

<210> SEQ ID NO 46
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 46
ugguggcugg acaacaaaaa                                              20

<210> SEQ ID NO 47
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 47
gcuggacaac aaaaauggau                                              20

<210> SEQ ID NO 48
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 48
guguuaauuu gucguacgua                                              20

<210> SEQ ID NO 49
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 49
aatcacattt ttccacttct tgaaaagtac tgtggcttcc atgaagataa cattccccag    60
ctggaagacg tttctcaatt cctgcagact tgcactggtc tccgcctccg acctgtggct   120
ggcctgcttt cctctcggga tttcttgggt ggcctggcct tccgagtctt ccactgcaca   180

<210> SEQ ID NO 50
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 50

Asn His Ile Phe Pro Leu Leu Glu Lys Tyr Cys Gly Phe His Glu Asp
1               5                   10                  15

Asn Ile Pro Gln Leu Glu Asp Val Ser Gln Phe Leu Gln Thr Cys Thr
            20                  25                  30

Gly Ser Arg Leu Arg Pro Val Ala Gly Leu Leu Ser Ser Arg Asp Phe
        35                  40                  45

Leu Gly Gly Leu Ala Phe Arg Val Phe His Cys Thr
    50                  55                  60

<210> SEQ ID NO 51
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 51
atgcctgcct ggggagccct gttcctgctc tgggccacag cagaggccac caaggactgc      60
cccagcccac gtacctgccg cgccctggaa accatggggc tgtgggtgga ctgcaggggc     120
cacggactca cggccctgcc tgccctgccg gcccgcaccc gccacttct gctggccaac     180

<210> SEQ ID NO 52
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 52

Met Pro Ala Trp Gly Ala Leu Phe Leu Leu Trp Ala Thr Ala Glu Ala
1               5                   10                  15

Thr Lys Asp Cys Pro Ser Pro Arg Thr Cys Arg Ala Leu Glu Thr Met
            20                  25                  30

Gly Leu Trp Val Asp Cys Arg Gly His Gly Leu Thr Ala Leu Pro Ala
        35                  40                  45

Leu Pro Ala Arg Thr Arg His Leu Leu Leu Ala Asn
    50                  55                  60

<210> SEQ ID NO 53
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 53
ggttatggtc ctgtctgccc tcctggtggc atacaagaag tcactatcaa ccagagccct      60
cttcagcccc tcaatgtgga gattgaccct gagatccaaa aggtgaagtc tcgagaaagg     120

<210> SEQ ID NO 54
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 54

Gly Tyr Gly Pro Val Cys Pro Pro Gly Gly Ile Gln Glu Val Thr Ile
1               5                   10                  15

Asn Gln Ser Pro Leu Gln Pro Leu Asn Val Glu Ile Asp Pro Glu Ile
            20                  25                  30

Gln Lys Val Lys Ser Arg Glu Arg

<210> SEQ ID NO 55
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 55
gtctccctgg ctgaggatcc ccagggagat gctgcccaga agacagatac atcccaccat    60
gatcaggatc acccaacctt caacaagatc accccaaacc cggctgagtt cgccttcagc   120
ctataccgcc agctggcaca ccagtccaac agcaccaata tcttcttctc cccagtgagc   180

<210> SEQ ID NO 56
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 56

Val Ser Leu Ala Glu Asp Pro Gln Gly Asp Ala Ala Gln Lys Thr Asp
1               5                   10                  15

Thr Ser His His Asp Gln Asp His Pro Thr Phe Asn Lys Ile Thr Pro
            20                  25                  30

Asn Pro Ala Glu Phe Ala Phe Ser Leu Tyr Arg Gln Leu Ala His Gln
        35                  40                  45

Ser Asn Ser Thr Asn Ile Phe Phe Ser Pro Val Ser
    50                  55                  60

<210> SEQ ID NO 57
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 57
ggccactgcc tcattatcaa caatgtgaac ttctgccgtg agtccgggct ccgcacccgc    60
actggctcca acatcgactg tgagaagttg cggcgtcgct tctcctcgcc gcatttcatg   120
gtggaggtga agggcgacct gactgccaag aaaatggtgc tggctttgct ggagctggcg   180

<210> SEQ ID NO 58
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 58

Gly His Cys Leu Ile Ile Asn Asn Val Asn Phe Cys Arg Glu Ser Gly
1               5                   10                  15

Leu Arg Thr Arg Thr Gly Ser Asn Ile Asp Cys Glu Lys Leu Arg Arg
            20                  25                  30

Arg Phe Ser Ser Pro His Phe Met Val Glu Val Lys Gly Asp Leu Thr
        35                  40                  45

Ala Lys Lys Met Val Leu Ala Leu Leu Glu Leu Ala
    50                  55                  60

<210> SEQ ID NO 59
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 59
actagagcta gatactttct agttgggagc aataatgcag aaacgaaata tcgtgtcttg    60
aagactgata gaacagaacc aaaagatttg gtcataattg atgacaggca tgtctatact   120
caacaagaag taagggaact tcttggccgc ttggatcttg gaaatagaac aaagatggga   180

<210> SEQ ID NO 60
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 60

Thr Arg Ala Arg Tyr Phe Leu Val Gly Ser Asn Asn Ala Glu Thr Lys
1               5                   10                  15

Tyr Arg Val Leu Lys Thr Asp Arg Thr Glu Pro Lys Asp Leu Val Ile
            20                  25                  30

Ile Asp Asp Arg His Val Tyr Thr Gln Gln Glu Val Arg Glu Leu Leu
        35                  40                  45

Gly Arg Leu Asp Leu Gly Asn Arg Thr Lys Met Gly
    50                  55                  60

<210> SEQ ID NO 61
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 61
acagatgccc cggtgagccc caccactctg tatgtggagg acatctcgga accgccgttg    60
cacgatttct accgcagcag gctactggac ctggtcttcc tgctggatgg ctcctccagg   120
ctgtccgagg ctgagtttga agtgctgaag gcctttgtgg tggacatgat ggagcggctg   180

<210> SEQ ID NO 62
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 62

Thr Asp Ala Pro Val Ser Pro Thr Thr Leu Tyr Val Glu Asp Ile Ser
1               5                   10                  15

Glu Pro Pro Leu His Asp Phe Tyr Arg Ser Arg Leu Leu Asp Leu Val
            20                  25                  30

Phe Leu Leu Asp Gly Ser Ser Arg Leu Ser Glu Ala Glu Phe Glu Val
        35                  40                  45

Leu Lys Ala Phe Val Val Asp Met Met Glu Arg Leu
    50                  55                  60

<210> SEQ ID NO 63
<211> LENGTH: 180
<212> TYPE: DNA

<213> ORGANISM: Artificial Sequence
<220> FEATURE:
<223> OTHER INFORMATION: Synthetic Polynucleotide

<400> SEQUENCE: 63

```
atctgtgctg ctgtcctcag caaattcatg tctgtgttct gcggggtata tgagcagcca    60
tactactact ctgatatcct gacggtgggc tgtgctgtgg gagtcggccg ttgttttggg   120
acaccacttg gaggagtgct atttagcatc gaggtcacct ccacctactt tgctgttcgg   180
```

<210> SEQ ID NO 64
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 64

```
Ile Cys Ala Ala Val Leu Ser Lys Phe Met Ser Val Phe Cys Gly Val
1               5                   10                  15

Tyr Glu Gln Pro Tyr Tyr Tyr Ser Asp Ile Leu Thr Val Gly Cys Ala
            20                  25                  30

Val Gly Val Gly Arg Cys Phe Gly Thr Pro Leu Gly Gly Val Leu Phe
        35                  40                  45

Ser Ile Glu Val Thr Ser Thr Tyr Phe Ala Val Arg
    50                  55                  60
```

<210> SEQ ID NO 65
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 65

```
tactttgaaa agtcaaagga gcagctgaca cccctgatca agaaggctgg aacggaactg    60
gttaacttct tgagctattt cgtggaactt ggaacacagc ctgccaccca gcgaagtgtc   120
cagcaccatt gtcttccaac cccagctggc ctctagaaca cccactggcc agtcctagag   180
```

<210> SEQ ID NO 66
<211> LENGTH: 59
<212> TYPE: PRT
<213> ORGANISM: Artificial Sequence
<220> FEATURE:
<223> OTHER INFORMATION: Synthetic Polypeptide

<400> SEQUENCE: 66

```
Tyr Phe Glu Lys Ser Lys Glu Gln Leu Thr Pro Leu Ile Lys Lys Ala
1               5                   10                  15

Gly Thr Glu Leu Val Asn Phe Leu Ser Tyr Phe Val Glu Leu Gly Thr
            20                  25                  30

Gln Pro Ala Thr Gln Arg Ser Val Gln His His Cys Leu Pro Thr Pro
        35                  40                  45

Ala Gly Leu Asn Thr His Trp Pro Val Leu Glu
    50                  55
```

<210> SEQ ID NO 67
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 67
ccgcacaagc gcctcacgct cagcggcatc tgcgccttca ttagtgaccg cttcccctac      60
taccgccgca agttccccgc ccggcagaac agcatccgcc acaacctctc gctgaacgac     120
tgcttcgtca agatccccccg cgagccgggc cgcccaggca agggcaacta ctggagcctg     180

<210> SEQ ID NO 68
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 68

Pro His Lys Arg Leu Thr Leu Ser Gly Ile Cys Ala Phe Ile Ser Asp
1               5                   10                  15

Arg Phe Pro Tyr Tyr Arg Arg Lys Phe Pro Ala Arg Gln Asn Ser Ile
            20                  25                  30

Arg His Asn Leu Ser Leu Asn Asp Cys Phe Val Lys Ile Pro Arg Glu
        35                  40                  45

Pro Gly Arg Pro Gly Lys Gly Asn Tyr Trp Ser Leu
    50                  55                  60

<210> SEQ ID NO 69
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 69
gctgaggacc tgtggctgag cccgctgacc atggaagatc ttgtctgcta cagcttccag      60
gtggccagag ggatggagtt cctggcttcc cgaaagtgca tccgcagaga cctggctgct     120
cggaacattc tgctgtcgga aagcgacgtg gtgaagatct gtgactttgg ccttgcccgg     180

<210> SEQ ID NO 70
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 70

Ala Glu Asp Leu Trp Leu Ser Pro Leu Thr Met Glu Asp Leu Val Cys
1               5                   10                  15

Tyr Ser Phe Gln Val Ala Arg Gly Met Glu Phe Leu Ala Ser Arg Lys
            20                  25                  30

Cys Ile Arg Arg Asp Leu Ala Ala Arg Asn Ile Leu Leu Ser Glu Ser
        35                  40                  45

Asp Val Val Lys Ile Cys Asp Phe Gly Leu Ala Arg
    50                  55                  60

<210> SEQ ID NO 71
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 71
gataccgaga ctgtgggcca gagagccctg cactcaattc tgaatgctgc catcatgatc      60
agtgtcgttg ttgtcatgac tatcctcctg gtggttctgt ataaatacag gtgctataag     120
gtcatccatg cctggcttat tatatcatct ctattgttgc tgttctttt ttcattcatt     180

<210> SEQ ID NO 72
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 72

Asp Thr Glu Thr Val Gly Gln Arg Ala Leu His Ser Ile Leu Asn Ala
1               5                   10                  15

Ala Ile Met Ile Ser Val Val Val Met Thr Ile Leu Leu Val Val
            20                  25                  30

Leu Tyr Lys Tyr Arg Cys Tyr Lys Val Ile His Ala Trp Leu Ile Ile
        35                  40                  45

Ser Ser Leu Leu Leu Leu Phe Phe Ser Phe Ile
    50                  55                  60

<210> SEQ ID NO 73
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 73
aagccgagta agccaaaaac caacatgaag cacatggctg gtgctgcagc agctggggca      60
gtggtggggg gccttggcgg ctacgtgctg gaagtgccat gagcaggcc catcatacat     120 ttcggcagtg actatgagga ccgttactat cgtgaaaaca tgcaccgtta ccccaaccaa    180

<210> SEQ ID NO 74
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 74

Lys Pro Ser Lys Pro Lys Thr Asn Met Lys His Met Ala Gly Ala Ala
1               5                   10                  15

Ala Ala Gly Ala Val Val Gly Gly Leu Gly Gly Tyr Val Leu Gly Ser
            20                  25                  30

Ala Met Ser Arg Pro Ile Ile His Phe Gly Ser Asp Tyr Glu Asp Arg
        35                  40                  45

Tyr Tyr Arg Glu Asn Met His Arg Tyr Pro Asn Gln
    50                  55                  60

<210> SEQ ID NO 75
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 75
cttcccagcc gagacgtgac agtccttctg gaaaactatg gcaaattcga aaagggtgt      60 ttgattttg ttgtacgttt cctctttggc ctggtaaacc aggagaggac ctcctacttg    120

<210> SEQ ID NO 76
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 76

Leu Pro Ser Arg Asp Val Thr Val Leu Glu Asn Tyr Gly Lys Phe
1               5                   10                  15

Glu Lys Gly Cys Leu Ile Phe Val Val Arg Phe Leu Phe Gly Leu Val
            20                  25                  30

Asn Gln Glu Arg Thr Ser Tyr Leu
        35                  40

<210> SEQ ID NO 77
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 77
gtgaagcact tctccccaga ggaactcaaa gttaaggtgt tgggagatgt gattgaggtg      60
catggaaaac atgaagagcg ccaggatgaa catggtttca tctccaggga gttccacggg     120
aaataccgga tcccagctga tgtagaccct ctcaccatta cttcatccct gtcatctgat     180

<210> SEQ ID NO 78
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 78

Val Lys His Phe Ser Pro Glu Glu Leu Lys Val Lys Val Leu Gly Asp
1               5                   10                  15

Val Ile Glu Val His Gly Lys His Glu Glu Arg Gln Asp Glu His Gly
            20                  25                  30

Phe Ile Ser Arg Glu Phe His Gly Lys Tyr Arg Ile Pro Ala Asp Val
        35                  40                  45

Asp Pro Leu Thr Ile Thr Ser Ser Leu Ser Ser Asp
    50                  55                  60

<210> SEQ ID NO 79
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 79
gagctgcact gtgacaagct gcacgtggat cctgagaact tcaggctcct gggcaacgtg      60
ctggtctgtg tgccggccca tcactttggc aaagaattca ccccaccagt gcaggctgcc     120
tatcagaaag tggtggctgg tgtggctaat gccctggccc acaagtatca ctaagctcgc     180

<210> SEQ ID NO 80
<211> LENGTH: 59
<212> TYPE: PRT
<213> ORGANISM: Artificial Sequence

```
<220> FEATURE:
<223> OTHER INFORMATION: Synthetic Polypeptide

<400> SEQUENCE: 80

Glu Leu His Cys Asp Lys Leu His Val Asp Pro Glu Asn Phe Arg Leu
1               5                   10                  15

Leu Gly Asn Val Leu Val Cys Val Pro Ala His Phe Gly Lys Glu
            20                  25                  30

Phe Thr Pro Pro Val Gln Ala Ala Tyr Gln Lys Val Val Ala Gly Val
        35                  40                  45

Ala Asn Ala Leu Ala His Lys Tyr His Ala Arg
    50                  55

<210> SEQ ID NO 81
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 81
aucggaauct auuuugacuc guuuuagagc uagaaauagc aaguuaaaau aaaggcuagu      60
ccguuaucaa cuugaaaaag uggcaccgag ucggugcuuu uu                       102

<210> SEQ ID NO 82
<211> LENGTH: 102
<212> TYPE: RNA
<213> ORGANISM: Artificial Sequence
<220> FEATURE:
<223> OTHER INFORMATION: Synthetic Polynucleotide

<400> SEQUENCE: 82
ucggaaucua uuuugacucg guuuuagagc uagaaauagc aaguuaaaau aaaggcuagu      60
ccguuaucaa cuugaaaaag uggcaccgag ucggugcuuu uu                       102

<210> SEQ ID NO 83
<211> LENGTH: 102
<212> TYPE: RNA
<213> ORGANISM: Artificial Sequence
<220> FEATURE:
<223> OTHER INFORMATION: Synthetic Polynucleotide

<400> SEQUENCE: 83
cuuagauaaa acugagcaag guuuuagagc uagaaauagc aaguuaaaau aaaggcuagu      60
ccguuaucaa cuugaaaaag uggcaccgag ucggugcuuu uu                       102

<210> SEQ ID NO 84
<211> LENGTH: 102
<212> TYPE: RNA
<213> ORGANISM: Artificial Sequence
<220> FEATURE:
<223> OTHER INFORMATION: Synthetic Polynucleotide

<400> SEQUENCE: 84
aucuauuuug acucguucuc guuuuagagc uagaaauagc aaguuaaaau aaaggcuagu      60
ccguuaucaa cuugaaaaag uggcaccgag ucggugcuuu uu                       102

<210> SEQ ID NO 85
<211> LENGTH: 102
<212> TYPE: RNA
<213> ORGANISM: Artificial Sequence
<220> FEATURE:
```

<223> OTHER INFORMATION: Synthetic Polynucleotide

<400> SEQUENCE: 85
uaaaacugag caagaggcuu guuuuagagc uagaaauagc aaguuaaaau aaaggcuagu    60
ccguuaucaa cuugaaaaag uggcaccgag ucggugcuuu uu    102

<210> SEQ ID NO 86
<211> LENGTH: 102
<212> TYPE: RNA
<213> ORGANISM: Artificial Sequence
<220> FEATURE:
<223> OTHER INFORMATION: Synthetic Polynucleotide

<400> SEQUENCE: 86
ugguggcugg acaacaaaaa guuuuagagc uagaaauagc aaguuaaaau aaaggcuagu    60
ccguuaucaa cuugaaaaag uggcaccgag ucggugcuuu uu    102

<210> SEQ ID NO 87
<211> LENGTH: 102
<212> TYPE: RNA
<213> ORGANISM: Artificial Sequence
<220> FEATURE:
<223> OTHER INFORMATION: Synthetic Polynucleotide

<400> SEQUENCE: 87
gcuggacaac aaaaauggau guuuuagagc uagaaauagc aaguuaaaau aaaggcuagu    60
ccguuaucaa cuugaaaaag uggcaccgag ucggugcuuu uu    102

<210> SEQ ID NO 88
<211> LENGTH: 102
<212> TYPE: RNA
<213> ORGANISM: Artificial Sequence
<220> FEATURE:
<223> OTHER INFORMATION: Synthetic Polynucleotide

<400> SEQUENCE: 88
guguuaauuu gucguacgua guuuuagagc uagaaauagc aaguuaaaau aaaggcuagu    60
ccguuaucaa cuugaaaaag uggcaccgag ucggugcuuu uu    102

<210> SEQ ID NO 89
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 89
gcctccgcca acgtggactt cgctttcagc ctgtacaagc agttagtcct gaaggcccct    60
gataagaatg tcatcttctc cccaccgagc atctccaccg ccttggcctt cctgtctctg   120
ggggcccata ataccaccct gacagagatt ctcaaaggcc tcaagttcta cctcacggag   180

<210> SEQ ID NO 90
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 90

Ala Ser Ala Asn Val Asp Phe Ala Phe Ser Leu Tyr Lys Gln Leu Val
1               5                   10                  15

```
Leu Lys Ala Pro Asp Lys Asn Val Ile Phe Ser Pro Ser Ile Ser
           20                  25                  30

Thr Ala Leu Ala Phe Leu Ser Leu Gly Ala His Asn Thr Thr Leu Thr
        35                  40                  45

Glu Ile Leu Lys Gly Leu Lys Phe Tyr Leu Thr Glu
    50                  55                  60
```

<210> SEQ ID NO 91
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 91

```
Gly Gly Gly Gly Ser
1               5
```

<210> SEQ ID NO 92
<211> LENGTH: 1636
<212> TYPE: PRT
<213> ORGANISM: Artificial Sequence
<220> FEATURE:
<223> OTHER INFORMATION: Synthetic Polypeptide

<400> SEQUENCE: 92

```
Ser Pro Lys Lys Lys Arg Lys Val Glu Ala Ser Met Thr Ser Glu Lys
1               5                   10                  15

Gly Pro Ser Thr Gly Asp Pro Thr Leu Arg Arg Arg Ile Glu Pro Trp
            20                  25                  30

Glu Phe Asp Val Phe Tyr Asp Pro Arg Glu Leu Arg Lys Glu Ala Cys
        35                  40                  45

Leu Leu Tyr Glu Ile Lys Trp Gly Met Ser Arg Lys Ile Trp Arg Ser
    50                  55                  60

Ser Gly Lys Asn Thr Thr Asn His Val Glu Val Asn Phe Ile Lys Lys
65                  70                  75                  80

Phe Thr Ser Glu Arg Asp Phe His Pro Ser Met Ser Cys Ser Ile Thr
                85                  90                  95

Trp Phe Leu Ser Trp Ser Pro Cys Trp Glu Cys Ser Gln Ala Ile Arg
            100                 105                 110

Glu Phe Leu Ser Arg His Pro Gly Val Thr Leu Val Ile Tyr Val Ala
        115                 120                 125

Arg Leu Phe Trp His Met Asp Gln Gln Asn Arg Gln Gly Leu Arg Asp
    130                 135                 140

Leu Val Asn Ser Gly Val Thr Ile Gln Ile Met Arg Ala Ser Glu Tyr
145                 150                 155                 160

Tyr His Cys Trp Arg Asn Phe Val Asn Tyr Pro Pro Gly Asp Glu Ala
                165                 170                 175

His Trp Pro Gln Tyr Pro Pro Leu Trp Met Met Leu Tyr Ala Leu Glu
            180                 185                 190

Leu His Cys Ile Ile Leu Ser Leu Pro Pro Cys Leu Lys Ile Ser Arg
        195                 200                 205

Arg Trp Gln Asn His Leu Thr Phe Phe Arg Leu His Leu Gln Asn Cys
    210                 215                 220

His Tyr Gln Thr Ile Pro Pro His Ile Leu Leu Ala Thr Gly Leu Ile
225                 230                 235                 240

His Pro Ser Val Ala Trp Arg Ser Pro Lys Lys Lys Arg Lys Val Glu
                245                 250                 255
```

```
Ala Ser Ser Pro Lys Lys Arg Lys Val Glu Ala Ser Asp Lys Lys
            260                 265             270

Tyr Ser Ile Gly Leu Ala Ile Gly Thr Asn Ser Val Gly Trp Ala Val
        275                 280             285

Ile Thr Asp Glu Tyr Lys Val Pro Ser Lys Phe Lys Val Leu Gly
    290                 295             300

Asn Thr Asp Arg His Ser Ile Lys Lys Asn Leu Ile Gly Ala Leu Leu
305             310             315                 320

Phe Asp Ser Gly Glu Thr Ala Glu Ala Thr Arg Leu Lys Arg Thr Ala
                325             330             335

Arg Arg Arg Tyr Thr Arg Arg Lys Asn Arg Ile Cys Tyr Leu Gln Glu
            340             345             350

Ile Phe Ser Asn Glu Met Ala Lys Val Asp Asp Ser Phe Phe His Arg
        355             360             365

Leu Glu Glu Ser Phe Leu Val Glu Glu Asp Lys Lys His Glu Arg His
    370             375             380

Pro Ile Phe Gly Asn Ile Val Asp Glu Val Ala Tyr His Glu Lys Tyr
385             390             395                 400

Pro Thr Ile Tyr His Leu Arg Lys Lys Leu Val Asp Ser Thr Asp Lys
                405             410             415

Ala Asp Leu Arg Leu Ile Tyr Leu Ala Leu Ala His Met Ile Lys Phe
            420             425             430

Arg Gly His Phe Leu Ile Glu Gly Asp Leu Asn Pro Asp Asn Ser Asp
        435             440             445

Val Asp Lys Leu Phe Ile Gln Leu Val Gln Thr Tyr Asn Gln Leu Phe
    450             455             460

Glu Glu Asn Pro Ile Asn Ala Ser Gly Val Asp Ala Lys Ala Ile Leu
465             470             475                 480

Ser Ala Arg Leu Ser Lys Ser Arg Arg Leu Glu Asn Leu Ile Ala Gln
            485             490             495

Leu Pro Gly Glu Lys Lys Asn Gly Leu Phe Gly Asn Leu Ile Ala Leu
        500             505             510

Ser Leu Gly Leu Thr Pro Asn Phe Lys Ser Asn Phe Asp Leu Ala Glu
    515             520             525

Asp Ala Lys Leu Gln Leu Ser Lys Asp Thr Tyr Asp Asp Asp Leu Asp
530             535             540

Asn Leu Leu Ala Gln Ile Gly Asp Gln Tyr Ala Asp Leu Phe Leu Ala
545             550             555             560

Ala Lys Asn Leu Ser Asp Ala Ile Leu Leu Ser Asp Ile Leu Arg Val
            565             570             575

Asn Thr Glu Ile Thr Lys Ala Pro Leu Ser Ala Ser Met Ile Lys Arg
        580             585             590

Tyr Asp Glu His His Gln Asp Leu Thr Leu Leu Lys Ala Leu Val Arg
    595             600             605

Gln Gln Leu Pro Glu Lys Tyr Lys Glu Ile Phe Phe Asp Gln Ser Lys
            610             615             620

Asn Gly Tyr Ala Gly Tyr Ile Asp Gly Gly Ala Ser Gln Glu Glu Phe
625             630             635             640

Tyr Lys Phe Ile Lys Pro Ile Leu Glu Lys Met Asp Gly Thr Glu Glu
                645             650             655

Leu Leu Val Lys Leu Asn Arg Glu Asp Leu Leu Arg Lys Gln Arg Thr
            660             665             670
```

```
Phe Asp Asn Gly Ser Ile Pro His Gln Ile His Leu Gly Glu Leu His
            675                 680                 685

Ala Ile Leu Arg Arg Gln Glu Asp Phe Tyr Pro Phe Leu Lys Asp Asn
        690                 695                 700

Arg Glu Lys Ile Glu Lys Ile Leu Thr Phe Arg Ile Pro Tyr Tyr Val
705                 710                 715                 720

Gly Pro Leu Ala Arg Gly Asn Ser Arg Phe Ala Trp Met Thr Arg Lys
                725                 730                 735

Ser Glu Glu Thr Ile Thr Pro Trp Asn Phe Glu Val Val Asp Lys
            740                 745                 750

Gly Ala Ser Ala Gln Ser Phe Ile Glu Arg Met Thr Asn Phe Asp Lys
        755                 760                 765

Asn Leu Pro Asn Glu Lys Val Leu Pro Lys His Ser Leu Leu Tyr Glu
    770                 775                 780

Tyr Phe Thr Val Tyr Asn Glu Leu Thr Lys Val Lys Tyr Val Thr Glu
785                 790                 795                 800

Gly Met Arg Lys Pro Ala Phe Leu Ser Gly Glu Gln Lys Lys Ala Ile
                805                 810                 815

Val Asp Leu Leu Phe Lys Thr Asn Arg Lys Val Thr Val Lys Gln Leu
            820                 825                 830

Lys Glu Asp Tyr Phe Lys Lys Ile Glu Cys Phe Asp Ser Val Glu Ile
        835                 840                 845

Ser Gly Val Glu Asp Arg Phe Asn Ala Ser Leu Gly Thr Tyr His Asp
    850                 855                 860

Leu Leu Lys Ile Ile Lys Asp Lys Asp Phe Leu Asp Asn Glu Glu Asn
865                 870                 875                 880

Glu Asp Ile Leu Glu Asp Ile Val Leu Thr Leu Thr Leu Phe Glu Asp
                885                 890                 895

Arg Glu Met Ile Glu Glu Arg Leu Lys Thr Tyr Ala His Leu Phe Asp
            900                 905                 910

Asp Lys Val Met Lys Gln Leu Lys Arg Arg Arg Tyr Thr Gly Trp Gly
        915                 920                 925

Arg Leu Ser Arg Lys Leu Ile Asn Gly Ile Arg Asp Lys Gln Ser Gly
    930                 935                 940

Lys Thr Ile Leu Asp Phe Leu Lys Ser Asp Gly Phe Ala Asn Arg Asn
945                 950                 955                 960

Phe Met Gln Leu Ile His Asp Asp Ser Leu Thr Phe Lys Glu Asp Ile
                965                 970                 975

Gln Lys Ala Gln Val Ser Gly Gln Gly Asp Ser Leu His Glu His Ile
        980                 985                 990

Ala Asn Leu Ala Gly Ser Pro Ala Ile Lys Lys Gly Ile Leu Gln Thr
    995                 1000                1005

Val Lys Val Val Asp Glu Leu Val Lys Val Met Gly Arg His Lys
    1010                1015                1020

Pro Glu Asn Ile Val Ile Glu Met Ala Arg Glu Asn Gln Thr Thr
    1025                1030                1035

Gln Lys Gly Gln Lys Asn Ser Arg Glu Arg Met Lys Arg Ile Glu
    1040                1045                1050

Glu Gly Ile Lys Glu Leu Gly Ser Gln Ile Leu Lys Glu His Pro
    1055                1060                1065

Val Glu Asn Thr Gln Leu Gln Asn Glu Lys Leu Tyr Leu Tyr Tyr
    1070                1075                1080

Leu Gln Asn Gly Arg Asp Met Tyr Val Asp Gln Glu Leu Asp Ile
```

-continued

```
            1085                1090                1095
Asn Arg Leu Ser Asp Tyr Asp Val Asp Ala Ile Val Pro Gln Ser
            1100                1105                1110
Phe Leu Lys Asp Asp Ser Ile Asp Asn Lys Val Leu Thr Arg Ser
            1115                1120                1125
Asp Lys Asn Arg Gly Lys Ser Asp Asn Val Pro Ser Glu Glu Val
            1130                1135                1140
Val Lys Lys Met Lys Asn Tyr Trp Arg Gln Leu Leu Asn Ala Lys
            1145                1150                1155
Leu Ile Thr Gln Arg Lys Phe Asp Asn Leu Thr Lys Ala Glu Arg
            1160                1165                1170
Gly Gly Leu Ser Glu Leu Asp Lys Ala Gly Phe Ile Lys Arg Gln
            1175                1180                1185
Leu Val Glu Thr Arg Gln Ile Thr Lys His Val Ala Gln Ile Leu
            1190                1195                1200
Asp Ser Arg Met Asn Thr Lys Tyr Asp Glu Asn Asp Lys Leu Ile
            1205                1210                1215
Arg Glu Val Lys Val Ile Thr Leu Lys Ser Lys Leu Val Ser Asp
            1220                1225                1230
Phe Arg Lys Asp Phe Gln Phe Tyr Lys Val Arg Glu Ile Asn Asn
            1235                1240                1245
Tyr His His Ala His Asp Ala Tyr Leu Asn Ala Val Val Gly Thr
            1250                1255                1260
Ala Leu Ile Lys Lys Tyr Pro Lys Leu Glu Ser Glu Phe Val Tyr
            1265                1270                1275
Gly Asp Tyr Lys Val Tyr Asp Val Arg Lys Met Ile Ala Lys Ser
            1280                1285                1290
Glu Gln Glu Ile Gly Lys Ala Thr Ala Lys Tyr Phe Phe Tyr Ser
            1295                1300                1305
Asn Ile Met Asn Phe Phe Lys Thr Glu Ile Thr Leu Ala Asn Gly
            1310                1315                1320
Glu Ile Arg Lys Arg Pro Leu Ile Glu Thr Asn Gly Glu Thr Gly
            1325                1330                1335
Glu Ile Val Trp Asp Lys Gly Arg Asp Phe Ala Thr Val Arg Lys
            1340                1345                1350
Val Leu Ser Met Pro Gln Val Asn Ile Val Lys Lys Thr Glu Val
            1355                1360                1365
Gln Thr Gly Gly Phe Ser Lys Glu Ser Ile Leu Pro Lys Arg Asn
            1370                1375                1380
Ser Asp Lys Leu Ile Ala Arg Lys Lys Asp Trp Asp Pro Lys Lys
            1385                1390                1395
Tyr Gly Gly Phe Asp Ser Pro Thr Val Ala Tyr Ser Val Leu Val
            1400                1405                1410
Val Ala Lys Val Glu Lys Gly Lys Ser Lys Lys Leu Lys Ser Val
            1415                1420                1425
Lys Glu Leu Leu Gly Ile Thr Ile Met Glu Arg Ser Ser Phe Glu
            1430                1435                1440
Lys Asn Pro Ile Asp Phe Leu Glu Ala Lys Gly Tyr Lys Glu Val
            1445                1450                1455
Lys Lys Asp Leu Ile Ile Lys Leu Pro Lys Tyr Ser Leu Phe Glu
            1460                1465                1470
Leu Glu Asn Gly Arg Lys Arg Met Leu Ala Ser Ala Gly Glu Leu
            1475                1480                1485
```

```
Gln Lys Gly Asn Glu Leu Ala Leu Pro Ser Lys Tyr Val Asn Phe
    1490                1495                1500

Leu Tyr Leu Ala Ser His Tyr Glu Lys Leu Lys Gly Ser Pro Glu
    1505                1510                1515

Asp Asn Glu Gln Lys Gln Leu Phe Val Glu Gln His Lys His Tyr
    1520                1525                1530

Leu Asp Glu Ile Ile Glu Gln Ile Ser Glu Phe Ser Lys Arg Val
    1535                1540                1545

Ile Leu Ala Asp Ala Asn Leu Asp Lys Val Leu Ser Ala Tyr Asn
    1550                1555                1560

Lys His Arg Asp Lys Pro Ile Arg Glu Gln Ala Glu Asn Ile Ile
    1565                1570                1575

His Leu Phe Thr Leu Thr Asn Leu Gly Ala Pro Ala Ala Phe Lys
    1580                1585                1590

Tyr Phe Asp Thr Thr Ile Asp Arg Lys Arg Tyr Thr Ser Thr Lys
    1595                1600                1605

Glu Val Leu Asp Ala Thr Leu Ile His Gln Ser Ile Thr Gly Leu
    1610                1615                1620

Tyr Glu Thr Arg Ile Asp Leu Ser Gln Leu Gly Gly Asp
    1625                1630                1635

<210> SEQ ID NO 93
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 93

Ser Gly Ser Glu Thr Pro Gly Thr Ser Glu Ser Ala Thr Pro Glu Ser
1               5                   10                  15

<210> SEQ ID NO 94
<211> LENGTH: 1600
<212> TYPE: PRT
<213> ORGANISM: Artificial Sequence
<220> FEATURE:
<223> OTHER INFORMATION: Synthetic Polypeptide

<400> SEQUENCE: 94

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
        50                  55                  60

Asn Phe Ile Glu Lys Phe Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Arg Asn Arg
            115                 120                 125

Gln Gly Leu Arg Asp Leu Ile Ser Ser Gly Val Thr Ile Gln Ile Met
```

```
            130                 135                 140
Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
    210                 215                 220

Ala Thr Gly Leu Lys Gly Gly Ser Met Asp Lys Lys Tyr Ser Ile Gly
225                 230                 235                 240

Leu Ala Ile Gly Thr Asn Ser Val Gly Trp Ala Val Ile Thr Asp Glu
                245                 250                 255

Tyr Lys Val Pro Ser Lys Lys Phe Lys Val Leu Gly Asn Thr Asp Arg
            260                 265                 270

His Ser Ile Lys Lys Asn Leu Ile Gly Ala Leu Leu Phe Asp Ser Gly
        275                 280                 285

Glu Thr Ala Glu Ala Thr Arg Leu Lys Arg Thr Ala Arg Arg Arg Tyr
    290                 295                 300

Thr Arg Arg Lys Asn Arg Ile Cys Tyr Leu Gln Glu Ile Phe Ser Asn
305                 310                 315                 320

Glu Met Ala Lys Val Asp Asp Ser Phe Phe His Arg Leu Glu Glu Ser
                325                 330                 335

Phe Leu Val Glu Glu Asp Lys Lys His Glu Arg His Pro Ile Phe Gly
            340                 345                 350

Asn Ile Val Asp Glu Val Ala Tyr His Glu Lys Tyr Pro Thr Ile Tyr
        355                 360                 365

His Leu Arg Lys Lys Leu Val Asp Ser Thr Asp Lys Ala Asp Leu Arg
    370                 375                 380

Leu Ile Tyr Leu Ala Leu Ala His Met Ile Lys Phe Arg Gly His Phe
385                 390                 395                 400

Leu Ile Glu Gly Asp Leu Asn Pro Asp Asn Ser Asp Val Asp Lys Leu
                405                 410                 415

Phe Ile Gln Leu Val Gln Thr Tyr Asn Gln Leu Phe Glu Glu Asn Pro
            420                 425                 430

Ile Asn Ala Ser Gly Val Asp Ala Lys Ala Ile Leu Ser Ala Arg Leu
        435                 440                 445

Ser Lys Ser Arg Arg Leu Glu Asn Leu Ile Ala Gln Leu Pro Gly Glu
    450                 455                 460

Lys Lys Asn Gly Leu Phe Gly Asn Leu Ile Ala Leu Ser Leu Gly Leu
465                 470                 475                 480

Thr Pro Asn Phe Lys Ser Asn Phe Asp Leu Ala Glu Asp Ala Lys Leu
                485                 490                 495

Gln Leu Ser Lys Asp Thr Tyr Asp Asp Asp Leu Asp Asn Leu Leu Ala
            500                 505                 510

Gln Ile Gly Asp Gln Tyr Ala Asp Leu Phe Leu Ala Ala Lys Asn Leu
        515                 520                 525

Ser Asp Ala Ile Leu Leu Ser Asp Ile Leu Arg Val Asn Thr Glu Ile
    530                 535                 540

Thr Lys Ala Pro Leu Ser Ala Ser Met Ile Lys Arg Tyr Asp Glu His
545                 550                 555                 560
```

```
His Gln Asp Leu Thr Leu Leu Lys Ala Leu Val Arg Gln Leu Pro
                565                 570                 575

Glu Lys Tyr Lys Glu Ile Phe Phe Asp Gln Ser Lys Asn Gly Tyr Ala
            580                 585                 590

Gly Tyr Ile Asp Gly Gly Ala Ser Gln Glu Glu Phe Tyr Lys Phe Ile
        595                 600                 605

Lys Pro Ile Leu Glu Lys Met Asp Gly Thr Glu Glu Leu Leu Val Lys
    610                 615                 620

Leu Asn Arg Glu Asp Leu Leu Arg Lys Gln Arg Thr Phe Asp Asn Gly
625                 630                 635                 640

Ser Ile Pro His Gln Ile His Leu Gly Glu Leu His Ala Ile Leu Arg
                645                 650                 655

Arg Gln Glu Asp Phe Tyr Pro Phe Leu Lys Asp Asn Arg Glu Lys Ile
            660                 665                 670

Glu Lys Ile Leu Thr Phe Arg Ile Pro Tyr Tyr Val Gly Pro Leu Ala
        675                 680                 685

Arg Gly Asn Ser Arg Phe Ala Trp Met Thr Arg Lys Ser Glu Glu Thr
    690                 695                 700

Ile Thr Pro Trp Asn Phe Glu Glu Val Val Asp Lys Gly Ala Ser Ala
705                 710                 715                 720

Gln Ser Phe Ile Glu Arg Met Thr Asn Phe Asp Lys Asn Leu Pro Asn
                725                 730                 735

Glu Lys Val Leu Pro Lys His Ser Leu Leu Tyr Glu Tyr Phe Thr Val
            740                 745                 750

Tyr Asn Glu Leu Thr Lys Val Lys Tyr Val Thr Glu Gly Met Arg Lys
        755                 760                 765

Pro Ala Phe Leu Ser Gly Glu Gln Lys Lys Ala Ile Val Asp Leu Leu
    770                 775                 780

Phe Lys Thr Asn Arg Lys Val Thr Val Lys Gln Leu Lys Glu Asp Tyr
785                 790                 795                 800

Phe Lys Lys Ile Glu Cys Phe Asp Ser Val Glu Ile Ser Gly Val Glu
                805                 810                 815

Asp Arg Phe Asn Ala Ser Leu Gly Thr Tyr His Asp Leu Leu Lys Ile
            820                 825                 830

Ile Lys Asp Lys Asp Phe Leu Asp Asn Glu Glu Asn Glu Asp Ile Leu
        835                 840                 845

Glu Asp Ile Val Leu Thr Leu Thr Leu Phe Glu Asp Arg Glu Met Ile
    850                 855                 860

Glu Glu Arg Leu Lys Thr Tyr Ala His Leu Phe Asp Asp Lys Val Met
865                 870                 875                 880

Lys Gln Leu Lys Arg Arg Arg Tyr Thr Gly Trp Gly Arg Leu Ser Arg
                885                 890                 895

Lys Leu Ile Asn Gly Ile Arg Asp Lys Gln Ser Gly Lys Thr Ile Leu
            900                 905                 910

Asp Phe Leu Lys Ser Asp Gly Phe Ala Asn Arg Asn Phe Met Gln Leu
        915                 920                 925

Ile His Asp Asp Ser Leu Thr Phe Lys Glu Asp Ile Gln Lys Ala Gln
    930                 935                 940

Val Ser Gly Gln Gly Asp Ser Leu His Glu His Ile Ala Asn Leu Ala
945                 950                 955                 960

Gly Ser Pro Ala Ile Lys Lys Gly Ile Leu Gln Thr Val Lys Val Val
                965                 970                 975
```

-continued

Asp Glu Leu Val Lys Val Met Gly Arg His Lys Pro Glu Asn Ile Val
              980                 985                 990

Ile Glu Met Ala Arg Glu Asn Gln Thr Thr Gln Lys Gly Gln Lys Asn
          995                 1000                1005

Ser Arg Glu Arg Met Lys Arg Ile Glu Glu Gly Ile Lys Glu Leu
        1010                1015                1020

Gly Ser Gln Ile Leu Lys Glu His Pro Val Glu Asn Thr Gln Leu
        1025                1030                1035

Gln Asn Glu Lys Leu Tyr Leu Tyr Tyr Leu Gln Asn Gly Arg Asp
        1040                1045                1050

Met Tyr Val Asp Gln Glu Leu Asp Ile Asn Arg Leu Ser Asp Tyr
        1055                1060                1065

Asp Val Asp Ala Ile Val Pro Gln Ser Phe Leu Lys Asp Asp Ser
        1070                1075                1080

Ile Asp Asn Lys Val Leu Thr Arg Ser Asp Lys Asn Arg Gly Lys
        1085                1090                1095

Ser Asp Asn Val Pro Ser Glu Glu Val Val Lys Lys Met Lys Asn
        1100                1105                1110

Tyr Trp Arg Gln Leu Leu Asn Ala Lys Leu Ile Thr Gln Arg Lys
        1115                1120                1125

Phe Asp Asn Leu Thr Lys Ala Glu Arg Gly Gly Leu Ser Glu Leu
        1130                1135                1140

Asp Lys Ala Gly Phe Ile Lys Arg Gln Leu Val Glu Thr Arg Gln
        1145                1150                1155

Ile Thr Lys His Val Ala Gln Ile Leu Asp Ser Arg Met Asn Thr
        1160                1165                1170

Lys Tyr Asp Glu Asn Asp Lys Leu Ile Arg Glu Val Lys Val Ile
        1175                1180                1185

Thr Leu Lys Ser Lys Leu Val Ser Asp Phe Arg Lys Asp Phe Gln
        1190                1195                1200

Phe Tyr Lys Val Arg Glu Ile Asn Asn Tyr His His Ala His Asp
        1205                1210                1215

Ala Tyr Leu Asn Ala Val Val Gly Thr Ala Leu Ile Lys Lys Tyr
        1220                1225                1230

Pro Lys Leu Glu Ser Glu Phe Val Tyr Gly Asp Tyr Lys Val Tyr
        1235                1240                1245

Asp Val Arg Lys Met Ile Ala Lys Ser Glu Gln Glu Ile Gly Lys
        1250                1255                1260

Ala Thr Ala Lys Tyr Phe Phe Tyr Ser Asn Ile Met Asn Phe Phe
        1265                1270                1275

Lys Thr Glu Ile Thr Leu Ala Asn Gly Glu Ile Arg Lys Arg Pro
        1280                1285                1290

Leu Ile Glu Thr Asn Gly Glu Thr Gly Glu Ile Val Trp Asp Lys
        1295                1300                1305

Gly Arg Asp Phe Ala Thr Val Arg Lys Val Leu Ser Met Pro Gln
        1310                1315                1320

Val Asn Ile Val Lys Lys Thr Glu Val Gln Thr Gly Gly Phe Ser
        1325                1330                1335

Lys Glu Ser Ile Leu Pro Lys Arg Asn Ser Asp Lys Leu Ile Ala
        1340                1345                1350

Arg Lys Lys Asp Trp Asp Pro Lys Lys Tyr Gly Gly Phe Asp Ser
        1355                1360                1365

Pro Thr Val Ala Tyr Ser Val Leu Val Val Ala Lys Val Glu Lys

-continued

```
                  1370                1375                1380

Gly Lys Ser Lys Lys Leu Lys Ser Val Lys Glu Leu Leu Gly Ile
            1385                1390                1395

Thr Ile Met Glu Arg Ser Ser Phe Glu Lys Asn Pro Ile Asp Phe
    1400                1405                1410

Leu Glu Ala Lys Gly Tyr Lys Glu Val Lys Lys Asp Leu Ile Ile
        1415                1420                1425

Lys Leu Pro Lys Tyr Ser Leu Phe Glu Leu Glu Asn Gly Arg Lys
    1430                1435                1440

Arg Met Leu Ala Ser Ala Gly Glu Leu Gln Lys Gly Asn Glu Leu
    1445                1450                1455

Ala Leu Pro Ser Lys Tyr Val Asn Phe Leu Tyr Leu Ala Ser His
    1460                1465                1470

Tyr Glu Lys Leu Lys Gly Ser Pro Glu Asp Asn Glu Gln Lys Gln
    1475                1480                1485

Leu Phe Val Glu Gln His Lys His Tyr Leu Asp Glu Ile Ile Glu
    1490                1495                1500

Gln Ile Ser Glu Phe Ser Lys Arg Val Ile Leu Ala Asp Ala Asn
    1505                1510                1515

Leu Asp Lys Val Leu Ser Ala Tyr Asn Lys His Arg Asp Lys Pro
    1520                1525                1530

Ile Arg Glu Gln Ala Glu Asn Ile Ile His Leu Phe Thr Leu Thr
    1535                1540                1545

Asn Leu Gly Ala Pro Ala Ala Phe Lys Tyr Phe Asp Thr Thr Ile
    1550                1555                1560

Asp Arg Lys Arg Tyr Thr Ser Thr Lys Glu Val Leu Asp Ala Thr
    1565                1570                1575

Leu Ile His Gln Ser Ile Thr Gly Leu Tyr Glu Thr Arg Ile Asp
    1580                1585                1590

Leu Ser Gln Leu Gly Gly Asp
    1595                1600

<210> SEQ ID NO 95
<211> LENGTH: 1606
<212> TYPE: PRT
<213> ORGANISM: Artificial Sequence
<220> FEATURE:
<223> OTHER INFORMATION: Synthetic Polypeptide

<400> SEQUENCE: 95

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
        50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
```

```
            115                 120                 125
Gln Gly Leu Arg Asp Leu Ile Ser Ser Gly Val Thr Ile Gln Ile Met
    130                 135                 140
Thr Glu Gln Glu Ser Gly Tyr Cys Trp Arg Asn Phe Val Asn Tyr Ser
145                 150                 155                 160
Pro Ser Asn Glu Ala His Trp Pro Arg Tyr Pro His Leu Trp Val Arg
                165                 170                 175
Leu Tyr Val Leu Glu Leu Tyr Cys Ile Ile Leu Gly Leu Pro Pro Cys
                180                 185                 190
Leu Asn Ile Leu Arg Arg Lys Gln Pro Gln Leu Thr Phe Phe Thr Ile
                195                 200                 205
Ala Leu Gln Ser Cys His Tyr Gln Arg Leu Pro Pro His Ile Leu Trp
    210                 215                 220
Ala Thr Gly Leu Lys Gly Gly Ser Gly Gly Ser Gly Gly Ser Met Asp
225                 230                 235                 240
Lys Lys Tyr Ser Ile Gly Leu Ala Ile Gly Thr Asn Ser Val Gly Trp
                245                 250                 255
Ala Val Ile Thr Asp Glu Tyr Lys Val Pro Ser Lys Lys Phe Lys Val
                260                 265                 270
Leu Gly Asn Thr Asp Arg His Ser Ile Lys Lys Asn Leu Ile Gly Ala
                275                 280                 285
Leu Leu Phe Asp Ser Gly Glu Thr Ala Glu Ala Thr Arg Leu Lys Arg
                290                 295                 300
Thr Ala Arg Arg Arg Tyr Thr Arg Arg Lys Asn Arg Ile Cys Tyr Leu
305                 310                 315                 320
Gln Glu Ile Phe Ser Asn Glu Met Ala Lys Val Asp Ser Phe Phe
                325                 330                 335
His Arg Leu Glu Glu Ser Phe Leu Val Glu Glu Asp Lys Lys His Glu
                340                 345                 350
Arg His Pro Ile Phe Gly Asn Ile Val Asp Glu Val Ala Tyr His Glu
                355                 360                 365
Lys Tyr Pro Thr Ile Tyr His Leu Arg Lys Lys Leu Val Asp Ser Thr
    370                 375                 380
Asp Lys Ala Asp Leu Arg Leu Ile Tyr Leu Ala Leu Ala His Met Ile
385                 390                 395                 400
Lys Phe Arg Gly His Phe Leu Ile Glu Gly Asp Leu Asn Pro Asp Asn
                405                 410                 415
Ser Asp Val Asp Lys Leu Phe Ile Gln Leu Val Gln Thr Tyr Asn Gln
                420                 425                 430
Leu Phe Glu Glu Asn Pro Ile Asn Ala Ser Gly Val Asp Ala Lys Ala
                435                 440                 445
Ile Leu Ser Ala Arg Leu Ser Lys Ser Arg Arg Leu Glu Asn Leu Ile
    450                 455                 460
Ala Gln Leu Pro Gly Glu Lys Lys Asn Gly Leu Phe Gly Asn Leu Ile
465                 470                 475                 480
Ala Leu Ser Leu Gly Leu Thr Pro Asn Phe Lys Ser Asn Phe Asp Leu
                485                 490                 495
Ala Glu Asp Ala Lys Leu Gln Leu Ser Lys Asp Thr Tyr Asp Asp Asp
                500                 505                 510
Leu Asp Asn Leu Leu Ala Gln Ile Gly Asp Gln Tyr Ala Asp Leu Phe
                515                 520                 525
Leu Ala Ala Lys Asn Leu Ser Asp Ala Ile Leu Leu Ser Asp Ile Leu
                530                 535                 540
```

```
Arg Val Asn Thr Glu Ile Thr Lys Ala Pro Leu Ser Ala Ser Met Ile
545                 550                 555                 560

Lys Arg Tyr Asp Glu His His Gln Asp Leu Thr Leu Leu Lys Ala Leu
                565                 570                 575

Val Arg Gln Gln Leu Pro Glu Lys Tyr Lys Glu Ile Phe Phe Asp Gln
            580                 585                 590

Ser Lys Asn Gly Tyr Ala Gly Tyr Ile Asp Gly Gly Ala Ser Gln Glu
        595                 600                 605

Glu Phe Tyr Lys Phe Ile Lys Pro Ile Leu Glu Lys Met Asp Gly Thr
    610                 615                 620

Glu Glu Leu Leu Val Lys Leu Asn Arg Glu Asp Leu Leu Arg Lys Gln
625                 630                 635                 640

Arg Thr Phe Asp Asn Gly Ser Ile Pro His Gln Ile His Leu Gly Glu
                645                 650                 655

Leu His Ala Ile Leu Arg Arg Gln Glu Asp Phe Tyr Pro Phe Leu Lys
            660                 665                 670

Asp Asn Arg Glu Lys Ile Glu Lys Ile Leu Thr Phe Arg Ile Pro Tyr
        675                 680                 685

Tyr Val Gly Pro Leu Ala Arg Gly Asn Ser Arg Phe Ala Trp Met Thr
    690                 695                 700

Arg Lys Ser Glu Glu Thr Ile Thr Pro Trp Asn Phe Glu Glu Val Val
705                 710                 715                 720

Asp Lys Gly Ala Ser Ala Gln Ser Phe Ile Glu Arg Met Thr Asn Phe
                725                 730                 735

Asp Lys Asn Leu Pro Asn Glu Lys Val Leu Pro Lys His Ser Leu Leu
            740                 745                 750

Tyr Glu Tyr Phe Thr Val Tyr Asn Glu Leu Thr Lys Val Lys Tyr Val
        755                 760                 765

Thr Glu Gly Met Arg Lys Pro Ala Phe Leu Ser Gly Glu Gln Lys Lys
    770                 775                 780

Ala Ile Val Asp Leu Leu Phe Lys Thr Asn Arg Lys Val Thr Val Lys
785                 790                 795                 800

Gln Leu Lys Glu Asp Tyr Phe Lys Lys Ile Glu Cys Phe Asp Ser Val
                805                 810                 815

Glu Ile Ser Gly Val Glu Asp Arg Phe Asn Ala Ser Leu Gly Thr Tyr
            820                 825                 830

His Asp Leu Leu Lys Ile Ile Lys Asp Lys Asp Phe Leu Asp Asn Glu
        835                 840                 845

Glu Asn Glu Asp Ile Leu Glu Asp Ile Val Leu Thr Leu Thr Leu Phe
    850                 855                 860

Glu Asp Arg Glu Met Ile Glu Glu Arg Leu Lys Thr Tyr Ala His Leu
865                 870                 875                 880

Phe Asp Asp Lys Val Met Lys Gln Leu Lys Arg Arg Arg Tyr Thr Gly
                885                 890                 895

Trp Gly Arg Leu Ser Arg Lys Leu Ile Asn Gly Ile Arg Asp Lys Gln
            900                 905                 910

Ser Gly Lys Thr Ile Leu Asp Phe Leu Lys Ser Asp Gly Phe Ala Asn
        915                 920                 925

Arg Asn Phe Met Gln Leu Ile His Asp Asp Ser Leu Thr Phe Lys Glu
    930                 935                 940

Asp Ile Gln Lys Ala Gln Val Ser Gly Gln Gly Asp Ser Leu His Glu
945                 950                 955                 960
```

His Ile Ala Asn Leu Ala Gly Ser Pro Ala Ile Lys Lys Gly Ile Leu
                965                 970                 975

Gln Thr Val Lys Val Val Asp Glu Leu Val Lys Val Met Gly Arg His
                980                 985                 990

Lys Pro Glu Asn Ile Val Ile Glu Met Ala Arg Glu Asn Gln Thr Thr
            995                1000                1005

Gln Lys Gly Gln Lys Asn Ser Arg Glu Arg Met Lys Arg Ile Glu
        1010                1015                1020

Glu Gly Ile Lys Glu Leu Gly Ser Gln Ile Leu Lys Glu His Pro
        1025                1030                1035

Val Glu Asn Thr Gln Leu Gln Asn Glu Lys Leu Tyr Leu Tyr Tyr
        1040                1045                1050

Leu Gln Asn Gly Arg Asp Met Tyr Val Asp Gln Glu Leu Asp Ile
        1055                1060                1065

Asn Arg Leu Ser Asp Tyr Asp Val Asp Ala Ile Val Pro Gln Ser
        1070                1075                1080

Phe Leu Lys Asp Asp Ser Ile Asp Asn Lys Val Leu Thr Arg Ser
        1085                1090                1095

Asp Lys Asn Arg Gly Lys Ser Asp Asn Val Pro Ser Glu Glu Val
        1100                1105                1110

Val Lys Lys Met Lys Asn Tyr Trp Arg Gln Leu Leu Asn Ala Lys
        1115                1120                1125

Leu Ile Thr Gln Arg Lys Phe Asp Asn Leu Thr Lys Ala Glu Arg
        1130                1135                1140

Gly Gly Leu Ser Glu Leu Asp Lys Ala Gly Phe Ile Lys Arg Gln
        1145                1150                1155

Leu Val Glu Thr Arg Gln Ile Thr Lys His Val Ala Gln Ile Leu
        1160                1165                1170

Asp Ser Arg Met Asn Thr Lys Tyr Asp Glu Asn Asp Lys Leu Ile
        1175                1180                1185

Arg Glu Val Lys Val Ile Thr Leu Lys Ser Lys Leu Val Ser Asp
        1190                1195                1200

Phe Arg Lys Asp Phe Gln Phe Tyr Lys Val Arg Glu Ile Asn Asn
        1205                1210                1215

Tyr His His Ala His Asp Ala Tyr Leu Asn Ala Val Val Gly Thr
        1220                1225                1230

Ala Leu Ile Lys Lys Tyr Pro Lys Leu Glu Ser Glu Phe Val Tyr
        1235                1240                1245

Gly Asp Tyr Lys Val Tyr Asp Val Arg Lys Met Ile Ala Lys Ser
        1250                1255                1260

Glu Gln Glu Ile Gly Lys Ala Thr Ala Lys Tyr Phe Phe Tyr Ser
        1265                1270                1275

Asn Ile Met Asn Phe Phe Lys Thr Glu Ile Thr Leu Ala Asn Gly
        1280                1285                1290

Glu Ile Arg Lys Arg Pro Leu Ile Glu Thr Asn Gly Glu Thr Gly
        1295                1300                1305

Glu Ile Val Trp Asp Lys Gly Arg Asp Phe Ala Thr Val Arg Lys
        1310                1315                1320

Val Leu Ser Met Pro Gln Val Asn Ile Val Lys Lys Thr Glu Val
        1325                1330                1335

Gln Thr Gly Gly Phe Ser Lys Glu Ser Ile Leu Pro Lys Arg Asn
        1340                1345                1350

Ser Asp Lys Leu Ile Ala Arg Lys Lys Asp Trp Asp Pro Lys Lys

| | | | | | | | | | |
|---|---|---|---|---|---|---|---|---|---|
| | | | | 1355 | | | 1360 | | 1365 |

Tyr Gly Gly Phe Asp Ser Pro Thr Val Ala Tyr Ser Val Leu Val
    1370                    1375                    1380

Val Ala Lys Val Glu Lys Gly Lys Ser Lys Lys Leu Lys Ser Val
    1385                    1390                    1395

Lys Glu Leu Leu Gly Ile Thr Ile Met Glu Arg Ser Ser Phe Glu
    1400                    1405                    1410

Lys Asn Pro Ile Asp Phe Leu Glu Ala Lys Gly Tyr Lys Glu Val
    1415                    1420                    1425

Lys Lys Asp Leu Ile Ile Lys Leu Pro Lys Tyr Ser Leu Phe Glu
    1430                    1435                    1440

Leu Glu Asn Gly Arg Lys Arg Met Leu Ala Ser Ala Gly Glu Leu
    1445                    1450                    1455

Gln Lys Gly Asn Glu Leu Ala Leu Pro Ser Lys Tyr Val Asn Phe
    1460                    1465                    1470

Leu Tyr Leu Ala Ser His Tyr Glu Lys Leu Lys Gly Ser Pro Glu
    1475                    1480                    1485

Asp Asn Glu Gln Lys Gln Leu Phe Val Glu Gln His Lys His Tyr
    1490                    1495                    1500

Leu Asp Glu Ile Ile Glu Gln Ile Ser Glu Phe Ser Lys Arg Val
    1505                    1510                    1515

Ile Leu Ala Asp Ala Asn Leu Asp Lys Val Leu Ser Ala Tyr Asn
    1520                    1525                    1530

Lys His Arg Asp Lys Pro Ile Arg Glu Gln Ala Glu Asn Ile Ile
    1535                    1540                    1545

His Leu Phe Thr Leu Thr Asn Leu Gly Ala Pro Ala Ala Phe Lys
    1550                    1555                    1560

Tyr Phe Asp Thr Thr Ile Asp Arg Lys Arg Tyr Thr Ser Thr Lys
    1565                    1570                    1575

Glu Val Leu Asp Ala Thr Leu Ile His Gln Ser Ile Thr Gly Leu
    1580                    1585                    1590

Tyr Glu Thr Arg Ile Asp Leu Ser Gln Leu Gly Gly Asp
    1595                    1600                    1605

<210> SEQ ID NO 96
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 96
attattatta ttccgcggat ttatttattt atttatttat tt                         42

<210> SEQ ID NO 97
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (10)..(12)
<223> OTHER INFORMATION: nucleotides may be repeated multiple times
<220> FEATURE:
<221> NAME/KEY: misc_feature

```
<222> LOCATION: (16)..(23)
<223> OTHER INFORMATION: n is a, c, g, or t
<220> FEATURE:
<221> NAME/KEY: misc_feature
<222> LOCATION: (30)..(35)
<223> OTHER INFORMATION: n is a, c, g, or t

<400> SEQUENCE: 97
atcttccnnn nncgtnnnnn nnncctcctn nnnnn                              35

<210> SEQ ID NO 98
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (13)..(20)
<223> OTHER INFORMATION: n is a, c, g, or t
<220> FEATURE:
<221> NAME/KEY: misc_feature
<222> LOCATION: (24)..(26)
<223> OTHER INFORMATION: n is a or t
<220> FEATURE:
<221> NAME/KEY: misc_feature
<222> LOCATION: (24)..(26)
<223> OTHER INFORMATION: nucleotides may be repeated multiple times
<220> FEATURE:
<221> NAME/KEY: misc_feature
<222> LOCATION: (27)..(28)
<223> OTHER INFORMATION: n is a, c, g, or t

<400> SEQUENCE: 98
nnnnnnagga ggnnnnnnnn acgnnnnngg aagat                              35

<210> SEQ ID NO 99
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 99
attattatta ttccgcggat ttatttattt atttatttat tt                      42

<210> SEQ ID NO 100
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 100
attattatta ttcugcggat ttatttattt atttatttat tt                      42

<210> SEQ ID NO 101
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 101
attattatta ttcgcggatt tatttattta tttatttatt t                       41
```

```
<210> SEQ ID NO 102
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 102
attattatta ttc                                                          13

<210> SEQ ID NO 103
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 103
gcggatttat ttatttattt atttattt                                          28

<210> SEQ ID NO 104
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 104
attattatta ttc                                                          13

<210> SEQ ID NO 105
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 105
gcggatttat ttatttattt atttattt                                          28

<210> SEQ ID NO 106
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(7)
<223> OTHER INFORMATION: these amino acids may be absent
<220> FEATURE:
<221> NAME/KEY: misc_feature
<222> LOCATION: (8)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: MISC_FEATURE
<222> LOCATION: (33)..(34)
<223> OTHER INFORMATION: these amnio acids may be absent
<220> FEATURE:
<221> NAME/KEY: misc_feature
<222> LOCATION: (35)..(35)
<223> OTHER INFORMATION: Xaa can be any naturally occurring amino acid
```

```
<400> SEQUENCE: 106

His Xaa Glu Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Pro Cys Xaa
            20                  25                  30

Xaa Xaa Xaa Cys
        35
```

What is claimed is:

1. A fusion protein comprising, in order, from N- to C-terminus:
   (i) a catalytic deaminase domain of an apolipoprotein B mRNA-editing complex (APOBEC) family deaminase comprising an amino acid sequence that is at least 95% identical to SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; and
   (ii) a nuclease-inactive Clustered Regulatory Interspaced Short Palindromic Repeat-associated protein 9 (dCas9) domain, wherein the dCas9 domain comprises an amino acid sequence that is at least 95% identical to the amino acid sequence of SEQ ID NO: 2,
   wherein the catalytic deaminase domain of (i) and the dCas9 domain of (ii) are fused via a linker comprising the amino acid sequence SGSETPGTSESATPES (SEQ ID NO: 93).

2. The fusion protein of claim 1, wherein the catalytic deaminase domain is a catalytic domain of an APOBEC1 family deaminase.

3. A method of DNA editing, the method comprising contacting a DNA molecule with
   (a) the fusion protein of claim 1; and
   (b) a single guide RNA (sgRNA) targeting the fusion protein of (a) to a target DNA sequence of the DNA molecule;
   wherein the DNA molecule is contacted with the fusion protein and the sgRNA in an amount effective and under conditions suitable for the deamination of a nucleotide base of the DNA molecule.

4. The method of claim 3, wherein the target DNA sequence comprises a sequence associated with a disease or disorder, and wherein the deamination of the nucleotide base results in a sequence that is not associated with the disease or disorder.

5. The method of claim 4, wherein the target DNA sequence comprises a point mutation associated with a disease or disorder, and wherein the deamination corrects the point mutation.

6. The method of claim 3, wherein the target DNA sequence comprises a T→C or A→G point mutation associated with a disease or disorder, and wherein the deamination of the mutant C or G base results in a sequence that is not associated with a disease or disorder.

7. The method of claim 4, wherein the sequence associated with the disease or disorder encodes a protein, and wherein the deamination introduces a stop codon into the sequence associated with the disease or disorder, resulting in a truncation of the encoded protein.

8. The method of claim 4, wherein the contacting is in vivo in a subject having or diagnosed with a disease or disorder.

9. The method of claim 4, wherein the disease or disorder is cystic fibrosis, phenylketonuria, epidermolytic hyperkeratosis (EHK), Charcot-Marie-Toot disease type 4J, neuroblastoma (NB), von Willebrand disease (vWD), myotonia congenital, hereditary renal amyloidosis, dilated cardiomyopathy (DCM), hereditary lymphedema, familial Alzheimer's disease, Prion disease, chronic infantile neurologic cutaneous articular syndrome (CINCA), desmin-related myopathy (DRM), or a neoplastic disease associated with a mutant PI3KCA protein.

10. The method of claim 3, wherein the method further comprises detecting the deamination of the nucleotide base.

11. The method of claim 10, wherein the detecting is via PCR.

12. A kit comprising
    a DNA or an RNA construct, comprising
      a sequence encoding the fusion protein of claim 1; and
      suitable reagents, buffers, and/or instructions.

13. The fusion protein of claim 1, wherein the catalytic deaminase domain of the APOBEC family deaminase is a catalytic domain of an APOBEC3 family deaminase.

14. The fusion protein of claim 2, wherein the APOBEC1 family deaminase comprises the amino acid sequence at least 95% identical to SEQ ID NO: 22, SEQ ID NO: 23, or SEQ ID NO: 24.

15. The fusion protein of claim 1 further comprising a nuclear localization signal (NLS).

16. The fusion protein of claim 15, wherein the NLS is fused to the C-terminus of the dCas9 domain.

17. The fusion protein of claim 1, wherein the dCas9 domain comprises an amino acid sequence that is at least 98% identical to the amino acid sequence of SEQ ID NO: 2.

18. The fusion protein of claim 1, wherein the dCas9 domain comprises an amino acid sequence at least 99% identical to SEQ ID NO: 2.

19. The fusion protein of claim 1, wherein the dCas9 domain comprises an alanine (A) at the residue corresponding to residue 10 in SEQ ID NO: 2.

20. The fusion protein of claim 13, wherein the catalytic deaminase domain of the APOBEC family deaminase comprises an amino acid sequence at least 98% identical to SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

21. The fusion protein of claim 1, wherein the catalytic deaminase domain of the APOBEC family deaminase comprises an amino acid sequence at least 98% identical to SEQ ID NO: 24.

22. The fusion protein of claim 1, wherein the catalytic deaminase domain of the APOBEC family deaminase comprises an amino acid sequence at least 99% identical to SEQ ID NO: 24.

23. A fusion protein comprising, in order, from N- to C-terminus:
   (i) a catalytic deaminase domain of an apolipoprotein B mRNA-editing complex (APOBEC) family deaminase comprising an amino acid sequence that is at least 95% identical to SEQ ID NO:
   10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; and
   (ii) a nuclease-inactive Clustered Regulatory Interspaced Short Palindromic Repeat-associated protein 9 (dCas9) domain, wherein the dCas9 domain comprises an amino acid sequence that is at least 95% identical to the amino acid sequence of SEQ ID NO: 37,
   wherein the catalytic deaminase domain of (i) and the dCas9 domain of (ii) are fused via a linker comprising the amino acid sequence SGSETPGTSESATPES (SEQ ID NO: 93).

24. The fusion protein of claim 23, wherein the catalytic deaminase domain is a catalytic domain of an APOBEC1 family deaminase.

25. A method of DNA editing, the method comprising contacting a DNA molecule with
   (a) the fusion protein of claim 23; and
   (b) a single guide RNA (sgRNA) targeting the fusion protein of (a) to a target DNA sequence of the DNA molecule;
   wherein the DNA molecule is contacted with the fusion protein and the sgRNA in an amount effective and under conditions suitable for the deamination of a nucleotide base of the DNA molecule.

26. The method of claim 25, wherein the target DNA sequence comprises a sequence associated with a disease or disorder, and wherein the deamination of the nucleotide base results in a sequence that is not associated with the disease or disorder.

27. The method of claim 26, wherein the target DNA sequence comprises a point mutation associated with a disease or disorder, and wherein the deamination corrects the point mutation.

28. The method of claim 25, wherein the target DNA sequence comprises a T→C or A→G point mutation associated with a disease or disorder, and wherein the deamination of the mutant C or G base results in a sequence that is not associated with a disease or disorder.

29. The method of claim 26, wherein the sequence associated with the disease or disorder encodes a protein, and wherein the deamination introduces a stop codon into the sequence associated with the disease or disorder, resulting in a truncation of the encoded protein.

30. The method of claim 26, wherein the contacting is in vivo in a subject having or diagnosed with a disease or disorder.

31. The method of claim 26, wherein the disease or disorder is cystic fibrosis, phenylketonuria, epidermolytic hyperkeratosis (EHK), Charcot-Marie-Toot disease type 4J, neuroblastoma (NB), von Willebrand disease (vWD), myotonia congenital, hereditary renal amyloidosis, dilated cardiomyopathy (DCM), hereditary lymphedema, familial Alzheimer's disease, Prion disease, chronic infantile neurologic cutaneous articular syndrome (CINCA), desmin-related myopathy (DRM), or a neoplastic disease associated with a mutant PI3KCA protein.

32. The method of claim 25, wherein the method further comprises detecting the deamination of the nucleotide base.

33. The method of claim 32, wherein the detecting is via PCR.

34. A kit comprising
   a DNA or an RNA construct, comprising
     a sequence encoding the fusion protein of claim 23; and
     suitable reagents, buffers, and/or instructions.

35. The fusion protein of claim 23, wherein the catalytic deaminase domain of the APOBEC family deaminase is a catalytic domain of an APOBEC3 family deaminase.

36. The fusion protein of claim 24, wherein the APOBEC1 family deaminase comprises the amino acid sequence at least 95% identical to SEQ ID NO: 22, SEQ ID NO: 23, or SEQ ID NO: 24.

37. The fusion protein of claim 23 further comprising a nuclear localization signal (NLS).

38. The fusion protein of claim 37, wherein the NLS is fused to the C-terminus of the dCas9 domain.

39. The fusion protein of claim 23, wherein the dCas9 domain comprises an amino acid sequence that is at least 98% identical to the amino acid sequence of SEQ ID NO: 37.

40. The fusion protein of claim 23, wherein the dCas9 domain comprises an amino acid sequence at least 99% identical to SEQ ID NO: 37.

41. The fusion protein of claim 23, wherein the dCas9 domain comprises an alanine (A) at the residue corresponding to residue 10 in SEQ ID NO: 37.

42. The fusion protein of claim 35, wherein the catalytic deaminase domain of the APOBEC family deaminase comprises an amino acid sequence at least 98% identical to SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

43. The fusion protein of claim 23, wherein the catalytic deaminase domain of the APOBEC family deaminase comprises an amino acid sequence at least 98% identical to SEQ ID NO: 24.

44. The fusion protein of claim 23, wherein the catalytic deaminase domain of the APOBEC family deaminase comprises an amino acid sequence at least 99% identical to SEQ ID NO: 24.

* * * * *